United States Patent
Perez et al.

(10) Patent No.: US 11,369,501 B2
(45) Date of Patent: *Jun. 28, 2022

(54) PERCUTANEOUS ELECTRICAL DERMAL PATCH FOR ENABLING APPETITE MODULATION AND/OR IMPROVING DIETARY COMPLIANCE

(71) Applicant: Elira, Inc., St. Louis, MO (US)

(72) Inventors: Raul E. Perez, St. Louis, MO (US); Peter I. Hong, Valencia, CA (US); Steven DiIanni, Amesbury, MA (US); Luis Jose Malave, San Marcos, CA (US); Brad Stengel, Kirkwood, MO (US); John L. Faul, Donnybrook (IE)

(73) Assignee: Elira, Inc., St. Louis, MO (US)

( * ) Notice: Subject to any disclaimer, the term of this patent is extended or adjusted under 35 U.S.C. 154(b) by 220 days.

This patent is subject to a terminal disclaimer.

(21) Appl. No.: 16/171,148

(22) Filed: Oct. 25, 2018

(65) Prior Publication Data

US 2019/0328565 A1    Oct. 31, 2019

Related U.S. Application Data

(63) Continuation of application No. 15/204,752, filed on Jul. 7, 2016, now Pat. No. 10,154,922, which is a
(Continued)

(51) Int. Cl.
*A61N 1/36* (2006.01)
*A61F 5/00* (2006.01)
(Continued)

(52) U.S. Cl.
CPC .......... *A61F 5/0026* (2013.01); *A61N 1/0502* (2013.01); *A61N 1/36017* (2013.01);
(Continued)

(58) Field of Classification Search
None
See application file for complete search history.

(56) References Cited

U.S. PATENT DOCUMENTS

| 4,646,744 A | 3/1987 | Capel |
| 5,067,495 A | 11/1991 | Brehm |

(Continued)

FOREIGN PATENT DOCUMENTS

WO    2014194200 A1    12/2014

OTHER PUBLICATIONS

Camilleri et al, "Effect of somatovisceral reflexes and selective dermatomal stimulation on postcibal antral pressure activity", Gastroenterology Unit, Mayo Clinic, Rochester, Minnesota 55905, Jul. 1984.

(Continued)

*Primary Examiner* — Kennedy Schaetzle
(74) *Attorney, Agent, or Firm* — Novel IP

(57) ABSTRACT

A wearable, percutaneous device for suppressing appetite or hunger in a patient includes a microprocessor, electrical stimulator and at least one percutaneous electrode implanted and configured to deliver electrical stimulation through the patient's skin. The percutaneous device includes a pad and at least one needle, in which the electrode is disposed, for secure placement of the device within the skin of a patient. The percutaneous device is adapted to provide electrical stimulation as per stimulation protocols and to communicate wirelessly with a companion control device configured to monitor and record appetite patterns of the patient. The control device is also configured to monitor, record, and modify stimulation parameters of the stimulation protocols.

9 Claims, 62 Drawing Sheets

Related U.S. Application Data continuation-in-part of application No. 15/052,784, filed on Feb. 24, 2016, now Pat. No. 10,143,840, and a continuation-in-part of application No. 15/052,791, filed on Feb. 24, 2016, now Pat. No. 10,118,035.

(60) Provisional application No. 62/248,059, filed on Oct. 29, 2015, provisional application No. 62/247,113, filed on Oct. 27, 2015, provisional application No. 62/246,526, filed on Oct. 26, 2015, provisional application No. 62/242,944, filed on Oct. 16, 2015, provisional application No. 62/242,957, filed on Oct. 16, 2015, provisional application No. 62/240,808, filed on Oct. 13, 2015, provisional application No. 62/237,356, filed on Oct. 5, 2015, provisional application No. 62/189,805, filed on Jul. 8, 2015, provisional application No. 62/189,800, filed on Jul. 8, 2015, provisional application No. 62/161,362, filed on May 14, 2015, provisional application No. 62/161,353, filed on May 14, 2015, provisional application No. 62/141,328, filed on Apr. 1, 2015, provisional application No. 62/141,333, filed on Apr. 1, 2015, provisional application No. 62/133,526, filed on Mar. 16, 2015, provisional application No. 62/133,530, filed on Mar. 16, 2015, provisional application No. 62/120,082, filed on Feb. 24, 2015, provisional application No. 62/120,067, filed on Feb. 24, 2015.

(51) Int. Cl.
| | | |
|---|---|---|
| *A61N 1/05* | (2006.01) | |
| *A61N 1/08* | (2006.01) | |
| *A61B 5/00* | (2006.01) | |
| *A61B 5/11* | (2006.01) | |
| *A61B 5/053* | (2021.01) | |
| *A61B 5/24* | (2021.01) | |

(52) U.S. Cl.
CPC .......... *A61N 1/36034* (2017.08); *A61B 5/053* (2013.01); *A61B 5/1118* (2013.01); *A61B 5/24* (2021.01); *A61B 5/4848* (2013.01); *A61B 5/4866* (2013.01); *A61N 1/36085* (2013.01); *A61N 2001/083* (2013.01)

(56) References Cited

U.S. PATENT DOCUMENTS

| | | | |
|---|---|---|---|
| 5,263,480 A | 11/1993 | Wernicke | |
| 5,514,175 A | 5/1996 | Kim | |
| 6,097,982 A | 8/2000 | Glegyak | |
| 6,179,756 B1 | 1/2001 | Bertolucci | |
| 6,192,889 B1 | 2/2001 | Morrish | |
| 6,228,103 B1 | 5/2001 | Grey | |
| 6,272,383 B1 | 8/2001 | Grey | |
| 6,282,443 B1 | 8/2001 | Mann | |
| 6,361,550 B2 | 3/2002 | Grey | |
| 6,366,813 B1 | 4/2002 | DiLorenzo | |
| 6,393,324 B2 | 5/2002 | Gruzdowich | |
| 6,535,760 B1 | 3/2003 | Grey | |
| 6,567,695 B1 | 5/2003 | Gruzdowich | |
| 6,582,449 B2 | 6/2003 | Grey | |
| 6,587,719 B1 | 7/2003 | Barrett | |
| 6,658,298 B2 | 12/2003 | Gruzdowich | |
| 6,671,557 B1* | 12/2003 | Gliner | A61N 1/36021 607/2 |
| 6,718,202 B2 | 4/2004 | Mann | |
| 6,735,480 B2 | 5/2004 | Giuntoli | |
| 6,819,956 B2 | 11/2004 | DiLorenzo | |
| 7,089,061 B2 | 8/2006 | Grey | |
| 7,127,288 B2 | 10/2006 | Sturman | |
| 7,171,266 B2 | 1/2007 | Gruzdowich | |
| 7,171,276 B2 | 1/2007 | Giuntoli | |
| 7,200,443 B2 | 4/2007 | Faul | |
| 7,209,787 B2 | 4/2007 | DiLorenzo | |
| 7,231,254 B2 | 6/2007 | DiLorenzo | |
| 7,242,984 B2 | 7/2007 | DiLorenzo | |
| 7,277,758 B2 | 10/2007 | DiLorenzo | |
| 7,324,851 B1 | 1/2008 | DiLorenzo | |
| 7,346,390 B1 | 3/2008 | Tumey | |
| 7,403,820 B2 | 7/2008 | DiLorenzo | |
| 7,529,582 B1 | 5/2009 | DiLorenzo | |
| 7,599,736 B2 | 10/2009 | DiLorenzo | |
| 7,623,928 B2 | 11/2009 | DiLorenzo | |
| 7,747,325 B2 | 6/2010 | DiLorenzo | |
| 7,853,329 B2 | 12/2010 | DiLorenzo | |
| 7,930,033 B2 | 4/2011 | Chen | |
| 7,930,035 B2 | 4/2011 | DiLorenzo | |
| 7,974,696 B1 | 7/2011 | DiLorenzo | |
| 7,983,761 B2 | 7/2011 | Giuntoli | |
| 8,260,439 B2 | 9/2012 | DiUbaldi | |
| 8,396,557 B2 | 3/2013 | DiLorenzo | |
| 8,574,164 B2 | 11/2013 | Mashiach | |
| 8,725,243 B2 | 5/2014 | DiLorenzo | |
| 8,762,065 B2 | 6/2014 | DiLorenzo | |
| 8,781,597 B2 | 7/2014 | DiLorenzo | |
| 8,852,238 B2* | 10/2014 | Nazeck | A61B 17/7085 606/264 |
| 8,862,238 B2 | 10/2014 | Rahimi | |
| 8,868,172 B2 | 10/2014 | Leyde | |
| 8,874,205 B2 | 10/2014 | Simon | |
| 8,880,175 B2 | 11/2014 | Simon | |
| 9,042,988 B2 | 5/2015 | DiLorenzo | |
| 9,113,801 B2 | 8/2015 | DiLorenzo | |
| 9,168,375 B2 | 10/2015 | Rahimi | |
| 9,320,900 B2 | 4/2016 | DiLorenzo | |
| 9,345,880 B1 | 5/2016 | DiLorenzo | |
| 9,375,573 B2 | 6/2016 | DiLorenzo | |
| 9,403,001 B2 | 8/2016 | Simon | |
| 9,415,222 B2 | 8/2016 | DiLorenzo | |
| 9,421,373 B2 | 8/2016 | DiLorenzo | |
| 9,466,919 B2 | 10/2016 | Kiani | |
| 9,630,004 B2* | 4/2017 | Rajguru | A61N 2/02 |
| 10,154,922 B1* | 12/2018 | Perez | A61N 1/36017 |
| 10,667,711 B1* | 6/2020 | Felix | A61B 5/0024 |
| 2001/0021869 A1* | 9/2001 | Bishay | A61N 1/36021 607/116 |
| 2002/0087192 A1 | 7/2002 | Barrett | |
| 2003/0181959 A1 | 9/2003 | Dobak | |
| 2007/0060971 A1 | 3/2007 | Glasberg | |
| 2007/0093870 A1 | 4/2007 | Maschino | |
| 2007/0123952 A1* | 5/2007 | Strother | A61N 1/36017 607/48 |
| 2007/0162085 A1 | 7/2007 | DiLorenzo | |
| 2007/0239224 A1 | 10/2007 | Bennett | |
| 2007/0255335 A1 | 11/2007 | Herbert | |
| 2008/0132962 A1 | 6/2008 | DiUbaldi | |
| 2009/0132018 A1 | 5/2009 | DiUbaldi | |
| 2009/0157149 A1* | 6/2009 | Wahlgren | A61N 1/0492 607/66 |
| 2011/0257711 A1 | 10/2011 | Lindner | |
| 2012/0101874 A1 | 4/2012 | Ben-Haim | |
| 2012/0121735 A1 | 5/2012 | Halford | |
| 2013/0096641 A1 | 4/2013 | Strother | |
| 2013/0110201 A1 | 5/2013 | Bonde | |
| 2013/0131753 A1 | 5/2013 | Simon | |
| 2013/0296996 A1 | 11/2013 | Wahlgren | |
| 2013/0338729 A1* | 12/2013 | Spector | A61N 1/36021 607/46 |
| 2014/0031895 A1 | 1/2014 | Rahimi | |
| 2014/0051906 A1 | 2/2014 | Chen | |
| 2014/0296935 A1 | 10/2014 | Ferree | |
| 2015/0005841 A1 | 1/2015 | Pal | |

(56) References Cited

U.S. PATENT DOCUMENTS

2016/0235352 A1  8/2016  DiLorenzo
2017/0203095 A1  7/2017  Bachinski

OTHER PUBLICATIONS

"Feasibility Assessment of Appetite Suppression Utilizing TENS Trial-1 (FAAST-1)", Protocol No. CD-001, Revision: Version Rev 02 (Nov. 20, 2015).
Hall WJ, O'Connor PC., "A pharmacological analysis of the response of dog anterior mesenteric vein to transmural electrical stimulation", Ir J Med Sci. Jul.-Sep. 1972;141(7):113-9.
Lee SK et al, "Electroacupuncture may relax the sphincter of Oddi in humans", Gastrointest Endosc. Feb. 2001;53(2):211-6.
Lee GT., "A study of electrical stimulation of acupuncture locus tsusanli (St-36) on mesenteric microcirculation", Am J Chin Med (Gard City N Y). Jan. 1974;2(1):53-66.
Obuchowicz A, Obuchowicz E., "Plasma beta-endorphin and insulin concentrations in relation to body fat and nutritional parameters in overweight and obese prepubertal children", Int J Obes Relat Metab Disord. Sep. 1997;21(9):783-8.
Giovannini et al, "Unresponsiveness of the endorphinergic system to its physiological feedback in obesity", Appetite. Feb. 1991;16(1):39-43.
Wan et al, "The effectiveness of purgation and electroacupuncture in extrahepatic bile duct stone complicated with acute biliary pancreatitis: management of biliary stone pancreatitis through traditional Chinese medicine", Pancreas. Apr. 2011;40(3):483-4. doi: 10.1097/MPA.0b013e318205e52f.
Blaut et al, "The effect of transcutaneous nerve stimulation on intraductal biliary pressure in post-cholecystectomy patients with T-drainage", Eur J Gastroenterol Hepatol. Jan. 2003;15(1):21-6.
Kim MH, "A brief commentary: electroacupuncture may relax the contraction of sphincter of Oddi". The Journal of Alternative and Complementary Medicine. vol. 7, Supplement 1, 2001, pp. S-119-S-120.
Liu et al, "Effects of acupuncture on myoelectric activity of Oddis sphincter in humans", J Tradit Chin Med. Sep. 1993;13(3):189-90.
"D4.3: Satiety Methodology", Work Package 4, Project No. KBBE-2011-5-289800, Project Title: SATIN (Satiety Innovation), Lead Partner: University of Leeds (UNIVLEEDS). Nov. 13, 2012.
Jing Wang et al, "Effects of Cutaneous Gastric Electrical Stimulation on Gastric Emptying and Postprandial Satiety and Fullness in Lean and Obese Subjects", J Clin Gastroenterol vol. 44, No. 5, May/Jun. 2010.
Mark Johnson, "Transcutaneous electrical nerve stimulation (TENS)".
"ACUSLIM Control Your Appetite the Natural Way", Simply Good Health, Australia. Natural Remedies for Healthy Living, Nov. 21, 1997.
Furgala et al, "The effect of Transcutaneous Nerve Stimulation (TENS) on gastric electrical activity", Oct. 18, 2001, http://www.jpp.krakow.pl/journal/archive/12_01/articles/07_article.html.
Wang et al, "Effects of Cutaneous Gastric Electrical Stimulation on Gastric Emptying and Postprandial Satiety and Fullness in Lean and Obese Subjects", J Clin Gastroenterol, vol. 44, No. 5, May/Jun. 2010.
JM Lacey et al, "Acupuncture for the treatment of obesity: a review of the evidence", International Journal of Obesity (2003) 27, 419-427.
Philip V. Peplow et al, "Electroacupuncture for Control of Blood Glucose in Diabetes: Literature Review", J Acupunct Meridian Stud 2012;5(1):1-10.
Mohammad Ma'ani et al, "Nerve Supply of the Stomach and the Small Intestines", Anatomy—7, Apr. 21, 2015.
Camilleri et al, "Relation between antral motility and gastric emptying of solids and liquids in humans", The American journal of physiology, Dec. 1985.

Liu Zhicheng et al, "Effect of acupuncture on weight loss evaluated by adrenal function", Journal of Traditional Chinese Medicine 13 (3): 169-173, 1993.
J F Bergmann et al, "Correlation between echographic gastric emptying and appetite: influence of psyllium", Gut 1992; 33: 1042-1043.
Janssen et al, "Review article: the role of gastric motility in the control of food intake", Aliment Pharmacol Ther 2011; 33: 880-894.
Eva Haker et al, "Effect of sensory stimulation (acupuncture) on sympathetic and parasympathetic activities in healthy subjects", Journal of the Autonomic Nervous System 79 (2000) 52-59.
Stein Knardahl et al, "Sympathetic nerve activity after acupuncture in humans", Pain 75 (1998) 19-25.
Monique Ernst et al, "Sympathetic effects of manual and electrical acupuncture of the Tsusnali Knee Point: Comparison with the Hoku Hand point sympathetic effects", Experimental Neurology 94, 1-10 (1986).
DiLorenzo, Daniel John, "Chronic Intraneural Electrical Stimulation for Prosthetic Sensory Feedback", Proc. 1st Intl IEEE EMBS Conf Neural Eng, Mar. 20-22, 2003.
Sven Andersson, "The functional background in acupuncture effects", Scand J Rehab Med, Suppl 29: 31-60, 1993.
Akio Sato et al, "Somatosympathetic Reflexes : Afferent Fibers, Central Pathways, Discharge Characteristics", Physiological Reviews, vol. 53, No. 4, Oct. 1973.
Kazushi Nishijo et al, "Decreased heart rate by acupuncture stimulation in humans via facilitation of cardiac vagal activity and suppression of cardiac sympathetic nerve", Neuroscience Letters 227 (1997) 165-168.
D. Thomas et al, "Somatic sympathetic vasomotor changes documented by medical thermographic imaging during acupuncture analgesia", Clinical reheumatology, 1992, 11, 55-59.
Monique Ernst et al, "Sympathetic vasomotor changes induced by manual and electrical acupuncture of the Hoku Point visualized by thermography", Pain 21 (1985), 25-33.
Will Rosellini, "FDA gives nod to first fully-removable percutaneous peripheral nerve stimulation device", Peripheral Nerve Stimulation, Posted on Jul. 28, 2016.
DiLorenzo, Daniel John, "Development of a Chronically Implanted Microelectrode Array for Intraneural Electrical Stimulation for Prosthetic Sensory Feedback",MIT SM Thesis,1999.
Zardetto-Smith et al., "Catecholamine and NPY Efferents From the Ventrolateral Medulla to the Amygdala in the Rat",Brain Research Bulletin, vol. 38, No. 3, 1995, pp. 253-260.
Barone et al., "Gastric Distension Modulates Hypothalamic Neurons Via a Sympathetic Afferent Path Through the Mesencephalic Periaqueductal Gray", Brain Research Bulletin, vol. 38, No. 3, 1995; pp. 239-251.
Brown et al., "Changes in Food Intake with Electrical Stimulation of the Ventromedial Hypothalamus in Dogs", Journal of Neurosurgery, vol. 60, 1984, pp. 1253-1257.
Daniel et al., "Criteria for Differentiation of Brown and White Fat in the Rat", Canadian Journal of Physiology and Pharmacology, vol. 47, Mar. 22, 1969; pp. 941-945.
Flaim et al., "Coupling of Signals to Brown Fat: .alpha.-and .beta.-Adrenergic Responses in Intact Rats", In Vivo Adrenergic Responses of Brown Adipose Tissue, 1976, pp. R101-R109.
Felton, D.L. and R.F. Jozefowicz, "Netter's Atlas of Human Neuroscience", Icon Learning Systems, Teterboro, NJ, 2004, p. 126.
Kolen et al., "Effects of spatially targeted transcutaneous electrical nerve stimulation using an electrode array that measures skin resistance on pain and mobility in patients with osteoarthritis in the knee: A randomized controlled trial." J. Pain, 153 (2012) 373-381, doi:10.1016/j.pain.2011.10.033.
Malesevic et al., "Classification of muscle twitch response using ANN: Application in multi-pad electrode optimization," IEEE 2010.
Malesevic et al., "Muscle twitch responses for shaping the multi-pad electrode for functional electrical stimulation," IEEE Journal of Automatic Control, University of Belgrade, vol. 20:53-58, 2010.
International Search Report for PCT Application No. PCT/US2016/019416, dated Jun. 21, 2016.

(56) References Cited

OTHER PUBLICATIONS

Li et al, "Acupuncture Effect and Central Autonomic Regulation", Hindawi Publishing Corporation, Evidence-Based Complementary and Alternative Medicine. vol. 2013, Article ID 267959, 6 pages.
"Obesity Treatment Using Neurostimulation", iRunway.com. Karthik Sankar. 2011, 7 pages.
Yao, Tai, "Acupuncture and Somatic Nerve Stimulation: Mechanism Underlying Effects on Cardiovascular and Renal Activities", Scand J Rehab Med, Suppl 29:7-18, 1993.
Derry et al., "Two Sympathetic Nerve Supplies to Brown Adipose Tissue of the Rat", Canadian Journal Of Physiology and Pharmacology, vol. 47, 1969, pp. 57-63.
Takahashi et al., "Hypothalamic Regulation of Lipid Metabolism in the Rat: Effect of Hypothalamic Stimulation on Lipogenesis", Journal of the Autonomic Nervous System, vol. 6, 1982, pp. 225-235.
Yuan et al, "Hypothalamic Unitary Responses to Gastric Vagal Input from the Proximal Stomach", Am J Physiol Gastrointest Liver Physiol 262:G74-G80, 1992.
Astrup A, Buemann B, Christensen NJ, Toubro S, Thorbek G, Victor OJ, Quaade F., "The effect of ephedrine/caffeine mixture on energy expenditure and body composition in obese women", Metabolism vol. 41, No. 7 (Jul. 1992), pp. 686-688.
Astrup A, Toubro S, Christensen NJ, Quaade F., "Pharmacology of thermogenic drugs", Am.J.Clin.Nutr. (1992), pp. 246S-248S.
Tian D et al, "Study on the effect of transcutaneous electric nerve stimulation on obesity", Beijing Da Xue Xue Bao. Jun 2003¾ 35(3):2779.
Berthoud HR, Niijima A, Sauter JF, Jeanrenaud B., "Evidence for a role of the gastric, coeliac and hepatic branches in vagally stimulated insulin secretion in the rat", J.Auton.Nerv.Syst. (1983), pp. 97-110.
Bray GA, "Obesity, a disorder of nutrient partitioning: the Mona Lisa hypothesis", American Institute of Nutrition (1991), pp. 1146-1162.
Bray GA, "Genetic, hypothalamic and endocrine features of clinical and experimental obesity", Prog.Brain Res. (1992), pp. 333-340.
Bray GA., "Reciprocal relation of food intake and sympathetic activity: experimental observations and clinical implications", Int. J.Obes.Relat Metab Disord. (2000), pp. S8-17.
Bray GA, Gallagher TF, Jr., "Manifestations of hypothalamic obesity in man: a comprehensive investigation of eight patients and a review of the literature", Medicine (Baltimore) (1975), pp. 301-330.
Bray GA, York DA, Fisler JS., "Experimental obesity: a homeostatic failure due to defective nutrient stimulation of the sympathetic nervous system", Vitam.Horm. (1989), pp. 1-125.
Bruch H., "The Frohlich syndrome: report of the original case", 1939. Obes. Res. (1939), pp. 329-331.
Cigaina V, V, Saggioro A, Rigo V, V, Pinato G, Ischai S., "Long-term Effects of Gastric Pacing to Reduce Feed Intake in Swine" Obes. Surg. (1996), pp. 250-253.
HANS—Han's Acupoint Nerve Stimulator, http://thehanssite.com. 2012. BioBalance LLC.
Greenway FL, "The safety and efficacy of pharmaceutical and herbal caffeine and ephedrine use as a weight loss agent", Obes.Rev. (2001), pp. 199-211.
Inoue S, Bray GA, "The effects of subdiaphragmatic vagotomy in rats with ventromedial hypothalamic obesity", Endocrinology (1977), pp. 108-114.
Inoue S, Bray GA, Mullen YS, "Transplantation of pancreatic beta-cells prevents development of hypothalamic obesity in rats", Am.J.Physiol (1978), pp. E266-E271.
Jeanrenaud B., "Energy fuel and hormonal profile in experimental obesities", Experientia Suppl (1983), pp. 57-76.
King BM, Frohman LA, "The role of vagally-medicated hyperinsulinemia in hypothalamic obesity", Neurosci.Biobehav. Rev. (1982), pp. 205-214. [28] Kral JG. Vagotomy.
Niijima A, Rohner-Jeanrenaud F, Jeanrenaud B., "Role of ventromedial hypothalamus on sympathetic efferents of brown adipose tissue", Am.J.Physiol (1984), pp. R650-R654.

Pasquali R, Casimirri F, Melchionda N, Grossi G. Bortoluzzi L, Morselli Labate AM, Stefanini C, Raitano A., "Effects of chronic administration of ephedrine during very-low-calorie diets on energy expenditure, protein metabolism and hormone levels in obese subjects", Clin.Sci.(Lond) (1992), pp. 85-92.
Perkins MN, Rothwell NJ, Stock MJ, Stone TW., "Activation of brown adipose tissue thermogenesis by the ventromedial hypothalamus", Nature (1981), pp. 401-402.
Pories WJ, Swanson MS, MacDonald KG, Long SB, Morris PG, Brown BM, Barakat HA, deRamon RA, Israel G, Dolezal JM, "Who would have thought it? An operation proves to be the most effective therapy for adult-onset diabetes mellitus", Ann.Surg. (1995), pp. 339-350.
Reeves AG, Plum F., "Hyperphagia, rage, and dementia accompanying a ventromedial hypothalamic neoplasm", Arch.Neurol. (1969), pp. 616-624.
De Graaf et al, "Biomarkers of satiation and satiety", Am J Clin Nutr 2004;79:946-61.
Sakaguchi T, Bray GA, Eddlestone G., "Sympathetic activity following paraventricular or ventromedial hypothalamic lesions in rats", Brain Res.Bull. (1988), pp. 461-465.
Sauter JF, Berthoud HR, Jeanrenaud B. ,"A simple electrode for intact nerve stimulation and/or recording in semi-chronic rats", Pflugers Arch. (1983), pp. 68-69.
Seydoux J. ssimacopoulos-Jeannet F, Jeanrenaud B, Girardier L., "Alterations of brown adipose tissue in genetically obese (ob/ob) mice. I. Demonstration of loss of metabolic response to nerve stimulation and catecholamines and its partial recovery after fasting or cold adaptation", Endocrinology (1982), pp. 432-438.
Shimizu H, Shargill NS, Bray GA., "Adrenalectomy and response to corticosterone and MSH in the genetically obese yellow mouse", Am.J.Physiol (1989), pp. R494-R500. [38] Smith DK, Sarfeh J, Howard L. Truncal vagotomy.
Tokunaga K, Fukushima M, Kemnitz JW, Bray GA., "Effect of vagotomy on serum insulin in rats with paraventricular or ventromedial hypothalamic lesions", Endocrinology (1986), pp. 1708-1711.
York DA, Bray GA., "Dependence of hypothalamic obesity on insulin, the pituitary and the adrenal gland", Endocrinology (1972), pp. 885-894.
Yoshida T, Bray GA., "Catecholamine turnover in rats with ventromedial hypothalamic lesions", Am.J.Physiol (1984), pp. R558-R565.
"Stimulation of auricular acupuncture points in weight loss", Richards et al., Aust. Fam. Physician, Jul. 1998, 27 Suppl 2:S73-77.
Gibbons et al, "Validation of a new hand-held electronic data capture method for continuous monitoring of subjective appetite sensations", International Journal of Behavioral Nutrition and Physical Activity 2011, 8:57.
Biggs et al., "A Comparison of the Hypoalgesic Effects of Transcutaneous Electrical Nerve Stimulation (TENS) and Non-invasive Interactive Neurostimulation (InterX.RTM.) on Experimentally Induced Blunt Pressure Pain Using Healthy Human Volunteers", Neuromodulation 2012; 15: 93-99.
Jordan Kahn, "Hands on with 'i-Massager' iPhone-controlled electrical nerve stimulation and other iOS massage accessories", 9TO5Mac, http://9to5mac.com/2013/01/09/hands-on-with-i-massager-iphone-controlled-electrical-nerve-stimulation-and-other-ios-massage-accessories/ Jan. 9, 2013.
Malesevic et al., "INTFES: A multi-pad electrode system for selective transcutaneous electrical muscle stimulation". Sep. 2011.
Sauter et al., "Current threshold for nerve stimulation depends on electrical impedance of the tissue: a study of ultrasound-guided electrical nerve stimulation of the median nerve." Anesth Analg. Apr. 2009;108(4):1338-43. doi: 10.1213/ane.0b013e3181957d84.
Ronald Melzack, "Pain and the Neuromatrix in the Brain", Journal of Dental Education, vol. 65, No. 12, Dec. 2001.
Harrold et al, "Measuring appetite in humans", KissieleffLaboratory for the Study of Human Ingestive Behaviour, School of Psychology, University of Liverpool. Jan. 29, 2008.
Jaime Ruiz-Tovar et al, "Percutaneous Electric Neurostimulation of Dermatome T7 Improves the Glycemic Profile in Obese and Type 2 Diabetic Patients", vol. 93. No. 07. Aug.-Sep. 2015, doi: 10.1016/j.cireng.2014.06.013.

(56) References Cited

OTHER PUBLICATIONS

Jaime Ruiz-Tovar et al, "Percutaneous Electrical Neurostimulation of Dermatome T6 for Appetite Reduction and Weight Loss in Morbidly Obese Patients", Obes Surg (2014) 24:205-211, DOI 10.1007/s11695-013-1091-z.
John K. DiBaise et al, "Impact of the Gut Microbiota on the Development of Obesity: Current Concepts", Am J Gastroenterol Suppl 2012; 1:22-27; doi: 10.1038/ajgsup.2012.5.
Lim et al, "Adipose Tissue: Ability to Respond to Nerve Stimulation in vitro", Department of Nutrition and Food Science, MIT, Cambirdge 39, Science, vol. 140. 1963.
Wenwen Zeng et al, "Sympathetic Neuro-adipose Connections Mediate Leptin-Driven Lipolysis", Cell 163, 84-94, Sep. 24, 2015, http://dx.doi.org/10.1016/j.cell.2015.08.055.
Kenneth Snow, "The Use of Transcutaneous Electrical Nerve Stimulationfor the Treatment of Painful Diabetic Neuropathy", 2012 NeuroMetrix, Inc., PN2203822 Rev C.
Diyar Hussein Tahir, "A comparison of high versus low intensity transcutaneous electrical nerve stimulation for chronic pain", Zanco J. Med. Sci., vol. 15, No. 2, 2011.
Obuchowicz A et al, "Plasma beta-endorphin and insulin concentrations in relation to body fat and nutritional parameters in overweight and obese prepubetral children", Int J Obes Relat Metab Disord. Sep. 1997, 21(9):783-8.
Livingstone et al, "Methodological issues in the assessment of satiety", Scandinavian Journal of NutritionlNaringsforskning vol. 44:98-1 03,2000.
Xing et al, "Gastric Electrical-Stimulation Effects on Canine Gastric Emptying, Food Intake, and Body Weight", Obesity Research vol. 11 No. 1 Jan. 2003.
Ruffin M et al, "Electrical stimulation of the ventromedial hypothalamus enhances both fat utilization and metabolic rate that precede and parallel the inhibition of feeding behavior", Brain Res. Oct. 30, 1999;846(1):23-9, PMID: 10536210.
Cigaina V, "Gastric pacing as therapy for morbid obesity: preliminary results", Obes Surg Jun. 2002;12(3):421, PMID: 11969102.
Shafshak TS, "Electroacupuncture and exercise in body weight reduction and their application in rehabilitating patients with knee osteoarthritis", Am J Chin Med. 1995;23(1):15-25, PMID: 7598088.
Michael Camilleri, "Peripheral Mechanisms in Appetite Regulation", Gastroenterology. May 2015 ; 148(6): 1219-1233. doi:10.1053/j.gastro.2014.09.016.
Guneli E, et al., "Possible involvement of ghrelin on pain threshold in obesity", Med Hypotheses, Mar. 2010;74(3):452-4, PMID 19883981.
Thomas O. Mundinger et al, "Direct Stimulation of Ghrelin Secretion by Sympathetic Nerves", Endocrinology, Jun. 2006, 147(6):2893-2901, doi: 10.1210/en.2005-1182.
Cigaina V et al, "Plasma ghrelin and gastric pacing in morbidly obese patients", Metabolism Clinical and Experimental 56 (2007) 1017-1021.
Flint et al, "Reproducibility, power and validity of visual analogue scales in assessment of appetite sensations in single test meal studies", International Journal of Obesity (2000) 24, 38-48.
Cigaina V et al, "Gastric Pacing for Morbid Obesity: Plasma Levels of Gastrointestinal Peptides and Leptin", Obesity Research vol. 11 No. 12 Dec. 2003.
Vander Tuig JG, Knehans AW, Romsos DR., "Reduced sympathetic nervous system activity in rats with ventromedial hypothalamic lesions", Life Sci. (1982), pp. 913-920.
Takahashi K, et al., "Methodology for detecting swallowing sounds", Dysphagia. 1994 Winter;9(1):54-62.
Brian Buntz, "Brain-Zapping Wearable Device Hits Market without FDA Clearance", Posted in Mobile Health by Brian Buntz on Jun. 4, 2015.
Biegler GMBH, Stivax Neurostimulation product brochure, http://www.biegler.com/en/stivax?file=files/biegler/manuals/stivax_brochure_en.pdf. Apr. 2016.
Eagle Advancement Institute, "Pulse Stimulation Treatment (PSTIM)", http://eagleadvancementinstitute.com/pstim/Overview.asp. 2014.
Ghoname et al, "The effect of stimulus frequency on the analgesic response to percutaneous electrical nerve stimulation in patients with chronic low back pain", Anesth Analg. Apr. 1999;88(4):841-6.
Takagi K1, Yamaguchi S, Ito M, Ohshima N., "Effects of electroacupuncture stimulation applied to limb and back on mesenteric microvascular hemodynamics", Jpn J Physiol. Jun. 2005;55(3):191-203. Epub Sep. 7, 2005.
Yamaguchi S1, Ito M, Ohshima N., "Effects of electrical stimulation of the dorsal skin on systemic and mesenteric microvascular hemodynamics in anesthetized rats", Jpn J Physiol. Jun. 2002;52(3):257-65.

\* cited by examiner

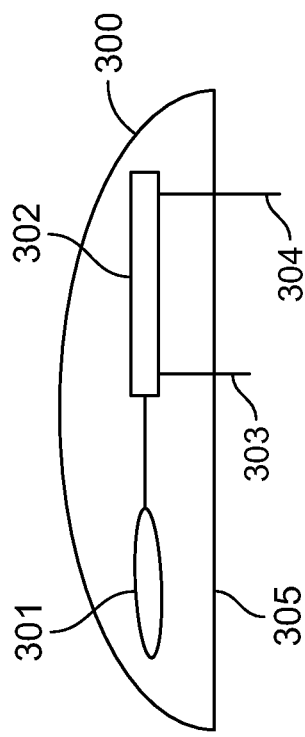
FIG. 3A
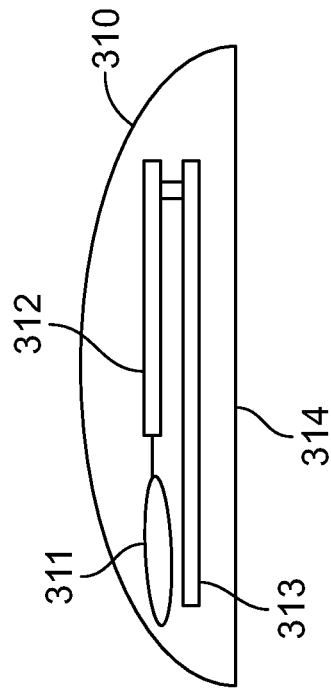
FIG. 3B
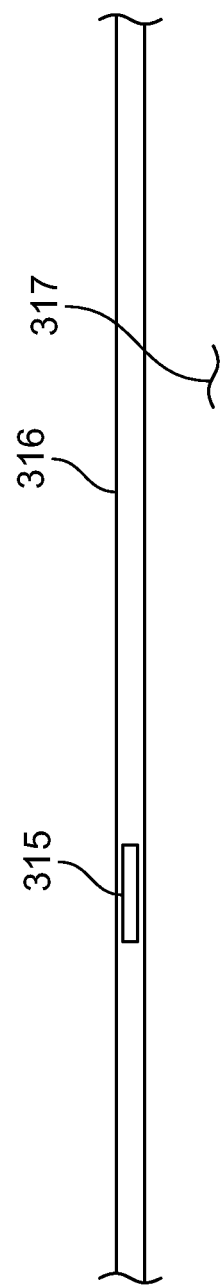

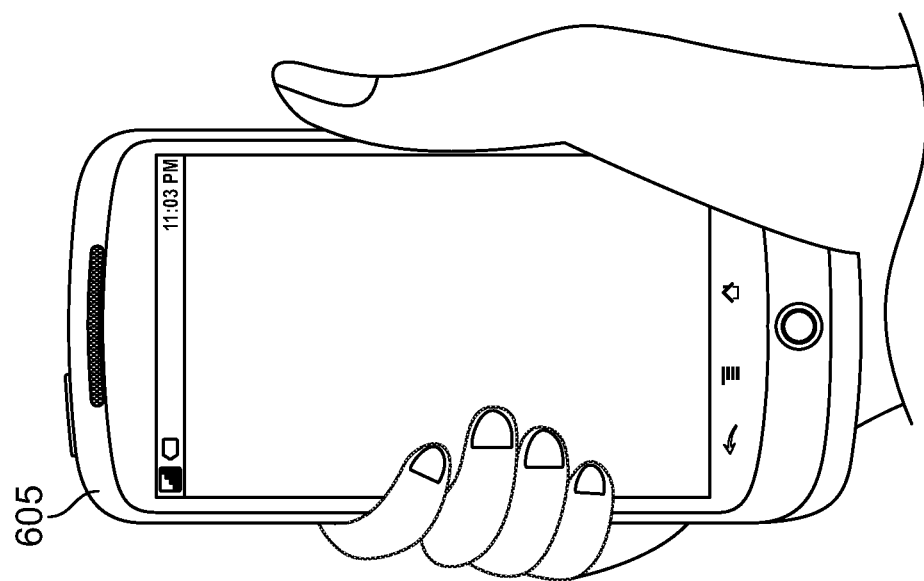
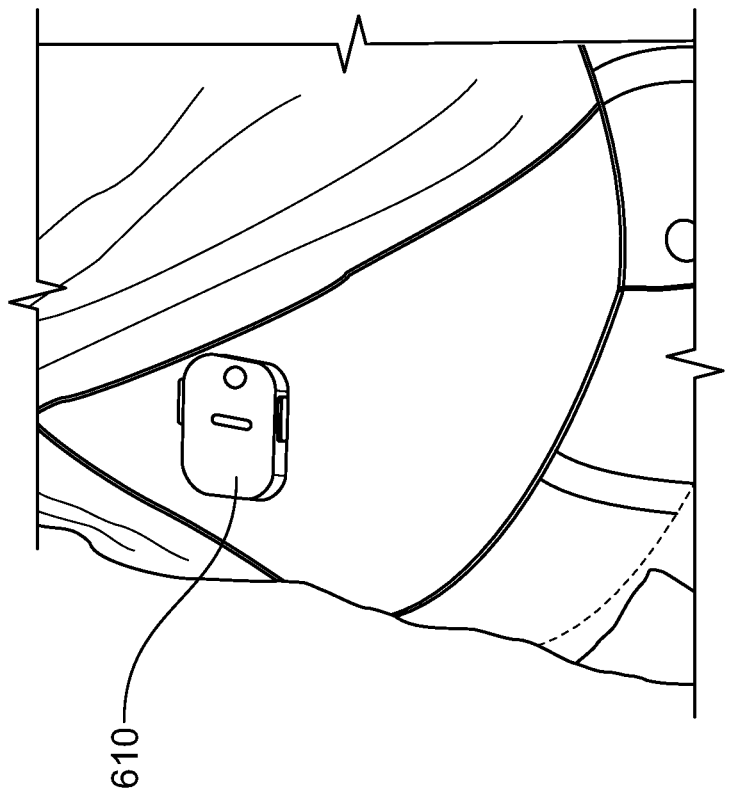
FIG. 6A

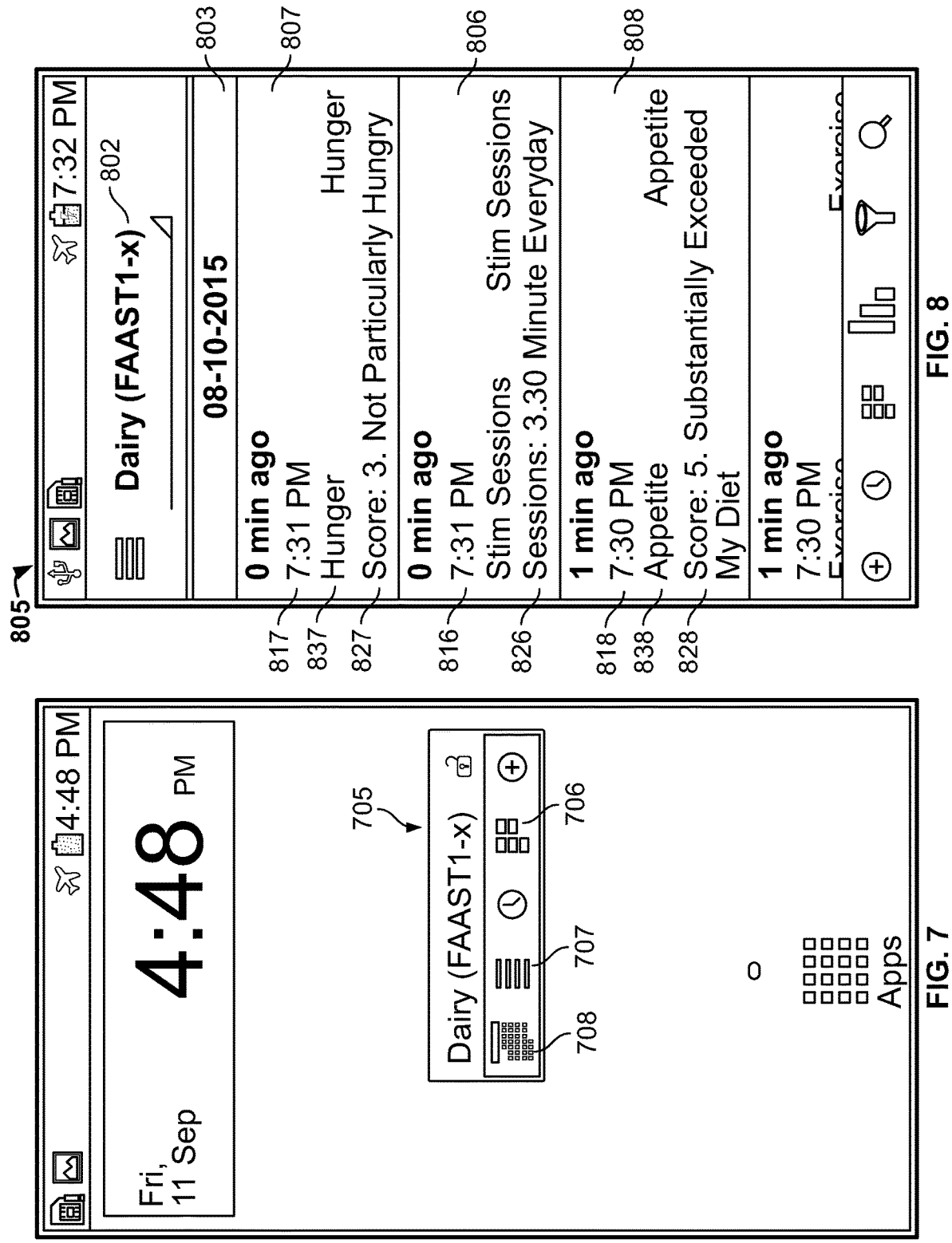

← Dairy (FAAST1-x) 1204 ⊗ 1201

Time 1203
08-10-2015 2:13 PM

Type
Exercise

Item
Exercise

Score
5. Less Than 2,500 St

5. Less Than 2,500 Steps Per Day 4. 2,500-5,000 Steps Per Day 1210

3. 5,000-7,500 Steps Per Day 2. 7,500-10,000 Steps Per Day

1. More Than 10,000 Steps Per Day

← Dairy (FAAST1-x) 1104 ⊗ 1101

Time 1103
08-10-2015 7:09 PM

Type
Appetite

Item
Appetite

Score
5. Substantially Excee

5. Substantially Exceeded My Diet

4. Somewhat Exceeded My Diet 1110

3. Followed My Diet

2. Ate A Little Less Than My Diet

1. Ate Substantially Less Than My Diet

- 1302 ← Dairy (FAAST1-x)
- Time
  - 1306 — 08-10-2015    7:09 PM
- Type
  - 1307 — Hunger
- Item
  - 1308 — Hunger
- Score
  - 5. Extremely Hungry Most of The Time
  - 1309 — 4. Frequently Hungry — 1310
  - 3. Not Particularly Hungry
  - 2. Almost Never Hungry
  - 1. Not Hungry At All

- 1402 ← Dairy (FAAST1-x)
- Time
  - 1406 — 08-10-2015 — 1403    2:14 PM
- Type
  - 1407 — Stim Sessions
- Item
  - 1408 — Stim Sessions
- Score
  - 1. 15 Minute E/O Day
  - 1409 — 2. 30 Minute E/O Day — 1410
  - 3. 30 Minute Everyday
  - 4. 30 Minute Twice/Day

🏠 🗓️  ✈️ 🔋 2:14 PM — 1501
← Diary (FAAST1-x)   1504  ⊗ 💾

Time
1502 — 08-10-2015   /—1503   2:14 PM

Type
1506 — Weight

Item
1507 — Weight

Weight (lbs)
1508 — Enter Weight (lbs)

✏️ ⭐ 📁 📷 🎤 ⊕

| 1 | 2 | 3 | ⌫ |
|---|---|---|---|
| 4 | 5 | 6 | Done |
| 7 | 8 | 9 | . |
| 123 Sym | 0 |  | ⚙️ |

🏠 🗓️  ✈️ 🔋 7:08 PM — 1601
← Diary (FAAST1-x)   1604  ⊗ 💾

Time
1602 — 08-10-2015  /—1603   7:08 PM

Type
1606 — Well Being

Item
1607 — Well-being

Score
1608 — 3. Experiencing Frequ

1609 — 3. Experiencing Frequent Nausea/A

2. Occasional Nausea/Abdominal Di — 1610

1. No Nausea/Abdominal Discomfor

✏️ ⭐ 📁 📷 🎤 ⊕

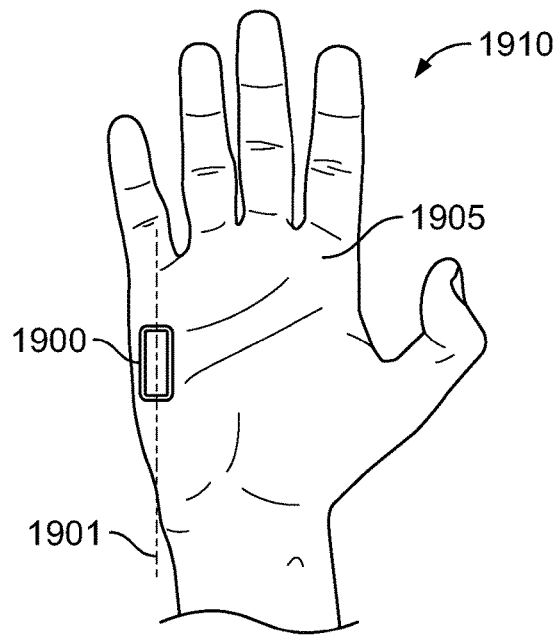
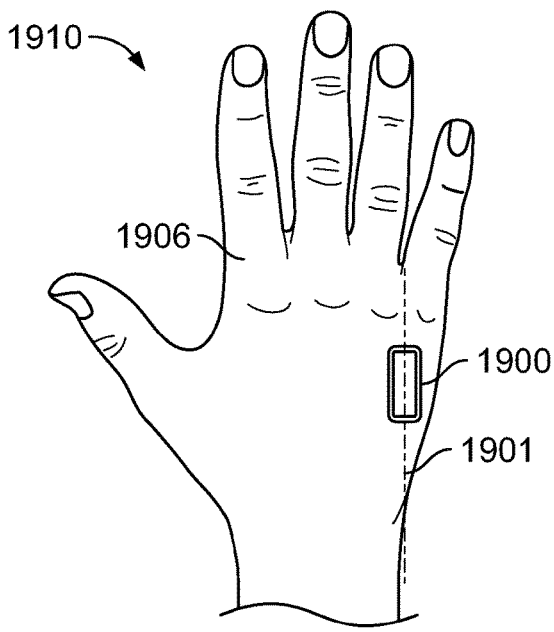
FIG. 19A  FIG. 19B
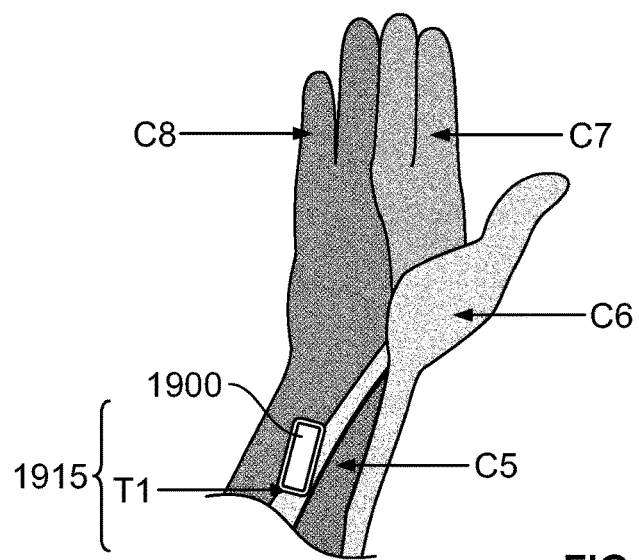
FIG. 19C

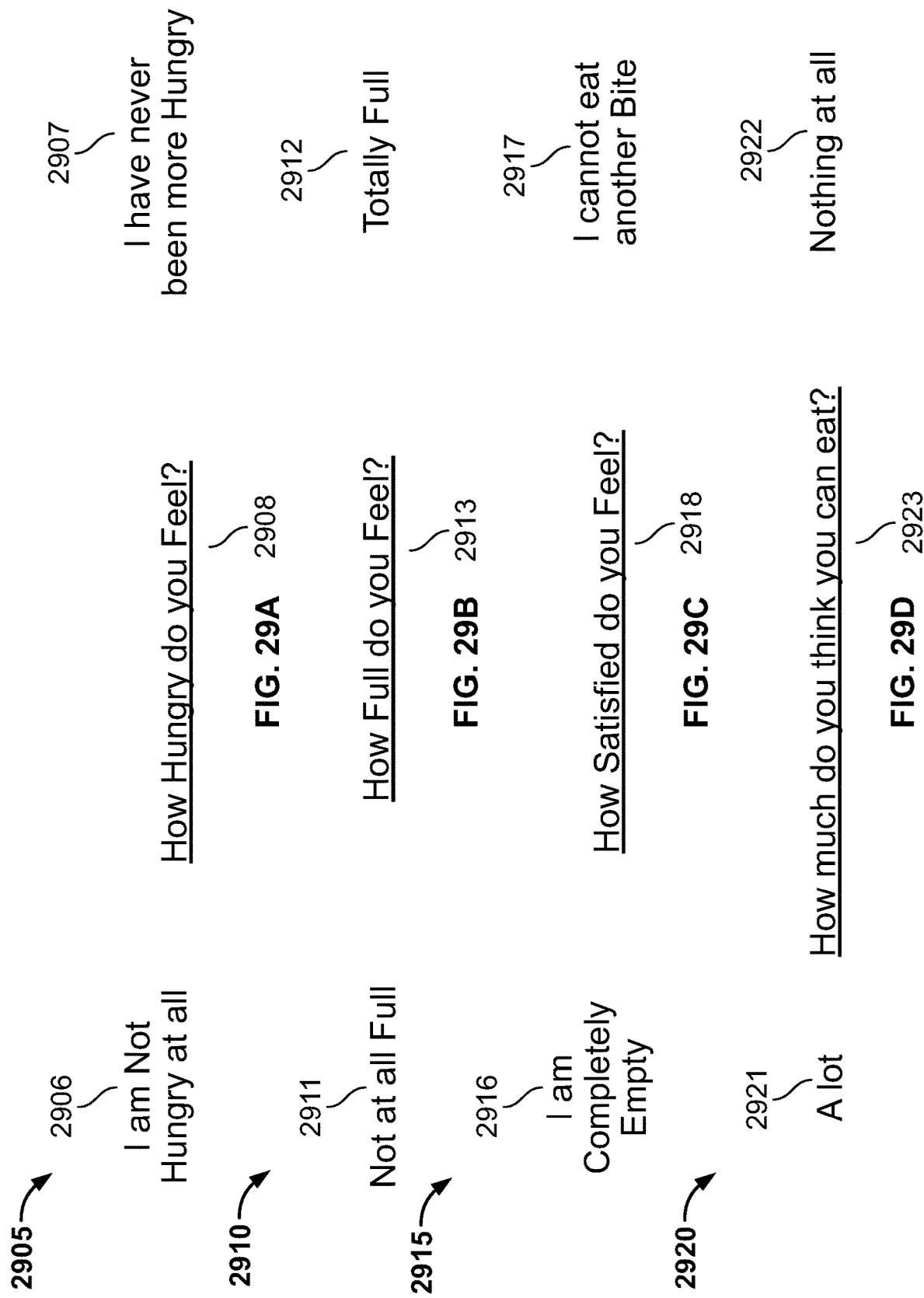

Patient 4

PERCUTANEOUS ELECTRICAL DERMAL PATCH FOR ENABLING APPETITE MODULATION AND/OR IMPROVING DIETARY COMPLIANCE

CROSS-REFERENCE

The present application is a continuation application of application Ser. No. 15/204,752, entitled "Systems and Methods for Enabling Appetite Modulation and/or Improving Dietary Compliance Using Percutaneous Electrical Neurostimulation" and filed on Jul. 7, 2016, which is a continuation-in-part of application Ser. No. 15/052,791, entitled "Systems and Methods for Enabling Appetite Modulation and/or Improving Dietary Compliance Using an Electro-Dermal Patch, filed on Feb. 24, 2016, which, in turn relies on U.S. Patent Provisional Application No. 62/120,067, entitled "Dermatome Stimulation System" and filed on Feb. 24, 2015, for priority.

The present specification is a continuation-in-part of application Ser. No. 15/052,784, entitled "Systems and Methods for Enabling Appetite Modulation and/or Improving Dietary Compliance Using an Electro-Dermal Patch, filed on Feb. 24, 2016, which, in turn, relies on U.S. Patent Provisional Application No. 62/120,082, entitled "Dermatome Stimulation Methods" and filed on Feb. 24, 2015, for priority.

The present specification also relies on U.S. Patent Provisional Application No. 62/189,800, entitled "Dermatome Stimulation Method" and filed on Jul. 8, 2015, for priority. The present specification also relies on U.S. Patent Provisional Application No. 62/189,805, entitled "Dermatome Stimulation System" and filed on Jul. 8, 2015, for priority.

In addition, the above-mentioned non-provisional U.S patent applications also rely on the following applications, for priority:

U.S. Patent Provisional Application No. 62/133,526, entitled "Dermatome Stimulation System" and filed on Mar. 16, 2015, for priority. U.S. Patent Provisional Application No. 62/133,530, entitled "Dermatome Stimulation Method" and filed on Mar. 16, 2015, for priority.

U.S. Patent Provisional Application No. 62/141,328, entitled "Dermatome Stimulation System" and filed on Apr. 1, 2015, for priority. U.S. Patent Provisional Application No. 62/141,333, entitled "Dermatome Stimulation Method" and filed on Apr. 1, 2015, for priority.

U.S. Patent Provisional Application No. 62/161,353, entitled "Dermatome Stimulation System" and filed on May 14, 2015, for priority.

U.S. Patent Provisional Application No. 62/161,362, entitled "Dermatome Stimulation Method" and filed on May 14, 2015, for priority.

The present specification also relies on U.S. Patent Provisional Application No. 62/237,356, entitled "Systems and Methods for Enabling Appetite Modulation Using Transcutaneous Electrical Neurostimulation" and filed on Oct. 5, 2015, for priority.

The present specification also relies on U.S. Patent Provisional Application No. 62/240,808, entitled "Systems and Methods for Enabling Appetite Modulation Using an Electro-Dermal Patch" and filed on Oct. 13, 2015, for priority.

The present specification also relies on U.S. Patent Provisional Application No. 62/242,944, entitled "Systems and Methods for Enabling Appetite Modulation Using an Electro-Dermal Patch" and filed on Oct. 16, 2015, for priority.

The present specification also relies on U.S. Patent Provisional Application No. 62/242,957, entitled "Systems and Methods for Enabling Appetite Modulation Using an Electro-Dermal Patch" and filed on Oct. 16, 2015, for priority.

The present specification also relies on U.S. Patent Provisional Application No. 62/246,526, entitled "Systems and Methods for Enabling Appetite Modulation Using an Electro-Dermal Patch" and filed on Oct. 26, 2015, for priority.

The present specification also relies on U.S. Patent Provisional Application No. 62/247,113, entitled "Systems and Methods for Enabling Appetite Modulation Using an Electro-Dermal Patch" and filed on Oct. 27, 2015, for priority.

The present specification also relies on U.S. Patent Provisional Application No. 62/248,059, entitled "Systems and Methods for Enabling Pain Management Using an Electro-Dermal Patch" and filed on Oct. 29, 2015, for priority.

All of the above-mentioned applications are herein incorporated by reference in their entirety.

FIELD

The present specification relates generally to systems and methods of modulating a patient's appetite, hunger, satiety level, satiation level, or fullness level in a user by delivering electrical stimulation to a predetermined area of the user's anatomy in a manner that is convenient, easy to use, and amenable to increased patient compliance. More particularly, the present specification relates to percutaneous electrical stimulation devices comprising low profile, wearable, disposable percutaneous skin patches that are easily programmable and monitorable using a mobile handheld device, and programmed to stimulate a patient's nerves in a manner that enables appetite or hunger control, modulation or suppression, avoids nausea, dyspepsia, minimizes habituation and enables increased compliance with a dietary regimen. The present specification further relates to a low profile, wearable, disposable percutaneous skin patch that is capable of integrating with, and being controlled by, a plurality of different hardware devices or software applications depending on the type, extent, nature and scope of the appetite, hunger, satiety level, satiation level, or fullness level modulation desired, the nature and degree of dietary compliance required, the amount of weight loss desired and/or the need for long term weight maintenance.

BACKGROUND

The potential benefits of enabling a user to modulate, suppress or control his appetite include decreasing a person's excess weight and, thereby potentially beneficially affecting all of the health problems associated therewith, as further discussed below. The same potential benefits apply to modulating or otherwise controlling a person's hunger, satiety level, satiation level, and degree of fullness.

Being obese, or overweight, is a condition that often results from an imbalance between food intake and caloric expenditure. Excessive weight increases the likelihood of several additional risks including cardiovascular complications (such as hypertension and hyperlipidemia), gallbladder disease, metabolic syndrome, cancer, polycystic ovary disease, pregnancy-related complications, arthritis-related complications and other orthopedic complications caused by stress on body joints. Obesity is also thought to be a primary cause of type 2 diabetes (T2DM) in many ethnicities.

In "Effect of Somatovisceral Reflexes and Selective Dermatomal Stimulation on Postcibal Antral Pressure Activity", Camilleri et al., sustained somatic stimulation by a transcutaneous electrical nerve stimulation (TENS) device was applied to the skin of human volunteers while simultaneously monitoring their upper gastrointestinal phasic pressure activity, extra-intestinal vasomotor indices, and plasma levels of putative humoral mediators of autonomic reflexes. Camilleri posits that "somatovisceral reflex alteration of gastric motility may also be elicited in humans . . . and suggests that a sustained somatic stimulus would also result in impaired antral phasic pressure response to a solid-liquid meal." However, Camilleri's approach requires sustained painful somatic stimulation and, accordingly, from a compliance standpoint, is simply not a feasible therapeutic approach.

U.S. Pat. No. 7,200,443 discloses "electrode pads . . . situated proximate to the thoracic vertebrae and the preganglionic greater splanchnic nerve fibers of the spine to stimulate the postganglionic sympathetic nerve pathways innervating the stomach." The electrode pads are "positioned at or near the top and bottom, respectively, of the thoracic spine". Because the electrodes are placed on the spine, it is difficult for a person to place, activate, or maintain the device on his own, reduces compliance, and is not practically sustainable as a therapy for people who are overweight.

Additionally such therapies require a medical professional to place the device and/or administer the therapy, including programming the device. The patient must visit the medical professional at the onset of treatment to have the device placed and then weekly thereafter to have the therapy administered and/or device programming modified. The requirement for such frequent doctor visits is inconvenient for most patients and can have a detrimental effect on patient compliance.

Additionally, such prior approaches using electrical, external stimulation to suppress appetite do not have a combination of the following characteristics effective to treat a patient: wearability; real-time or near real-time feedback from the patient (e.g. food intake, exercise, hunger) or from wearable devices, for example, a device, with physiological sensors, configured to be worn on the human body, such as around the wrist, in order to monitor, acquire, record, and/or transmit the physiological data; the ability to stimulate multiple times per day or week; daily, or on-demand, feedback from the device to the patient with respect to dietary compliance, exercise, calories burned; storage of stimulation parameters and other real-time inputs; and an electrical stimulation profile and a footprint conducive to wearability. In addition, prior art therapies which have some degree of flexibility include an electrode which must be tethered via cables to a control or power box. Prior art therapies which are wireless are typically bulky, inflexible, and not amenable to being worn for long periods of time.

Because successful weight loss is, in the end, a matter of achieving a high degree of compliance with a dietary regimen, it is absolutely critical for a successful device to go beyond mere appetite suppression and combine wearability, physical comfort, ease of use, and integration of numerous data sources to provide a holistic and real-time view into a person's dietary compliance, in addition to effectively modulating the individual's appetite, hunger, satiety level, satiation level, or fullness.

Therefore, there is a need for a low profile, long lasting electrical neuro-stimulation device which is programmable, and is effective to cause appetite or hunger control, modulation or suppression while minimizing any accompanying nausea, dyspepsia and habituation. There is also a need for a device that can effectively integrate appetite management data with conventional weight management information, such as caloric expenditure and consumption.

There is a need for an electrical neuro-stimulation device which is wearable and can be controlled and programmed. There is also a need for an electrical neuro-stimulation device which includes real-time or near real-time feedback from patient parameters including, but not limited to, exercise, diet, hunger, appetite, well-being and which will be able to obtain real-time or near real-time feedback from other wearable devices, for example, a device, with physiological sensors, configured to be worn on the human body, such as around the wrist, in order to monitor, acquire, record, and/or transmit the physiological data, allowing for frequent adjustability and customization of therapy to suppress appetite and therefore treat conditions of obesity, over-weight, eating disorders, metabolic syndrome. There is a need for an electro-stimulation device configured to intelligently trigger and initiate stimulation automatically and without on-going management by a user. There is a need for an electrical neuro-stimulation device having the ability to stimulate multiple times per day or per week, accelerating treatment effect and efficacy. There is a need for an electrical neuro-stimulation device which provides daily feedback from the device to the patient on such parameters as dietary compliance, and calories burned.

In addition, there is a need for an electrical neuro-stimulation device capable of storing stimulation parameters and other real-time inputs, such as diary and exercise monitoring, to provide a physician and the patient with real-time records and treatment profiles. Inputs from the electrical neuro-stimulation device and from other sources of information, for example, a device, with physiological sensors, configured to be worn on the human body, such as around the wrist, in order to monitor, acquire, record, and/or transmit the physiological data would be stored.

There is also a need to allow physicians to be able to flexibly program an electrical neuro-stimulation device and still direct the patient, allowing the patient to adjust device parameters (for greater patient independence) but within restricted bounds or predetermined parameters.

There is also a need for an electrical neuro-stimulation device which targets appetite or hunger suppression, does not require implantation, and does not require wires or remote electrodes to provide stimulation. There is a need for an electrical neuro-stimulation device which is remotely programmable, yet wireless, can flex at any point along its body, is waterproof, and is configured for extended or permanent wearability. There is also a need for a wearable electrical neuro-stimulation device directed toward suppressing post-prandial glucose levels and effectively modulating a plurality of hormones and microbiota related to gastrointestinal functionality. There is a need for an electrical neuro-stimulation device having a size, shape, and weight, and being composed of materials that effectively allow the device to be wearable. Such a device would eliminate the need for stimulation parameters requiring large power needs (which would make wearability impractical or impossible). There is also a need for an electrical neuro-stimulation device which is controllable by a companion device (such as a smartphone) and includes no visible or tactile user interface on the stimulation device itself. There is a need for an electrical neuro-stimulation device having unique electrical stimulation and footprint, based on electrode design and stimulation parameters, which would allow users to comfortably wear the device.

There is also a need for a holistic approach to managing a patient's caloric consumption and expenditure profile. Conventional approaches focus on caloric intake but do not analyze, monitor, or otherwise gather data on the important precursor to caloric intake, namely appetite or hunger levels. There are untapped benefits to integrating data relating to the appetite, hunger and/or craving levels, active suppression or control over appetite, caloric intake, weight gain, and caloric expenditure. These and other benefits shall be described in relation to the detailed description and figures.

SUMMARY

The following embodiments and aspects thereof are described and illustrated in conjunction with systems, tools and methods, which are meant to be exemplary and illustrative, and not limiting in scope. The present application discloses numerous embodiments.

The device may be used to treat a condition including any one of obesity, excess weight, eating disorders, metabolic syndrome and diabetes. In accordance with various aspects of the present specification, the neuro-stimulation device enables treating people with BMI (Body Mass Index) of 25 or greater (overweight being 25-30, obese being 30 and above, and morbid obesity being above 35).

In some embodiments, the present specification discloses an electrical stimulation system configured to modulate at least one of a patient's appetite, hunger, level of satiety, or level of satiation level comprising: a percutaneous electrical dermal patch adapted to be adhered to the patient's epidermal layer, wherein said electrical dermal patch comprises a controller, at least one electrode adapted to be implanted to a depth of 0.1 mm to 30 mm within said patient's skin, a pulse generator in electrical communication with the controller and said at least one electrode; and a transceiver in communication with at least one of said controller and pulse generator; and a plurality of programmatic instructions, stored in a non-transient computer readable memory of a device physically separate from said percutaneous electrical dermal patch, wherein, when executed, said programmatic instructions acquire patient status data, generate a modulation signal based upon said patient status data, wherein said modulation signal comprises instructions for modulating at least one of a pulse width, a pulse amplitude, a pulse frequency, a pulse shape, a duty cycle, a session duration, and a session frequency, and wirelessly transmit said modulation signal from the device to the transceiver.

Optionally, the electrical stimulation system further comprises a second electrode positioned on a surface of the patient's epidermal layer.

Optionally, the electrical stimulation system further comprises a second percutaneous electrode adapted to be implanted to a depth of 0.1 mm to 30 mm within said patient's skin.

Optionally, the pulse generator is configured to generate a plurality of electrical pulses and a corresponding electrical field, wherein the electrical field is adapted to penetrate a range of 0.1 mm to 30 mm through the patient's skin.

Optionally, the plurality of electrical pulses comprise a pulse width in a range of 10 μsec to 100 msec, a pulse amplitude in a range of 100 μA to 500 mA, and a pulse frequency in a range of 1 Hz to 10,000 Hz.

Optionally, at least one of said pulse width, said pulse amplitude, and said pulse frequency are defined such that a post-stimulation daily caloric intake of said patient decreases relative to a pre-stimulation daily caloric intake of said patient, wherein said pre-stimulation daily caloric intake is a function of an amount of calories consumed by the patient over a first predefined period of time prior to stimulation, and wherein said post-stimulation daily caloric intake is a function of an amount of calories consumed by the patient over a second predefined period of time equal in duration to the first predefined period of time, after stimulation is initiated.

Optionally, at least one of said pulse width, said pulse amplitude, and said pulse frequency are defined such that a post-stimulation daily caloric intake of said patient is less than 99% of a pre-stimulation daily caloric intake of said patient, wherein said pre-stimulation daily caloric intake is a function of an amount of calories consumed by the patient over a first predefined period of time prior to stimulation, and wherein said post-stimulation daily caloric intake is a function of an amount of calories consumed by the patient over a second predefined period of time equal in duration to the first predefined period of time, after stimulation is initiated.

Optionally, at least one of said pulse width, said pulse amplitude, and said pulse frequency are defined such that, after at least one stimulation, the patient's compliance with a target daily caloric intake increases relative to the patient's compliance with the target daily caloric intake before stimulation.

Optionally, said patient status data comprises at least one of the patient's hunger, the patient's hunger appetite, the patient's satiety level, the patient's satiation level, and a degree of well-being being experienced by the patient.

Optionally, said well-being level comprises at least one of a degree of nausea being experienced by the patient and a degree of dyspepsia being experienced by the patient.

Optionally, when executed, said programmatic instructions acquire a first stimulation protocol and use said first stimulation protocol to generate the modulation signal.

Optionally, when executed, said programmatic instructions acquire a second stimulation protocol, wherein said second stimulation protocol is different from the first stimulation protocol, and, using said second stimulation protocol, generate a second modulation signal, wherein said second modulation signal comprises instructions for modulating at least one of the pulse width, the pulse amplitude, the pulse frequency, the pulse shape, the duty cycle, the session duration, and the session frequency.

Optionally, when executed, said programmatic instructions wirelessly transmit said second modulation signal from the device to the electrical dermal patch.

Optionally, the percutaneous electrical dermal patch is configured to use the second modulation signal to modify at least one of said pulse width, pulse amplitude, pulse frequency, pulse shape, duty cycle, session duration, and session frequency to yield a second pulse width, a second pulse amplitude, a second pulse frequency, a second pulse shape, a second duty cycle, a second session duration, or a second session frequency, wherein at least one of the second pulse width is different from the first pulse width, the second pulse amplitude is different from the first pulse amplitude, the second pulse frequency is different from the first pulse frequency, the second pulse shape is different from the first pulse shape, the second duty cycle is different from the first duty cycle, the second session duration is different from the first session duration, and the second session frequency is different from the first session frequency.

Optionally, said controller, pulse generator, and transceiver are positioned in a first housing and the at least one electrode is positioned outside said first housing.

Optionally, said controller and transceiver are positioned in a first housing and said pulse generator and the at least one electrode are positioned outside said first housing.

Optionally, the electrical field is adapted to contact at least one of the patient's T2 frontal and lateral thoracic dermatome, T3 frontal and lateral thoracic dermatome, T4 frontal and lateral thoracic dermatome, T5 frontal and lateral thoracic dermatome, T6 frontal and lateral thoracic dermatome, T7 frontal and lateral thoracic dermatome, T8 frontal and lateral thoracic dermatome, T9 frontal and lateral thoracic dermatome, or T10 frontal and lateral thoracic dermatome.

Optionally, the electrical field is adapted to contact at least one of the patient's T2 frontal and lateral thoracic dermatome, T3 frontal and lateral thoracic dermatome, T4 frontal and lateral thoracic dermatome, T5 frontal and lateral thoracic dermatome, T6 frontal and lateral thoracic dermatome, T7 frontal and lateral thoracic dermatome, T8 frontal and lateral thoracic dermatome, T9 frontal and lateral thoracic dermatome, and T10 frontal and lateral thoracic dermatome and is not positioned within a range of 0.1 mm to 25 mm from any one of the patient's T2 posterior thoracic dermatome, T3 posterior thoracic dermatome, T4 posterior thoracic dermatome, T5 posterior thoracic dermatome, T6 posterior thoracic dermatome, T7 posterior thoracic dermatome, T8 posterior thoracic dermatome, T9 posterior thoracic dermatome, and T10 posterior thoracic dermatome.

Optionally, the electrical field is adapted to contact at least one of the patient's C8 anterior or posterior dermatome located on the patient's hand, wrist, elbow, and fingers, C8 anterior or posterior dermatome located on the patient's arm, C8 dermatome located on the patient's upper trunk, T1 anterior or posterior dermatome located on the patient's arm, T1 anterior or posterior dermatome located on the patient's wrist, elbow, and hand, and T1 anterior or posterior dermatome located on the patient's upper trunk is electrically stimulated.

Optionally, the electrical stimulation system further comprises an adhesive layer positioned on the bottom surface of the electrical dermal patch, such that when the adhesive layer is adhered to the patient's skin, the electrical dermal patch has an average minimum peel strength in a range of 1.3 to 1.7 newtons.

Optionally, at least one of said pulse width, said pulse amplitude, and said pulse frequency are defined such that, after receiving at least one stimulation session, the appetite of said patient is less than the appetite of said patient prior to receiving said at least one stimulation session.

Optionally, at least one of said pulse width, said pulse amplitude, and said pulse frequency are defined such that, after at least one stimulation, the patient's appetite decreases, over a predefined period of time, relative to the patient's appetite before stimulation and a nausea level of the patient does not increase, over said predefined period of time, relative to the nausea level of the patient before stimulation.

Optionally, at least one of said pulse width, said pulse amplitude, and said pulse frequency are defined such that, after at least one stimulation, the patient's appetite decreases, over a predefined period of time, relative to the patient's appetite before stimulation, wherein at least one of a dyspepsia level of the patient or a nausea level of the patient does not increase, over said predefined period of time, relative to at least one of the dyspepsia level or the nausea level of the patient before stimulation, and wherein said at least one stimulation does not cause the patient to experience a pain sensation.

Optionally, at least one of said pulse width, said pulse amplitude, and said pulse frequency are defined such that, after at least one stimulation, a total body weight of the patient reduces by at least 1% relative to a total body weight of the patient before stimulation.

Optionally, at least one of said pulse width, said pulse amplitude, and said pulse frequency are defined such that, after at least one stimulation, an excess body weight of the patient reduces by at least 1% relative to an excess body weight of the patient before stimulation.

Optionally, at least one of said pulse width, said pulse amplitude, and said pulse frequency are defined such that, after at least one stimulation, a total body weight of the patient reduces by at least 1% relative to a total body weight of the patient before stimulation and a well-being level of the patient does not reduce more than 5% relative to a well-being level of the patient before stimulation.

Optionally, at least one of said pulse width, said pulse amplitude, and said pulse frequency are defined such that, after at least one stimulation, the patient's appetite decreases, over a predefined period of time, relative to the patient's appetite before stimulation and a nausea level of the patient does not increase by more than 10%, over said predefined period of time, relative to the nausea level of the patient before stimulation.

Optionally, at least one of said pulse width, said pulse amplitude, and said pulse frequency are defined such that, after at least one stimulation, the patient's hunger decreases, over a predefined period of time, relative to the patient's hunger before stimulation and a nausea level of the patient does not increase by more than 10%, over said predefined period of time, relative to the nausea level of the patient before stimulation.

Optionally, said housing is covered by at least one polymer having a hardness measure of 30-70 on a subzero shore scale.

Optionally, said housing is encased in at least one polymer having a tensile modulus of 15 to 55 psi.

Optionally, the housing has a substantially linear profile, a width of 4 inches or less, a length of 8 inches or less, and a height of 1 inches or less.

Optionally, the percutaneous electrical dermal patch has a volume in a range of 0.25 in$^3$ to 10 in$^3$.

Optionally, the percutaneous electrical dermal patch has a weight in a range of 5 grams to 250 grams.

Optionally, the percutaneous electrical dermal patch further comprises a power source.

Optionally, the percutaneous electrical dermal patch further comprises an impedance sensor configured to determine an electrode integrity of the at least one electrode.

Optionally, the pulse generator is configured to generate a plurality of electrical pulses and a corresponding electrical field, wherein the electrical field is adapted to contact at least one of the patient's C5, C6, C7, C8, T1, T2, T3, T4, T5, T6, T7, T8, T9, T10, T11, and T12 dermatomes.

Optionally, the pulse generator is configured to generate a plurality of electrical pulses and a corresponding electrical field, wherein the electrical field is adapted to contact a portion of at least one of the patient's C5, C6, C7, C8, T1, T2, T3, T4, T5, T6, T7, T8, T9, T10, T11, and T12 frontal and lateral dermatomes and wherein the electrical field is not adapted to contact any portion of the patient's C5, C6, C7, C8, T1, T2, T3, T4, T5, T6, T7, T8, T9, T10, T11, and T12 posterior dermatomes.

Optionally, at least one of said pulse width, said pulse amplitude, and said pulse frequency are defined such that, after at least one stimulation, a fasting glucose level of the patient reduces to a level equal to or below 100 mg/dl from a level above 100 mg/dl before stimulation.

Optionally, at least one of said pulse width, said pulse amplitude, and said pulse frequency are defined such that, after at least one stimulation, a pre-prandial ghrelin level of the patient reduces by at least 1% relative to a pre-prandial ghrelin level of the patient before stimulation.

Optionally, at least one of said pulse width, said pulse amplitude, and said pulse frequency are defined such that, after at least one stimulation, a post-prandial ghrelin level of the patient reduces by at least 1% relative to a post-prandial ghrelin level of the patient before stimulation.

Optionally, at least one of said pulse width, said pulse amplitude, and said pulse frequency are defined such that, after at least one stimulation, a glucagon-like peptide-1 level of the patient increases by at least 1% relative to a glucagon-like peptide-1 level of the patient before stimulation.

Optionally, at least one of said pulse width, said pulse amplitude, and said pulse frequency are defined such that, after at least one stimulation, a leptin level of the patient increases by at least 1% relative to a leptin level of the patient before stimulation.

Optionally, at least one of said pulse width, said pulse amplitude, and said pulse frequency are defined such that, after at least one stimulation, a peptide YY level of the patient increases by at least 1% relative to a peptide YY level of the patient before stimulation.

Optionally, at least one of said pulse width, said pulse amplitude, and said pulse frequency are defined such that, after at least one stimulation, a lipopolysaccharide level of the patient reduces by at least 1% relative to a lipopolysaccharide level of the patient before stimulation.

Optionally, at least one of said pulse width, said pulse amplitude, and said pulse frequency are defined such that, after at least one stimulation, a motilin-related peptide level of the patient reduces by at least 1% relative to a motilin-related peptide level of the patient before stimulation.

Optionally, at least one of said pulse width, said pulse amplitude, and said pulse frequency are defined such that, after at least one stimulation, a cholecystokinin level of the patient increases by at least 1% relative to a cholecystokinin level of the patient before stimulation.

Optionally, at least one of said pulse width, said pulse amplitude, and said pulse frequency are defined such that, after at least one stimulation, a resting metabolic rate of the patient increases by at least 1% relative to a resting metabolic rate of the patient before stimulation.

Optionally, at least one of said pulse width, said pulse amplitude, and said pulse frequency are defined such that, after at least one stimulation, a plasma-beta endorphin level of the patient increases by at least 1% relative to a plasma-beta endorphin level of the patient before stimulation.

Optionally, the electrical dermal patch further comprises a housing and wherein at least one of the controller and the pulse generator is located within the housing.

Optionally, the at least one electrode is removably connected to an exterior surface of the housing.

Optionally, the electrical stimulation further comprises a circuit board positioned within said housing, wherein the controller and the pulse generator are positioned on the circuit board and wherein the circuit board has a maximum area of 5 in$^2$.

Optionally, the circuit board comprises a dielectric laminate having no more than three layers and having a thickness no greater than 0.05 inches.

Optionally, said power source is two stacked batteries having a voltage in a range of 1.0 V to 8.0 V.

Optionally, the electrical dermal patch has an ingress protection rating of at least IPX4.

Optionally, at least one of said pulse width, said pulse amplitude, and said pulse frequency are defined such that, after at least one stimulation, the patient's daily caloric intake decreases to a range of 600 to 1600 calories.

Optionally, at least one of said pulse width, said pulse amplitude, and said pulse frequency are defined such that, after at least one stimulation, the patient's daily caloric intake decreases from over 2000 calories per day to under 2000 calories per day.

Optionally, at least one of said pulse width, said pulse amplitude, and said pulse frequency are defined such that, after at least one stimulation, an amount of the patient's antral motility reduces relative to the patient's antral motility before stimulation.

Optionally, at least one of said pulse width, said pulse amplitude, and said pulse frequency are defined such that, after at least one stimulation, an amount of the patient's gastric motility reduces relative to the patient's gastric motility before stimulation.

Optionally, at least one of said pulse width, said pulse amplitude, and said pulse frequency are defined such that, after at least one stimulation, a rate of the patient's gastric emptying reduces relative to a rate of the patient's gastric emptying before stimulation.

The aforementioned and other embodiments of the present specification shall be described in greater depth in the drawings and detailed description provided below.

BRIEF DESCRIPTION OF THE DRAWINGS

These and other features and advantages of the present specification will be further appreciated, as they become better understood by reference to the following detailed description when considered in connection with the accompanying drawings:

FIG. 3A is a side view illustration of a neuro-stimulation percutaneous electrical dermal patch (PEDP) device, in accordance with one embodiment;

FIG. 3B is a side view illustration of another neuro-stimulation PEDP device, in accordance with one embodiment;

FIG. 6A illustrates an neuro-stimulation device of the present specification, configured as a percutaneous skin patch, placed at a lateral thoracic dermatome and being wirelessly controlled by a smartphone, in accordance with various embodiments;

FIG. 7 is a screen shot of a companion device depicting a diary widget, in accordance with one embodiment of the present specification;

FIG. 8 is a screen shot of a companion device depicting a list view of diary entries, in accordance with one embodiment of the present specification;

FIG. 11 is a screen shot of a companion device depicting an appetite entry screen, in accordance with one embodiment of the present specification;

FIG. 12 is a screen shot of a companion device depicting an exercise entry screen, in accordance with one embodiment of the present specification;

FIG. 13 is a screen shot of a companion device depicting a hunger entry screen, in accordance with one embodiment of the present specification;

FIG. 14 is a screen shot of a companion device depicting a stimulation session entry screen, in accordance with one embodiment of the present specification;

FIG. 15 is a screen shot of a companion device depicting a weight entry screen, in accordance with one embodiment of the present specification;

FIG. 16 is a screen shot of a companion device depicting a well-being entry screen, in accordance with one embodiment of the present specification;

FIG. 19A illustrates C8 stimulation position of the ventral or front (palm) side of a user's hand using a percutaneous electro-dermal patch, in accordance with certain embodiments;

FIG. 19B illustrates C8 stimulation position of the dorsal or back side of the user's hand using a percutaneous electro-dermal patch, in accordance with certain embodiments;

FIG. 19C illustrates C8 and T1 stimulation position of the ventral side of the user's lower arm or wrist regions using a percutaneous electro-dermal patch, in accordance with certain embodiments;

FIG. 29A is a Visual Analogue Scale (VAS) questionnaire for assessing a feeling of hunger or appetite, in accordance with an embodiment;

FIG. 29B is a VAS questionnaire for assessing a feeling of fullness, in accordance with an embodiment;

FIG. 29C is a VAS questionnaire for assessing a feeling of satiation, in accordance with an embodiment;

FIG. 29D is a VAS questionnaire for assessing a feeling of satiety, in accordance with an embodiment;

DETAILED DESCRIPTION

Figure 1A:
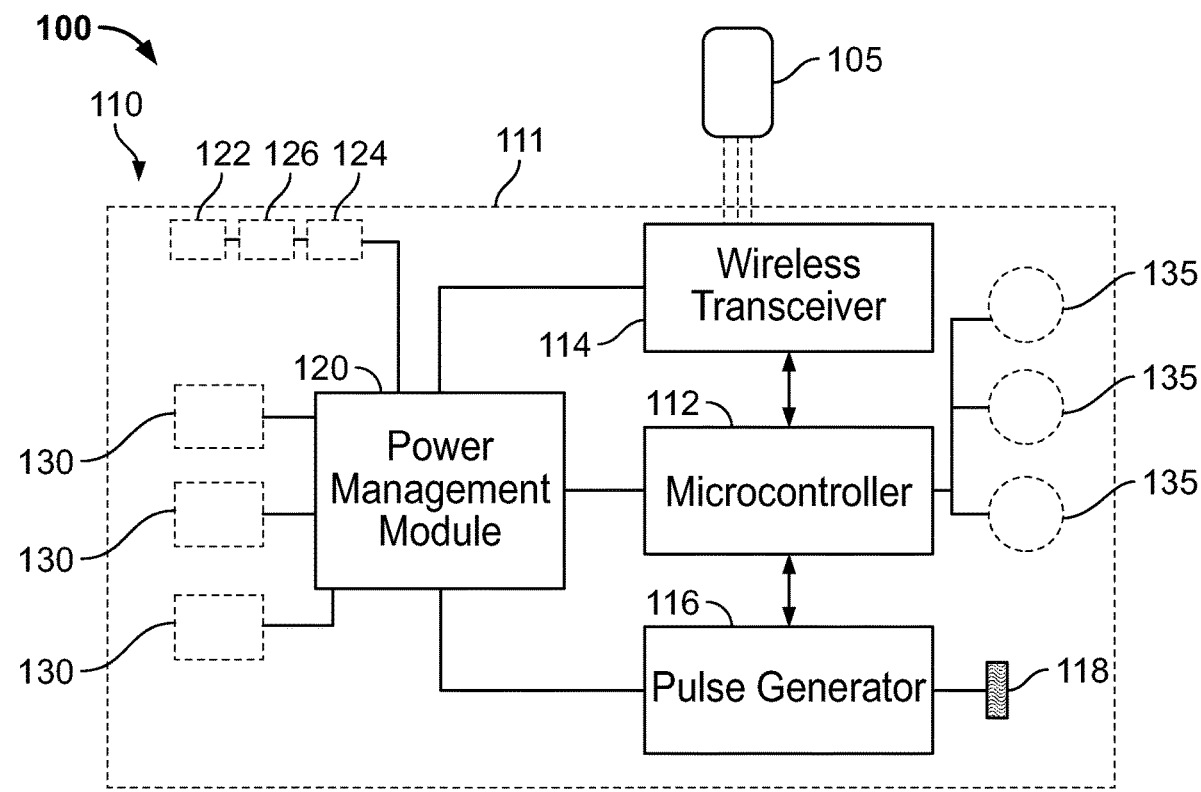
FIG. 1A is a block diagram of a system for stimulating nerves and nerve endings in body tissue, in accordance with various embodiments of the present specification.

The present specification is directed toward systems and methods of modulating a patient's appetite, hunger, satiety level, satiation level, or fullness level by delivering electrical stimulation to a predetermined area of the user's anatomy in a manner that is convenient, easy to use, and amenable to increased patient compliance. The term "modulating" refers to any form of regulation, manipulation or control to change a given variable from one state to another state. More particularly, the present specification relates to electrical stimulation devices comprising low profile, wearable, disposable percutaneous skin patches that are configured for placement and/or implantation on a patient's front, lateral and back T2 to T12 and/or C5-T1 dermatomes, programmable and monitorable using a mobile handheld device, and programmed to stimulate, nerves located proximate to the front, lateral and back T2 to T12 and/or C5-T1 dermatomes in a manner that enables modulation of a patient's appetite, hunger, satiety level, satiation level or fullness level, and that avoids nausea, dyspepsia and minimizes habituation. In some embodiments, a stimulation depth through the patient's skin ranges from 0.1 mm to 60 mm, with the stimulation electrodes being placed percutaneously at a depth through the patient's skin ranging from 0.1 mm to 60 mm. In various embodiments, a stimulation depth through the patient's skin ranges from 0.1 mm to 30 mm, with the stimulation electrodes being placed percutaneously at a depth through the patient's skin ranging from 0.1 mm to 30 mm. The present specification further relates to a low profile, wearable, disposable percutaneous skin patch that is capable of integrating with, and being controlled by, a plurality of different hardware devices or software applications depending on the type, extent, nature and scope of the appetite, hunger, satiety level, satiation level or fullness level modulation desired, including immediate, large weight loss or long term weight maintenance.

An electrical neuro-stimulation device, in the form of a percutaneous electro-dermal patch (PEDP) is disclosed that, in various embodiments, is configured as a discrete, disposable and waterproof adhesive patch or pad for placement on a user's skin (while one or more electrodes lay percutaneously just underneath the user's skin), particularly on the regions encompassing the front, lateral and back T2-T12 dermatomes and/or C5-T1 dermatomes. In accordance with various aspects of the present specification, the PEDP device is configured to be self-implanted or self-administered by the user or implanted by a physician or medical personnel. In various embodiments, the PEDP is wireless and incorporates flexible circuits and elastomeric overmolding, making the device waterproof and flexible enough to be able to mold to body contours for greater comfort and permanent wearability. In some embodiments, the PEDP device also modulates ghrelin production.

In accordance with various aspects of the present specification, the resultant benefits of modulating appetite, hunger, satiety level, satiation level or fullness level include treating conditions associated with persons who are overweight or those with metabolic syndrome, treating obesity and T2DM prevention or management. In accordance with various aspects of the present specification, the neuro-stimulation device treats people having a BMI (Body Mass Index) of 25 or greater (overweight being 25-30, obese being 30 and above, and morbid obesity being above 35). In embodiments of the present specification, the neuro-stimulation device is wearable and can be controlled and programmed by the patient, allowing the patient to administer therapy and eliminating the need for frequent patient visits to a medical professional. In embodiments, the neuro-stimulation device is designed to be placed on the front, lateral and back thoracic dermatomes and/or C5-T1 dermatomes of the patient.

In embodiments, the neuro-stimulation device is wirelessly coupled to a companion device (e.g. smartphone, watch, glove, wristband or tablet) which can be used to program the neuro-stimulation device. In some embodiments, all therapy provided by the neuro-stimulation device is coupled with a storage or recording (for keeping a log of the therapy) and patient compliance reminders. The benefits provided by having a wearable neuro-stimulation device include, among others, greater patient independence and improved patient compliance to stimulation protocols, with resultant increased dietary compliance and overall efficacy, and the ability to modify stimulation parameters based on real-time feedback provided to the neuro-stimulation device by the patient and other devices. In some embodiments, the neuro-stimulation device is driven by an algorithm derived from patient input data and monitored data (e.g. exercise monitored by a separate device). Adjustments to the algorithm, and therefore stimulation, are made both manually by the patient and automatically by the device itself or the companion device. In some embodiments, the neuro-stimulation device is driven by an algorithm derived from patient input data and monitored data (e.g. exercise monitored by a separate device). In some embodiments, the algorithm is also derived from monitored parameters, such as leptin (for ghrelin suppression), glucagon-like peptide 1 (GLP-1), hemoglobin A1C, and blood glucose levels (for diabetes treatment), lipids, and triglycerides. These parameters are measured at baseline and over time during treatment and are used as inputs to titrate therapy. Adjustments to the algorithm, and therefore stimulation, are made either manually by the patient or automatically by the neuro-stimulation device itself or the companion device or both. In accordance with some aspects of the present specification, a medical professional can flexibly program the percutaneous electro-dermal patch and still direct the patient, only allowing the patient to adjust device parameters (for greater patient independence) but within restricted bounds or predetermined parameters.

The present specification is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

For purposes of the present specification, the terms "trigger" and "triggering" do not necessarily imply immediately triggering stimulation. "Trigger" and "triggering" are defined as initiating or starting the execution of a protocol that will result in stimulation over a predefined period.

In the description and claims of the application, each of the words "comprise" "include" and "have", and forms thereof, are not necessarily limited to members in a list with which the words may be associated.

As used herein, the indefinite articles "a" and "an" mean "at least one" or "one or more" unless the context clearly dictates otherwise.

The terms "patient", "individual", "person", and "user" are used interchangeably throughout this specification and refer to the person that is receiving treatment or stimulation from the devices and methods of the present specification.

The term "hunger" is defined as a physical sensation indicative of a person's physical need for food and may be related to low levels of glucose in the person's blood and/or concentrations of ghrelin and/or hunger-inducing gut hormones.

The term "appetite" is defined as a desire for food, possibly prompted by an emotional, psychological, and/or sensory reaction to the look, taste, or smell of food.

The term "satiation" is defined as a sensation of fullness that results in cessation of eating.

The term "fullness" is defined as a sensation of an adequate amount of food present in the stomach. It should be appreciated that the term "fullness" refers to a psychological or perceptive sensation by the patient, which may be objectively measured using the scales described herein. The term "physiological fullness" shall refer to a physical measurement of the actual contents of a person's stomach.

The term "satiety" is defined as a sense of fullness that prolongs the time between meals (the more satiety, the longer duration between two meals). It is intended to refer to a patient's perception of a sense of fullness that prolongs the time between meals.

The phrase "change in satiety" is defined as an alteration in the patient's perception of gastric fullness or emptiness.

The term "dietary compliance" is defined as a patient's ability to adhere to a prescribed regimen of caloric intake, whether defined in terms of total permissible calories or a type or amount of nutritional intake, or some combination thereof, in order to achieve a targeted daily, weekly, or monthly calorie consumption and/or a targeted type or amount of nutritional intake.

The phrase "weight maintenance" means adjusting an appetite or hunger suppression/decrease goal in order to maintain a certain amount of weight loss that has already been achieved and to now avoid gaining weight. In some embodiments, weight loss maintenance entails engaging in a surgical procedure (such as various bariatric surgeries), applying the PEDP of the present specification and using appetite or hunger suppression/decrease in order to maintain the weight loss achieved by surgery.

The term "microbiota" is defined as an ensemble of microorganisms that reside in a previously established environment, such as the stomach or gastrointestinal system. The term "gut microbiota" or "gut flora is the name given to the microbiota living in a person's intestine.

The term "glycemic index (GI)" is defined as a number associated with a particular type of food that indicates the food's effect on a person's blood glucose (also called blood sugar) level. A value of 100 represents the standard, an equivalent amount of pure glucose. The glycemic index is calculated by determining the incremental area under the blood glucose response curve of a specific portion of a test food expressed as a percent of the response to the same amount of carbohydrate from a standard food taken by the same subject.

The term "glycemic load (GL)" is defined as the glycemic index multiplied by grams of carbohydrate per serving size. GL is based on a specific quantity and carbohydrate content of a test food and calculated by multiplying the weighted mean of the dietary glycemic index by the percentage of total energy from the test food. When the test food contains quantifiable carbohydrates, the GL=GI (%)×grams of carbohydrate per serving.

The term "epidermal layer" means the outer most layer of a person's skin and shall be construed to cover all variants of the word "epidermal", including epidermis.

Throughout this specification, the term "power source" is used to represent any energy providing device, including a lithium-ion battery, a betavoltaic battery, a solar cell, nickel-cadmium battery, a fuel cell, a mobile phone, or remote charging station.

The term "controller" is used to denote a processing unit configured to control the initiation of stimulation, termination of stimulation, and type and/or extent of stimulation and shall include the terms "control unit", "processing unit", "microcontroller", "microprocessor", or "processor".

The term "pulse generator" means a device configured to generate electrical pulses in accordance with instructions from a controller. It should be appreciated that the pulse generator and controller can be integrated into a single device or multiple devices.

The term "electrode" is used to refer to a conducting material that is capable of receiving electrical pulses and communicating them to another surface.

The term "modulation" or "modulating" means any form of regulation, manipulation or control to change a given variable from one state to another state.

Any increases or decreases in levels or rates are determined by the following formula [(New Level or Rate)−(Old Level or Rate)]/(Old Level or Rate).

The phrase "at least one of x, y, and z" means that only one of x or y or z need to be true or present in order to satisfy that limitation.

The term "dermatome" refers to an area of skin that is primarily innervated and/or supplied by a specific spinal nerve.

The term "meridian" refers to low resistance fluid channels where various chemical and physical transports take place and are individual pathways which exist among the subcutaneous tissues and serve as channels for the flow of interstitial microscopic fluid throughout the body.

Nerve Stimulation System

FIG. 1A is a block diagram illustration of a system 100 for stimulating or modulating nerves and nerve endings in body tissues, in accordance with an embodiment of the present specification. The system 100 comprises a neuro-stimulation device 110 in data communication with a companion device 105. In one embodiment, the neuro-stimulation device 110 is in the form of a percutaneous electro-dermal patch (PEDP). In various embodiments, the companion device 105 is further capable of being in data communication with a remote patient care facility, data server and/or patient care personnel. The companion device 105, comprising a computer readable medium and processor, can be any type of computing and communication device, including a computer, server, mobile phone, gateway, laptop, desktop computer, netbook, personal data assistant, remote control device or any other device capable of accessing a cellular, Internet, TCP/IP, Ethernet, Bluetooth, wired, or wireless network.

The neuro-stimulation device 110, in various embodiments, has a housing 111 comprising a microprocessor or microcontroller 112 electronically connected to a transceiver 114 to wirelessly communicate with the companion device 105, a pulse generator 116 to generate a plurality of electrical pulses for application through one or more electrodes 118 and a power management module 120, such as a lithium-ion battery, a betavoltaic battery, a solar cell, nickel-cadmium battery, or a fuel cell. In an embodiment, at least one electrode 118 is percutaneous. In an embodiment, at least one electrode 118 is transcutaneous. In an embodiment, electrodes 118 are a combination of percutaneous and transcutaneous. In an embodiment, electrodes 118 are percutaneous. In an embodiment, electrodes 118 are percutaneous electrodes that lay just underneath a user's skin. In some embodiments, the power management module 120 comprises a battery having a voltage in a range of 1.5 V to 4.5 V (for a single battery). The voltage depends on the chemistry of the battery being used. In other embodiments, the power management module 120 includes a plurality of batteries stacked in series to increase the voltage supply, wherein per battery voltage ranges from 1.5 V to 4.5 V. The power management module 120 has one or more additional receptor slots 130 to enable snap on or clip on attachment of a disposable electronic assembly that includes a battery for providing additional backup charge to the neuro-stimulation device 110.

Optionally, the housing 111 also comprises one or more actuators 122 such as push buttons or switches to switch the device 110 on/off and to enable user control or settings of a plurality of stimulation therapy protocols such as for toggling stimulation up or down, one or more visual indicators 124, such as LEDs (Light Emitting Diodes), and one or more tactile and audio indicators 126, such as a vibrator, buzzer or beeper to provide feedback to a user, such as about the on/off state of the neuro-stimulation device 110, commencement or conclusion of therapy, battery charge/discharge, and/or malfunction of the neuro-stimulation device 110, among other information. In one embodiment, the one or more actuators 122 includes a touch sensitive screen that enables (using an accelerometer) the user to finger-tap to control and adjust stimulation therapy protocols while the neuro-stimulation device 110 is still worn by the user. Still further embodiments may include (additionally or alternatively) control interfaces on the PEDP such as, but not limited to, a slider on the surface of the PEDP, an infrared interface wherein communication between the PEDP 110 and the companion device 105 is achieved by transmission of infrared radiation, a magnetic interface wherein an external magnet or electromagnet activates a reed switch or GMR (giant magnetoresistance) device or sensor positioned on the PEDP 110, or an audible (speaker) command input interface. It should also be appreciated that, in one embodiment, the PEDP comprises no such on/off actuators or stimulation toggling actuators and is entirely controlled by an external device, as described below.

In various embodiments, the housing 111 is sealed so that it is waterproof or water-resistant. In some embodiments, the housing 111 is hermetically sealed to be airtight. In various embodiments, the housing 111 is molded from polymeric materials such as, but not limited to, polyolefins, PET (Polyethylene Terephthalate), polyurethanes, polynorbornenes, polyethers, polyacrylates, polyamides (Polyether block amide also referred to as Pebax®), polysiloxanes, polyether amides, polyether esters, trans-polyisoprenes, polymethyl methacrylates (PMMA), cross-linked trans-polyoctylenes, cross-linked polyethylenes, cross-linked polyisoprenes, cross-linked polycyclooctenes, inorganic-organic hybrid polymers, co-polymer blends with polyethylene and Kraton®, styrene-butadiene co-polymers, urethane-butadiene co-polymers, polycaprolactone or oligo caprolactone co-polymers, polylactic acid (PLLA) or polylactide (PL/DLA) co-polymers, PLLA-polyglycolic acid (PGA) co-polymers, and photocrosslinkable polymers. In some embodiments, the housing 111 is of transparent polymeric material to allow visibility of the contained electronic components and circuitry.

In various embodiments, the microprocessor 112 is in electronic communication with one or more sensors 135 to generate data representative of various physiological parameters of an individual, such as the individual's heart rate, pulse rate, beat-to-beat heart variability, EKG or ECG, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and/or UV radiation exposure and absorption. In certain cases, the data representative of the various physiological parameters are the signal or signals themselves generated by the one or more sensors 135 and in certain other cases the data is calculated by the microprocessor 112 based on the signal or signals generated by the one or more sensors 135. Methods for generating data representative of various physiological parameters and sensors to be used therefor are well known to persons of ordinary skill in the art.

Table 1 provides several examples of well-known parameters and the sensor used to measure the parameter. The types of data listed in Table 1 are intended to be examples of the types of data that can be generated by the one or more sensors 135. It is to be understood that other types of data relating to other parameters can be generated by the neuro-stimulation device 110 without departing from the scope of the present specification. It is further understood that the sensors may be located in the housing 111, as shown in FIG. 1A, or remotely positioned from the housing 111 and configured to be electronic communication, via the wireless transceiver 114, with the microcontroller 112.

TABLE 1

| Parameter | Sensor |
| --- | --- |
| Heart Rate/Pulse Rate | EKG (2 Electrodes)/BVP (LED Emitter and Optical Sensor) |
| Beat-to-Beat Variability | EKG (2 Electrodes) |
| EKG Skin Surface Potential | EKG (3-10 Electrodes) |
| Respiration Rate | Chest Volume Change (Strain Gauge) |
| Skin Temperature | Surface Temperature Probe (Thermistors) |
| Core Temperature | Esophageal or Rectal Probe (Thermistors) |
| Heat Flow | Heat Flux (Thermopile) |
| Galvanic Skin Response | Skin Conductance (2 Electrodes) |
| EMG Skin Surface Potential | EMG (3 Electrodes) |
| EEG Skin Surface Potential | EEG (Multiple Electrodes) |
| EOG Eye Movement | Thin Film Piezoelectric Sensors |
| Blood Pressure | Electronic Sphygmomanometer |
| Body Fat | Body Impedance (2 Active Electrodes) |
| Activity | Accelerometer |
| Oxygen Consumption | Oxygen Uptake (Electro-chemical) |
| Glucose Level | Electro-chemical sensors, Optical techniques, Aqueous techniques (tears, saliva, and sweat), and Iontophoresis techniques. |
| Body Position | Mercury Switch Array, Accelerometer |
| Muscle Pressure | Thin Film Piezoelectric Sensors |
| UV Radiation | UV Sensitive Photo Cells |
| Blood oxygen saturation | Pulse oximeter |

The microprocessor 112 is programmed to summarize and analyze the data representative of the physiological parameters of the individual. For example, the microprocessor 112 can be programmed to calculate an average, minimum or maximum heart rate or respiration rate over a defined period of time, such as ten minutes. The neuro-stimulation device 110 is also able to derive information relating to the individual's physiological state based on the data representative of one or more physiological parameters. The microprocessor 112 is programmed to derive such information using known methods based on the data representative of one or more physiological parameters. Table 2 provides examples of the type of information that can be derived, and indicates some of the types of data that can be used therefor.

TABLE 2

| Derived Information | Data Used |
| --- | --- |
| Activity level | Heart rate, pulse rate, respiration rate, heat flow, activity, oxygen consumption |
| Basal metabolic rate | Heart rate, pulse rate, respiration rate, heat flow, activity, oxygen consumption, glucose level |
| Basal temperature | Skin temperature, core temperature |
| Calories burned | Heart rate, pulse rate, respiration rate, heat flow, activity, oxygen consumption |
| Maximum oxygen consumption rate | EKG, heart rate, pulse rate, respiration rate, heat flow, blood pressure, activity, oxygen consumption |
| Relaxation Level | EKG, beat-to-beat variability, heart rate, pulse rate, respiration rate, skin temperature, heat flow, galvanic skin response, EMG, EEG, blood pressure, activity, oxygen consumption |
| Sleep onset/wake | Beat-to-beat variability, heart rate, pulse rate, respiration rate, skin temperature, core temperature, heat flow, galvanic skin response, EMG, EEG, EOG, blood pressure, oxygen consumption |
| Stress level | EKG, beat-to-beat variability, heart rate, pulse rate, respiration rate, skin temperature, heat flow, galvanic skin response, EMG, EEG, blood pressure, activity, oxygen consumption |

Additionally, the neuro-stimulation device 110 may also generate data indicative of various contextual parameters relating to the environment surrounding the individual. For example, the neuro-stimulation device 110 can generate data representative of the air quality, sound level/quality, light quality or ambient temperature near the individual, or the global positioning of the individual. The neuro-stimulation device 110 may include one or more sensors for generating signals in response to contextual characteristics relating to the environment surrounding the individual, the signals ultimately being used to generate the type of data described above. Such sensors are well known, as are methods for generating contextual parametric data such as air quality, sound level/quality, ambient temperature and global positioning.

In one embodiment, the neuro-stimulation device 110 includes at least one or a combination of the following three sensors 135:

1) an impedance or bio-impedance sensor to determine electrode integrity, i.e. whether the electrode is functioning properly or damaged, to detect and confirm contact integrity of the one or more electrodes 118 with tissues to be stimulated, or to estimate body fat or Body Mass Index (BMI) and accordingly modify or manage stimulation therapy. In another embodiment, a first impedance or bio-impedance sensor is used to detect and confirm contact integrity of the one or more electrodes 118 with tissues to be stimulated and a second impedance or bio-impedance sensor is used to estimate body fat or Body Mass Index (BMI). In embodiments the impedance or bio-impedance sensor, on determination of successful contact integrity of electrodes with tissues, and therefore confirmation that the PEDP device is worn by the user, switches the PEDP device 'on' for therapy;

2) an accelerometer or inclinometer to monitor user activity such as walking, running, exercises, distance covered, sleep detection and monitoring, sensing user input to the neuro-stimulation device 110, and/or 3) a neural activity monitor to detect presence of neural activity as well as an amount of neural activity (firing rate).

In one embodiment, the neuro-stimulation device 110 only includes one or a combination of the following three sensors 135, and no other sensors:

1) an impedance or bio-impedance sensor to determine electrode integrity, i.e. whether the electrode is functioning properly or damaged, to detect and confirm contact integrity of the one or more electrodes 118 with tissues to be stimulated, or to estimate body fat or Body Mass Index (BMI) and accordingly modify or manage stimulation therapy. In another embodiment, a first impedance or bio-impedance sensor is used to detect and confirm contact integrity of the one or more electrodes 118 with tissues to be stimulated and a second impedance or bio-impedance sensor is used to estimate body fat or Body Mass Index (BMI). In embodiments, the impedance or bio-impedance sensor on determination of successful contact integrity of electrodes with tissues, and therefore ascertaining that the PEDP device is worn by the user, switches the PEDP device 'on' for therapy, 2) an accelerometer or inclinometer to monitor user activity such as walking, running, exercises, distance covered, sleep detection and monitoring, sensing user input to the neuro-stimulation device 110, 3) a neural activity monitor to detect presence of neural activity as well as an amount of neural activity (firing rate). With respect to confirming contact integrity, it should be appreciated that, in one embodiment, sufficient contact integrity of the one or more electrodes 118 is defined in terms of achieving a predefined amount of electrode impedance with the patient's epidermal layer, such as in the range of 200 to 1000 ohms, as measured by the impedance sensor.

The neural sensor is used to generate a plurality of feedback such as, but not limited to, an indication that the neuro-stimulation device 110 is placed in the right location or area, an indication that the neuro-stimulation device 110 is increasing neural-activity in line with, and in accordance with, a stimulation protocol or an indication that the neural response rate is too slow or insufficient and, therefore, the stimulation protocol needs to be modified. Such plurality of feedback generated by the neural sensor is provided to the user through a Health Management software application running on the user's hand-held computing device such as a smartphone, PDA, tablet that, in various embodiments, functions as the companion device 105. In some embodiments, the neural sensor connects to at least one of the one or more stimulation electrodes 118 while in some alternate embodiments, the neural sensor connects to at least one additional sensing electrode in addition to the one or more stimulation electrodes 118. In some embodiments, the neuro-stimulation device 110 also includes a glucose sensor to monitor the user's blood glucose level.

In some embodiments, at least a portion of the electrodes 118 are removably connectable to the housing 111. In one embodiment, at least one of the electrodes 118 is configured to be partially positioned in the housing 111 and extend outward. In another embodiment, at least one of the electrodes 118 is configured to be a snap-on electrode where the electrode 118 is removably connectable to an exterior surface of the housing 111. This allows for the electrode 118 to be removed and replaced with a new electrode 118, thereby reusing the electrical dermal patch device 110 with a new electrode and minimizing the cost of electrodes that fail after just a few days of use.

Figure 1B:
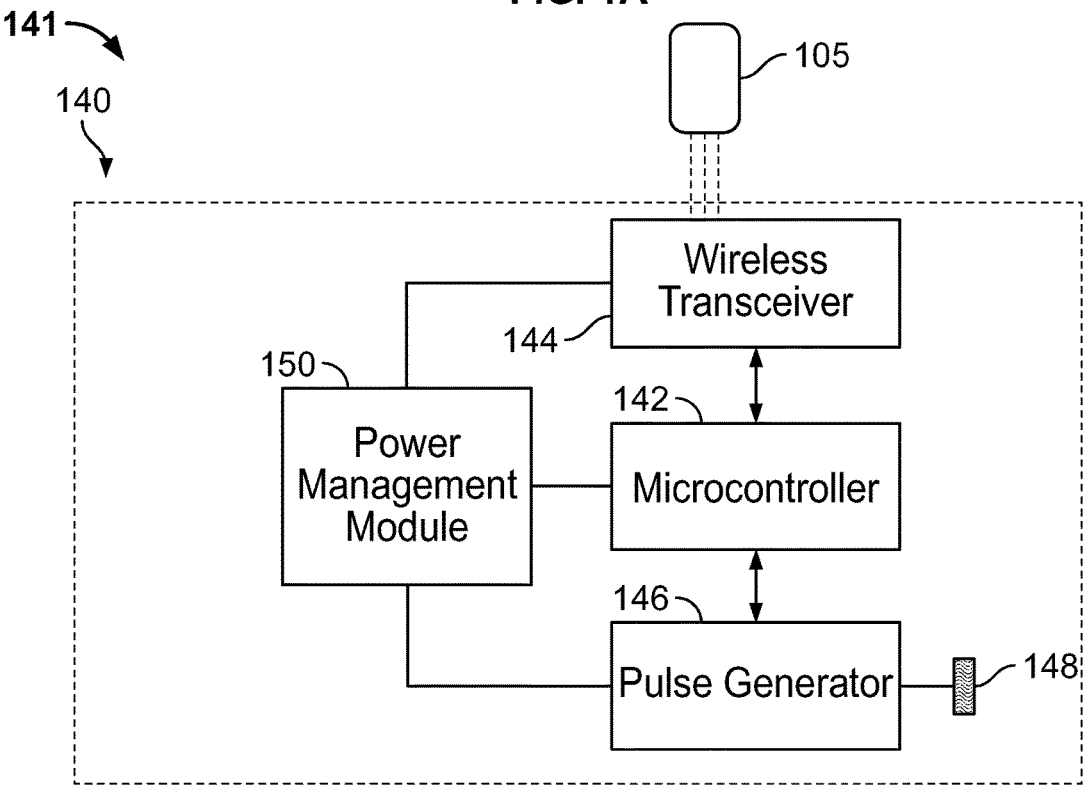
FIG. 1B is a block diagram of a system for stimulating or modulating nerves and nerve endings in body tissues, in accordance with another embodiment of the present specification.

FIG. 1B is a block diagram illustration of a system 141 for stimulating or modulating nerves and nerve endings in body tissues, in accordance with another embodiment of the present specification. In some embodiments, referring to FIG. 1B, the neuro-stimulation device (PEDP) 140 includes a microcontroller 142, wireless transceiver 144, a power management module 150, such as a lithium-ion battery, a betavoltaic battery, a solar cell, nickel-cadmium battery, or a fuel cell, a pulse generator 146, and at least one electrode 148, and includes no other physical inputs or sensors on the PEDP 140 itself. The remaining inputs are on the companion device 105 and are actuated through the wireless coupling of the companion device 105 and PEDP 140.

In an embodiment, at least one electrode 148 is percutaneous. In an embodiment, at least one electrode 148 is transcutaneous. In an embodiment, electrodes 148 are a combination of percutaneous and transcutaneous. In an embodiment, electrodes 148 are percutaneous electrodes that lay just underneath a user's skin.

In some embodiments, rather than including a physical on/off switch, the PEDP 140 depicted in FIG. 1B is always using at least a minimum amount of power such that an 'off' state refers to a low power state. While no stimulation is being provided, there is, at a minimum, a periodic 'wake-up' of the PEDP 140 to check for communication from the companion device 105. The 'wake-up' places the device in an 'on' state and, in some embodiments, includes no stimulation wherein the PEDP 140 runs diagnostics for reporting to the companion device 105. Therefore, while in the 'off' state, the PEDP 140 is constantly using a very low amount of power, is not providing stimulation, and is either awaiting a signal from the companion device or is performing diagnostics or other non-stimulation activities requiring very little power. In some embodiments, the energy usage is less than 5 µA average current or in the range of 0.1 µA to 5 µA average current while in the 'off' state and greater than 10 µA average current while in the 'on' state. In some embodiments, the energy usage is at least 1 µA greater while in the 'on' state than while in the 'off' state. Once the PEDP 140 receives a signal from the companion device 105 to initiate stimulation, it enters the 'on' state and uses an amount of energy associated with the level of stimulation. In another embodiment, the PEDP 140 uses no energy while in an 'off' state and must be awakened, or switched to an 'on' state, by a signal from the companion device.

Figure 1C:
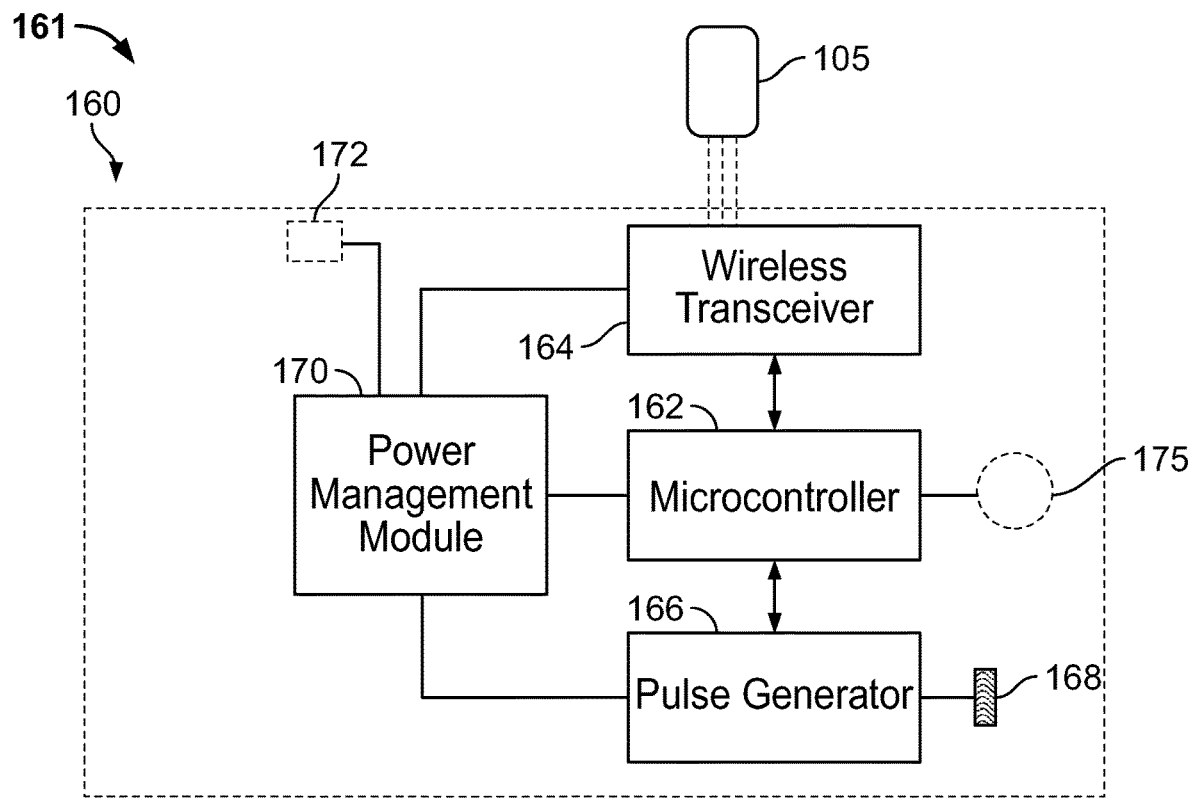
FIG. 1C is a block diagram of a system for stimulating or modulating nerves and nerve endings in body tissues, in accordance with yet another embodiment of the present specification.

FIG. 1C is a block diagram illustration of a system 161 for stimulating or modulating nerves and nerve endings in body tissues, in accordance with yet another embodiment of the present specification. In some embodiments, referring to FIG. 1C, the neuro-stimulation device (PEDP) 160 includes a microcontroller 162, wireless transceiver 164, a power management module 170, such as a lithium-ion battery, a betavoltaic battery, a solar cell, nickel-cadmium battery, or a fuel cell, a pulse generator 166, one electrode 168, an optional single actuator 172 to turn the PEDP 160 on or off, one sensor 175 for sensing a physiological parameter of the patient, and includes no other physical inputs on the PEDP 160 itself. In one embodiment, the sensor 175 is a neural sensor. The remaining inputs are on the companion device 105 and are actuated through the wireless coupling of the companion device 105 and PEDP 160.

In accordance with various aspects of the present specification, each component (power management module, microprocessor or microcontroller, pulse generator, transceiver, and one or more electrodes) of the percutaneous electro-dermal patch may be positioned in a separate housing, in a separate device, or otherwise physically remote from each other. For example, as described with reference to FIG. 1A, the neuro-stimulation device 110 comprises a power management module 120, microprocessor or microcontroller 112, pulse generator 116, transceiver 114, and one or more electrodes 118 in a housing 111.

Figure 1D:
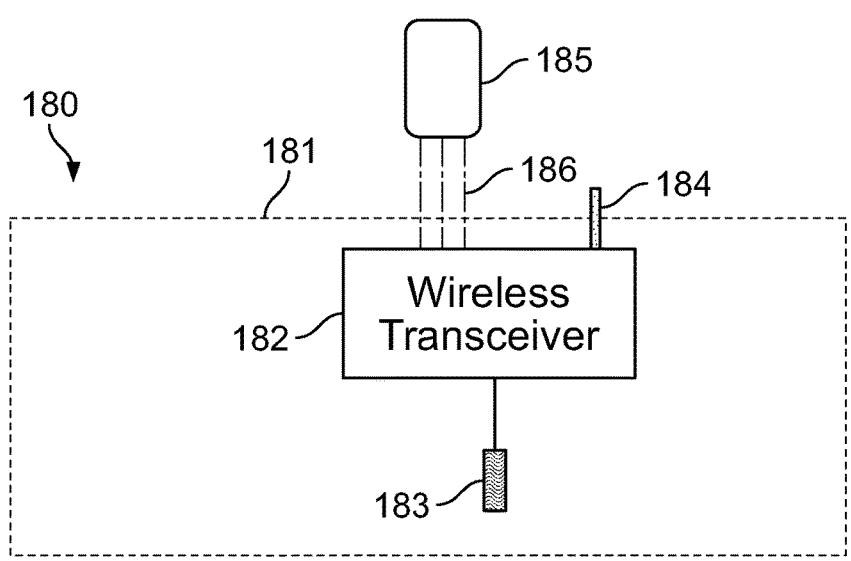
FIG. 1D is a block diagram of a system for stimulating or modulating nerves and nerve endings in body tissues, in accordance with yet another embodiment of the present specification.

However, in a first alternative embodiment as shown in FIG. 1D, the neuro-stimulation device 180 comprises a transceiver 182 having an antenna 184 for receiving electrical pulse signals 186 and an electrode 183. A housing 181 may be positioned around the transceiver 182 and optionally at least one electrode 183 or a substrate carrier may be used to support a low-profile transceiver and/or electrode circuit without any additional housing structure. In this embodiment, an external device 185 comprises the power source, controller, and pulse generator adapted to generate a plurality of electrical pulses, as described earlier with reference to FIGS. 1A through 1C. The external device 185 may be a watch, mobile phone, a sensor pod configured to attach to the patient using a strap or band, or other wearable device. The external device 185 wirelessly transmits the electrical pulses 186 to the transceiver 182 which, in turn, transmits the electrical pulses to the electrode 183 and, thereafter, to the patient.

Figure 1E:
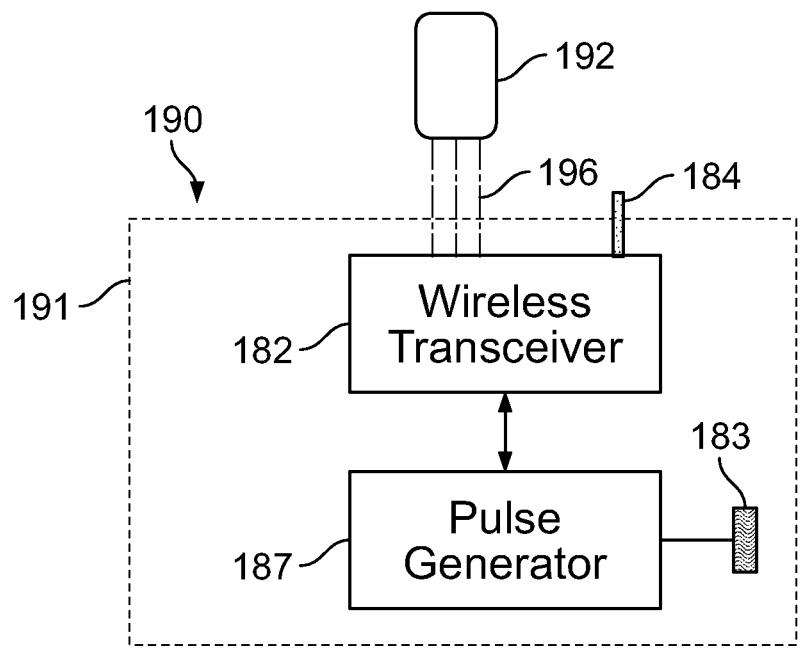
FIG. 1E is a block diagram of a system for stimulating or modulating nerves and nerve endings in body tissues, in accordance with still another embodiment of the present specification.

In a second alternative embodiment, as shown in FIG. 1E, the PEDP device 190 comprises a transceiver 182 having an antenna 184 for receiving signals 196, a pulse generator 187, and an electrode 183. A housing 191 may be positioned around the transceiver 182, pulse generator 187, and optionally at least one electrode 183. In this embodiment, an external device 192 comprises the power source and controller adapted to generate an electrical signal, power signal, or data signal 196 that is wirelessly transmitted to transceiver 182 and, in turn, to the pulse generator 187 and used by the pulse generator 187 to generate a plurality of electrical pulses. The external device 192 may be a watch, mobile phone, a sensor pod configured to attach to the patient using a strap or band, or other wearable device. The electrical pulses are communicated to the electrode 183 and, thereafter, to the patient.

Figure 1F:
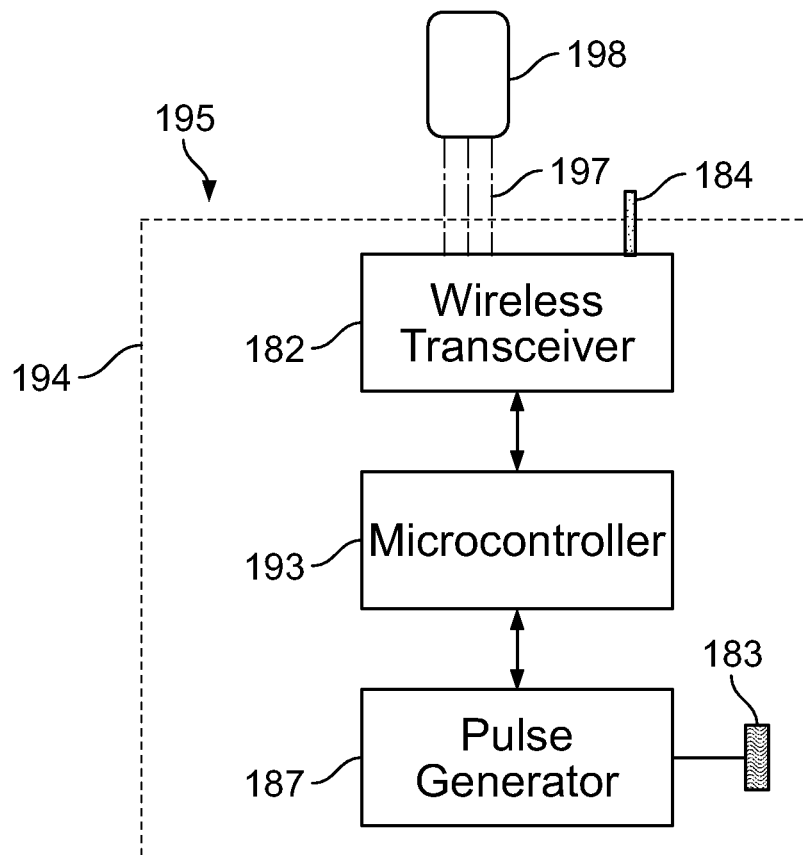
FIG. 1F is a block diagram of a system for stimulating or modulating nerves and nerve endings in body tissues, in accordance with yet another embodiment of the present specification.

In a third alternative embodiment, as shown in FIG. 1F, the PEDP device 195 comprises a transceiver 182 having an antenna 184 for receiving power signals 197, a microprocessor or microcontroller 193, a pulse generator 187, and an electrode 183. A housing 194 may be positioned around the transceiver 182, microcontroller 193, pulse generator 187, and optionally at least one electrode 183. In this embodiment, an external device 198 comprises a power source and transceiver adapted to generate the power signal 197 that is wirelessly transmitted to the transceiver 182 of the PEDP device 195 and, in turn, to the microcontroller 193 and pulse generator 187 which generates a plurality of electrical pulses. The external device 198 may be a watch, mobile phone, a sensor pod configured to attach to the patient using a strap or band, or other wearable device. The electrical pulses are communicated to the electrode 183 and, thereafter, to the patient.

In a fourth alternative embodiment, each of the power source, controller, pulse generator, transceiver, and optionally at least one electrode are combined altogether in a single housing.

In a fifth alternative embodiment, the controller, pulse generator, and/or transceiver are combined together in a first housing while the electrode and power source are in a disposable second housing, thereby allowing the electrode and the power source to be disposed of when exhausted. Accordingly, the controller, pulse generator, and/or transceiver could be reused and connected to a replacement electrode and power source, yielding a refreshed device.

It should be appreciated that each of the above embodiments can be implemented without a transceiver, replacing the wireless communication with a wired connection between the external device and the electro-dermal patch. It should also be appreciated that, for each embodiment, signal processing to determine data indicative of a physiological condition can be done at the sensor level, i.e. in the impedance or other sensor, at the controller level in the PEDP device, or at the external device level using a mobile application software or other program.

Percutaneous Electro-Dermal Patch (PEDP) Device Configurations

In accordance with an aspect of the present specification, the neuro-stimulation device 110 is configured as a wearable and disposable percutaneous skin patch that is adhesively attached to the user's skin. In one embodiment, the entire assembly is disposed of once the battery depletes. In accordance with an aspect of the present specification, the neuro-stimulation device 110 is configured to be worn for prolonged usage, such as for at least 1, 2, 3, 4, 5, 6, 7, 8, 9, 10, 11, 12, 13, 14 days or up to 3 months continuously or any increment therein, and removed solely for the purpose of recharging and/or replacing the electrodes. The adhesive of the patch is preferably biocompatible to prevent skin irritation due to prolonged usage of the patch. Loctite®, manufactured by Henkel, is a non-limiting example of a medical or biocompatible adhesive. The adhesive of the pads provides sufficient attachment integrity of the PEDP to the user's skin. In various embodiments, the PEDP has an average minimum 'peel strength' in a range of 1.3 to 1.7 Newton and preferably 1.5 Newton on living skin. Persons of ordinary skill in the art would appreciate that 'peel strength' is the force required to remove or peel off the PEDP, having adhesive pads, from the user's skin and is a measure of the attachment integrity of the PEDP. 'Peel strength' is typically quantified by pulling the device from a flexible end or edge at an angle of 90 degrees from the skin surface at a peel rate that ranges from 100 to 500 mm/minute. In alternate embodiments, placement of the neuro-stimulation device 110 is accomplished using a band, strap or a belt (for example, at the user's arm or wrist regions). It should be appreciated that the term "adhered" is intended to encompass all forms of achieving device-to-skin contact, including adhesives, bands, straps, or belts.

Referring back to FIG. 1A, in accordance with some embodiments, the one or more electrodes 118 are placed or inserted percutaneously up to a depth, ranging from 0.1 mm to 30 mm, in the skin and enable the neuro-stimulation device 110 to provide electrical stimulation therapy to a user. In various embodiments, a stimulation depth through the patient's skin ranges from 0.1 mm to 30 mm.

For percutaneous electrical stimulation, in an embodiment, the present specification employs a first electrode configured as a transcutaneous electrode pad for placing on the user's skin surface and a second electrode configured as a percutaneous electrode. In another embodiment, both the first and the second electrodes are configured as percutaneous electrodes. In various embodiments, the percutaneous electrode is a fine wire that is inserted to a depth into the user's skin to stimulate deep musculature and nerves along with other tissues. The wire is substantially coated with an electrical insulator except for a distal end, which remains uncovered to create an electrode. In various embodiments, the length of the second electrode, that is the percutaneous electrode, ranges from 0.1 mm to 60 mm and preferably from 0.1 mm to 30 mm, or any increment therein. In various embodiments, the depth of insertion of the percutaneous electrodes ranges from 0.1 mm to 30 mm, at an angle of insertion ranging from 10 degrees to 90 degrees (with reference to the dermal layer), or any increment therein, to deliver stimulation through the skin, wherein the stimulated area ranges from 0.1 mm to 30 mm (with reference to the dermal layer), or any increment therein. In some embodiments, the percutaneous electrode is inserted into the skin to a depth of up to 10 mm.

Optionally, in embodiments where two or more electrodes are configured as percutaneous electrodes, the two or more percutaneous electrodes may optionally be implanted at the same depths and/or the same angles of insertion, independently of each other, to deliver a desired stimulation.

It should be appreciated that in embodiments where two or more electrodes are configured as percutaneous electrodes, the two or more percutaneous electrodes may optionally be implanted at different depths and/or at different angles of insertion, independently of each other, to deliver a desired stimulation. For example, a first electrode may be implanted at a depth of 0.2 mm while the second electrode may be implanted at a depth of 4 mm. In another example, the first electrode may be inserted at an angle of 90 degrees and implanted at a depth of 2 mm while the second electrode may be inserted at an angle of 15 degrees and implanted at a depth of 4 mm.

Optionally, in embodiments where two or more electrodes are configured as percutaneous electrodes, the two or more percutaneous electrodes may optionally be implanted at different depths and/or the same angles of insertion, independently of each other, to deliver a desired stimulation.

Optionally, in embodiments where two or more electrodes are configured as percutaneous electrodes, the two or more percutaneous electrodes may optionally be implanted at the same depths and/or different angles of insertion, independently of each other, to deliver a desired stimulation.

In accordance with various aspects of the present specification, the PEDP device is configured to be self-implanted or self-administered by the user or implanted by a physician or medical personnel.

Figure 1G:
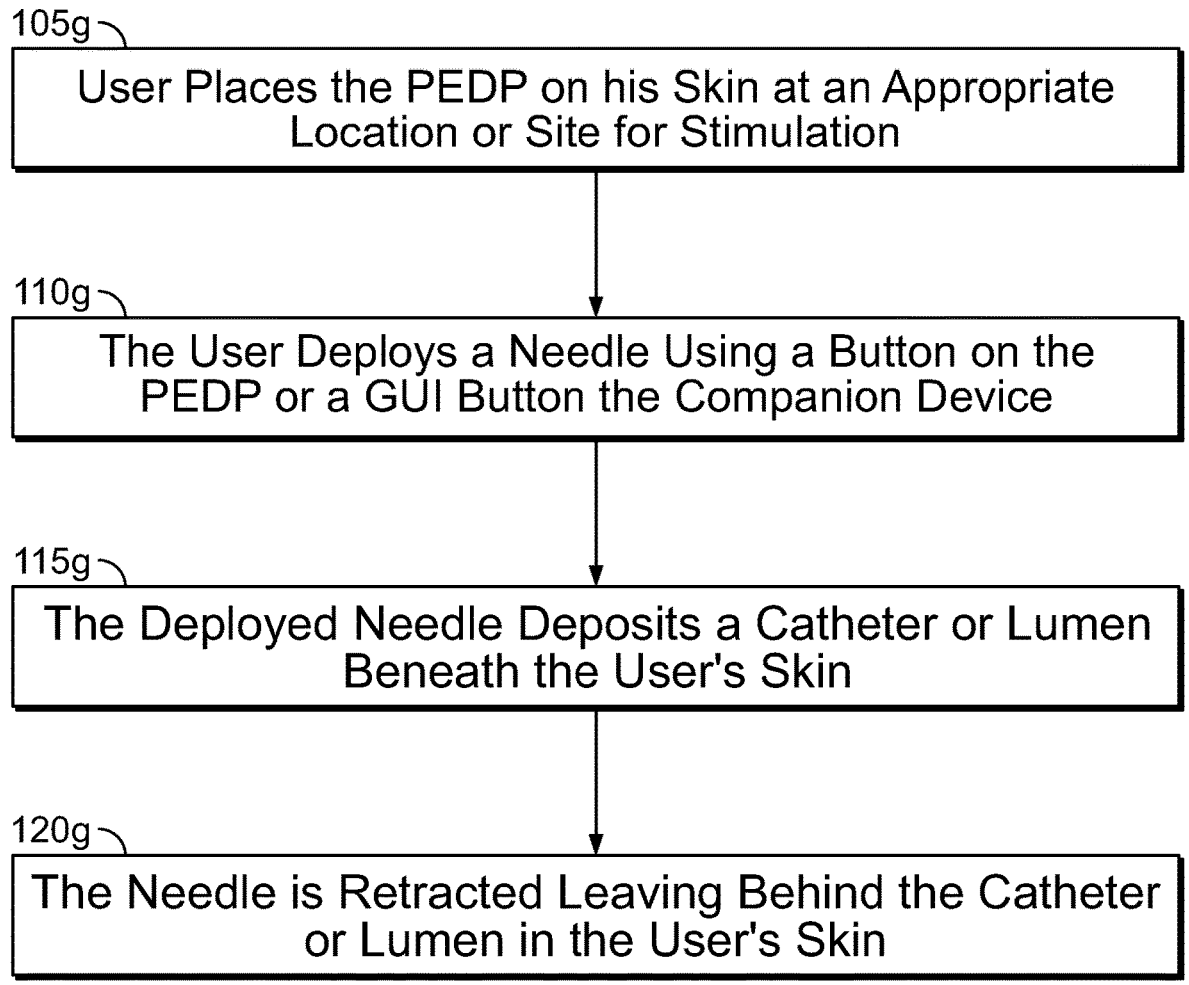
FIG. 1G is a flowchart illustrating a plurality of exemplary steps of a method of self-implantation of a neuro-stimulation PEDP device, in accordance with an embodiment of the present specification.

In a first embodiment, the PEDP device is self-implanted or self-administered by the patient. In such an embodiment, the user places a PEDP device on his skin at an appropriate site or location whereby the PEDP device includes a deployable retractable needle positioned on the bottom surface of the device, which is in contact with the user's skin. When deployed, the needle punctures the user's skin and implants an electrically conductive lumen underneath the skin. The needle is then retracted. FIG. 1G is a flowchart illustrating a plurality of steps of a method of self-implantation of the PEDP by a user, in accordance with an embodiment. At step 105g, the user places the PEDP on the skin at an appropriate site or location for stimulation. Selection or identification of the appropriate site is described in greater detail below. The user then, at step 110g, deploys a needle positioned at the bottom surface (touching the user's skin) of the PEDP, by either actuating a button on the PEDP or using a GUI based button or icon on a companion device, such as the user's smartphone. When deployed, the needle punctures and penetrates the user's skin up to an appropriate depth, such as 0.1 mm to 30 mm, and at a desired angle of insertion ranging from 10 to 90 degrees (as described with reference to FIG. 2B in this specification). At step 115g, the deployed or inserted needle deposits, underneath the skin, a catheter or lumen that is electrically conductive and malleable and capable of delivering stimulation. Once the catheter or lumen is deposited, the needle is retracted, at step 120g, leaving the catheter or lumen behind. In some embodiments, the needle is automatically retracted. In other embodiments, the needle may be retracted using a button or GUI-based button or icon. In some embodiments, the needle may only be retracted when an adequate implantation is confirmed by the device or companion device.

Figure 1H:
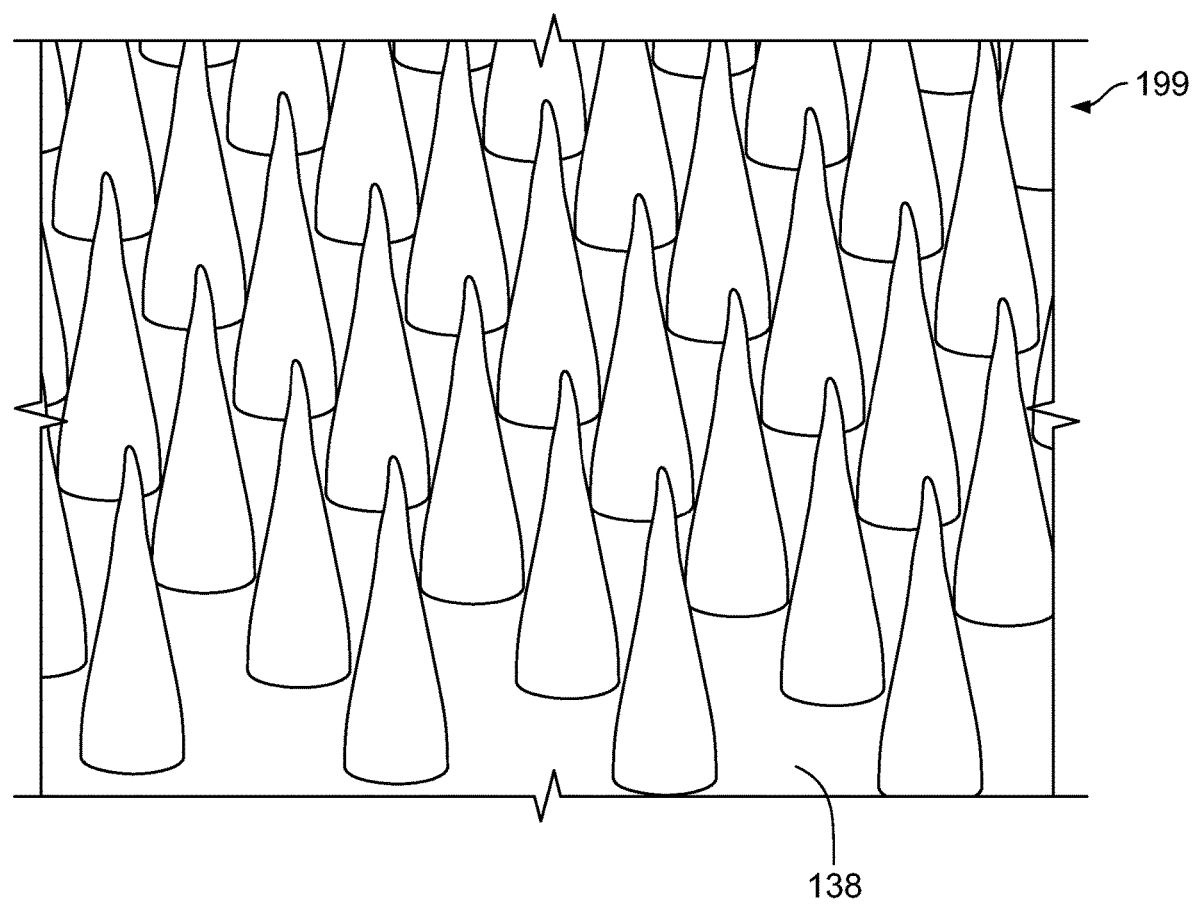
FIG. 1H is a perspective view of an array of micro-needle based electrodes mounted on a base.

In a second embodiment of the present specification, referring back to FIG. 1A, the PEDP device includes one or more electrodes 118 configured as an array of micro-needles that enable a patient-friendly intradermal stimulation delivery solution that can be self-implanted and positioned by the user. FIG. 1H shows an array of micro-needles 199 mounted on a base 138. The micro-needles 199, in some embodiments, are positioned using springs for insertion into the patient's skin. The array of micro-needle electrodes 199 penetrate the skin barrier and deliver stimulation with reduced tissue damage, reduced pain, and reduced or no bleeding. In some embodiments, the depth of insertion of penetration of the micro-needle electrodes 199 ranges from 0.1 mm to 30 mm. In some embodiments, the depth of insertion or penetration of the micro-needle electrodes 199 ranges from 0.1 mm to 4 mm.

In a third embodiment, the PEDP device of the present specification is implanted by a physician or medical personnel. FIG. 2C is a perspective view of a percutaneous electrode insertion system 230 utilized by a physician to implant one or more percutaneous electrodes underneath the patient's skin. The system 230 comprises a housing 232 with a mounting surface 235 adapted for application to the skin of the patient, in accordance with some embodiments. The mounting surface 235 is defined by a plane and has a hollow needle 238 protruding therefrom. In various embodiments, the needle 238 is surrounded by springs that are utilized to deploy a percutaneous electrode (such as the electrode 211 of FIG. 2A), inserted through the hollow needle 238, automatically at a desired angle of insertion.

Figure 2A:
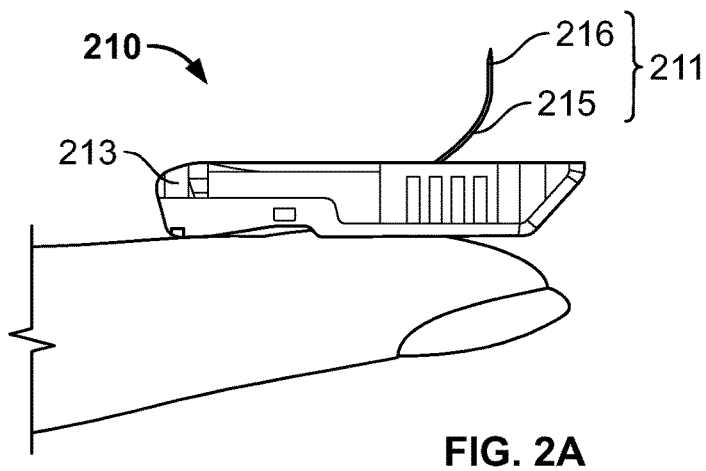
FIG. 2A is a perspective view of a neuro-stimulation device configured to provide electrical stimulation therapy, in accordance with some embodiments.

FIG. 2A shows a neuro-stimulation device 210 configured to provide percutaneous electrical stimulation therapy, in accordance with some embodiments. The device 210 includes an electrode pad or skin patch (not visible) for placing on the user's skin surface and a percutaneous electrode 211 in the form of an insulated fine wire 215 extending from a bottom surface of the housing 213. A distal end 216 of the insulated fine wire is bared or "stripped" of insulation to create an electrode. The housing 213 includes the microcontroller, pulse generator, wireless transceiver, and power management module of the system described with reference to FIGS. 1A through 1C.

Figure 2B:
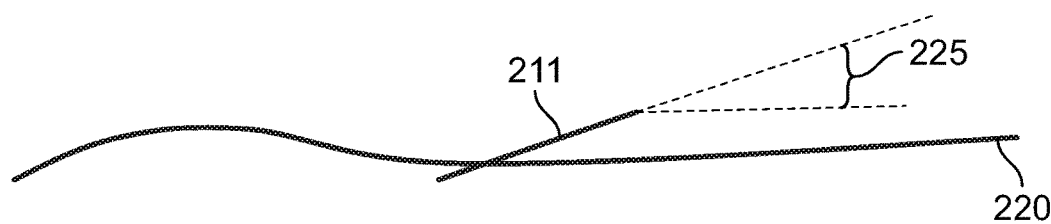
FIG. 2B illustrates an angle of insertion of a percutaneous electrode into a user's epidermal layer.
Figure 2C:
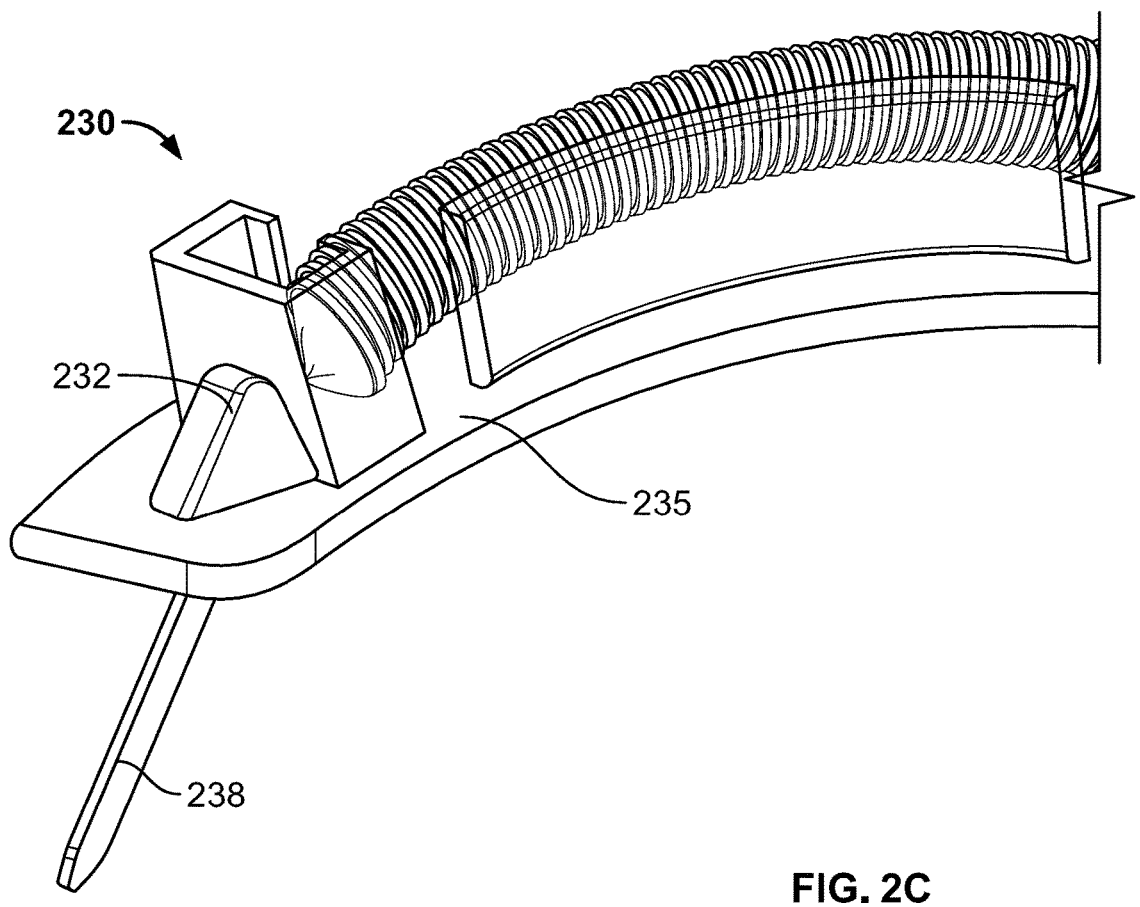
FIG. 2C is a perspective view of a percutaneous electrode insertion system, in accordance with some embodiments.

In various embodiments, a depth of insertion of the percutaneous electrode 211, into the user's skin, is governed by an angle at which the percutaneous electrode 211 enters the user's epidermal layer. FIG. 2B illustrates the percutaneous electrode 211 entering the user's epidermal layer 220 at an angle 225 of insertion (with reference to the epidermal layer 220). In various embodiments, the angle 225 of insertion ranges from 10 degrees, corresponding to a shallow insertion scenario, to 90 degrees, corresponding to a most protruding scenario of insertion of the percutaneous electrode 211.

Optionally, in various embodiments, the neuro-stimulation device 210 comprises a retractable needle coupled to the bottom surface of the housing 213. In embodiments where the user self-implants the device 210, the device 210 is positioned on the user's skin and the retractable needle is deployed to penetrate the user's skin to a desired depth and at a desired angle of insertion and deposit a conductive catheter or lumen underneath the user's skin. The needle is thereafter retracted leaving the catheter or lumen behind. In some embodiments, the device 210 comprises an actuator, such as a button, which when triggered by the user causes the retractable needle to be deployed. In additional or alternative embodiments, the retractable needle is deployable by actuating a GUI based icon or button the user's smartphone that functions as a companion device.

In some embodiments, all of the components of neuro-stimulation device 210 are positioned in a single patch such that neuro-stimulation device 210 has a substantially flat profile. The lower profile of neuro-stimulation device 210 facilitates patient comfort. In various embodiments, the neuro-stimulation device 210, has a width w of 4 inches or less, a length l of 8 inches or less, and a height h of 1.5 inches, and preferably 1 inch or less and still preferably 0.35 inches or less. In various embodiments, the neuro-stimulation device 210 has a weight ranging from 5 grams to 250 grams. In various embodiments, the neuro-stimulation device 210 has a weight of 145 grams or less. In various embodiments, these dimensions include the percutaneous electrode or micro-needle array portions. In various embodiments, these dimensions do not include the percutaneous electrode or micro-needle array portions.

In various embodiments, the dimensions and/or form factor of the percutaneous electro-dermal patch device of the present specification has any one or a combination of the following attributes: a substantially linear profile, a width of 4 inches or less, a length of 8 inches or less and a height of 1 inch or less; a volume in a range of 0.25 inches$^3$ to 10 inches$^3$; a weight in a range of 5 grams to 250 grams; a physical aspect ratio of width to thickness in a range of 1:1 to 6:1; a footprint of the PEDP device in a range of 3.5 inches' (1:1 aspect ratio) to 6 inches' (6:1 aspect ratio); an electrical aspect ratio in a range of 1:1 to 1.5:1.

It should be appreciated that, while different physical configurations may exist for the percutaneous electrical dermal patch, it is important that the device deliver enough electrical stimulation in a reasonably sized patch structure, namely one that is not so large that it would be uncomfortable to wear.

In various embodiments, the neuro-stimulation device 210 has an ingress protection rating (IPX) of at least IPX7, allowing the patient to take showers and swim for at least 30 minutes while the neuro-stimulation device 210 is positioned on the body without water damage to the neurostimulation device 210. In some embodiments, the adhesive portion (of the percutaneous electro-dermal patch) is surrounded along the perimeter with a closed cell foam to prevent water ingress to the adhesive and adhesion reduction in a long shower and/or a 30 minute swim. In various alternate embodiments, the PEDP device 210 has an ingress protection rating (IP) ranging from IP3 to IP5 and preferably a waterproof rating of IP4 (that is, protection from water splashing from any direction for 5 minutes) per IEC standard 60529. The neuro-stimulation device 210 is composed of a flexible, rubber or silicone material with sufficient structural strength to remain on the body once positioned while still flexible enough to be peeled back by its edges. The neuro-stimulation device 210 is storable when not in use. In other embodiments, the neuro-stimulation device 210 has an ingress protection rating (IPX) of at least IPX1, IPX2, IPX3, IPX4, IPX5, or IPX6, as known to persons of ordinary skill in the art.

In one embodiment, the neuro-stimulation device 210 includes no visible or tactile user interface and all communication with the neuro-stimulation device 210 is achieved wirelessly using a companion device as described further below.

In some embodiments, the neuro-stimulation device 210 includes a disposable battery which provides operating power for at least 90 days of usage. In one embodiment, the neuro-stimulation device electronic circuitry, in combination with the electrodes, is used to sense skin placement and to turn therapy on and off automatically as further described below. In one embodiment, the neuro-stimulation device electronic core and adhesive pad with electrodes are all combined in one flat component configured to provide therapy for at least 3 months. In an alternate embodiment, the neuro-stimulation device electronic core is located within a housing separate from the pad and, in some embodiments, is easily replaceable by the patient or a medical professional.

FIG. 3A illustrates a side view of a neuro-stimulation PEDP device in accordance with one embodiment. The neuro-stimulation device (PEDP device) 300 has all electronics 302, power 301, a power transfer mechanism 303, such as a coil, and electrode 304 captured within a single unit structure. The PEDP device 300 contains at least one electrode 304, in the form of a very fine wire that passes through the cutaneous tissue (skin) to reach the dermatome. The wire is completely coated with an electrical insulator except for the distal end where it is open to create an electrode. This portion is designed to be inserted into or near the dermatome of interest.

The PEDP device 300, aside from at least one percutaneous electrode, is intended to be placed on, and adhered to, the skin over a dermatome of interest. The device 300 can have different shapes and sizes for different body types. Placement can be accomplished via a biocompatible adhesive on its surface, 305, a band, a belt, or other such fixturing methods. The proper location of the electrode 304 may be determined by a sensing mechanism. This sensing mechanism can be feedback from the patient, an electronic sensing mechanism (e.g., biopotential amplifier with analog filtering), or both. Once the proper location is found, the patient can be tattooed to mark the spot for future device placements.

Optionally, in various embodiments, the PEDP device 300 comprises a retractable needle coupled to the bottom surface 305. In embodiments where the user self-implants the device 300, the device 300 is positioned on the user's skin and the retractable needle is deployed to penetrate the user's skin to a desired depth and at a desired angle of insertion and deposit a conductive catheter or lumen underneath the user's skin. The needle is thereafter retracted leaving the catheter or lumen behind. In some embodiments, the device 300 comprises an actuator, such as a button, which when triggered by the user causes the retractable needle to be deployed. In additional or alternative embodiments, the retractable needle is deployable by actuating a GUI based icon or button the user's smartphone that functions as a companion device.

FIG. 3B illustrates another embodiment for a neuro-stimulation PEDP device whereby electrodes are fully implanted. The target dermatome(s) are stimulated through a small structure 315 that has a plurality of anodes and a plurality of cathodes and is placed in the subcutaneous region 316 of a patient's body 317 proximate the target dermatome(s). This structure 315 also has a receiving mechanism to receive power from outside the patient's body 317. Power is transferred to structure 315 from the PEDP device 310 which contains a battery 311, electronics 312, a power transfer mechanism 313, such as a coil. The PEDP device 310 is placed with its bottom surface 314 in close proximity to said subcutaneous region 316 to enable transfer of power from power transfer mechanism 313 to structure 315.

Optionally, in various embodiments, the PEDP device 310 comprises a retractable needle coupled to the bottom surface 314. In embodiments where the user self-implants the device 310, the device 310 is positioned on the user's skin and the retractable needle is deployed to penetrate the user's skin to a desired depth and at a desired angle of insertion and deposit a conductive catheter or lumen underneath the user's skin. The needle is thereafter retracted leaving the catheter or lumen behind. In some embodiments, the device 310 comprises an actuator, such as a button, which when triggered by the user causes the retractable needle to be deployed. In additional or alternative embodiments, the retractable needle is deployable by actuating a GUI based icon or button the user's smartphone that functions as a companion device.

Figure 3C:
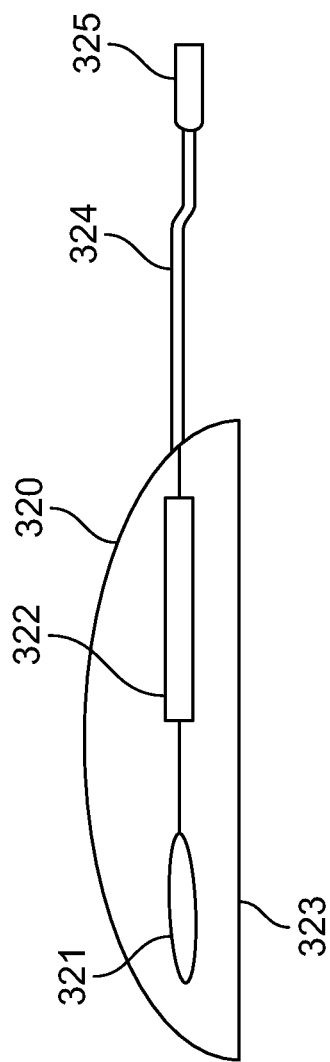
FIG. 3C is a side view illustration of yet another neuro-stimulation PEDP device configured to provide electrical stimulation therapy, in accordance with one embodiment.

FIG. 3C illustrates another embodiment for a neuro-stimulation PEDP device whereby the electrodes 325 are not part of the main device housing. The target dermatome(s) are stimulated through these electrodes 325, which are operably connected to the PEDP device 320 via a cable 324. The cable 324 can either be permanently connected to the device 320 or detachable. The electrodes can be either percutaneous or a combination of cutaneous and percutaneous. It should be understood that other portions of the device 320 could be detachable as well. For example, the unit could be constructed such that the power source 321 and electrodes 325 are both detachable. This would make the electronics 322 a reusable element of the device 320 while the power source 321 and electrodes 325 can be disposable. Other such configurations can be envisioned. Optionally, the device 320 also includes a power transfer mechanism, such as a coil. A bottom surface 323 of the device includes an adhesive for securing the device 320 to a skin surface of a patient.

Optionally, in various embodiments, the PEDP device 320 comprises a retractable needle coupled to the bottom surface 323. In embodiments where the user self-implants the device 320, the device 320 is positioned on the user's skin and the retractable needle is deployed to penetrate the user's skin to a desired depth and at a desired angle of insertion and deposit a conductive catheter or lumen underneath the user's skin. The needle is thereafter retracted leaving the catheter or lumen behind. In some embodiments, the device 320 comprises an actuator, such as a button, which when triggered by the user causes the retractable needle to be deployed. In additional or alternative embodiments, the retractable needle is deployable by actuating a GUI based icon or button the user's smartphone that functions as a companion device.

Figure 3D:
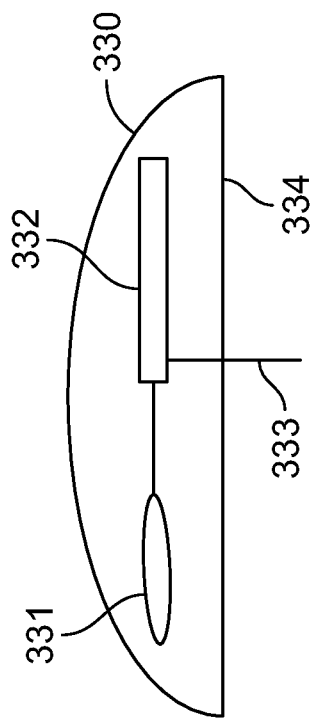
FIG. 3D is a side view illustration of yet another neuro-stimulation PEDP device, in accordance with another embodiment of the present specification.

FIG. 3D is another embodiment for a PEDP device 330 whereby there are no electrodes disposed on the surface of the device and only one percutaneous element 333 that extends outward from the surface of the device. The device 330 contains a battery 331, electronics 332 and, optionally, a power transfer mechanism. This embodiment allows for a plurality of electrodes, for example in the form of an array of micro-needles, to be on the percutaneous element 333. A bottom surface 334 of the device includes an adhesive for securing the device 330 to a skin surface of a patient.

Optionally, in various embodiments, the PEDP device 330 comprises a retractable needle coupled to the bottom surface 334. In embodiments where the user self-implants the device 330, the device 330 is positioned on the user's skin and the retractable needle is deployed to penetrate the user's skin to a desired depth and at a desired angle of insertion and deposit a conductive catheter or lumen underneath the user's skin. The needle is thereafter retracted leaving the catheter or lumen behind. In some embodiments, the device 330 comprises an actuator, such as a button, which when triggered by the user causes the retractable needle to be deployed. In additional or alternative embodiments, the retractable needle is deployable by actuating a GUI based icon or button the user's smartphone that functions as a companion device.

Figure 3E:
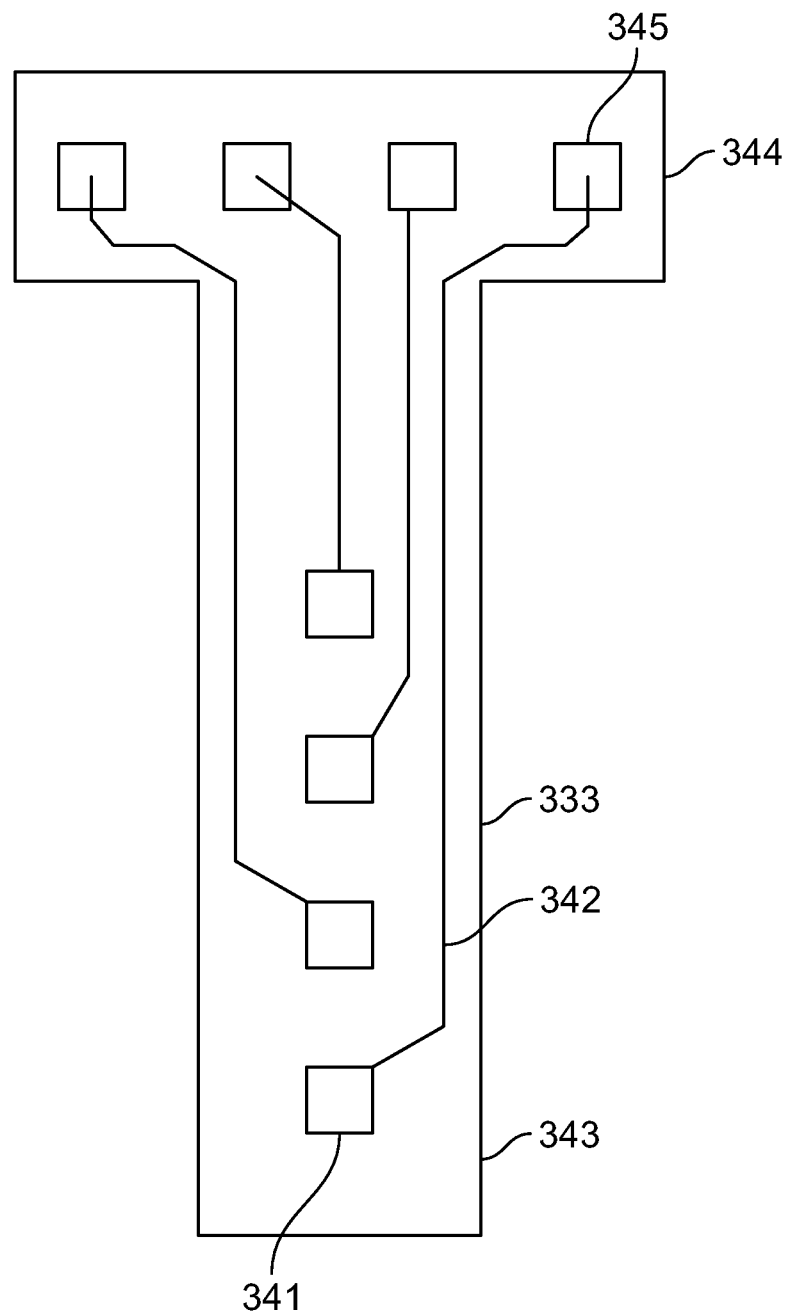
FIG. 3E is an illustration of a percutaneous multi-electrode array that may be employed with the devices of the present specification.

FIG. 3E is an embodiment of the percutaneous element 333 of FIG. 3D. The element 333 has four electrodes 341 connected to four pads 345 via conductors 342. The element substrate 343 can be made from a flexible material such as Kapton® (polyimide film) or other such material, and the electrodes 341 and traces can be made of gold, platinum, etc. An insulate material such as polyimide or parylene can be used to prevent short circuiting of the electrode conductors in tissue.

Figure 4:
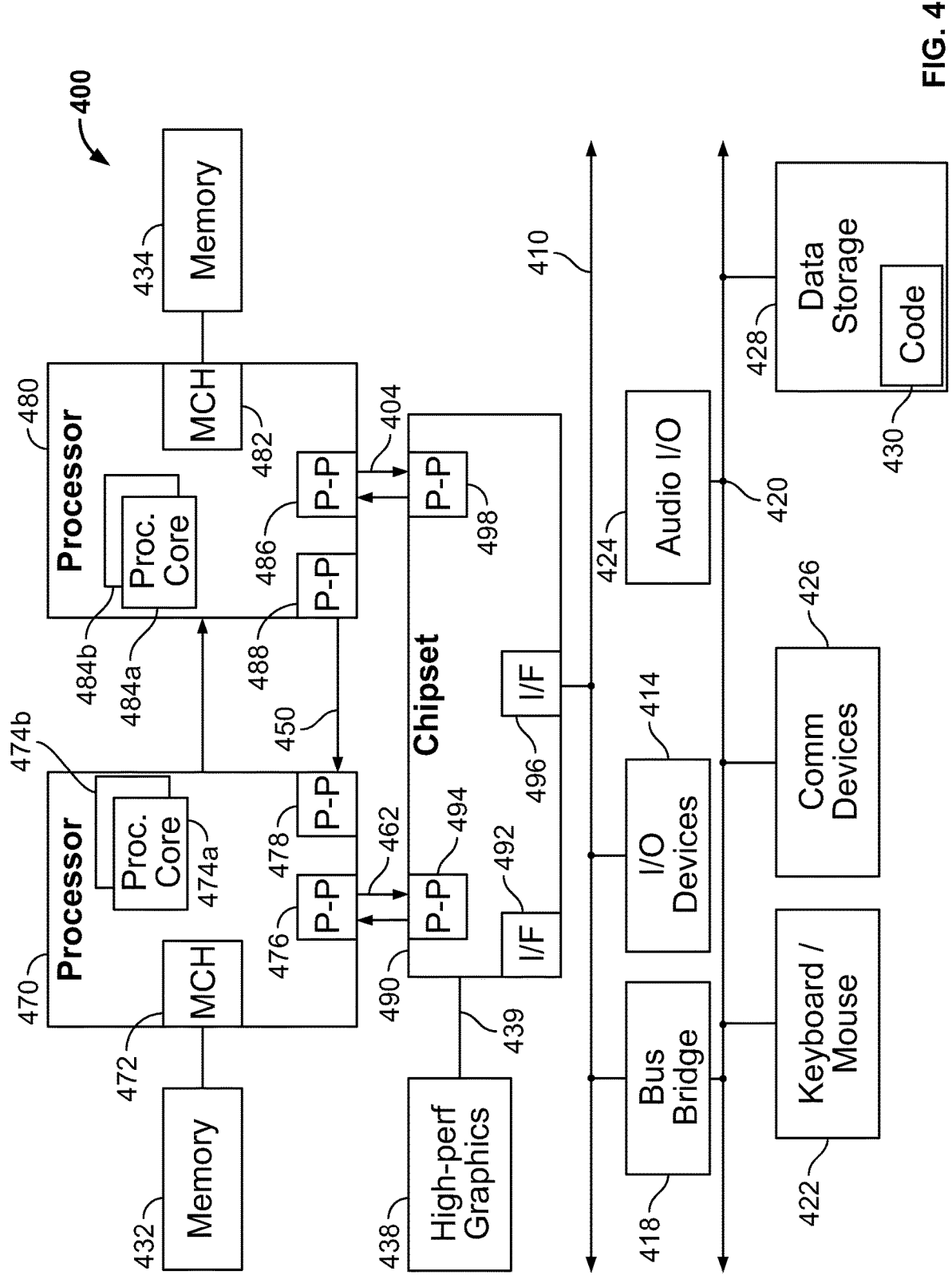
FIG. 4 is a block diagram of a mobile electronics platform that may be employed with the devices of the present specification.

FIG. 4 is a block diagram of a mobile electronics platform 400 that may be employed with the devices of the present specification. System 400 may be included in, for example, a mobile computing node such as a cellular phone, smartphone, tablet, Ultrabook®, notebook, laptop, personal digital assistant, and mobile processor based platform. However, in other embodiments portions thereof may be included in the electronics of the devices of FIGS. 3A-3E (e.g., leaving out one of the two cores, the keyboard, and the like).

Shown in FIG. 4 is a multiprocessor system 400 that includes a first processing element 470 and a second processing element 480. While two processing elements 470 and 480 are shown, it is to be understood that an embodiment of system 400 may also include only one such processing element. System 400 is illustrated as a point-to-point interconnect system, wherein the first processing element 470 and second processing element 480 are coupled via a point-to-point interconnect 450. It should be understood that any or all of the interconnects illustrated may be implemented as a multi-drop bus rather than point-to-point interconnect. As shown, each of processing elements 470 and 480 may be multicore processors, including first and second processor cores (i.e., processor cores 474a and 474b and processor cores 484a and 484b). Such cores 474a, 474b, 484a, 484b may be configured to execute instruction code in a manner similar to methods discussed herein.

Each processing element 470, 480 may include at least one shared cache. The shared cache may store data (e.g., instructions) that are utilized by one or more components of the processor, such as the cores 474a, 474b and 484a, 484b, respectively. For example, the shared cache may locally cache data stored in a memory 432, 434 for faster access by components of the processor. In one or more embodiments, the shared cache may include one or more mid-level caches, such as level 2 (L2), level 3 (L3), level 4 (L4), or other levels of cache, a last level cache (LLC), and/or combinations thereof.

While shown with only two processing elements 470, 480, it is to be understood that the scope of the present specification is not so limited. In other embodiments, one or more additional processing elements may be present in a given processor. Alternatively, one or more of processing elements 470, 480 may be an element other than a processor, such as an accelerator or a field programmable gate array. For example, additional processing element(s) may include additional processors(s) that are the same as a first processor 470, additional processor(s) that are heterogeneous or asymmetric to first processor 470, accelerators (such as, e.g., graphics accelerators or digital signal processing (DSP) units), field programmable gate arrays, or any other processing element. There can be a variety of differences between the processing elements 470, 480 in terms of a spectrum of metrics of merit including architectural, micro-architectural, thermal, power consumption characteristics, and the like. These differences may effectively manifest themselves as asymmetry and heterogeneity amongst the processing elements 470, 480. For at least one embodiment, the various processing elements 470, 480 may reside in the same die package.

First processing element 470 may further include memory controller logic (MC) 472 and point-to-point (P-P) interfaces 476 and 478. Similarly, second processing element 480 may include a MC 482 and P-P interfaces 486 and 488. MC's 472 and 482 couple the processors to respective memories, namely a memory 432 and a memory 434, which may be portions of main memory locally attached to the respective processors. While MC logic 472 and 482 is illustrated as integrated into the processing elements 470, 480, for alternative embodiments the MC logic may be discreet logic outside the processing elements 470, 480 rather than integrated therein.

First processing element 470 and second processing element 480 may be coupled to an I/O subsystem 490 via P-P interfaces 476, 486 via P-P interconnects 462, 404, respectively. As shown, I/O subsystem 490 includes P-P interfaces 494 and 498. Furthermore, I/O subsystem 490 includes an interface 492 to couple I/O subsystem 490 with a high performance graphics engine 438. In one embodiment, a bus may be used to couple graphics engine 438 to I/O subsystem 490. Alternately, a point-to-point interconnect 439 may couple these components.

In turn, I/O subsystem 490 may be coupled to a first bus 410 via an interface 496. In one embodiment, first bus 410 may be a Peripheral Component Interconnect (PCI) bus, or a bus such as a PCI Express bus or another third generation I/O interconnect bus, although the scope of the present invention is not so limited.

As shown, various I/O devices 414, 424 may be coupled to first bus 410, along with a bus bridge 418 which may couple first bus 410 to a second bus 420. In one embodiment, second bus 420 may be a low pin count (LPC) bus. Various devices may be coupled to second bus 420 including, for example, a keyboard/mouse 422, communication device(s)

426 (which may in turn be in communication with a computer network), and a data storage unit 428 such as a disk drive or other mass storage device which may include code 430, in one embodiment. The code 430 may include instructions for performing embodiments of one or more of the methods described above. Further, an audio I/O 424 may be coupled to second bus 420.

Note that other embodiments are contemplated. For example, instead of the point-to-point architecture shown, a system may implement a multi-drop bus or another such communication topology. Also, the elements of FIG. 4 may alternatively be partitioned using more or fewer integrated chips than shown in the FIG. 4.

Figure 5A:
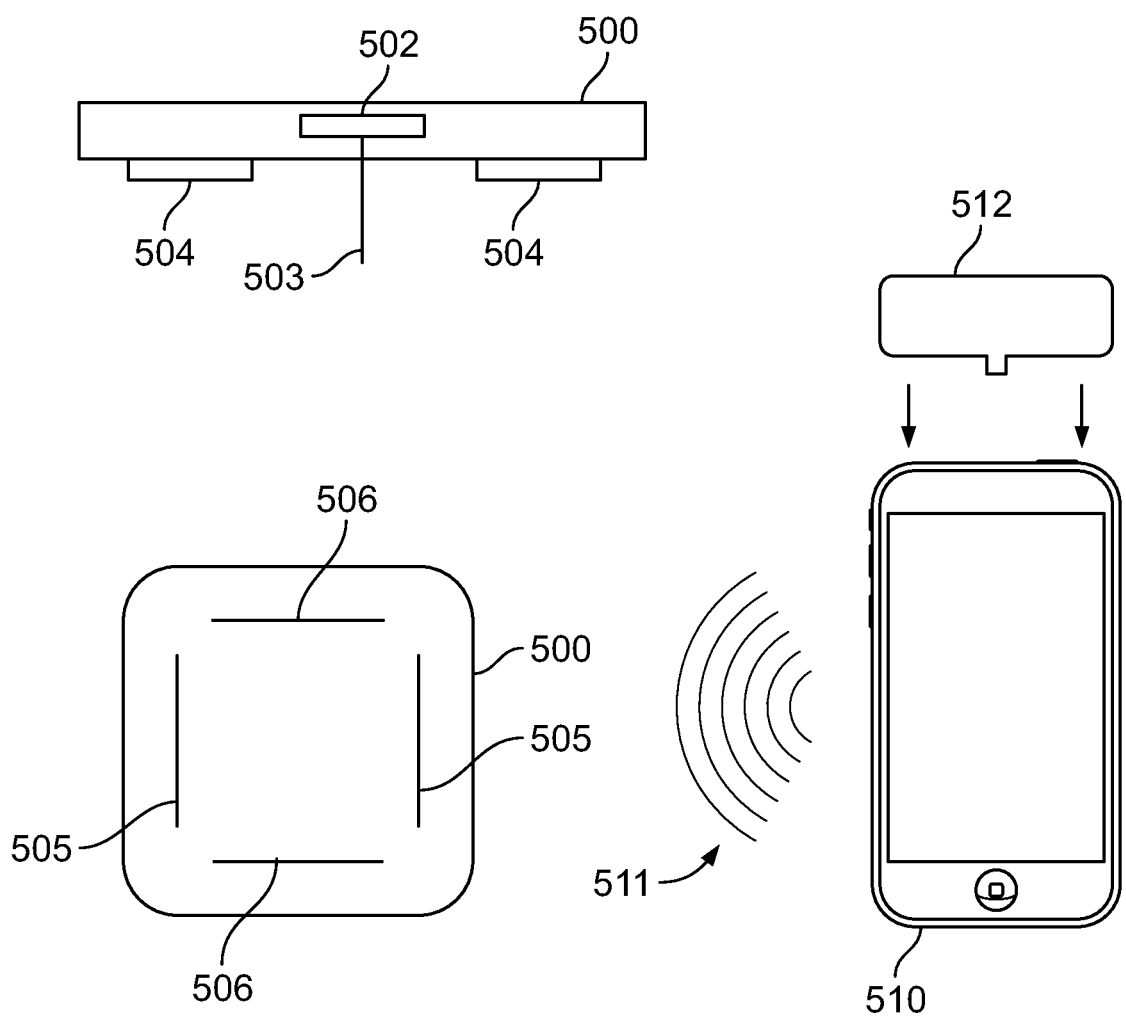
FIG. 5A is an illustration of a PEDP device that receives wireless energy for stimulation, in accordance with one embodiment.

FIG. 5A is another embodiment of a PEDP device 500, wherein there are no active electronics incorporated. Instead, an antenna 505 is connected to a simple passive rectifier circuit 502 to convert an RF signal 511 to energy that is delivered to the electrodes 503 and 504. The antenna 505 can be of various designs, such as a dipole antenna, inverted-F antenna, fractal antenna, or other such antenna that can efficiently receive the transmitted RF power. An external wireless device 510 transmits the RF signal 511 to the PEDP device 500. It should be appreciated that wireless energy, in the form of electromagnetic energy, RF energy, ultrasound energy, or any combination thereof, is transferred from the external wireless device 510 (such as a smartphone, for example) to the PEDP device 500. An embodiment can use a half-wave rectifier, a full-wave rectifier, or any other passive rectifier circuits known in the art, for the passive rectifier circuit. An embodiment can have one antenna 505 or an additional second antenna 506 to account for RF signal polarization. The electrodes 503, 504 can be percutaneous and/or skin surface electrodes. An embodiment would contain sufficient electronic intelligence to avoid unintended stimulation from another external wireless device, whether that be another patient controller or some other wireless device; e.g., airport security scanner, etc. Such intelligence can be in the form of reading a specific data packet encoded in the RF transmission by means of modulation, such as amplitude modulation, frequency shift keying modulation, or other such conventional techniques.

An embodiment for an external wireless device 510 is a battery powered portable device. An embodiment for the external wireless device can be a smartphone or any other commercially-available mobile electronics platform (such as that shown in FIG. 4). An embodiment can include an attachment 512 to a smartphone or commercially-available mobile electronics platform which includes one or more of the following: an antenna, an RF signal generator circuit, an RF communication circuit, and an additional portable power source (e.g., battery). An embodiment for the external wireless device can be portable, thereby incorporating a portable power source. An embodiment for the external wireless device can be non-portable, thereby not requiring a portable power source and able to rely on the use of AC mains (connection to electrical wall socket). An embodiment includes the ability to encode data in the RF transmission to enable pairing to a desired PEDP device only.

Figure 5B:
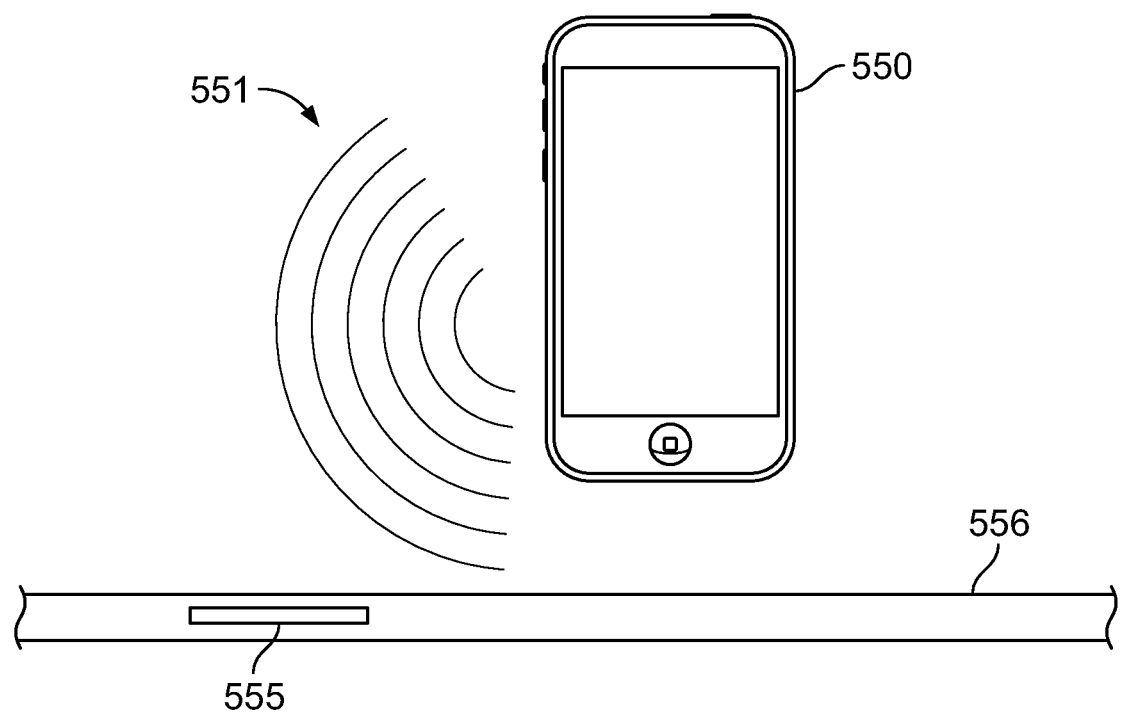
FIG. 5B is an illustration of another PEDP device that receives wireless energy for stimulation, in accordance with one embodiment.

FIG. 5B is another embodiment of a PEDP device that receives wireless energy for stimulation, and has elements of FIGS. 3B and 5A combined. More specifically, the PEDP device 5505 has the electrodes, antenna, and rectifier circuit fully implanted. The target dermatome(s) are stimulated through this small structure that has a plurality of anodes and a plurality of cathodes and is placed in the subcutaneous region 5506 of patient's body 5507 proximate the target dermatome(s). Wireless energy 5501, in the form of electromagnetic energy, RF energy, ultrasound energy, or any combination thereof, is transferred from an external wireless device 5500 with embodiments as described in FIG. 5A.

Companion Device/Control

Referring back to FIG. 1A, the neuro-stimulation device 110 is in data communication with and controlled by the companion device 105 in accordance with an aspect of the present specification. The companion device 105 is further capable of being in data communication with a remote patient care facility and/or patient care personnel. The companion device 105 is in data communication with the neuro-stimulation device 110 through a direct link to drive therapy. In accordance with a preferred embodiment, the companion device 105 is a hand-held computing device such as a watch, wristband, smartphone, tablet, or PDA that controls the neuro-stimulation device 110 through a wireless connection, such as Bluetooth, WiFi or any other private/public cellular or TCP/IP network such as the Internet. In some embodiments, the companion device is physically separated from and external to the PEDP, hence referred to as a separate or external device. In some embodiments, the companion device may be a wearable activity monitor that tracks heart rates, movement, and other physiological data. In some embodiments, the PEDP may be integrated into a wearable activity monitor and communicate with an external device, such as a smartphone, that is executing a software application in data communication with the wearable activity monitor.

The companion device 105 is configured to monitor and record ('learn') a patient's appetite patterns and monitor and record, learn, and modify the stimulation parameters of the stimulation protocols delivered by the neuro-stimulation device 110. In some embodiments, all therapy provided by the neuro-stimulation device 110 is coupled with recording (keeping a log of the therapy) and patient compliance reminders provided by the companion device 105. FIG. 6A shows the neuro-stimulation device 610 of the present specification, configured as a percutaneous skin patch and placed at a lateral thoracic dermatome, in accordance with an embodiment, and being wirelessly controlled by a smartphone 605, for example.

With reference to FIG. 1A, in accordance with an aspect, the companion device 105, which is a hand-held computing device (such as a smartphone, tablet, PDA) in various embodiments, runs or implements a Health Management software application. The Health Management application activates, deactivates and controls the neuro-stimulation device 110 to provide a plurality of stimulation therapies or protocols in accordance with various embodiments. In some embodiments, this is enabled by pairing or syncing the hand-held computing device (wirelessly or through a wired connection) with the neuro-stimulation device 110. In some embodiments, the Health Management application pairs or syncs and controls more than one neuro-stimulation device 110 worn by the user for treating a combination of conditions.

In still further embodiments, the Health Management application is capable of also communicating (via pairing or syncing) with a third party device (including a third party application software on an external device), with physiological sensors, configured to be worn on the human body, such as around the wrist, in order to monitor, acquire, record, and/or transmit the physiological data, to receive and integrate exercise and weight loss information, along with one or more neuro-stimulation devices 110 of the present specification.

In some embodiments, multiple percutaneous electrodermal patch (PEDP) devices 110 are networked together with a single companion device 105 to aggregate data feedback from the PEDP devices 110. The aggregated data is then used to modify stimulation parameters and develop more precise stimulation algorithms. In various embodiments, the companion device 105 enables social networking with friends and family, provides voice recognition and voice feedback, and includes anti-hacking data protection for HIPAA compliance. In some embodiments, the wireless connection (for pairing or syncing) is optionally compliant with HIPAA and other regulatory body requirements and laws relating to OUS (Outside United States) countries for patient data privacy. In various embodiments, the wireless connection is encrypted to prevent hacking of the device to retrieve patient data and/or inappropriately stimulate the patient and/or destroy the device.

Figure 6B:
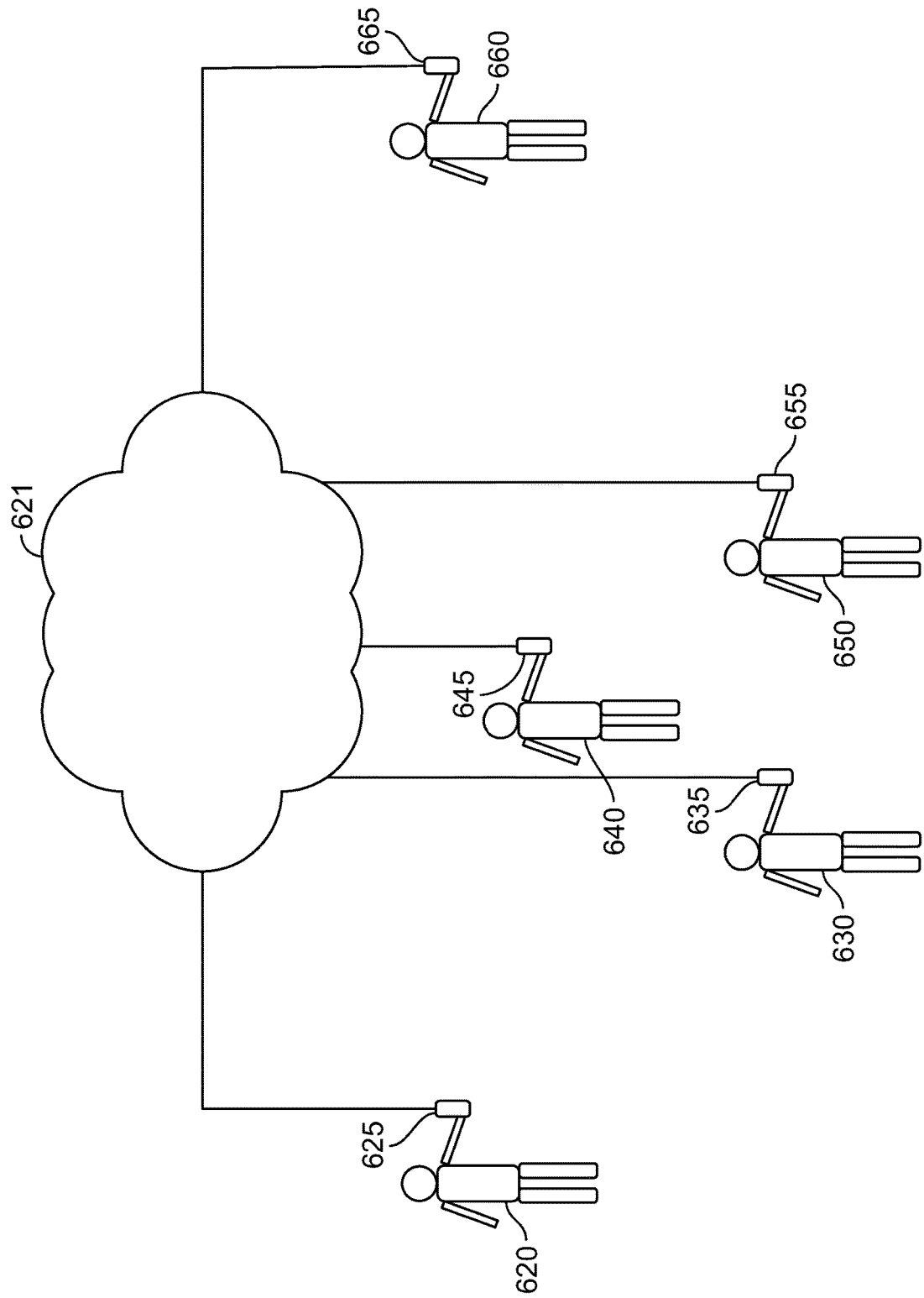
FIG. 6B is a schematic diagram of a plurality of percutaneous electro-dermal patch users with companion devices shared over a common network connection, in accordance with one embodiment of the present specification.

In various embodiments, as shown in FIG. 6B, using a companion device 625, 635, 645, 655, 665 multiple PEDP users 620, 630, 640, 650, 660 can network with one another and communicate regarding their therapy over a shared network connection 621, such as a cloud-based connection, which can lead to improved patient compliance to stimulation protocols, with resultant increased dietary compliance. For example, networked PEDP users could share and exchange experiences, progress, dietary ideas, and success stories. In some embodiments, networked exchanges are automatically input into companion devices, resulting in changes to therapy provided by the PEDP devices. For example, in one embodiment, aggregated dosing data is used to reset baseline default dosing settings to provide different dietary recommendations. Traditionally, small group clinical studies are performed to obtain data used for creating dosing strategies. By networking PEDP users through companion devices, larger amounts of aggregated user settings can be obtained automatically, for example, via a cloud based connection, and used to automatically fine tune dosing settings. In some embodiments, PEDP users have the ability, over a network connection, to share data among friends and family who are also users. In some embodiments, PEDP users can be segmented into diet clubs based on their connected friends and/or based on the type of diet they have chosen. Therefore, in various embodiments, users can connect with friends and also connect into "groups" defined around the type of diet plan, i.e. Atkins, Mediterranean, and intermittent fasting, they are following. Further, in some embodiments, users connected to a group, for example, Weight Watchers, can receive "group therapy" support in the form of input, as needed or at periodic intervals, from a moderator or therapist. In embodiments, the "groups" also enable communication between PEDP devices, between users, and between users and a moderator or therapist. Such interconnectivity among friends, groups, and moderators/therapists provides a larger support network for PEDP users and promotes user compliance.

Figure 6C:
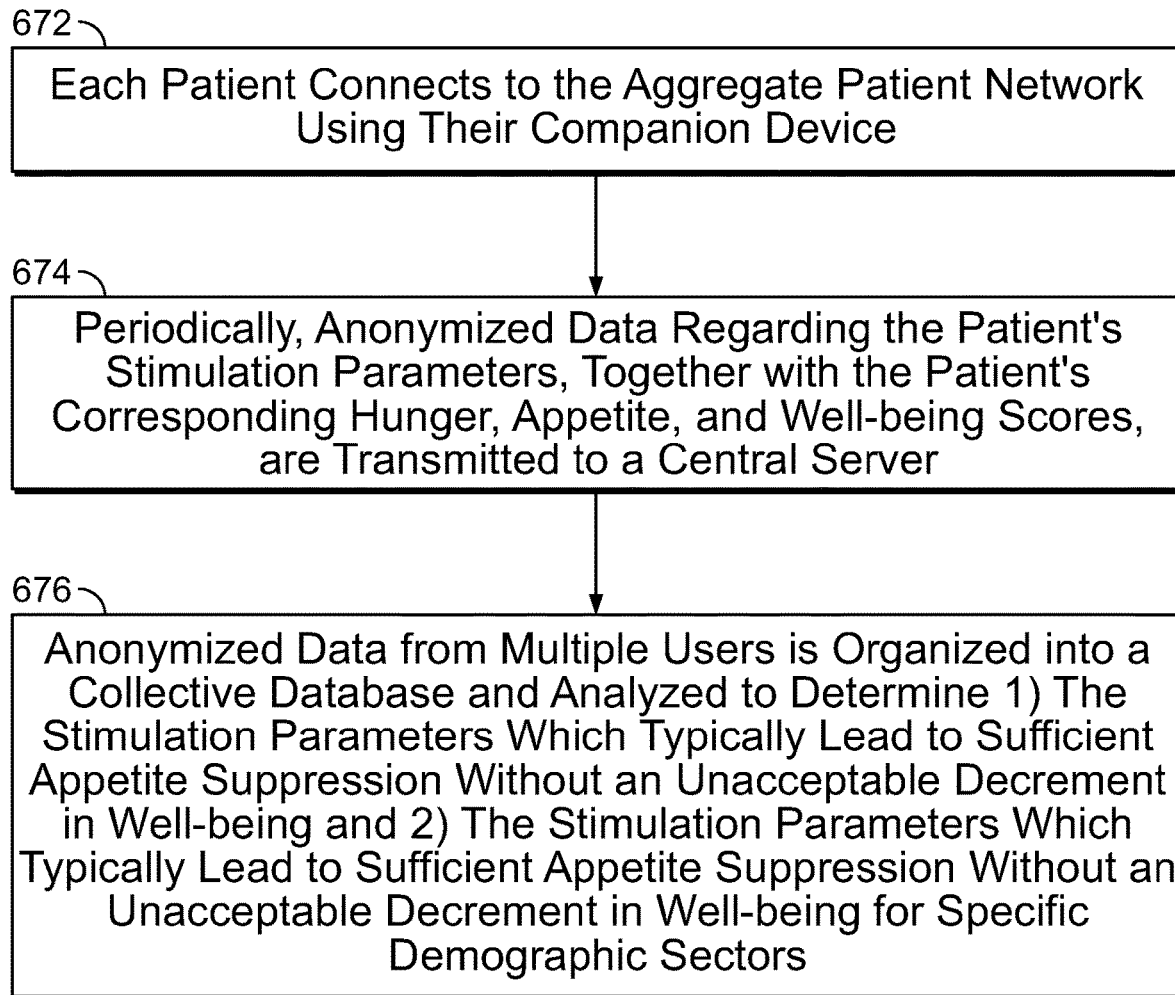
FIG. 6C is a flow chart listing the steps in one embodiment of a method of aggregating, organizing, and analyzing stimulation parameters and patient hunger, appetite, and well-being scores for a plurality of patients, each having a PEDP device with linked companion device connected to an aggregate patient network.

In some embodiments, a PEDP user network functions as a dosing settings and dietary information exchange. For example, in an aggregate patient data network, multiple different patients have a PEDP communicating with a personal companion device. FIG. 6C is a flow chart listing the steps in one embodiment of a method of aggregating, organizing, and analyzing stimulation parameters and patient hunger, appetite, and well-being scores for a plurality of patients, each having a PEDP device with linked companion device connected to an aggregate patient network. At step 672, each patient connects to the aggregate patient network using their companion device. At step 674, periodically, e.g. several times a day, once a day, 2-6 times a week, or any such increment, anonymized data regarding the patient's stimulation parameters including, but not limited to, stimulation pulse width, pulse amplitude, pulse frequency, pulse shape, duty cycle, session duration, and session frequency, together with the patient's corresponding hunger, appetite, and well-being scores (the hunger, appetite, and well-being scores being collectively referred to as patient status data), are transmitted to a central server, or set of servers.

At the central server, at step 676, the anonymized data from multiple users are organized into a collective database and analyzed to determine 1) the stimulation parameters including, but not limited to, stimulation pulse width, pulse amplitude, pulse frequency, pulse shape, duty cycle, session duration, and session frequency, which typically lead to sufficient appetite suppression without an unacceptable decrement in well-being and 2) the stimulation parameters including, but not limited to, stimulation pulse width, pulse amplitude, pulse frequency, pulse shape, duty cycle, session duration, and session frequency, which typically lead to sufficient appetite suppression without an unacceptable decrement in well-being for specific demographic sectors. In some embodiments, patient status data such as the hunger and appetite scores are aggregated into a composite score, also referred to as a satiety score. In some embodiments, exercise scores reflective of calories expended are also factored into the composite or satiety score. The user can share her composite score (along with treatment or stimulation settings that led to the composite score) with friends and family via social networking, to illicit advice, encouragement and compare progress with fellow dieters.

It should be appreciated that while in some embodiments data regarding the patients' stimulation parameters is anonymized, in some embodiments the data may not be anonymized if the patients sign away their respective privacy rights.

In various embodiments, hunger and appetite scores across demographic profiles are analyzed to determine what stimulation settings achieve optimum appetite and hunger levels or scores for a given age, gender, BMI, ethnicity, weight loss goal, or bacterial microbiome profile. Thus, for a given user, once the optimum stimulation settings are identified, it is then determined how stimulation settings for the given user must be modified in order to match those optimum stimulation settings, and a modulation signal is transmitted in order to establish those new (optimum) stimulation settings.

Figure 6D:
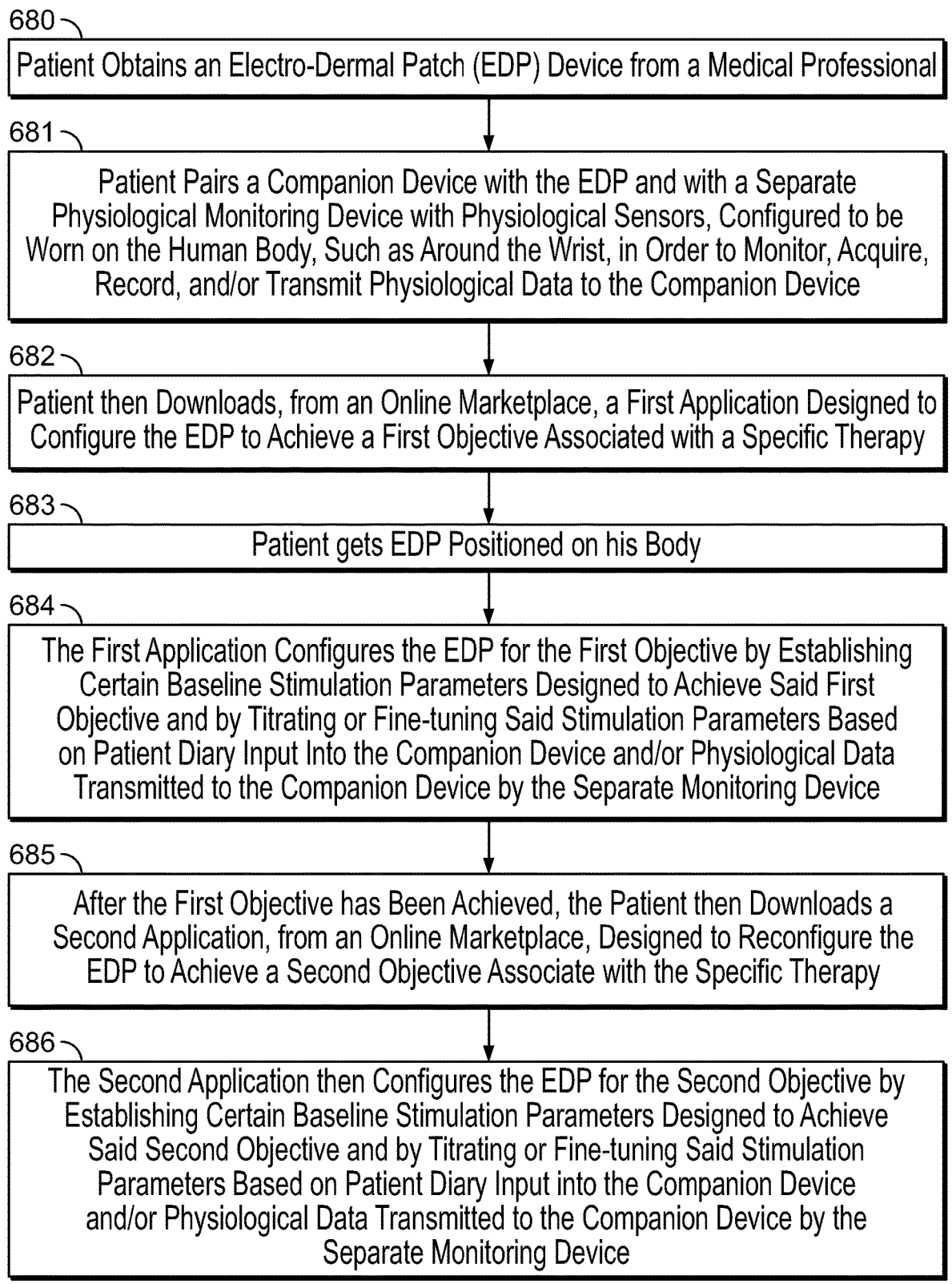
FIG. 6D is a flow chart illustrating the steps involved in using one or more downloadable applications to configure and reconfigure stimulation provided by a percutaneous electro-dermal patch (PEDP) device, in accordance with one embodiment of the present specification.

In various embodiments, the PEDP device, and the electrical stimulation it delivers, is configurable and re-configurable for different therapies and for different aspects within a specific therapy. For example, regarding weight loss and management, the patient and/or companion device can configure the PEDP to deliver electrical stimulation in an effort to promote active weight loss in the patient and then, once a target weight is achieved, reconfigure the PEDP to deliver electrical stimulation to maintain the patient at the target weight. This can be accomplished via one or more applications downloaded to the companion device. FIG. 6D is a flow chart illustrating the steps involved in using one or more downloadable applications to configure and reconfigure stimulation provided by a percutaneous electro-dermal patch (PEDP) device, in accordance with one embodiment of the present specification. At step 680, a patient obtains or has a PEDP implanted by a medical professional. At step 681, the patient pairs a companion device with the PEDP and with a separate physiological monitoring device with physiological sensors, configured to be worn on the human body, such as around the wrist, in order to monitor, acquire, record, and/or transmit physiological data to the companion device, wherein the companion device is adapted to create and modify stimulation parameters based on the monitored physiological data. At step 682, the patient then downloads, from an online marketplace, a first application designed to configure the PEDP to achieve a first objective associated with a specific therapy, for example, weight loss for weight management. The patient positions the PEDP on his body at step 683. The first application, at step 684, configures the PEDP for the first objective by establishing certain baseline stimulation parameters designed to achieve said first objective and by titrating or fine-tuning said stimulation parameters based on patient diary input into the companion device and/or physiological data transmitted to the companion device by the separate monitoring device. After the first objective has been achieved, at step 685, the patient then downloads a second application, from an online marketplace, designed to reconfigure the PEDP to achieve a second objective associated with the specific therapy, for example, maintaining weight for weight management.

In various embodiments, one or both of the first and second applications is available from the online marketplace for a fee. Additionally, both the first and second applications may be separate and distinct applications which reside on the companion device, are separately obtained by accessing the on-line application marketplace associated with the companion device, and are activated, and executed, by clicking on separate and distinct icons from the companion device's home screen. In another embodiment, the first application may be downloaded from the on-line application marketplace associated with the companion device and may be activated, and executed, by clicking on separate and distinct icons from the companion device's home screen while the second application, and all subsequent applications responsible for modulating the PEDP's stimulation parameters, are downloaded by accessing a marketplace of such applications through the first application. Specifically, the first application provides a gateway to a database, or library, of additional applications which may provide for different stimulation parameters based on inputs, weights, and other criteria that differ from the first application, or each other.

The second application, at step 686, then configures the PEDP for the second objective by establishing certain baseline stimulation parameters designed to achieve said second objective and by titrating or fine-tuning said stimulation parameters based on patient diary input into the companion device and/or physiological data transmitted to the companion device by the separate monitoring device. In one embodiment, for weight management, the stimulation parameters for the first objective (weight loss) are more focused on patient diary record of well-being and hunger as inputs to titrate therapy while the stimulation parameters for the second objective (weight maintenance) are more focused on daily body weight as an input to titrate therapy. While weight management has been used to describe the method above for modifying therapy provided by the PEDP, in various embodiments, the method of using one or more online applications to configure and reconfigure the stimulation parameters of the PEDP can be used on any condition receptive to electrical stimulation therapy.

In various embodiments, the PEDP and companion device are open source to allow for the creation of applications for the devices designed to enact therapy methods similar to the one described above. In another embodiment, a single master application downloadable to a companion device is responsible for controlling the PEDP and setting initial stimulation parameters. This master application may come with the PEDP upon initial purchase or may be separately purchasable or downloadable for free from an online marketplace. In various embodiments, further software upgrades, such as in-application or "in-app" purchases, can be obtained, for a fee, within the master application and used to fine-tune therapy. In various embodiments, such software upgrades include, for example, new diet plans, new exercise plans, and improved fitness tracking, among others. In various embodiments, these software upgrades are created by third parties or by the creator of the master application. In some embodiments, new applications or software upgrades to a master application reconfigure the PEDP to provide electrical stimulation targeting different conditions. For example, in various embodiments, applications or upgrades reconfigure baseline PEDP stimulation parameters to treat other conditions including, but not limited to, dysmenorrhea, back pain, urinary incontinence, and peripheral neuropathy, including diabetic peripheral neuropathy. In some embodiments, the electrical components of the device are the same and the patient uses a different, disposable electrode patch portion and repositions the device on his or her body. These applications and upgrades modify the algorithms used by the companion device to change the stimulation parameters for the PEDP to treat the different conditions. For example, in one embodiment, a patient initially uses the PEDP for weight management in a method similar to that described above. She then downloads a fee based online application to the companion device which then reconfigures the PEDP stimulation to treat her dysmenorrhea. She can then use her initial application to return the PEDP back to weight management settings. She could continually download new applications and upgrades and reconfigure the PEDP to treat a plurality of different conditions and go back and forth between different conditions. It would be preferred that, for the non-weight loss applications, such as urinary incontinence, back pain, dysmenorrhea and peripheral neuropathy, including diabetic peripheral neuropathy, a completely different application be downloaded while for new or different weight loss plans, it would be preferred to download additional applications through the first downloaded weight loss application itself, thereby avoiding having multiple different and distinct weight loss applications on the companion device's home screen.

Because the presently disclosed embodiments are directed to medical treatments, it is imperative that patient specific data, such as data representing specific stimulation settings and patient status data, are stored, transmitted, and verified in a manner that is secure and subject to authentication. In one embodiment, data transmissions between the PEDP, the companion device, and any remote server(s) are subject to verification and authentication, such as by using checksums, private and public keys, and other forms of verification known in the art. If, at any time, one or more of the data transmissions fail to be properly verified or authenticated, any new or modulated stimulation settings associated with such data transmissions are discarded or otherwise set aside and only a previous stimulation setting associated with a fully verified and/or authenticated complete set of data transmissions is used. Alternatively, the system may lock the use of any stimulation setting until such data transmissions can be fully verified, along with any new or modulated stimulation settings associated therewith.

Figure 6E:
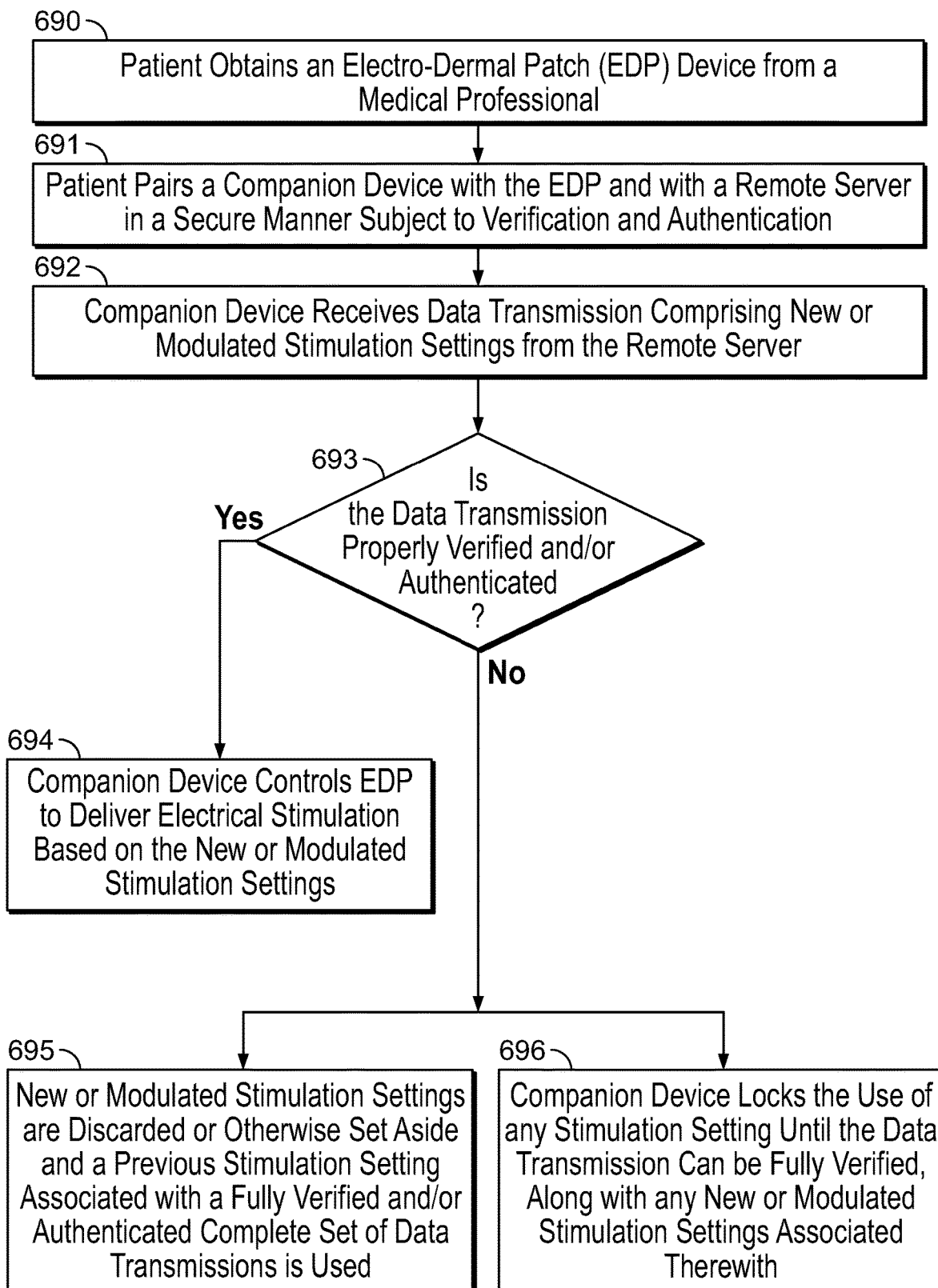
FIG. 6E is a flow chart illustrating the steps involved in a method of a companion device verifying and/or authenticating data transmission received from a remote server, in accordance with some embodiments of the present specification.

FIG. 6E is a flow chart illustrating the steps involved in a method of a companion device verifying and/or authenticating data transmission received from a remote server, in accordance with some embodiments of the present specification. At step 690, a patient obtains a percutaneous electrodermal patch (PEDP) device from a medical professional. The patient pairs a companion device with the PEDP and with a remote server, in a secure manner subject to verification and authentication, at step 691. At step 692, the companion device receives a data transmission comprising new or modulated stimulation settings from the remote server. The companion device then checks if the data transmission is properly verified and/or authenticated at step 693. In one embodiment, if the data transmission is properly verified and/or authenticated, the companion device controls the PEDP to deliver electrical stimulation based on the new or modulated stimulation settings at step 694. In one embodiment, if the data transmission is not properly verified and/or authenticated, the new or modulated stimulation settings are discarded or otherwise set aside and a previous stimulation setting associated with a fully verified and/or authenticated complete set of data transmissions is used at step 695. In another embodiment, if the data transmission is not properly verified and/or authenticated, the companion device locks the use of any stimulation setting until the data transmission can be fully verified, along with any new or modulated stimulation settings associated therewith at step 696.

In another embodiment, communications between a PEDP, companion device and any remote server(s) may comprise an indication, such as a packet header, identifier, tag, or other representation, of whether the specific PEDP involved in the data transmissions is a device that has been sold subject to FDA regulatory approval or whether it is a device that has not been sold subject to FDA regulatory approval. Depending on such an identifier (indicative of government regulatory governance, or some extent thereof), different data processing may occur. For example, if the companion device or remote server(s) determine the PEDP in question is subject to FDA approval (based on an identifier being stored in a memory within the PEDP), it may cause a different or higher level of encryption, authentication, and/or verification to be applied to the stored data or to data transmissions. In one case, all data transmissions to and from the PEDP, between the PEDP and companion device, and/or between the companion device and remote server(s) are encrypted, authenticated, and anonymized subject to verification. In another case, only data transmissions containing patient-specific stimulation settings or patient status data are encrypted, authenticated, and/or subject to verification while all other data transmissions are not encrypted.

If, on the other hand, the companion device or remote server(s) determines the PEDP in question is not subject to FDA approval (based on an identifier being stored in a memory within the PEDP), it may cause a lower level of encryption, authentication, and/or verification to be applied to the stored data or to data transmissions relative to the FDA case. In one embodiment, no data transmissions to and from the PEDP, between the PEDP and companion device, and/or between the companion device and remote server(s) are encrypted, authenticated, and subject to verification. In another case, only data transmissions containing patient-specific stimulation settings or patient status data are authenticated and/or subject to verification and no data transmissions are encrypted.

Figure 6F:
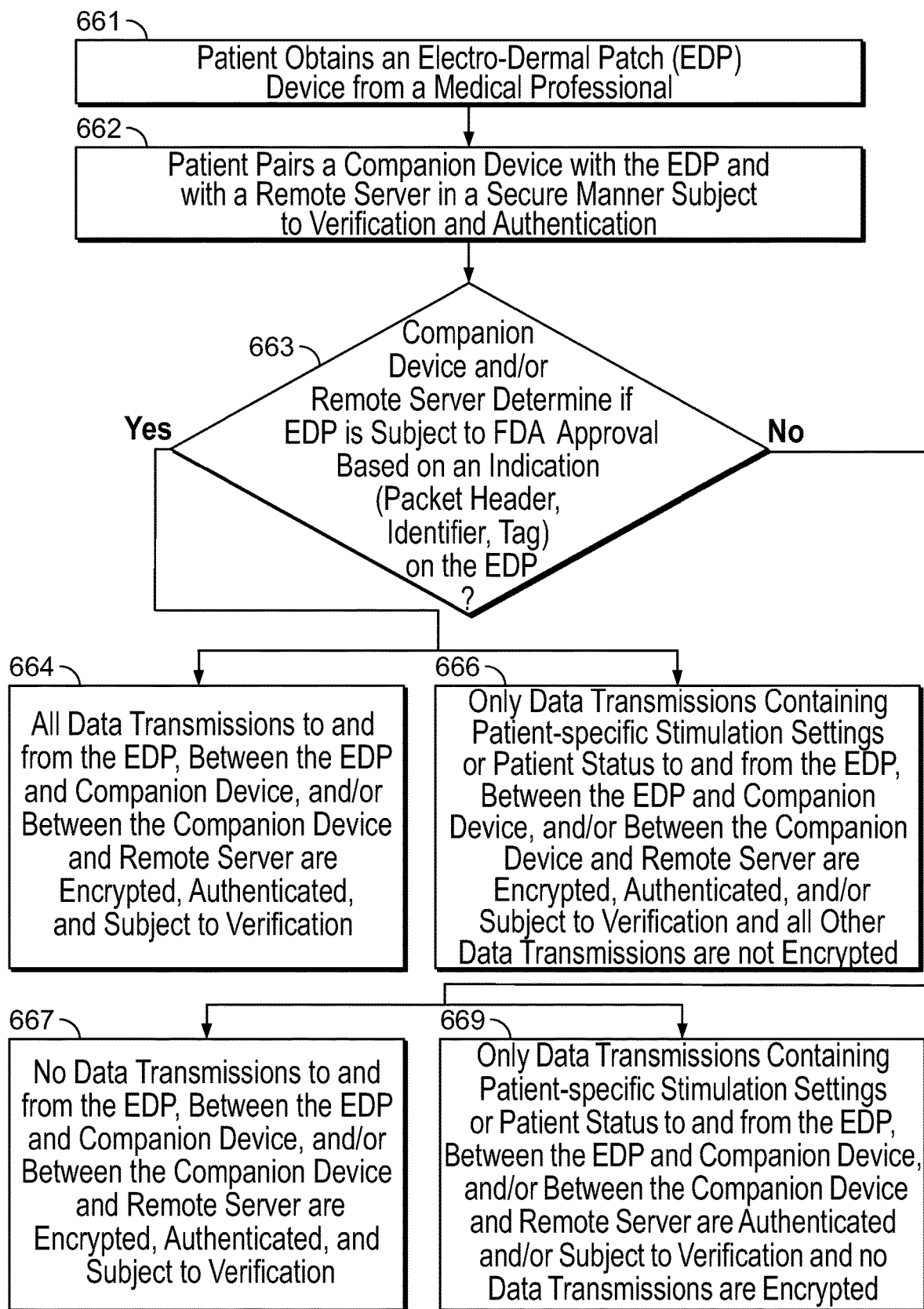
FIG. 6F is a flow chart illustrating the steps involved in a method of encrypting, authenticating, and/or verifying data transmissions between a PEDP, companion device, and remote server based on FDA approval status of the PEDP, in accordance with some embodiments of the present specification.

FIG. 6F is a flow chart illustrating the steps involved in a method of encrypting, authenticating, and/or verifying data transmissions between a PEDP, companion device, and remote server based on FDA approval status of the PEDP, in accordance with some embodiments of the present specification. At step 661, a patient obtains a percutaneous electrodermal patch (PEDP) device from a medical professional. The patient pairs a companion device with the PEDP and with a remote server, in a secure manner subject to verification and authentication, at step 662. At step 663, the companion device and/or remote server determine if the PEDP is subject to FDA approval based on an indication (packet header, identifier, tag) on the PEDP. In one embodiment, if it is determined that the PEDP is subject to FDA approval, then all data transmissions to and from the PEDP, between the PEDP and companion device, and/or between the companion device and remote server are encrypted, authenticated, and subject to verification at step 664. In another embodiment, at step 666, if it is determined that the PEDP is subject to FDA approval, only data transmissions containing patient-specific stimulation settings or patient status to and from the PEDP, between the PEDP and companion device, and/or between the companion device and remote server are encrypted, authenticated, and/or subject to verification and all other data transmissions are not encrypted. In another embodiment, if it is determined that the PEDP is not subject to FDA approval, then no data transmissions to and from the PEDP, between the PEDP and companion device, and/or between the companion device and remote server are encrypted, authenticated, and subject to verification at step 667. In another embodiment, at step 669, if it is determined that the PEDP is not subject to FDA approval, only data transmissions containing patient-specific stimulation settings or patient status to and from the PEDP, between the PEDP and companion device, and/or between the companion device and remote server are authenticated and/or subject to verification and no data transmissions are encrypted.

In accordance with an aspect of the present specification, patient status data and, if needed, stimulation setting, parameters and protocols are transmitted to insurance companies to support medical treatments, such as bariatric surgeries, or other insurance claims, or for other general insurance data needs. In some embodiments, such data transmission may be subjected to encryption, authentication and verification as described at step 666.

The Health Management Application (hereinafter also referred to as 'HMA') of the present specification comprises a plurality of programmatic instructions and algorithms and implements a plurality of GUIs (Graphical User Interface) to enable a plurality of functions, non-limiting examples of which are described henceforth.

Referring back to FIG. 1A, in various embodiments, the HMA enables confirming linkup to the neuro-stimulation device 110 and displaying battery life of the neuro-stimulation device 110.

The HMA enables generating an audio and/or visual indicator on the hand-held computing device 105 indicating that a) the neuro-stimulation device 110 has been properly placed on and implanted within the user's body by, for example, confirming sufficient electrode and tissue contact or integrity, b) the one or more electrodes 118 is aged or compromised (ascertained by, for example, impedance measurements) and needs to be replaced. In some embodiments, electrode and tissue contact integrity and electrode integrity, i.e. whether the electrode is functioning properly or damaged, are checked through at least one impedance or bio-impedance sensor of the neuro-stimulation device 110. In other embodiments, an acoustic sensor, capable of sensing specific acoustic signals unique to an area of the human body, is used to determine if the neuro-stimulation device 110 has been properly positioned on the user's body. In various embodiments, sufficient electrode and tissue contact or integrity is defined as achieving electrode impedance in a range of 200 ohms to 1000 ohms. In one embodiment, pulse amplitude is automatically adjusted by virtue of there being a constant current source (from one or more batteries). A constant current source circuit automatically adjusts the pulse to maintain a programmed amplitude in the event of electrode-tissue interface impedance changes. This automatic adjustment may be programmed to occur for voltages ranging from 0.1V to 500V. Accordingly, the pulse amplitude is automatically modulated in order to maintain a constant current source.

The HMA also enables analyzing sensed neural activity prior to the commencement of a stimulation therapy to assess and indicate to the user that the neuro-stimulation device 110 has been placed at an appropriate location, such as the T2-T12 and/or C5-T1 dermatomes for eating disorders. In various embodiments, the accuracy or appropriateness of the neuro-stimulation device location is assessed through the neural activity monitor of the neuro-stimulation device 110. In various embodiments, neural activity sensing or monitoring is accomplished by using a sense amplifier circuit to measure neural activity and output a representative signal to the microcontroller or microprocessor of the neuro-stimulation device 110. The microcontroller algorithmically processes the data to determine if there is neural activity. In some embodiments, the sense amplifier circuit measures neural activity signals directly using the same electrodes used for stimulation. In other embodiments, the sense amplifier circuit measures neural activity signals separately using different electrodes than those used for stimulation. In still other embodiments, the sense amplifier circuit measures neural activity signals using both the same electrodes used for stimulation and different electrodes than those used for stimulation. In various embodiments, the sense amplifier circuit incorporates a gain in a range of 1 to 100,000,000 and all values in between, and incorporates a bandpass filter of 0.1 Hz to 10,000 Hz and all combinations in between. These functions are accomplished using conventional analog circuitry known in the art, such as operational amplifier circuits and transistor circuits. In one embodiment, a process used by the microprocessor to process the sensed neural activity comprises counting the number of events within a predetermined time period. In other embodiments, the process is modified to add moving averages in the form of finite impulse response (FIR) or infinite impulse response (IIR) digital filters.

The HMA also enables analyzing sensed neural activity during a stimulation therapy to assess effectiveness of the stimulation. Depending upon the effectiveness, the Health Management application may automatically recommend and/or implement adjustments or modifications to a plurality of stimulation parameters. In some embodiments, the recommended adjustments to the plurality of stimulation parameters must be accepted or authorized for implementation by at least one of the user (that is, the patient) and/or the remote patient care facility or personnel. In various embodiments, neural activity is sensed using a sense amplifier circuit as described above.

The HMA enables the user to self-administer therapy, including the ability to stimulate multiple times per day or per week, thereby accelerating treatment effect and efficacy. In various embodiments, the self-administration is on-demand and is actuated via a button on the companion device 105 used to trigger the neuro-stimulation device 110. Triggering the neuro-stimulation device 110 is defined as triggering a protocol that may result in stimulation over a predefined period and does not necessarily indicate electrical stimulation begins immediately. The companion device 105 and/or neuro-stimulation device 110 include pre-programmed restrictions which prevent the patient from over-stimulating. In addition, the companion device 105 and/or neuro-stimulation device 110 include triggers which prompt the patient to stimulate based upon time of day, historical trends in appetite, caloric intake, and exercise data.

The HMA enables the user to input his current weight per day through a GUI screen and provides real-time or near real-time integration of feedback from patient parameters such as, but not limited to, exercise and fitness, diet, hunger, appetite, and well-being, recorded in a patient daily diary, from the patient and obtaining real-time or near real-time integration of feedback, such as steps taken as an indicator of calories burned, from other wearable devices, for example, a device, with physiological sensors, configured to be worn on the human body, such as around the wrist, in order to monitor, acquire, record, and/or transmit the physiological data, allowing for frequent adjustability and customization of therapy as needed. The integration of feedback from the patient and from other devices allows for modification of therapy, as needed, to suppress appetite and treat conditions such as obesity, over-weight, and/or metabolic syndrome. In accordance with various aspects of the present specification, the neuro-stimulation device enables treating people with BMI (Body Mass Index) of 25 or greater (overweight being 25-30, obese being 30 and above, with morbid obesity being above 35).

The HMA enables providing recording, storage and display of all stimulation parameters and other real-time inputs, such as diary and exercise monitoring, to provide the physician and patient real-time records and treatment profiles. The information stored includes a combination of inputs from the stimulation device and from other sources of information, for example, from a device, with physiological sensors, configured to be worn on the human body, such as around the wrist, in order to monitor, acquire, record, and/or transmit the physiological data.

The HMA enables presenting GUI screens to enable the user to provide inputs such as, but not limited to, eating information and activities information. In various embodiments, eating information comprises standard regular eating and meals profile or routine of the user such as the number of meals per day typically consumed and the types and amounts of food eaten at each of the meals per day. The standard regular eating and meals profile is typically input only once by the user as it represents the general eating habit of the user and is likely to be modified by the user over long periods of time. In some embodiments, the standard regular eating and meals profile is representative of a standard diet plan such as, but not limited to, Mediterranean, Intermittent Fasting, Jenny Craig, Weight Watchers, SlimFast and Custom Plan.

In various embodiments, eating information additionally or alternatively comprises real time actual eating and meals profile of the user such as the time of consumption of a meal in a day and the type and amount of food eaten at the meal. In other words, each time the user consumes a meal he (in real time) records the occurrence of the meal event, which is automatically time stamped by the application, as well as the type and amount of food eaten. If the meal being consumed and the type and amount of food are in line with the user's standard regular eating profile, he may simply select the meal and types and amounts of food from the pre-stored eating profile of the user.

In accordance with an aspect of the present specification, the real time eating and meals profile is utilized to calculate the actual amount of calories consumed by the user in a day. On the other hand, the standard regular eating and meals routine of the user is utilized to calculate a forecasted or expected amount of calories likely to be consumed by the user in a day. A difference between the daily, weekly or monthly expected and actual calories consumption value may prompt a plurality of recommendations from the Health Management application to the user.

In accordance with some aspects of the present specification, it is advantageous to also assess the quality of meal or diet consumed along with the amount of calories consumed as a result of the meal or diet in a day. In some embodiments, the quality of a meal or diet is determined based on a mix of macronutrients such as carbohydrates (also referred to as "carbs"), proteins and fats present in the meal or diet. Thus, the user's standard diet plan may propose an acceptable ratio for each macronutrient. For example, the Zone Diet (by Barry Sears, PhD) proposes a meal of 40% carbs, 30% protein and 30% fats, the Atkins Diet proposes a meal of 5% carbs, 25% protein and 75% fats, while the Ketogenic Diet proposes a meal of 10% carbs, 45% protein and 45% fats. Thus, for a user who is endeavoring to follow a standard diet plan or a custom diet plan designed around a specific ratio of macronutrients, the expected ratio of macronutrients and the expected calories likely to be consumed in a day are known and pre-stored by the Health Management application.

In various embodiments, the actual or real time eating and meals profile of the user is indicative of the time of consumption of a meal in a day as well as the type and amount of food eaten at the meal. The type and amount of food eaten enables calculating the calories consumed as well as a ratio of macronutrients, that is, carbs, protein and fats consumed. It should be appreciated that while in some embodiments, the Health Management application calculates the ratio of all three macronutrients, (carbs, proteins and fats) consumed in a meal, in various alternate embodiments, an amount and effect of any one or two macronutrients may be monitored and calculated. For example, in some embodiments, the Health Management application is focused on monitoring and determining the effect of carbohydrates consumed compared to an acceptable amount of carbohydrates allowed based on the standard diet plan being followed by the user.

Thus, in accordance with an aspect, carbohydrate containing foods are rated on a scale called the glycemic index (GI) and the glycemic index is used to calculate a glycemic load (GL) associated with the food consumed. The GI ranks carbohydrate containing foods based on their effect on blood sugar levels over a period of time. Carbohydrate containing foods are compared with glucose or white bread as a reference food, which is given a GI score of 100. The GI compares foods that have the same amount of carbohydrate, gram for gram. Carbohydrates that break down quickly during digestion have a higher glycemic index (say, GI more than 70). These high GI carbohydrates, such as a baked potato, release their glucose into the blood quickly. Carbohydrates that break down slowly, such as oats, release glucose gradually into the bloodstream. They have low glycemic indexes (say, GI less than 55). The blood glucose response is slower and flatter. Low GI foods prolong digestion due to their slow break down and may help with satiety.

The glycemic index compares the potential of foods containing the same amount of carbohydrate to raise blood glucose. However, the amount of carbohydrate consumed also affects blood glucose levels and insulin responses. The glycemic load (GL) takes into account both the GI of the food and the amount of carbohydrate in a portion or serving consumed. GL is based on the idea that a high GI food consumed in small quantities would give the same effect on blood glucose levels as larger quantities of a low GI food. GL is calculated by multiplying the GI by the amount of carbohydrates (in grams) in a serving of food.

Thus, in accordance with another aspect of the present specification, the real time eating and meals profile is utilized to calculate the ratio of macronutrients, that is, carbs, proteins and fats, consumed in a day or at least the glycemic load (GL) associated with the meals profile. On the other hand, the standard regular eating and meals routine of the user is utilized to calculate a forecasted, allowed or expected ratio of the macronutrients consumed by the user in a day or at least the allowable glycemic load. A difference between the daily, weekly or monthly expected and actual macronutrient ratio or a difference between the daily, weekly or monthly expected and actual glycemic load may prompt a plurality of recommendations from the Health Management application to the user.

Activities information relates to how much and when a person moves around and/or exercises during the day and utilizes both data input by the user and data sensed by the one or more sensors 135. The data input by the user may include details regarding the user's daily activities, for example the fact that the user worked at a desk from 9 a.m. to 5 p.m. and then took an aerobics class from 6:30 p.m. to 7:30 p.m. Relevant data sensed by the sensors 135 may include heart rate, movement as sensed by an accelerometer, heat flow, respiration rate, calories burned, and galvanic skin response (GSR). Accordingly, calories burned or spent (calories expenditure) maybe calculated in a variety of manners, including: the multiplication of the type of exercise input by the user by the duration of exercise input by the user; sensed motion multiplied by time of motion multiplied by a filter constant; and sensed heat flux multiplied by time multiplied by a filter constant or on the basis of metabolic equivalents (METs). In some embodiments, the user's RMR (Resting Metabolic Rate) or BMR (Basal Metabolic Rate) is also calculated to estimate the amount of calories consumed by the user which is then used to calculate a daily caloric balance. As known to persons of ordinary skill in the art, RMR or BMR is the rate at which you burn energy or calories when resting and is a function of at least the user's age, gender, height and weight. This helps fulfill the basic requirements of the body to function optimally.

The amount of calories actually consumed by the individual is compared to the amount of calories expended or burned by the individual for daily, weekly or monthly periods and is referred to hereinafter as energy balance of the user. A positive or surplus energy balance is representative of more actual calories consumed in comparison to the calories expended and is considered to be indicative of a potential weight gain scenario for the user over a period of time. A negative energy balance is representative of less actual calories consumed in comparison to the calories expended and is considered to be indicative of a potential weight loss scenario for the user over a period of time.

Continuing with various non-limiting examples of the plurality of functions of the HMA, in various embodiments the HMA also enables presenting GUI screens to enable the user to record his hunger or appetite profile. Hunger or appetite profile includes data such as the time of day when the user feels hungry and the intensity of hunger felt. In some embodiments, the intensity of hunger is recorded by the user by selecting from a scale of, for example, 1 to 5, where 1 is indicative of light hunger and 5 is indicative of very high hunger intensity. In various embodiments, the hunger profile includes only those times when the user feels hungry but should ideally not consume a meal. This may include, for example, times that do not match the user's standard regular eating and meals profile or routine.

The HMA further enables providing daily feedback from the neuro-stimulation device to the patient on dietary compliance, calories burned and displaying diet plans.

The HMA also enables receiving, processing and analyzing glucose data generated by a glucose sensor, included as one of the sensors 135, in some embodiments. In various embodiments, the glucose data is analyzed to detect conditions such as a hyperglycemic rush, resulting from, for example, a large carbohydrate meal, and titrate stimulation to treat or manage a condition where there is a surplus of insulin secretion that may trigger hunger in non-diabetic users.

The HMA enables generating and displaying a plurality of charts or graphs representative of the user's standard regular eating and meals profile, actual eating and meals profile, energy balance information, weight trend including a rate of weight loss or gain, glucose data trend and hunger profile over a period of time such as daily, weekly or monthly.

The HMA enables managing and generating prompts (audio, visual and/or tactile) with respect to a plurality of compliance aspects such as, but not limited to: stimulation therapy compliance—prompts the user if the user forgets to apply the neuro-stimulation device and/or disables a recommended duration or frequency of stimulation therapy; prompts the user with respect to a stimulation protocol that a scheduled stimulation is going to begin in the next T minutes, 10 minutes for example, and presenting the user with an option to disable the scheduled stimulation which if not disabled allows the scheduled stimulation to begin after T minutes; dietary compliance or guidance—the user either selects a predefined standard dietary plan (from a drop down list of multiple predefined dietary plans, such as but not limited to Mediterranean Zone diet, Atkins diet, or Jenny Craig) or inputs a customized plan as part of the standard regular eating and meals routine. The user also records details of the actual meals taken and time of meals. Audio, visual and/or tactile alert(s) may be generated, for example, if the user is not in compliance with the selected dietary plan. The compliance prompts are intended to encourage patient compliance and, in some embodiments, include composite scores and displays for overall patient progress.

The HMA enables recommending and/or implementing modification to stimulation patterns or protocols when receiving an input from the user that the user is encountering a feeling of nausea, dyspepsia, heartburn, or sensation at the stimulation site during and/or after stimulation.

The HMA further enables assessing stimulation habituation, nausea and/or dyspepsia scenarios in the user and accordingly modifying the stimulation patterns or protocols. In various embodiments, these events are input into the neuro-stimulation device or companion device by the patient. For example, in one embodiment, the patient can input, via a GUI on one or both devices, nausea events, dyspepsia events or hunger events. The microprocessor then algorithmically processes these events and accordingly modifies stimulation.

The HMA enables the remote patient care facility and/or patient care personnel to access (via cellular and/or private or public wired or wireless networks such as the Internet) a plurality of user's health related information such as the user's hunger profile, standard eating and meals profile, actual eating and meals profile, energy balance, weight trends, glucose data and stimulation induced nausea, dyspepsia, habituation events. In some embodiments, the Health Management application periodically transmits the user's health related information apart from enabling the remote patient care facility and/or patient care personnel to access such information in real time or on demand, if required. In various embodiments, the user's authorization is needed to allow such access to the user's health related information.

The HMA also enables detecting removal of the neuro-stimulation device—the impedance or bio-impedance electrode enables the Health Management application to regularly or continuously monitor electrode activity. This allows the Health Management application to detect whether the neuro-stimulation device has been removed or worn by the user. This enables the neuro-stimulation device to stimulate only when it is confirmed that the device is being worn by the user. In some embodiments, where the neuro-stimulation device is configured for use as a 24/7 wearable device, detection of removal of the neuro-stimulation device corresponds to missing of the user's health related information. However, in other embodiments, where the neuro-stimulation device is configured for use on as-needed or on-demand basis, any missing user health related information is treated as non-occurrence of any stimulation event.

The HMA also enables providing unique electrical stimulation characteristics and 'footprints', based on electrode design and stimulation parameters, allowing the patient to use a variety of methodologies for stimulation.

In still a further non-limiting example, the HMA enables providing a weight loss graph along with the patient's pictures corresponding to various milestones on the weight loss graph.

In still a further non-limiting example, the HMA enables; enables bariatric surgeons, doctors, dieticians or medical personnel to tell new patients about their medical practice.

In still a further non-limiting example, the HMA enables patients to keep time intervals between meals and fluids. For example, the HMA may notify users when enough time has passed after drinking to eat and vice versa.

In still further non-limiting examples, the HMA enables patients to view their medical personnel and request an appointment with the office; enables setting of daily reminders for prescribed vitamins and supplements; enables patients to pose queries to their dietician; enables communicating schedules of weight loss seminars and support groups, to the patients; enables medical personnel to communicate healthy recipes with the patients to support their continued weight loss success; enables bariatric surgery patients to stay on track with reminders and a pre-populated checklist—Psych Eval, Insurance Pre-approval, Physician Supervised Diet; enables medical personnel as well as patients to journalize daily thoughts and progress notes; enables information exchange with third party applications; enables patients to track their water intake along with food consumed; enables automatic tracking of calories, protein, fat and carbohydrates consumed by patients; enables scanning of barcodes of package food to allow patients to see the nutritional information, and have it logged automatically to the feed consumed daily diary; enables physicians or medical personnel to enter specific goals for their patients; enables physicians to share their patient status data, with approval from their patients, with the fellow practice/department physicians to solicit better recommendations for the patients; enables instilling weight management habits in the patients since monitoring of food/calories intake leads to better dietary compliance; enables physicians, dieticians and other medical personnel to send out push notifications to their patients to keep the patients engaged and motivated towards their health goals.

It should be appreciated that in various embodiments, the user's plurality of health related information is utilized by the Health Management application to suggest and/or implement a plurality of recommendations comprising stimulation patterns or protocols, medication (such as an amount of insulin intake, for example), dietary and/or activities plans. For example, if the user's actual calories consumption is found to be higher than the expected calories consumption, consistently over a period of time, the Health Management application may recommend any one or a combination of: a specific standard diet plan to the user; a change from a first standard diet plan to a second standard diet plan or prescribe customization of an existing standard diet plan that the user may be following; recommend or change an existing stimulation protocol to suppress the user's appetite and/or suggest to the user to increase his activity levels such as walking, exercising.

In some embodiments, the plurality of recommendations is auto-generated by the Health Management application and presented to the user for his authorization for implementation. In some embodiments, the plurality of recommendations auto generated by the Health Management application are presented to the remote patient care facility and/or personnel for authorization or approval and thereafter either implemented or presented again to the user for a final authorization for implementation. In some embodiments, the Health Management application receives a plurality of recommendations prescribed by the remote patient care facility and/or personnel based on the user's plurality of health related information.

In various embodiments, the user is presented, on one or more GUIs, a plurality of recommendations, which are auto generated by the Health Management application as well as those received as prescriptions or recommendations from the remote patient care facility or personnel, the reasons for each of the plurality of recommendations, authorizations/approvals or disapprovals against each of the plurality of recommendations as received from the remote patient care facility or personnel, and annotations or notes from the remote patient care facility or personnel describing reasons for approving or disapproving each of the plurality of recommendations that were generated by the Health Management application. The user then reviews and authorizes/approves or disapproves implementation of each of the plurality of recommendations. In some embodiments, however, authorizations to implement the plurality of recommendations may not be required from the user and/or the remote patient care facility or personnel. For example, in one embodiment wherein the neuro-stimulation device is worn 24 hours per day, the number of stimulation sessions per a specified time period is automatically titrated up or down based on the recommendations. In another embodiment, the duration of stimulation is automatically titrated up or down based on the recommendations. In other embodiments, other stimulation parameters are changed automatically based on the recommendations.

In various embodiments, the companion device includes a 'diary' for the patient to input, track, record, and display patient parameters. FIG. 7 is a screen shot of a companion device depicting a diary widget 705, in accordance with one embodiment of the present specification. The diary widget 705 includes icons enabling the patient to input and view entries in the diary. The diary widget 705 includes a quick entry buttons icon 706 which, when pressed, causes the companion device to display buttons for making diary entries. The diary widget 705 also includes a list view of diary entries icon 707 which, when pressed, causes the companion device to display the diary in a list format. The diary widget 705 also includes a calendar view of diary entries icon 708 which, when pressed, causes the companion device to display the diary in a calendar format.

FIG. 8 is a screen shot of a companion device depicting a list view of diary entries 805, in accordance with one embodiment of the present specification. The list view of diary entries 805 is accessed by pressing the list view of diary entries icon 707 as shown on FIG. 7. In various embodiments, the list view of diary entries 805 displays entries input by the patient for instances such as stimulation sessions 806 and patient parameters, for example, hunger 807 and appetite 808. The stimulation session entry 806 displays the time 816 of the entry and details 826 of the stimulation session. Each patient parameter entry 807, 808 displays the time 817, 818 of the entry, the type of parameter 837, 838, and a score with description 827, 828 associated with the entry. The list view of diary entries 805 also displays the date 803 and the name of the diary 802 being viewed.

Figure 9:
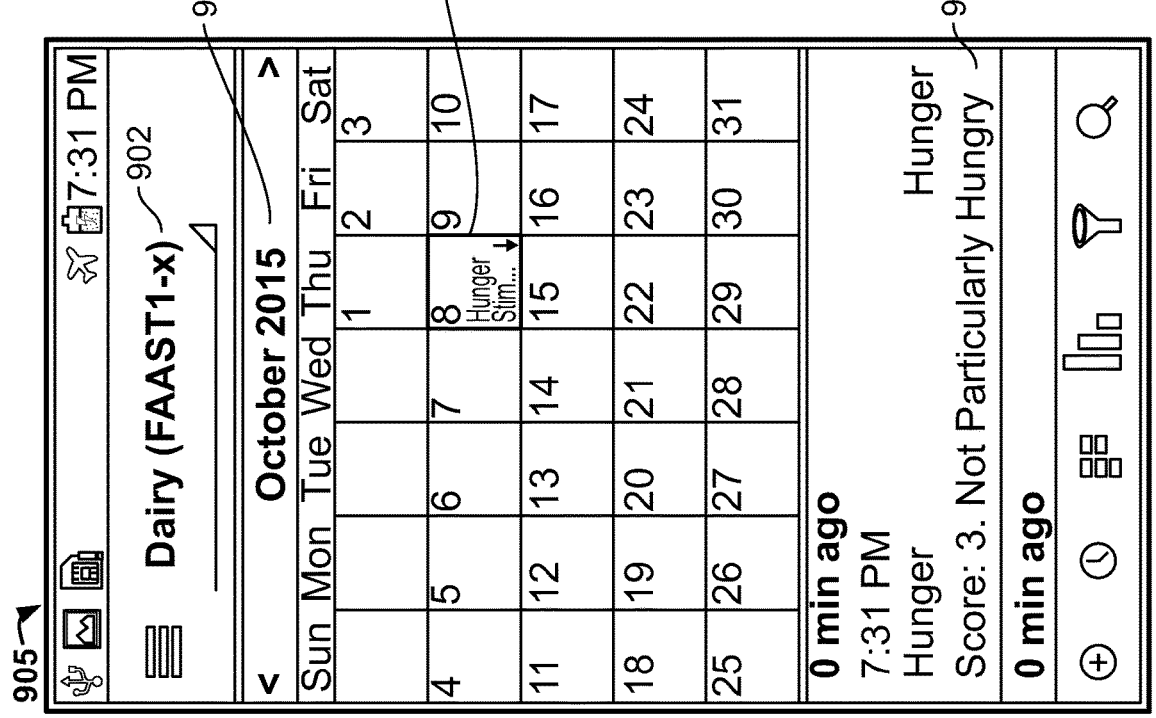
FIG. 9 is a screen shot of a companion device depicting a calendar view of diary entries, in accordance with one embodiment of the present specification.

FIG. 9 is a screen shot of a companion device depicting a calendar view of diary entries 905, in accordance with one embodiment of the present specification. The calendar view of diary entries 905 is accessed by pressing the calendar view of diary entries icon 708 as shown on FIG. 7. The calendar view of diary entries 905 displays the days 906 of the month being viewed. Pressing on an individual day displays the diary entries for that day as a list 907. The patient can scroll through the list 907 to view entries. The calendar view of diary entries 905 also displays the month and year 903 and the name of the diary 902 being viewed.

Figure 10:
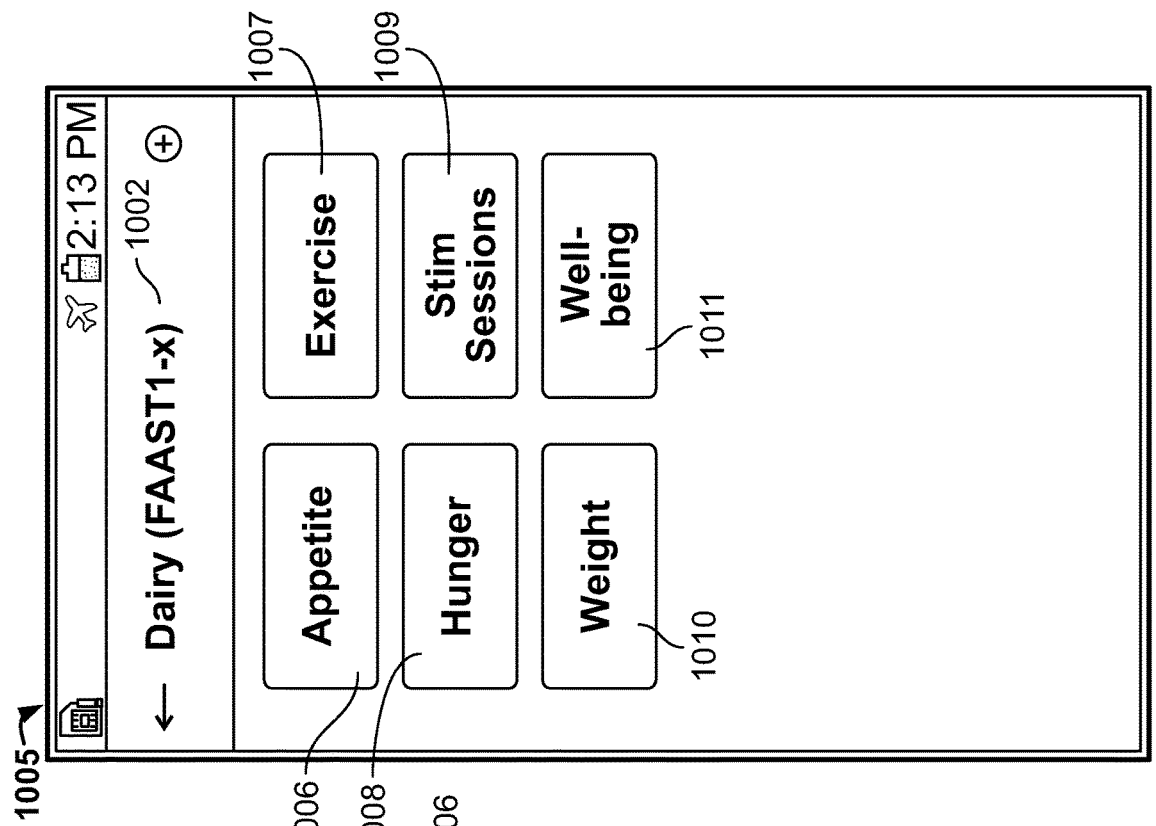
FIG. 10 is a screen shot of a companion device depicting a quick entry buttons view, in accordance with one embodiment of the present specification.

FIG. 10 is a screen shot of a companion device depicting a quick entry buttons view 1005, in accordance with one embodiment of the present specification. The quick entry buttons view 1005 is accessed by pressing the quick entry buttons icon 706 as shown on FIG. 7. In one embodiment, the quick entry buttons view 1005 includes six quick entry buttons: appetite 1006, exercise 1007, hunger 1008, stim (that is, stimulation) sessions 1009, weight 1010, and well-being 1011. The quick entry buttons depicted in FIG. 10 are exemplary only and not intended to be limiting. In other embodiments, fewer or additional quick entry buttons are included on the quick entry buttons view. Pressing on any one of the quick entry buttons 1006, 1007, 1008, 1009, 1010, 1011 causes the companion device to display an entry screen for the chosen button. The quick entry button view 1005 also displays the name of the diary 1002 being viewed.

FIG. 11 is a screen shot of a companion device depicting an appetite entry screen 1105, in accordance with one embodiment of the present specification. The appetite entry screen 1105 allows the user to enter the type 1106 and item 1107 of patient parameter, in this case appetite, and a score 1108 associated with the parameter. The score 1108 has a numerical value 1109 and a description 1110 associated therewith to help the patient determine which score best fits the current parameter. In some embodiments, for appetite, the description relates to how much the patient ate compared to the amount recommended by the patient's diet. In some embodiments, the score ranges from 1 to 5. The appetite entry screen 1105 also displays the time and date 1103 the entry is being entered and the name of the diary 1102. The patient can save the entry by pressing the disk icon 1101 or cancel the entry by pressing the X icon 1104.

FIG. 12 is a screen shot of a companion device depicting an exercise entry screen 1205, in accordance with one embodiment of the present specification. The exercise entry screen 1205 allows the user to enter the type 1206 and item 1207 of patient parameter, in this case exercise, and a score 1208 associated with the parameter. The score 1208 has a numerical value 1209 and a description 1210 associated therewith to help the patient determine which score best fits the current parameter. In some embodiments, for exercise, the description relates to how many steps the patient took per day. In some embodiments, the score ranges from 1 to 5. The exercise entry screen 1205 also displays the time and date 1203 the entry is being entered and the name of the diary 1202. The patient can save the entry by pressing the disk icon 1201 or cancel the entry by pressing the X icon 1204.

FIG. 13 is a screen shot of a companion device depicting a hunger entry screen 1305, in accordance with one embodiment of the present specification. The hunger entry screen 1305 allows the user to enter the type 1306 and item 1307 of patient parameter, in this case hunger, and a score 1308 associated with the parameter. The score 1308 has a numerical value 1309 and a description 1310 associated therewith to help the patient determine which score best fits the current parameter. In some embodiments, for hunger, the description relates to the level of hunger the patient is experiencing. In some embodiments, the score ranges from 1 to 5. The hunger entry screen 1305 also displays the time and date 1303 the entry is being entered and the name of the diary 1302. The patient can save the entry by pressing the disk icon 1301 or cancel the entry by pressing the X icon 1304.

FIG. 14 is a screen shot of a companion device depicting a stimulation session entry screen 1405, in accordance with one embodiment of the present specification. The stimulation session entry screen 1405 allows the user to enter the type 1406 and item 1407 of session, in this case a stimulation session, and a level 1408 associated with the session. The level 1408 has a numerical value 1409 and a description 1410 associated therewith to help the patient determine which level best represents what was applied during the current session. In some embodiments, for stimulation session, the description relates to how often stimulation was delivered per day and for how long the stimulation was applied during each session. In some embodiments, the level ranges from 1 to 4. The stimulation session entry screen 1405 also displays the time and date 1403 the entry is being entered and the name of the diary 1402. The patient can save the entry by pressing the disk icon 1401 or cancel the entry by pressing the X icon 1404.

FIG. 15 is a screen shot of a companion device depicting a weight entry screen 1505, in accordance with one embodiment of the present specification. The weight entry screen 1505 allows the user to enter the type 1506 and item 1507 of patient parameter, in this case weight, and a weight in pounds 1508 associated with the parameter. The weight entry screen 1505 includes a numeric keypad 1509 for the patient to use to enter the weight. The weight entry screen 1505 also displays the time and date 1503 the entry is being entered and the name of the diary 1502. The patient can save the entry by pressing the disk icon 1501 or cancel the entry by pressing the X icon 1504.

FIG. 16 is a screen shot of a companion device depicting a well-being entry screen 1605, in accordance with one embodiment of the present specification. The well-being entry screen 1605 allows the user to enter the type 1606 and item 1607 of patient parameter, in this well-being, and a score 1608 associated with the parameter. The score 1608 has a numerical value 1609 and a description 1610 associated therewith to help the patient determine which score best fits the current parameter. In some embodiments, for well-being, the description relates to a level of nausea, dyspepsia and/or abdominal discomfort the patient is experiencing. In some embodiments, the score ranges from 1 to 3. The well-being entry screen 1605 also displays the time and date 1603 the entry is being entered and the name of the diary 1602. The patient can save the entry by pressing the disk icon 1601 or cancel the entry by pressing the X icon 1604.

It should be appreciated that the HMA incorporates GUIs that present scales, surveys, or questionnaires designed to quantitatively assess one or more of a person's appetite, hunger, level of satiety, level of satiation, level of fullness, level of well-being, level of nausea, feelings of pain, level of dyspepsia, perception of food, and changes thereto.

For example, SNAQ (Simplified Nutritional Appetite Questionnaire) is an appetite assessment tool that predicts weight loss. SNAQ includes questions that rank, on a scale of 1 to 5, the strength of appetite, feelings of fullness after eating, taste of food and number of meals eaten each day. A SNAQ score of less than or equal to 14 predicts high likelihood of at least 5% weight loss within six months. The Ghrelin Hunger Scale (G-scale) is a two dimensional scale wherein a first scale of 1 to 7 on the y-axis is used to assess the feeling of hunger/fullness and a second scale of 1 to 7 on the x-axis is used to assess the time elapsed since a last meal (breakfast, lunch, snack, or dinner).

In general, each such scale is a form of a visual analog scale (VAS). A VAS is question-based assessment mechanism, where a visual measure is associated with each question and where answering the question requires selecting a quantifiable position within that visual measure, indicative of a particular level or degree. The scale is typically composed of lines (of varying length) with words anchored at each end, describing the extremes (that is, 'I am not hungry at all' on the left to 'I have never been more hungry' on the right). Patients are asked to make a mark across the line corresponding to their feelings. Quantification of the measurement is done by measuring the distance from the left end of the line to the mark. In some embodiments, VAS may be used to assess sensations of pain (due to stimulation, for example), hunger, appetite, satiation, fullness, satiety, overall quality of life, degree of nausea, degree of well-being, degree of dyspepsia, perception of food, food aversions, and perceptions of dietary compliance.

FIG. 29A illustrates a VAS questionnaire 2905 for assessing hunger sensations or appetite. The questionnaire 2905 presents a patient with a leading question, such as, "how hungry do you feel 48" while the two extremities 2906, 2907 of the scale line 2908 are anchored with words that describe the feeling of least and maximum hunger. In one embodiment the two extremities 2906, 2907 are described as "I am not hungry at all" and "I have never been more hungry", respectively.

FIG. 29B illustrates a VAS questionnaire 2910 for assessing a feeling of fullness. The questionnaire 2910 presents the patient with a leading question, such as, "how full do you feel?" while the two extremities 2911, 2912 of the scale line 2913 are anchored with words that describe the feeling of least and maximum fullness. In one embodiment the two extremities 2911, 2912 are described as "Not at all full" and "Totally full", respectively.

FIG. 29C illustrates a VAS questionnaire 2915 for assessing a feeling of satiation. The questionnaire 2915 presents the patient with a leading question, such as, "how satisfied do you feel?" while the two extremities 2916, 2917 of the scale line 2918 are anchored with words that describe the feeling of least and maximum satiation. In one embodiment the two extremities 2916, 2917 are described as "I am completely empty" and "I cannot eat another bite", respectively.

FIG. 29D illustrates a VAS questionnaire 2920 for assessing a feeling of satiety. The questionnaire 2920 presents the patient with a leading question, such as, "how much do you think you can eat?" while the two extremities 2921, 2922 of the scale line 2923 are anchored with words that describe the feeling of least and maximum satiety. In one embodiment, the two extremities 2921, 2922 are described as "A lot" and "Nothing at all", respectively.

Persons of ordinary skill in the art should appreciate that the leading question and anchoring words at the two extremities of the scale, for each questionnaire of FIGS. 29A through 29D, may be linguistically modified in alternate embodiments without departing from the assessment objective or the feeling to be assessed. For example, in an alternate embodiment the questionnaire 2920 the leading question is "How strong is your desire to eat now?" while the two extremities 2921, 2922 are described as "Extremely" and "Not at all". Additionally, other intermediate language may be used between the two extremes.

Also, VAS questionnaires can be designed to assess aspects such as, but not limited to, health-related overall quality of life, degree of nausea, degree of pain felt, degree of well-being, and degree of dyspepsia. For example, in one embodiment, to assess nausea levels a VAS questionnaire may present a leading question, such as, "Do you feel nauseous?" while the two extremities of the scale are described as "A lot" and "Not at all". In another embodiment, to assess health-related overall quality of life or degree of well-being a VAS questionnaire may present a leading question, such as, "How satisfied are you with your health as whole?" with the two extremities of the scale being described as "completely dissatisfied" and "completely satisfied". In yet another embodiment, to assess degree of dyspepsia a VAS questionnaire may present a leading question, such as, "Has your ability to eat or drink (including when, what, and how much) been disturbed by your stomach problems in the last 2 weeks?" with the two extremities of the scale being described as "Extremely" and "Not at all".

As discussed earlier, the Health Management application is capable of communicating (via pairing or syncing) with a third party device (including a third party application software on an external device), with physiological sensors, configured to be worn on the human body, such as around the wrist, in order to monitor, acquire, record, and/or transmit the physiological data, to receive and integrate exercise and weight loss information, along with one or more neuro-stimulation devices of the present specification. It should be appreciated that the third party device, whether it is a third party application software on an external device or a second external device entirely (such as, but not limited to, a watch, a diabetes wearable pump, or another medical device), is enabled to obtain information from the PEDP device of the present specification, either directly from the PEDP device, directly from the Health Management application, or directly from a server in data communication with the PEDP device or the Heath Management application of the present specification. Consequently, the third party application or the second external device can display any information gathered by the PEDP device and/or Health Management application, including patient diary inputs, the patient's level of hunger, the patient's level of wellbeing, the patient's level of appetite, the stimulation settings, or an aggregate/composite weight management performance score which aggregates any of the data tracked by the third party device with any of the data tracked by the PEDP device and/or Health Management application to yield a single composite score.

The third party device, in various embodiments, may track one or any combination of the following patient related data: heart rate, pulse rate, beat-to-beat heart variability, EKG or ECG, respiration rate, skin temperature, core body temperature, heat flow off the body, galvanic skin response or GSR, EMG, EEG, EOG, blood pressure, body fat, hydration level, activity level, oxygen consumption, glucose or blood sugar level, body position, pressure on muscles or bones, and/or UV radiation exposure and absorption or any other parameter listed in Tables 1 and Table 2 above, data representative of the air quality, sound level/quality, light quality or ambient temperature near the patient, or the global positioning of the patient, patient's weight, food consumed, type and amount of activity or exercise (such as steps take, swimming, running).

Neuro-Stimulation Device Placement

In various embodiments, the neuro-stimulation device (such as the neuro-stimulation device 110 of FIG. 1A through 1C) of the present specification is placed and/or implanted at or near an 'area of interest' on the user's body to provide stimulation therapies for a plurality of conditions or treatments.

In various embodiments, the 'area of interest' comprises a dermatome. As understood by persons of ordinary skill in the art, a dermatome is an area of skin supplied by sensory neurons that arise from a spinal nerve ganglion. There are 8 cervical nerves (C1 being an exception with no dermatome), 12 thoracic nerves, 5 lumbar nerves and 5 sacral nerves. Each of these nerves relays sensation from a particular region of skin to the brain.

In some embodiments, the 'area of interest' comprises a thoracic dermatome, such as the user's front, lateral and back T2 to T12 dermatomes. In other embodiments, the 'area of interest' comprises a dermatome, such as the user's front (anterior) and/or back (posterior) C5-T1 dermatomes in the hand and arm along with the front (anterior) C5-T1 dermatomes on the upper chest region (hereinafter together referred to as 'hand dermatomes'). In various embodiments, the 'area of interest' expressly excludes the back (posterior) C5-T1 dermatomes of the upper chest region since the back portions are inaccessible to the user and therefore would need a medical practitioner to apply the devices of the present specification.

In some embodiments, the 'area of interest' comprises at least one of the patient's T2 frontal, lateral and back thoracic dermatome, T3 frontal, lateral and back thoracic dermatome, T4 frontal, lateral and back thoracic dermatome, T5 frontal, lateral and back thoracic dermatome, T6 frontal, lateral and back thoracic dermatome, T7 frontal, lateral and back thoracic dermatome, T8 frontal, lateral and back thoracic dermatome, T9 frontal, lateral and back thoracic dermatome, or T10 frontal, lateral and back thoracic dermatome.

In some embodiments, the 'area of interest' comprises at least one of the patient's C8 anterior or posterior dermatome located on the patient's hand, wrist, elbow, and fingers, C8 anterior or posterior dermatome located on the patient's arm, C8 dermatome located on the patient's upper trunk, T1 anterior or posterior dermatome located on the patient's arm, T1 anterior or posterior dermatome located on the patient's wrist, elbow, and hand, and T1 anterior or posterior dermatome located on the patient's upper trunk.

In some embodiments, the 'area of interest' comprises at least one of the patient's front, lateral and/or back C5, C6, C7, C8, T1, T2, T3, T4, T5, T6, T7, T8, T9, T10, T11, and T12 dermatomes.

In alternate yet less preferred embodiments, the 'area of interest' comprises one or more meridians.

Figure 17A:
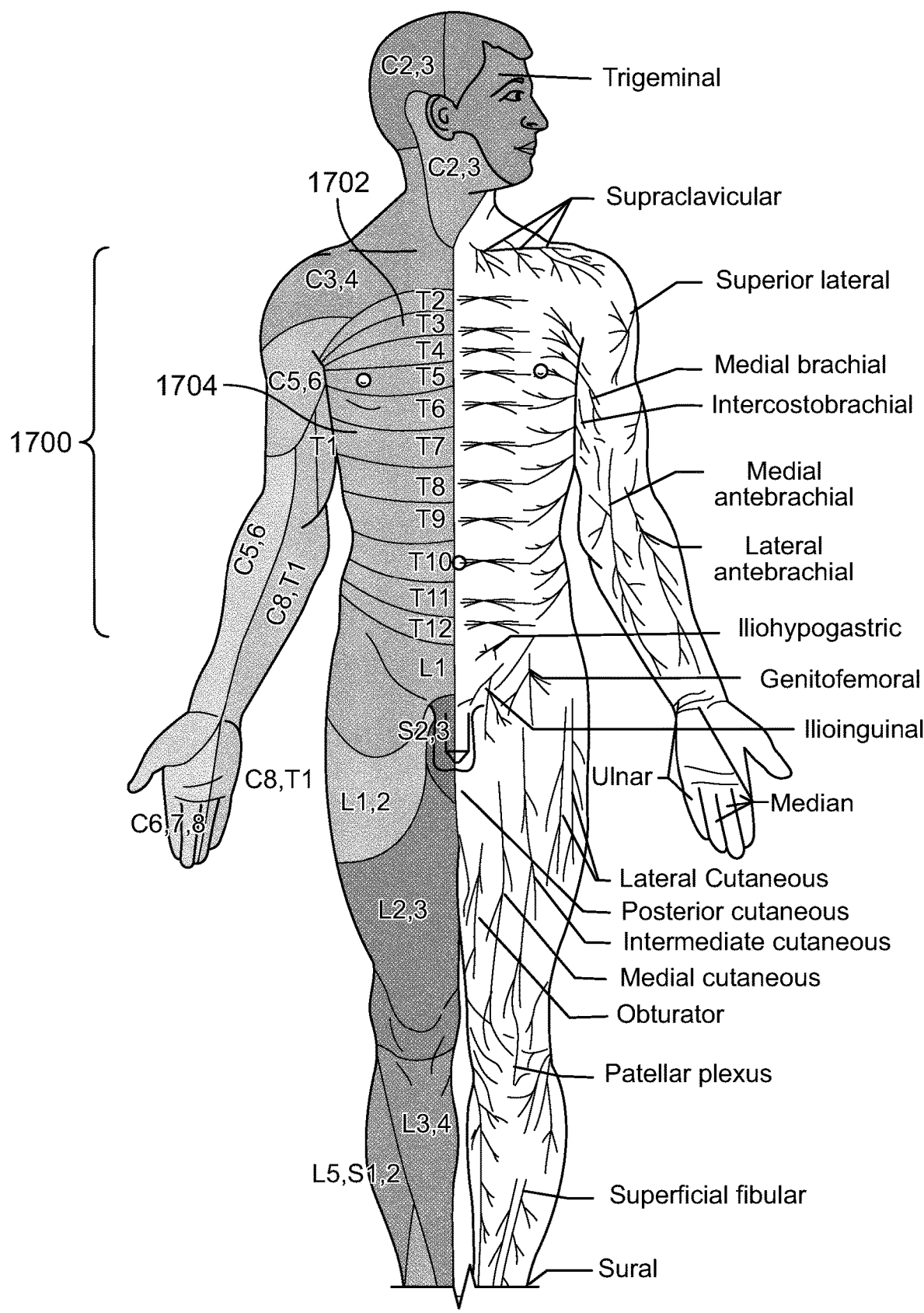
FIG. 17A is an illustration depicting the distribution of the front and lateral T2-T12 dermatomes across a thorax and abdomen of a human body.
Figure 17B:
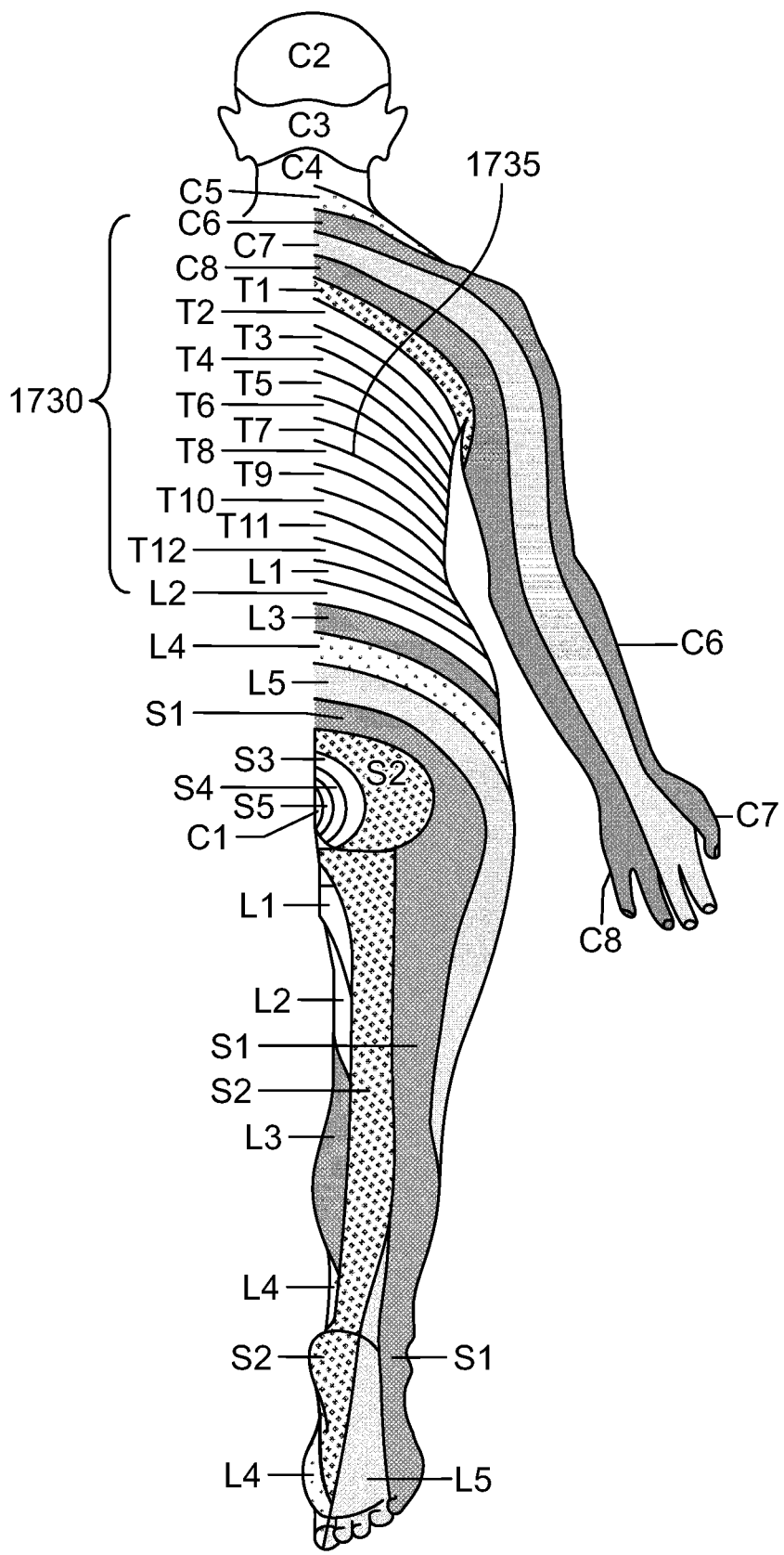
FIG. 17B is an illustration depicting the distribution of the posterior or back T2-T12 dermatomes across a trunk of the human body.

FIG. 17A is an illustration depicting the distribution 1700 of the front and lateral, or frontal, T2-T12 dermatomes across a thorax and abdomen, that is trunk, of a human body while FIG. 17B is an illustration depicting the distribution 1730 of the posterior or back T2-T12 dermatomes across the trunk. In various embodiments, the neuro-stimulation devices of the present specification are positioned just underneath the surface of the epidermis on the front portion 1702, lateral portion 1704 and/or posterior or back portion 1735 of the T2-T12 dermatomes, at a distance ranging from 0.1 to 30 mm below the skin surface. The electrode(s) positioned within the pads or percutaneous skin patches of the neuro-stimulation device are then implanted underneath the skin to provide electrical stimulation to the targeted dermatome(s).

The T2 to T12 dermatomes are anatomically identifiable as follows:

T2—At the apex of the axilla.
T3—Intersection of the midclavicular line and the third intercostal space.
T4—Intersection of the midclavicular line and the fourth intercostal space, located at the level of the nipples.
T5—Intersection of the midclavicular line and the fifth intercostal space, horizontally located midway between the level of the nipples and the level of the xiphoid process.
T6—Intersection of the midclavicular line and the horizontal level of the xiphoid process.
T7—Intersection of the midclavicular line and the horizontal level at one quarter the distance between the level of the xiphoid process and the level of the umbilicus.
T8—Intersection of the midclavicular line and the horizontal level at one half the distance between the level of the xiphoid process and the level of the umbilicus.
T9—Intersection of the midclavicular line and the horizontal level at three quarters of the distance between the level of the xiphoid process and the level of the umbilicus.
T10—Intersection of the midclavicular line, at the horizontal level of the umbilicus.
T11—Intersection of the midclavicular line, at the horizontal level midway between the level of the umbilicus and the inguinal ligament.
T12—Intersection of the midclavicular line and the midpoint of the inguinal ligament.

Figure 17C:
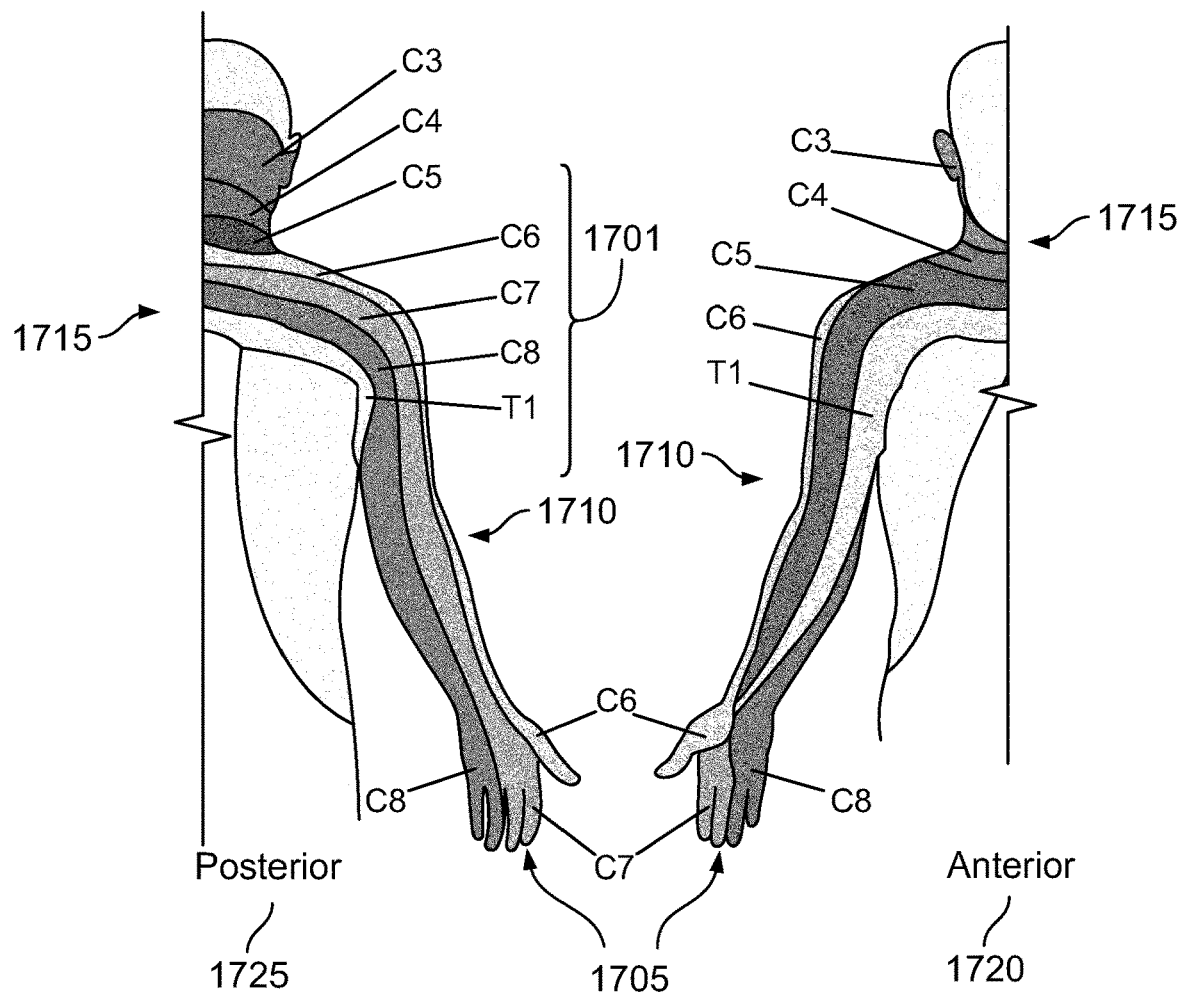
FIG. 17C is an illustration depicting the distribution of the anterior and posterior C5-T1 dermatomes across a hand, arm and upper chest regions of a human body.

FIG. 17C is an illustration depicting the distribution 1701 of the front and back, C5-T1 dermatomes across the hand 1705, arm 1710 and upper chest 1715 regions of a human body. In various embodiments, the PDEP neuro-stimulation devices of the present specification are positioned just underneath the surface of the epidermis on the front portion 1720 and/or back portion 1725 of the C5-T1 dermatomes on the hand 1705 and arm 1710 along with the front (anterior) C5-T1 dermatomes on the upper chest 1715, at a distance ranging from 0.1 to 30 mm below the skin surface.

Figure 17D:
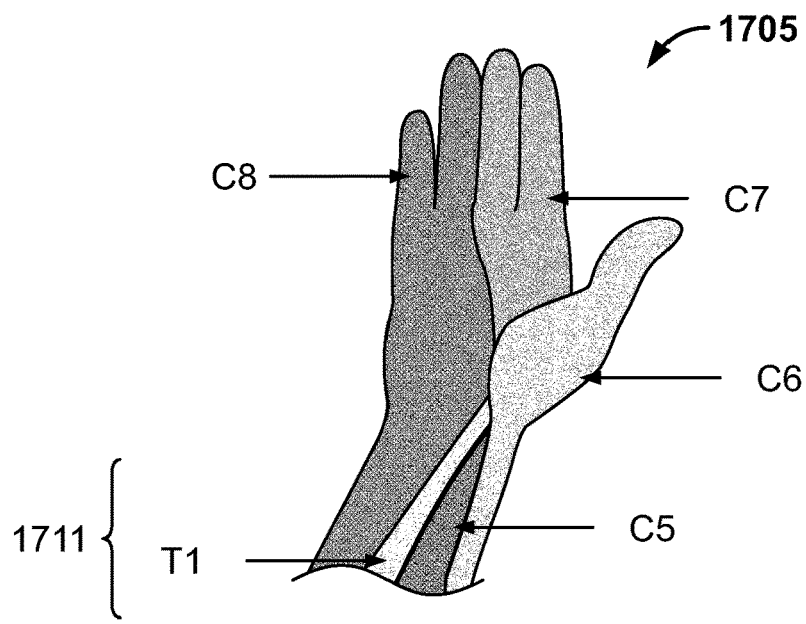
FIG. 17D is an illustration depicting the distribution of the C5-T1 dermatomes across the ventral side of the hand and lower arm of the human body.

FIG. 17D is an illustration depicting the distribution of the C5-T1 dermatomes across the hand 1705 and lower arm 1711 regions. In various embodiments, the neuro-stimulation devices of the present specification are positioned just underneath the surface of the epidermis on the front (palm) and/or back side of the hand 1705 targeting the C6-C8 dermatomes or on the front and/or back side of the lower arm 1711 (such as at a wrist region, for example) targeting the C5 and T1 dermatomes, at a distance ranging from 0.1 to 30 mm below the skin surface.

Thus, the electrode(s) positioned on the pads or percutaneous skin patches of the neuro-stimulation device are implanted underneath the skin to provide electrical stimulation to the targeted dermatome(s).

The C5-T1 dermatomes are anatomically identifiable as follows:

C5—On the lateral (radial) side of the antecubital fossa, just proximally to the elbow.
C6—On the dorsal surface of the proximal phalanx of the thumb.
C7—On the dorsal surface of the proximal phalanx of the middle finger.
C8—On the dorsal surface of the proximal phalanx of the little finger.
T1—On the medial (ulnar) side of the antecubital fossa, just proximally to the medial epicondyle of the humerus.

Figure 17E:
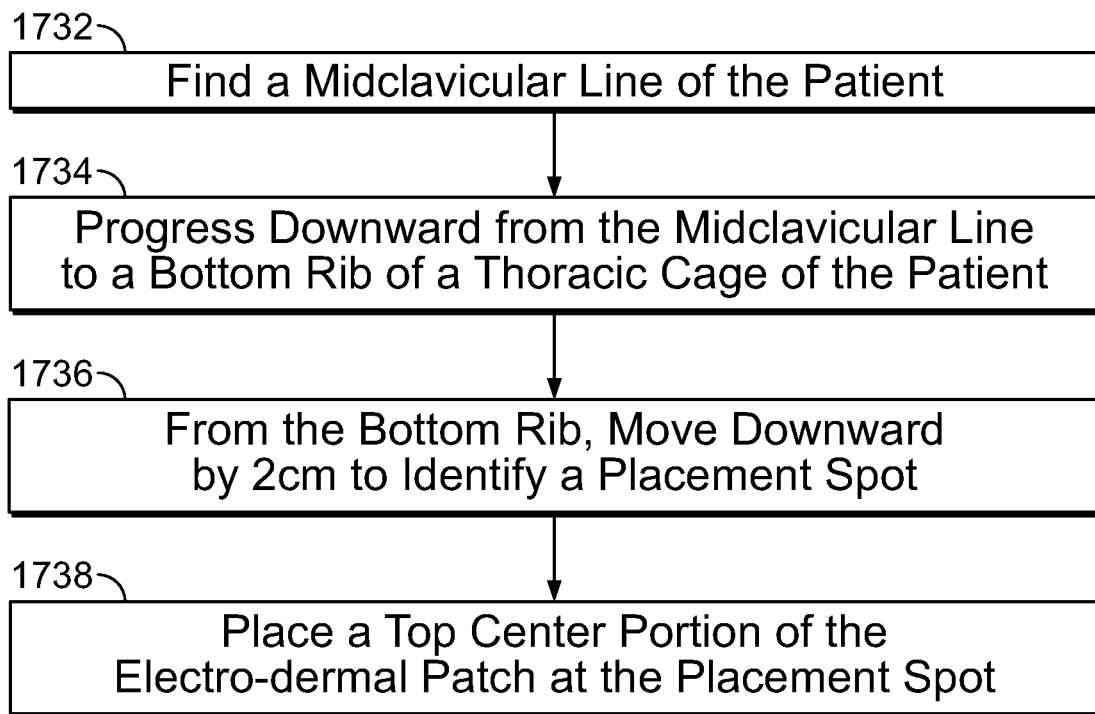
FIG. 17E is a flow chart listing the steps involved in one method of identifying a proper placement location for a percutaneous electro-dermal patch on a front thoracic surface of a patient, in accordance with one embodiment of the present specification.

FIG. 17E is a flow chart listing the steps involved in one method of identifying a proper placement location for a percutaneous electro-dermal patch on a front thoracic surface of a patient, in accordance with one embodiment of the present specification. At step 1732, the physician or medical technician finds a midclavicular line of the patient. The person applying the device then progresses downward from the midclavicular line to a bottom rib of a thoracic cage of the patient at step 1734. From the bottom rib, at step 1736, the person applying the device moves downward by 2 cm to identify a placement spot. At step 1738, the person applying the device places a top center portion of the percutaneous electro-dermal patch at the placement spot. It should be appreciated that the person applying the device may be the user himself or a physician, depending upon the embodiment, as described above. In other words, the PEDP device of the present specification may be self-implanted or self-administered by the user or implanted by a physician or medical personnel so that one or more electrodes are placed or inserted percutaneously at an angle of insertion ranging from 10 degrees to 90 degrees and up to a depth, ranging from 0.1 mm to 30 mm to enable stimulation depth through the user's skin ranging from 0.1 mm to 30 mm.

Referring back to FIG. 1A, in various embodiments, at least one thoracic dermatome, from T2 to T12 and/or 'arm dermatome' or 'hand dermatome' C5-T1, is stimulated by the neuro-stimulation device 110 to provide electrical stimulation therapy by means of electrodes 118 placed percutaneously within the skin.

In some embodiments, the neuro-stimulation device 110 stimulates areas in the T6 and/or T7 dermatome. In some embodiments, the neuro-stimulation device 110 stimulates areas in the C8 and/or T1 dermatome on the hand of a patient. In still other embodiments, the neuro-stimulation device 110 stimulates areas in the T6, T7, C8 and/or T1 dermatomes.

Figure 18C:
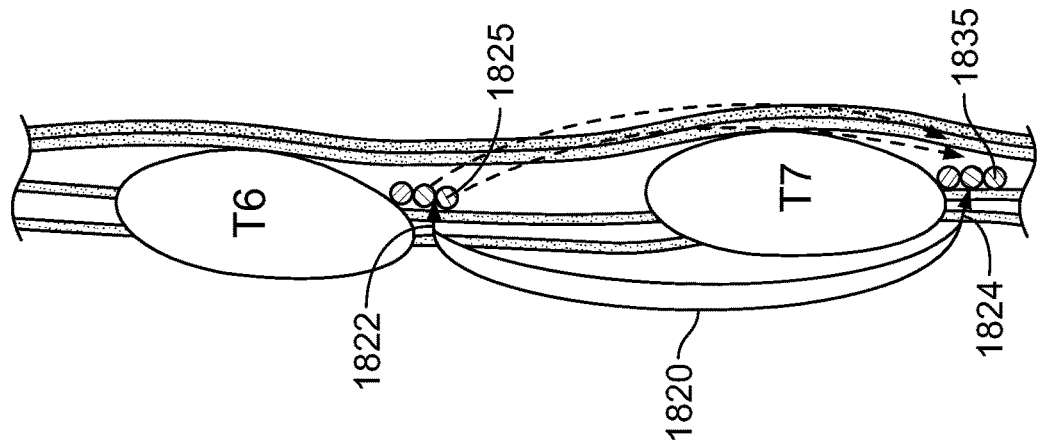
FIG. 18C illustrates T6 and T7 stimulation using an neuro-stimulation device, in accordance with certain embodiments.
Figure 18B:
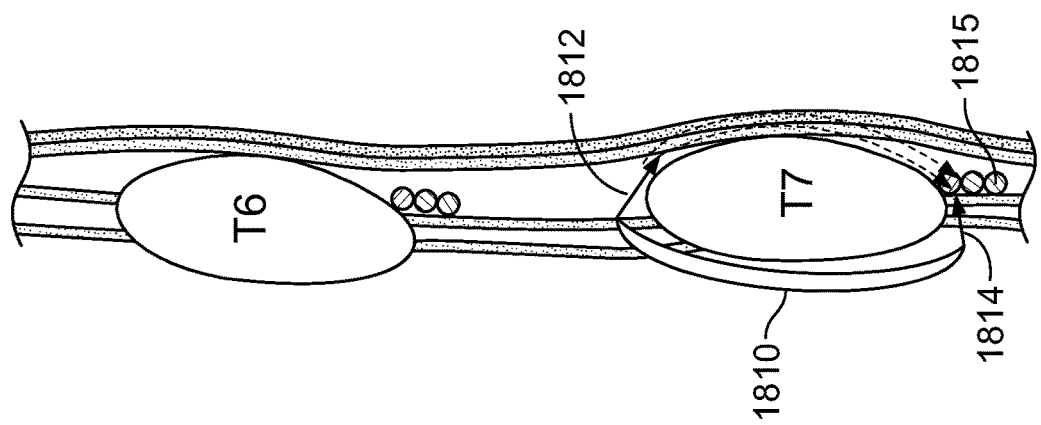
FIG. 18B illustrates T7 stimulation using an neuro-stimulation device, in accordance with certain embodiments.
Figure 18A:
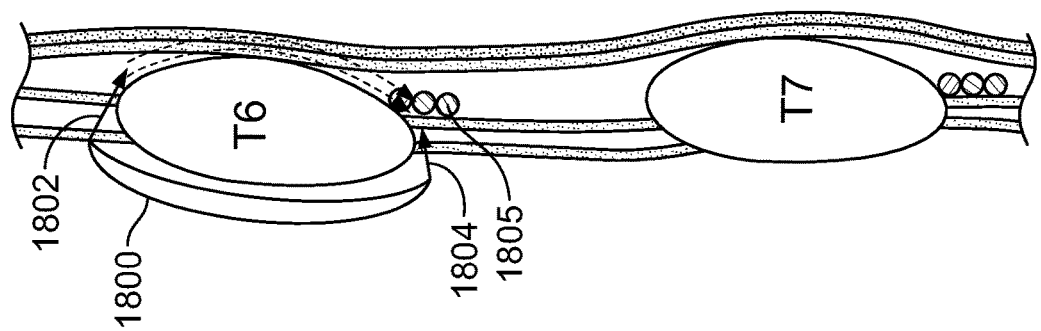
FIG. 18A illustrates T6 stimulation using an neuro-stimulation device, in accordance with certain embodiments.

In one embodiment, as shown in FIG. 18A, the neuro-stimulation device 1800 stimulates the T6 dermatome, including meridians. In another embodiment, as shown in FIG. 18B, the neuro-stimulation device 1810 stimulates the T7 dermatome. In yet another embodiment, as shown in FIG. 18C, the neuro-stimulation device 1820 stimulates both the T6 and T7 dermatomes. In some embodiments, referring to FIG. 18A, an neuro-stimulation device 1800 delivers, through one or more electrodes positioned within a pad or percutaneous skin patch, electrical stimulation 1802 above a rib (T6) and electrical stimulation 1804 below the rib (T6) to stimulate an intercostal nerve 1805 and the T6 dermatome. In other embodiments, referring to FIG. 18B, an neuro-stimulation device 1810 delivers, through one or more electrodes disposed in a pad or percutaneous skin patch, electrical stimulation 1812 above a rib (T7) and electrical stimulation 1814 below the rib (T7) to stimulate an intercostal nerve 1815 and the T7 dermatome. In yet other embodiments, referring to FIG. 18C, an neuro-stimulation device 1820 delivers, through one or more electrodes disposed in a pad or percutaneous skin patch, electrical stimulation 1822 below a rib (T6) and above a rib (T7) and electrical stimulation 1824 below a rib (T7) to stimulate intercostal nerves 1825, 1835 and the T6 and T7 dermatomes.

In one embodiment, the neuro-stimulation device 1800 is positioned on a very specific portion of the patient's T6 dermatome. Specifically, the PEDP device 1800 is positioned on the left upper quadrant along the mid-clavicular line, 2 cm below the ribcage at a 90 degree angle towards the abdominal wall at a depth of approximately 0.1 mm to 1 cm and preferably at a depth of approximately 2 mm to 1 cm. In other words, the PEDP device 1800 is positioned at the intersection of two lines drawn on a standing patient: a first line vertically down from a mid-clavicle and a second line horizontally across from the xyphoid process. The first and second lines would form an angle of 90 degrees on the right side and left side of the anterior trunk of the patient.

In accordance with an aspect of the present specification, the T6 dermatome is stimulated to treat conditions such as obesity, over-weight, eating disorders, metabolic syndrome and/or for appetite suppression. In accordance with another aspect of the present specification, the T7 dermatome is stimulated to treat T2DM (Type 2 Diabetes Mellitus). In accordance with yet another aspect of the present specification, up to two dermatomes, such as T6 and T7, are simultaneously or alternatingly stimulated to treat multiple conditions (e.g., appetite suppression and T2DM). In accordance with another aspect of the present specification, the C8 or T1 dermatome is stimulated to treat conditions such as obesity, over-weight, eating disorders, metabolic syndrome and/or for appetite suppression. In accordance with yet another aspect of the present specification, up to two dermatomes, such as C8 and T1, are simultaneously or alternatingly stimulated. In still further embodiments, T6, C8 and/or T1 dermatome is stimulated to treat conditions such as obesity, over-weight, eating disorders, metabolic syndrome and/or for appetite suppression, while the T7 dermatome is stimulated to treat T2DM (Type 2 Diabetes Mellitus). In still additional embodiments, multiple dermatomes are simultaneously stimulated, for example any one or any combination of T6, T7, C8 and/or T1 dermatomes are stimulated simultaneously.

In some embodiments, the neuro-stimulation device 110 stimulates areas in the C8 and/or T1 dermatome on the hand of a patient. In one embodiment, as shown in FIG. 19A, the neuro-stimulation device 1900, through one or more electrodes implanted in the user's skin, stimulates the C8 dermatome on the front (palm) or ventral side 1905 of the hand 1910. In another embodiment, as shown in FIG. 19B, the neuro-stimulation device 1900, through one or more electrodes disposed in a pad or percutaneous skin patch and implanted into the skin, stimulates the C8 dermatome on the back or dorsal side 1906 of the hand 1910. In yet another embodiment, as shown in FIG. 19C, the neuro-stimulation device 1900, through one or more electrodes implanted in the user's skin, stimulates both the C8 and T1 dermatomes by being placed on the front or ventral side of the lower arm or wrist region 1915.

It should be appreciated that, in various embodiments, the neuro-stimulation device 1900 is placed in-line with the patient's fingers, such that a longitudinal axis 1901 of the neuro-stimulation device 1900 is approximately in the direction of the fingers. However, in various alternate embodiments the neuro-stimulation device may not be placed in-line with the patient's fingers. In various embodiments, the neuro-stimulation device 1900 is placed on a non-dominant hand of the patient. In some embodiments, the neuro-stimulation device 1900 is preferably placed on the back or dorsal side of the hand (as shown in FIG. 19B) as the patient's palm (ventral side) comes into contact with many surfaces in daily routine that may cause damage to the neuro-stimulation device 1900.

In accordance with an aspect, the neuro-stimulation device 1900 is sufficiently flexible so that it conforms to the contour of the user's hand 1910 and does not interfere in free movement of the hand 1910. Referring back to FIG. 1A, to enable sufficient flexibility of the neuro-stimulation device 110 (that is, neuro-stimulation device 1800 configured as a percutaneous skin patch as shown in FIGS. 19A through 19C) the underlying electronics such as the microcontroller 112, transceiver 114, the pulse generator 116 and the power management module 120 including the receptor slots 130 are mounted on flexible plastic substrates, such as polyimide, PEEK (Polyether Ether Ketone) or transparent conductive polyester film—to form flex circuits. Alternatively, the underlying electronics are substantially miniature so that their rigid substrate, in some embodiments, do not need to flex over their small area. In some embodiments, the power management module 120 including the receptor slots 130, the actuators 122 and the indicators 124, 126 are physically separated or at a distance from the electronic circuitry such as the microcontroller 112, transceiver 114, and the pulse generator 116 to enable increased flexibility. In various embodiments, the housing 111 of the neuro-stimulation device 110 is of a flexible material such as silicone, rubber or any other flexible polymer known to persons of ordinary skill in the art.

Figure 20B:
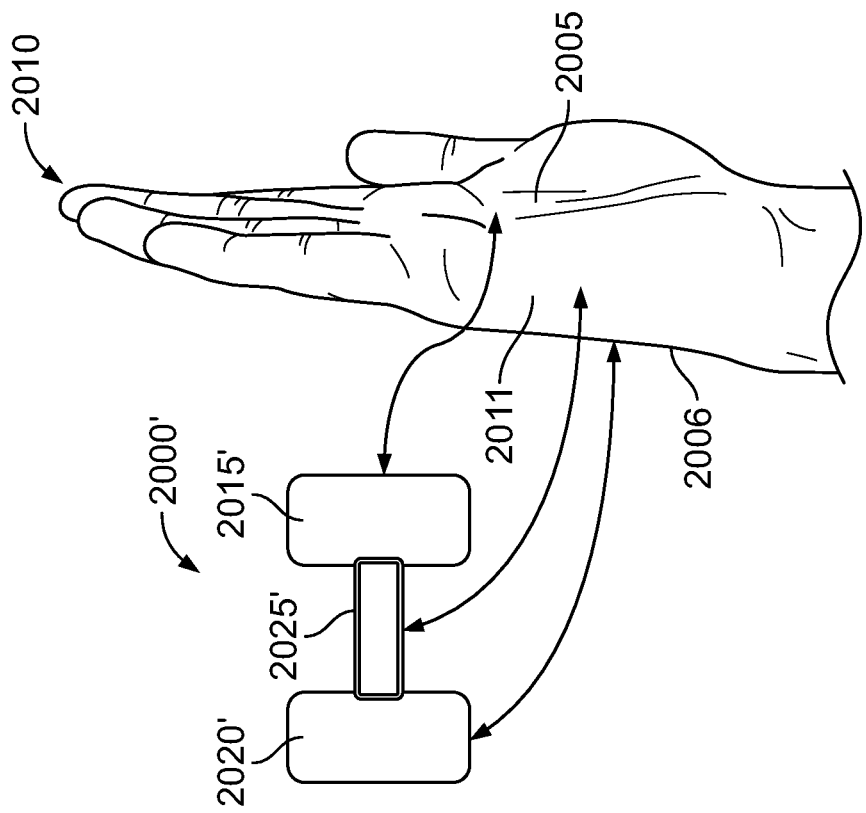
FIG. 20B illustrates another embodiment of an neuro-stimulation device of the present specification wrapped around the edge of the user's hand for stimulating the C8 dermatome.
Figure 20A:
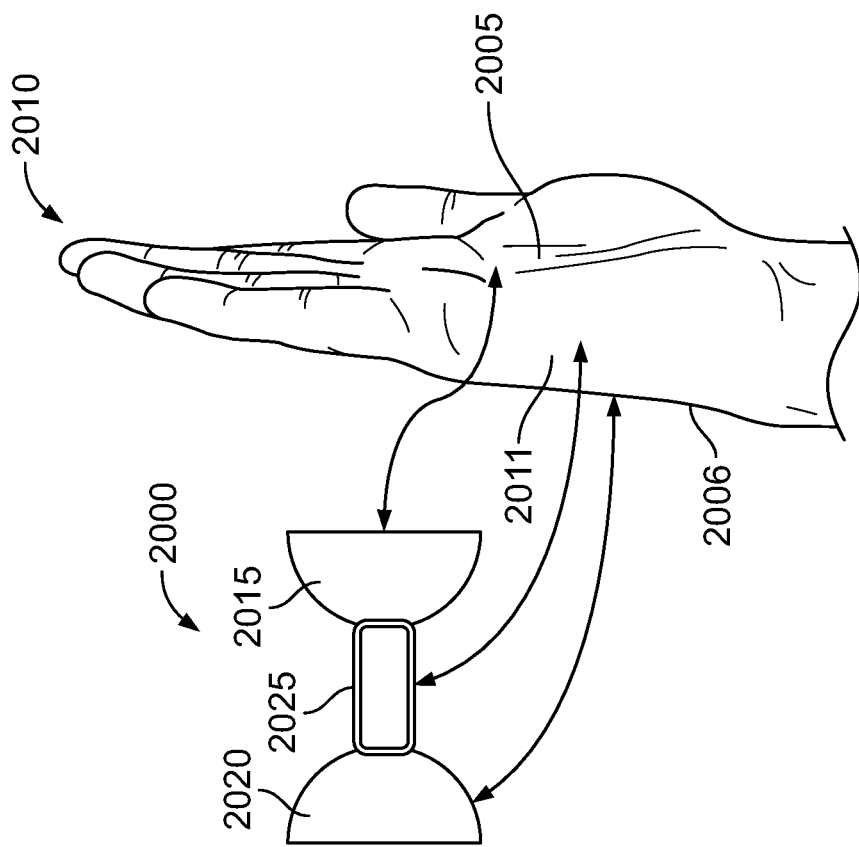
FIG. 20A illustrates an embodiment of an neuro-stimulation device of the present specification wrapped around the edge of the user's hand for stimulating the C8 dermatome.

In some embodiments, the neuro-stimulation device, through one or more electrodes implanted in the user's skin, is configured to stimulate the C8 dermatome on the front (palm side) or ventral side as well as the back or dorsal side of the user's hand. In one embodiment, as shown in FIG. 20A, the neuro-stimulation device 2000 comprises a first patch portion 2015, a second patch portion 2020 and a third patch portion or bridge 2025 connecting the first and second patch portions 2015, 2020. In some embodiments, the first and second patch portions 2015, 2020 are substantially semi-circular shaped that are connected by a substantially rectangular bridge 2025 such that the neuro-stimulation device 2000 forms an approximate 'hourglass' shape. In another embodiment, as shown in FIG. 20B, the first and second patch portions 2015', 2020' are substantially rectangular that are connected by a substantially rectangular bridge 2025' such that the neuro-stimulation device 2000' forms an approximate 'H' shape. In various embodiments, the bridge 2025, 2025' is narrow (that is, the width is substantially less than the length of the bridge) to increase flexibility of this segment of the neuro-stimulation device 2000, 2000'. It should be appreciated that the 'hourglass' and 'H' shaped configurations of FIGS. 20A, 20B are non-limiting examples of the various shapes that the neuro-stimulation device may have in various embodiments.

In some embodiments, all three patch portions 2015, 2020 and 2025 are adhesive. However, in alternate embodiments only the first and second patch portions 2015, 2020 are adhesive while the bridge portion 2025 is non-adhesive to improve comfort, wearability tolerance and overall flexibility of the patches 2000, 2000'. The non-adhesive bridge portion 2025 may be configured into a thinner portion relative to the adhesive first and second adhesive patch portions 2015, 2020.

During use, the neuro-stimulation devices 2000, 2000' respectively wrap around the edge 2011 of the hand 2010 such that the first patch portion 2015 adheres to or lies on the front (palm) or ventral side 2005, the second patch portion 2020 adheres to or lies on the back or dorsal side 2006 while the bridge 2025 wraps around the edge 2011 of the hand 2010. In accordance with an aspect of the present specification, a first electrode is disposed in the first patch portion 2015 to stimulate the C8 dermatome on the ventral side 2005 and a second electrode is disposed in the second patch portion 2020 to stimulate the C8 dermatome on the dorsal side 2006 of the hand 2010.

In some embodiments, the neuro-stimulation devices 2000, 2000' are configured such that the underlying electronic circuitry including the power management module are disposed on one of the first or second patch portions 2015, 2020. Thus, referring to FIGS. 1A, 20A, 20B the neuro-stimulation device 110 is configured or disposed as patches 2000, 2000' of FIGS. 20A, 20B such that the microcontroller 112, transceiver 114, pulse generator 116, the power management module 120 including the receptor slots 130, actuators 122 and the indicators 124, 126 are located on either the first or the second patch portions 2015, 2020. In one embodiment, the microcontroller 112, transceiver 114, pulse generator 116, the power management module 120 including the receptor slots 130, actuators 122 and the indicators 124, 126 are located on the second patch portion 2020 i.e., the patch portion that adheres to the back or dorsal side 2006 of the hand 2010 to avoid damage to the electronic components from daily use.

In other embodiments, the neuro-stimulation devices 2000, 2000' are configured such that the underlying circuitry and the power management module are distributed between the first and second patch portions 2015, 2020. Thus, referring to FIGS. 1A, 20A, 20B the neuro-stimulation device 110 is configured or disposed as patches 2000, 2000' of FIGS. 20A, 20B such that the microcontroller 112, transceiver 114, pulse generator 116 the power management module 120 including the receptor slots 130, actuators 122 and the indicators 124, 126 are distributed and therefore physically separated between the first and second patch portions 2015, 2020 to improve flexibility of the neuro-stimulation devices 2000, 2000'. In one embodiment, the microcontroller 112, transceiver 114, pulse generator 116, actuators 122 and the indicators 124, 126 are located on, say, the first patch portion 2015 (that adheres to the ventral or palm side 2005 of the hand 2010) whereas the power management module 120 including the receptor slots 130 is located on the second patch portion 2020 (that adheres to the dorsal or back side 2006 of the hand 2010). In another embodiment, the microcontroller 112, transceiver 114, pulse generator 116, actuators 122 and the indicators 124, 126 are located on, say, the second patch portion 2020 (that adheres to the dorsal or back side 2006 of the hand 2010) whereas the power management module 120 including the receptor slots 130 is located on the first patch portion 2015 (that adheres to the ventral or palm side 2005 of the hand 2010).

Still referring to FIGS. 1A, 20A, 20B, in one embodiment, the first and second electrodes 118 as well as the sensors 135 are disposed on the first patch portion 2015 i.e., the patch portion that adheres to the front (palm) or ventral side 2005 of the hand 2010. In another embodiment, the first and second electrodes 118 are disposed on the first patch portion 2015 while the sensors 135 are located on the second patch portion 2020. In yet another embodiment, the first and second electrodes 118 are disposed on the second patch portion 2020 while the sensors 135 are located on the first patch portion 2020. In still further embodiments, the first and second electrodes 118 are respectively disposed on the first and second patch portions 2015, 2020 while the sensors 135 are located on either the first or the second patch portion 2015, 2020.

It should be noted that while in various embodiments, the neuro-stimulation devices of FIGS. 19A, 19B, 19C, 20A and 20B have been illustrated as being placed at locations on the hand of the user, in various alternate embodiments these neuro-stimulation devices may be placed at other points to stimulate the C5-C8 and/or T1 dermatomes on the user's arms or upper chest regions as well.

Thus, in accordance with some aspects of the present specification, electrical stimulation to a depth ranging from 0.1 mm to 30 mm of the patient's dermis (using the neuro-stimulation device 110 of FIG. 1A) provides for treatment of appetite suppression, ghrelin production modulation, eating disorders, excessive weight or over-weight, obesity, metabolic syndrome and diabetes. In various embodiments, a stimulation depth through the patient's skin ranges from 0.1 mm to 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 mm or any increment therein.

Mechanisms of Action

The therapeutic objectives of the presently disclosed embodiments may be effectuated by one or more of the following mechanisms of action. In a first mechanism of action, the pain of hunger is negated, operating under one or more predefined stimulation parameters. Small diameter nerve fibers carry pain stimuli through a theoretical "gate mechanism" but larger diameter nerve fibers can inhibit the transmission of pain stimuli by the smaller nerves, in effect blocking or closing this theoretical gate. It is believed that by stimulating the large nerve fibers, the gate can be closed to block the pain and thereby block any sensation of hunger. In a second mechanism of action, the production of endorphins, which are natural pain relieving hormones produced by the body, may be upregulated or increased, operating under one or more predefined stimulation parameters, again thereby blocking any sensation of hunger.

In a third mechanism of action, the present embodiments, operating under one or more stimulation parameters, causes a somato-somatic, somato-autonomic and/or a somato-visceral reflex with resulting afferent central as well as efferent visceral effects. In various embodiments, electrical stimulation through the dermis of the dermatomes disclosed herein creates a somato-autonomic reflex with sensory nerves that connect specifically to the stomach as an efferent pathway. As a consequence of this parasympathetic stimulation, the stomach slows down its emptying process and increases the feeling of fullness or satiation, which translates into a reduction in appetite. Similarly, in various embodiments, electrical stimulation through the dermis of certain dermatomes, such as the T7 dermatome, also creates a somato-autonomic reflex with sensory nerve endings to dermatome T7 as an afferent pathway and parasympathetic branches of the sensory nerves which stimulate the pancreatic gland as an efferent pathway.

In a fourth mechanism of action, the present application discloses a method of modifying an individual's perception of food, or otherwise undermining their association of positive feelings with food, and thereby increasing his or her aversion to food intake comprising: providing a percutaneous electrical dermal patch adapted to adhere to the patient's epidermal layer, wherein said electrical dermal patch comprises a controller, at least one electrode adapted to be implanted into said patient's skin, and a pulse generator in electrical communication with the controller and said at least one electrode, defining a plurality of stimulation parameters, and programming the pulse generator to generate a plurality of electrical pulses using said plurality of stimulation parameters, wherein said plurality of stimulation parameters are defined such that, after applying at least one stimulation to the patient's nerves, the patient has an increased aversion to food intake. In this regard, the stimulation parameters may be defined such that a) the stimulation is painful, b) the stimulation is coordinated with, and automatically triggered during, the person's actual food intake times, such times being programmed into the controller or pulse generator either directly or from an external device and automatically triggering a stimulation at the appropriate times, c) the stimulation is coordinated with, and automatically triggered during, times of day other than the person's actual food intake times, such times being programmed into the controller or pulse generator either directly or from an external device and automatically triggering a stimulation at such times, and d) the stimulation is manually triggered at any given time by the patient, either directly via an interface on the PEDP or via the external device, as the patient may require. The benefit of this method is that it achieves, in addition to the physiological effects of appetite modulation, the psychological effect of associating a negative sensation (electrical stimulation) with food intake, thereby undermining the otherwise positive associations the individual has with food and, therefore, one of the key psychological impetuses for compulsive eating. In this regard, the present invention achieves an aversion to food intake, in addition to a decrease in appetite.

In a fifth mechanism of action, the presently disclosed embodiments selectively cause electrical central nervous stimulation over electrical spinal stimulation. Electrical stimulation in the perceptive range is central (sensory) and in the non-perceptive range is spinal (autonomic). Electrical stimulation above a sensation reaction threshold results in selective central stimulation while electrical stimulation below the sensation reaction threshold results in selective spinal stimulation. Therefore, determining the sensation reaction threshold in a patient allows for the adjustment of electrical stimulation parameters for selective central or spinal stimulation to modulate the patient's appetite level.

Figure 21A:
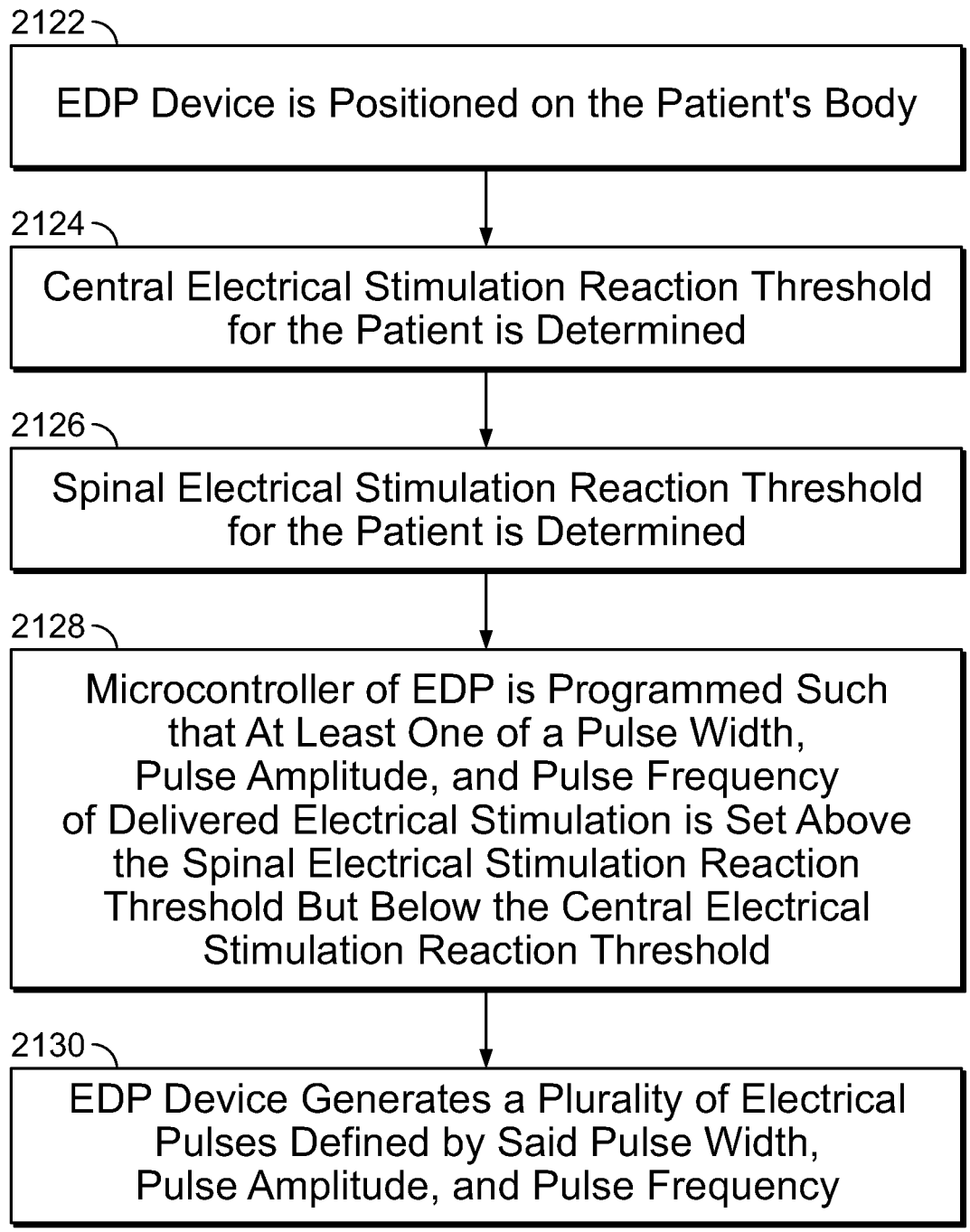
FIG. 21A is a flow chart illustrating the steps involved in a method of determining stimulation reaction thresholds and using a percutaneous electro-dermal patch (PEDP) device to suppress appetite in a patient, in various embodiments of the present specification.

FIG. 21A is a flow chart illustrating the steps involved in one embodiment of a method of determining stimulation reaction thresholds and using a percutaneous electro-dermal patch (PEDP) device to suppress appetite in a patient. At step 2122, the PEDP device is positioned on the patient's body, such that the at least one electrode can be implanted just underneath the patient's skin. In various embodiments, the PEDP device is either self-implanted by the patient himself or is implanted by a physician or medical personnel. At step 2124, a central electrical stimulation reaction threshold for the patient is determined. Then, at step 2126, a spinal electrical stimulation reaction threshold for the patient is determined. A microcontroller of the PEDP device is then programmed, at step 2128, such that at least one of a pulse width, pulse amplitude, and pulse frequency of delivered electrical stimulation is set above the spinal electrical stimulation reaction threshold but below the central electrical stimulation reaction threshold. At step 2130, the PEDP device then generates a plurality of electrical pulses defined by the pulse width, pulse amplitude, and pulse frequency set at step 2128.

Figure 21B:
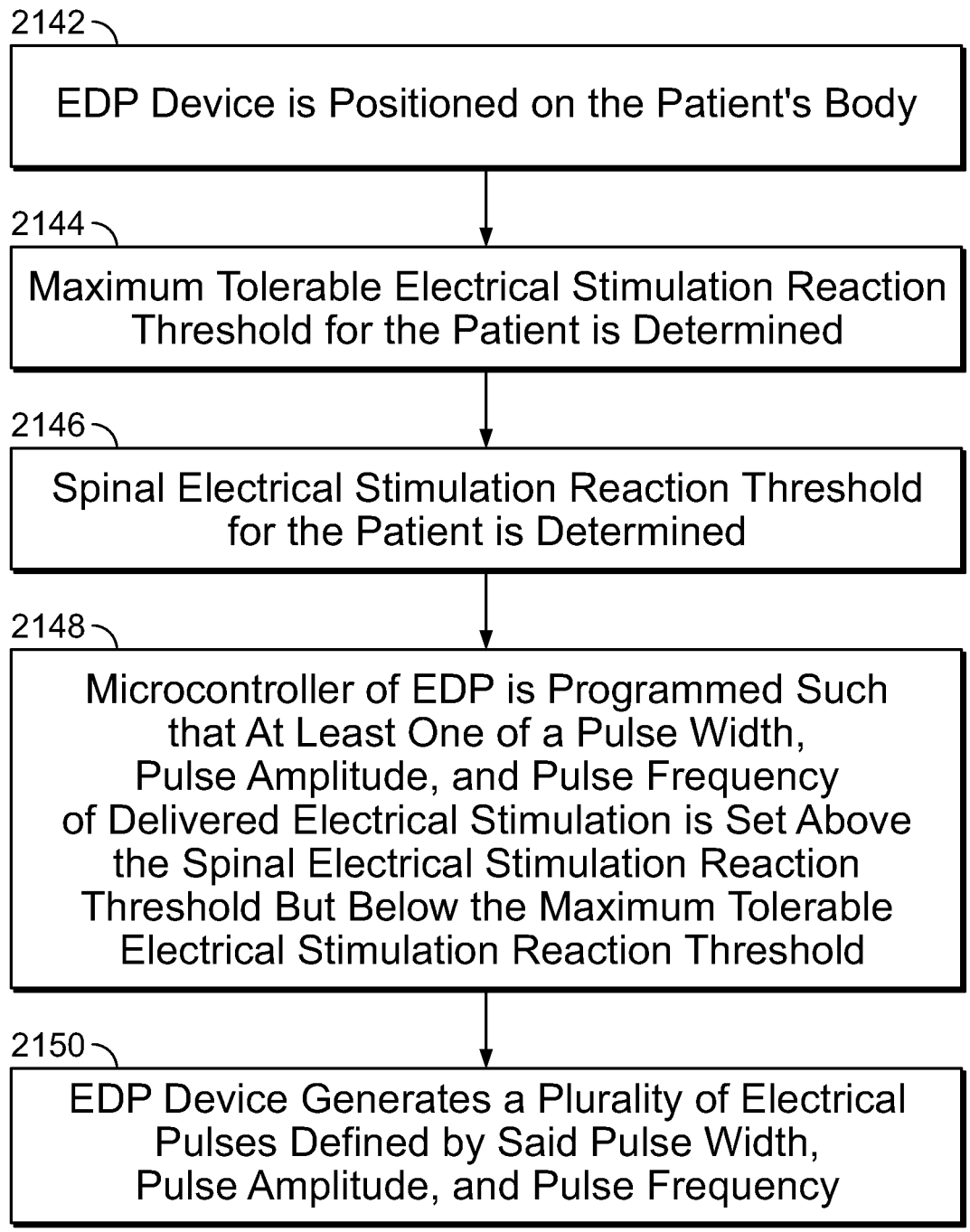
FIG. 21B is a flow chart illustrating the steps involved in a method of determining stimulation reaction thresholds and using a PEDP device to suppress appetite in a patient, in various embodiments of the present specification.

FIG. 21B is a flow chart illustrating the steps involved in another embodiment of a method of determining stimulation reaction thresholds and using a percutaneous electro-dermal patch (PEDP) device to suppress appetite in a patient. At step 2142, the PEDP device is positioned on the patient's body, such that the at least one electrode can be implanted just underneath the patient's skin. In various embodiments, the PEDP device is either self-implanted by the patient himself or is implanted by a physician or medical personnel. At step 2144, a maximum tolerable electrical stimulation reaction threshold, which can be measured as a pain sensation, for the patient is determined. Then, at step 2146, a spinal electrical stimulation reaction threshold for the patient is determined. A microcontroller of the PEDP device is then programmed, at step 2148, such that at least one of a pulse width, pulse amplitude, and pulse frequency of delivered electrical stimulation is set above the spinal electrical stimulation reaction threshold but below the maximum tolerable electrical stimulation reaction threshold. At step 2150, the PEDP then generates a plurality of electrical pulses defined by the pulse width, pulse amplitude, and pulse frequency set at step 2148.

In a sixth mechanism of action, the percutaneous electro-dermal patch (PEDP) devices of the present specification stimulate specific dermatomes as described above to modulate ghrelin and suppress appetite. The gastric mucosa plays a role in ghrelin-induced gastric contractions. Intrinsic primary afferent neurons (IPAN), which comprise multi-axonal interneurons, may be involved in passing signals from the mucosa to the myenteric plexus. Ghrelin may stimulate and modulate gastric contractions through cholinergic, adrenergic, serotonergic, and/or opioidergic actions and/or via nitric oxide synthase in the myenteric plexus. The stimulatory effects of ghrelin on gastric motility are mediated by the direct stimulation of the intrinsic enteric neural pathway and capsaicin-sensitive afferent neurons. There exists a close interaction between ghrelin and enteric neurotransmission, involving the stimulation of the excitatory neural system and/or the suppression of the inhibitory neural system via ghrelin receptors, under stimulation of the intrinsic neural pathways. Ghrelin secretion during fasting is induced by adrenergic agents (locally released norepinephrine), released by sympathetic neurons acting directly on B1 receptors on ghrelin secreting cells of the stomach, resulting in fasting-induced elevation in plasma ghrelin levels.

Sympathetic stimulation at certain dermatomes, such as dermatome T6, causes a somato-visceral arc reflex which causes inhibition of the B1 adrenergic (sympathetic) neurons that produce ghrelin. This results in a decrease in ghrelin levels. This decrease in ghrelin causes activity in the enteric nervous system and intrinsic primary afferent neurons contained in the gastric mucosa (necessary as a final step in ghrelin's action on gastric and antral motility).

Therefore, in various embodiments of the present specification, the PEDP devices are believed to suppress appetite via the following mechanism. To begin, a PEDP device delivers electrical stimulation to the cutaneous nerves at dermatome T6 (or any of the other dermatomes described in the present specification), activating the somato-visceral reflex described above. In some embodiments, the PEDP device delivers electrical stimulation to the cutaneous nerves at dermatomes T5-T10. Stimulation of the B1 adrenergic plexus (neurons), which is inhibitory in nature, results in decreased production of fasting ghrelin. This leads to decreased activity in the enteric nervous system and in intrinsic primary afferent neurons (responsible for the final steps necessary for ghrelin action on gastrointestinal motility). The decreased plasma ghrelin levels result in appetite suppression as well as decreased gastric motility and decreased gastric emptying time.

Figure 33A:
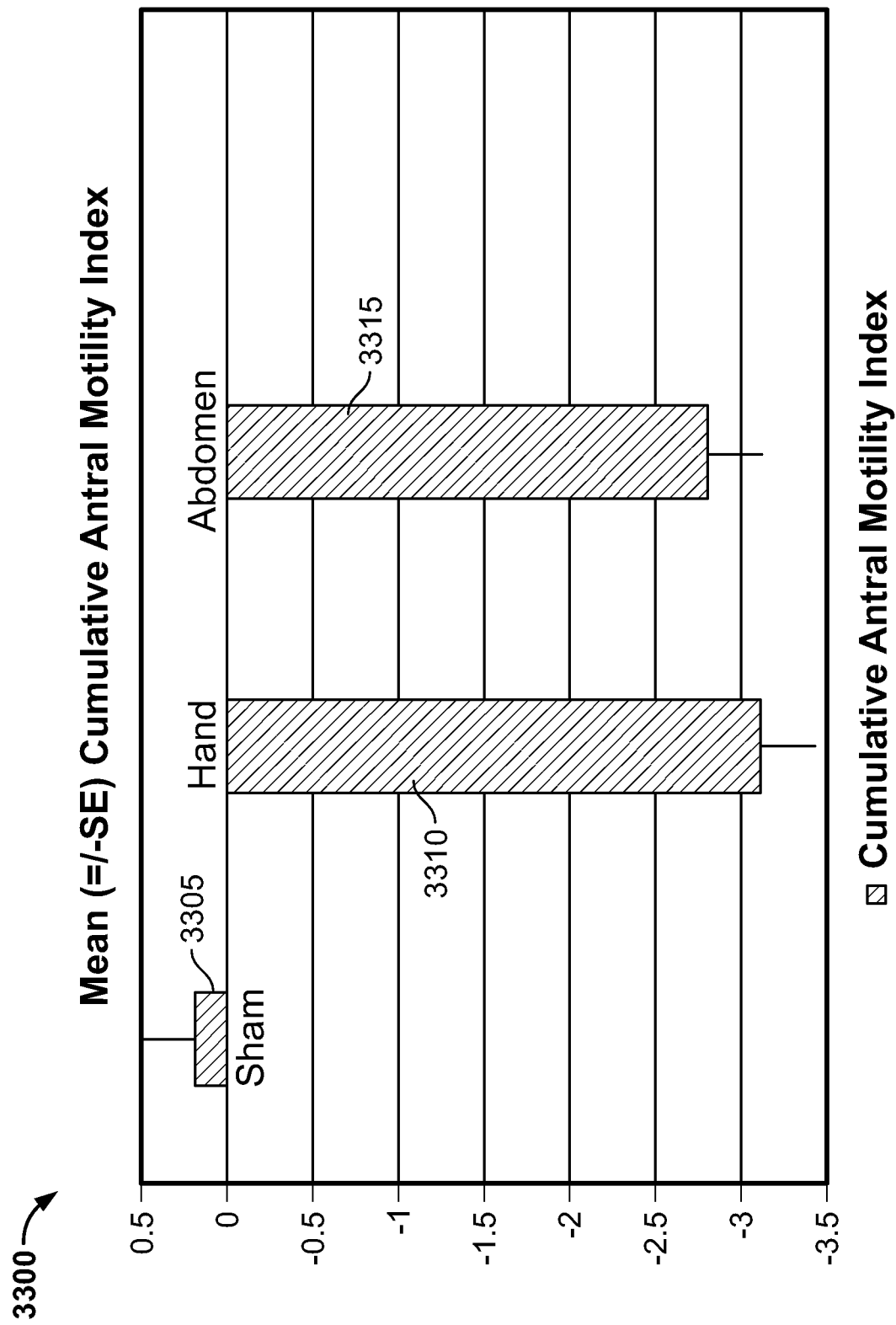
FIG. 33A is a bar graph illustrating mean cumulative changes of antral motility indices for various stimulation sessions, in accordance with an embodiment.
Figure 33B:
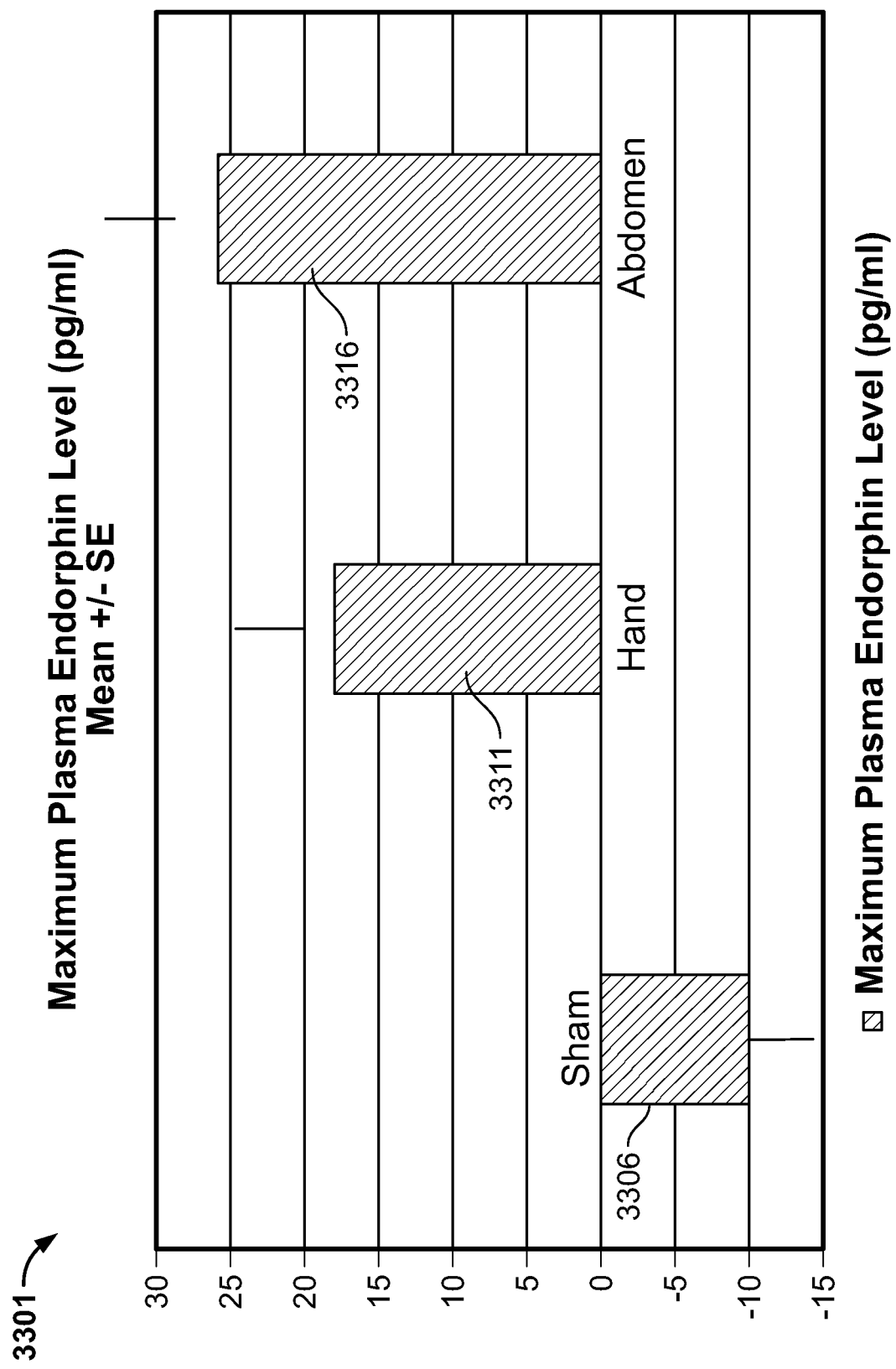
FIG. 33B is a bar graph illustrating maximum plasma endorphin levels measured for various stimulation sessions, in accordance with an embodiment.

In a sixth mechanism of action, the percutaneous electro-dermal patch (PEDP) devices of the present specification use electrical stimulation to effect a reduction in antral activity resulting in reduction in gastric motility and slowing of gastric emptying. Somatic stimulation of the T2-T12 and/or C5-T1 dermatomes, using the neuro-stimulation device of the present specification, affects modulation of the gastro-intestinal phasic pressure activity resulting in reduction in antral motility and an increase in plasma beta-endorphin levels. Thus, somatic stimulation causes reduced post-prandial antral phasic pressure activity, slowing of gastric emptying and therefore a feeling of satiety over increased periods of time between meals. FIG. 33A is a chart 3300 illustrating mean cumulative changes (in 20 minutes increments) of antral motility indices during sham stimulation sessions 3305, stimulation sessions 3310 targeted to hand dermatomes C8 and/or T1 and stimulation sessions 3315 targeted to thoracic dermatomes T2-T12. Note the effect on antral motility of the hand and abdomen stimulation sessions. FIG. 33B is a chart 3301 illustrating maximum plasma endorphin levels in µg/ml related to sham stimulation sessions 3306, stimulation sessions 3311 targeted to hand dermatomes C5-C8 and/or T1 and stimulation sessions 3316 targeted to thoracic dermatomes T2-T12. Note the increase in endorphin levels as a result of the hand and abdomen stimulation sessions. In additional mechanisms of action, the percutaneous electro-dermal patch (PEDP) devices of the present specification use electrical stimulation to modulate gut microbiota to improve the ratio of favorable to unfavorable gut bacteria, modulate secretions of a plurality of hormones such as serotonin, glucagon-like peptide 1 (GLP1), and leptin, reduce serum levels of lipopolysaccharide (LPS), improve metabolic inflammation and insulin resistance, modulate resting metabolic rate (RMR) and by improving glucose homeostasis. The specific therapeutic objectives related to each of the above listed hormones and other physiological markers are further discussed below.

Stimulation Patterns/Protocols to Drive Therapy

As discussed earlier, the user's plurality of health related information, such as the user's hunger profile, standard eating and meals profile, actual eating and meals profile, energy balance, weight trends, glucose data, stimulation induced nausea, dyspepsia and habituation events—is utilized by the Health Management application to suggest and/or implement a plurality of recommendations comprising stimulation patterns or protocols, medication (such as an amount of insulin intake, for example), dietary and/or activities plans. It should be appreciated that this integrated system provides users with a degree of independence and encourages patient compliance. Notwithstanding the above, however, the present application does apply to having physicians set or modify the stimulation protocols, either directly programming the PEDP, programming the PEDP through the companion device, or remotely communicating a desired protocol from a remote server or third party computing device to either the PEDP directly or via the companion device.

In various embodiments, recommendations related to stimulation patterns or protocols comprise driving, setting, customizing or adjusting a plurality of stimulation parameters such as, but not limited to, the number of stimulation sessions per day; duration of each stimulation; time or moment of application of the stimulation sessions; intensity of stimulations, stimulation pulse shape, frequency, width and amplitude; stimulation duty cycle; stimulation continuity profile; minimum and maximum overall duration or course of stimulation treatment in days, weeks or months. Following are exemplary standard setting ranges for some of the stimulation parameters:

Pulse Width: 10 µsec to 10 msec
Pulse Amplitude: 100 µA to 500 mA, less than 60 mA, 100 µA to 500 mA, 1 mA to 30 mA, 15 mA to 30 mA, 5 mA to 45 mA, and any increment therein
Pulse Frequency: 1 Hz to 10,000 Hz, preferably 1 Hz to 100 Hz
Pulse Shape: Monophasic, biphasic, sinusoidal
Duty Cycle: 1% to 100%
Stimulation Session Duration: 1 min to 120 min or 50 ms to 120 min or substantially continuously
Number of Stimulation Sessions/Day: 1 to 24
Number of Sessions/Week: 1 to 168 or 1 to substantially continuously
Daily Pre-Prandial Stimulations: half hour to an hour prior to each meal every day, as most patients typically report hunger peaking just prior to meals
Burst Mode (that is, a burst of programmable pulses at a rate): 0.1 Hz to 100 Hz
Ramp Up/Down Mode (that is, the time it takes to go from no stimulation to a peak or steady state (Ramp Up) and the time it takes to go from peak or steady state stimulation to no stimulation (Ramp Down)): 0.1 sec to 60 sec
Modulated Mode: Range between 1%-100% amplitude, modulating up/down over a period of 0.1 sec-60 sec; modulation can be linear or sinusoidal; that is, in "modulated mode" the amplitude varies between 1% and 100% of a target amplitude (such as 10 mA) and this amplitude variation occurs over a period of 0.1 seconds to 60 seconds
Electrode impedance (that is, the electrode-tissue interface impedance): 100 ohms to 5 kilo-ohms, 10 ohms to 5 kilo-ohms, 200 ohms to 1000 ohms, or 1 kilo-ohms to 100 kilo-ohms In some embodiments, the neuro-stimulation device provides electrical stimulation having the following parameters which are adjustable by the patient using the companion device:

Monophasic pulse shape with an active charge balancing phase
Pulse Width: 25 µsec to 400 µsec in steps of 25 µsec
Pulse Amplitude: 1 mA to 50 mA in steps of 1 mA
Pulse Frequency: from 1 Hz, 5 Hz, 10 Hz, 15 Hz, 20 Hz, 25 Hz, 30 Hz, 40 Hz, 50 Hz, 60 Hz, 70 Hz, 80 Hz, 90 Hz, 100 Hz, 150 Hz, 200 Hz
Stimulation Session Duration: from 5 min to 60 min in steps of 5 min In some embodiments, the neuro-stimulation device provides electrical stimulation having the following parameters which are adjustable by the patient using the companion device:

Pulse Width: 100 µsec to 500 msec, preferably 10 µsec to 100 msec
Pulse Amplitude: 1 µA to 1 mA
Pulse Frequency: 0.1 Hz to 1 kHz Stimulation Session Duration: 1 min to 24 hr
Number of Stimulation Sessions/Day: 1 to 24
Number of Sessions/Week: 1 to substantially continuously It should be appreciated that any initial or default stimulation parameters, which are implemented upon starting the device and without the benefit of any user input regarding their appetite, hunger, satiety level, satiation level, fullness level, well-being status, nausea status or other information, may be universally fixed for all persons or may be based upon any one or a combination of the following parameters of the person: age, gender, ethnicity, weight, body mass index, body fat percentage, and/or race. Therefore, stimulation dosing may be initially based on categorizing the individual into one or more template groups and choosing a corresponding protocol. For example, one may classify individuals into various groups (a BMI greater than 40, a BMI of 35 to 39, a BMI of 30 to 34, and a BMI of 25 to 29) and apply a standard stimulation scheme for all individuals within that classification. The same could apply to a combination of age and gender for example (females 65 and over, females 55 to 64, females 45 to 54, females 35 to 44, females 25 to 34, females 24 and under, males 65 and over, males 55 to 64, males 45 to 54, males 35 to 44, males 25 to 34, males 24 and under). Additionally, the initial stimulation settings may be based on any parameters indicative of the patient's extent of appetite, or hunger, satiety level, satiation level, or fullness level.

It should further be appreciated that any selected stimulation parameters may be titrated for a given patient. Specifically, they may be adjusted upward or downward based on the amount of stimulation felt by the patient and/or immediately reported feelings of pain, nausea, or other discomfort.

In some embodiments, the stimulation continuity profile may be, for each stimulation session duration the stimulation profile applied, continuous; intermittent including short intervals of Y seconds of no stimulation; step-up stimulation wherein the stimulation amplitude and/or frequency increases at a predefined rate from commencement to completion of a stimulation session duration; or step-down stimulation wherein the stimulation amplitude and/or frequency decreases at a predefined rate from commencement to completion of a stimulation session duration. In some embodiments, the stimulation continuity profile may vary on a day to day basis. For example, for a treatment duration of, say, 4 weeks the stimulation profile applied may be at least one of continuous wherein the number and/or intensity of stimulation does not vary throughout the treatment; step-up stimulation wherein the intensity and number of sessions per day increase at a predefined rate on a daily or weekly basis; step-down stimulation wherein the intensity and number of sessions per day decrease at a predefined rate on a daily or weekly basis.

In some embodiments, the time or moment of application of stimulation sessions may be, for example, 't' minutes before meals such as breakfast, lunch, snack, dinner, wherein T is within a range of 1 min to 150 min; right before going to bed; at the onset of hunger and/or right before an expected hunger event based on the user's recorded hunger profile.

In accordance with an aspect of the present specification, the user as well as the remote patient care facility or personnel are able to control and adjust the plurality of stimulation parameters through the Health Management application and/or by the user via actuators 122 such as buttons or switches of FIG. 1A. In some embodiments, the remote patient care facility or personnel is authorized to control and adjust all stimulation parameters while the user is enabled to control and adjust a subset of the stimulation parameters with or without authorization/approval of the remote patient care facility or personnel. For example, the user may be allowed to change the number of stimulation sessions per day from, for example, 2 sessions per day to 1 session per day; stimulation session duration from, for example, 30 minutes to 15 minutes; and/or stimulation pulse amplitude from, for example, 20 mA to 150 µA. In one embodiment, the maximum change is limited to a predefined amount or multiple of the prior settings.

In a preferred embodiment, the user is able to increase the stimulation pulse amplitude from a minimal default amplitude setting of, say, 100 µA to a 'sensory threshold' corresponding to amplitude where the user can just feel the stimulation. The user may then save the 'sensory threshold' setting and continue stimulation at this setting. The sensory perception varies from person to person and therefore in various embodiments the 'sensory threshold' ranges from about 5 mA to 10 mA on the lower side and from about 20 mA to 30 mA on the higher side.

In some embodiments, a stimulation protocol includes alternating stimulation sessions between a first session having a low pulse frequency, for example, less than 50 Hz, followed by a second session having a high pulse frequency, for example, greater than 50 Hz.

In still further embodiments, the user may be able to control and adjust the subset of stimulation parameters within the standard settings ranges, such as those described above, or within a narrower band of range or constrained range within the standard settings ranges. For example, the user may be allowed to modify the stimulation pulse width, amplitude and frequency by no more than +/−50% from the original, default or standard setting. In another example, the user may be allowed to modify all stimulation parameters by +/−10% (from the original, default or standard setting) except for allowing the amplitude to decrease unbounded in order to address safety and/or comfort reasons User modification of the stimulation parameters beyond the constrained range may require authorization from the remote patient care facility or personnel. In some embodiments, the range within which the user is able to control and adjust the subset of stimulation parameters is set by the remote patient care facility or personnel. Also, in some embodiments, the user may be allowed to control and adjust stimulation parameters within a first range at the onset of therapy, but as therapy progresses (for example, after 2 to 3 weeks) the user is allowed to control and adjust stimulation parameters within a second range wherein the second range is narrower, limited or constrained compared to the first range.

It should be appreciated that the type and number of stimulation parameters that the user is allowed to control and adjust can vary in multiple embodiments.

In accordance with an aspect of the present specification, the Health Management software application provides a plurality of pre-configured default or standard stimulation protocols to drive therapy for a plurality of conditions such as obesity, over-weight, eating disorders, metabolic syndrome or appetite suppression and T2DM, as examples.

Example Stimulation Protocols for Treating Conditions of Obesity, Over-Weight, Eating Disorders, Metabolic Syndrome or Appetite Suppression and/or T2DM In various embodiments, a standard stimulation protocol, for stimulating the T6, C8 and/or T1 dermatome for treating conditions of obesity, over-weight, eating disorders, metabolic syndrome or for appetite suppression and the T7 dermatome for treating T2DM, may comprise a plurality of pre-configured standard settings such as at least three setting options, for example mild, optimal, intense. For example, an embodiment of a standard optimal stimulation protocol comprises two 30 minute sessions a day, 30 to 45 minutes before lunch and right before bed or after a specific time, say, after 8 or 9 pm, at an intensity that doesn't bother patient, but can still be felt by them, such as at a frequency of 20 Hz and at a 'sensory threshold' amplitude of 10 mA. A standard mild stimulation protocol comprises one 20 minute session a day, 30 to 45 minutes before lunch or right before bed or after a specific time, say, after 8 or 9 pm, at a frequency of 20 Hz and at a 'sensory threshold' amplitude of 5 to 35 mA. A standard intense stimulation protocol comprises three 30 minute sessions a day, 30 to 45 minutes before lunch, right before bed and also after a specific time, say, after 8 or 9 pm, at a frequency of 40 Hz and at a 'sensory threshold' amplitude of 10 mA. In some embodiments, a latency effect is encountered with stimulation wherein the stimulation is provided for a specific amount of time and the effect is not witnessed until a certain amount of time has passed and/or the effect remains for a certain amount of time post stimulation. For example, in one embodiment, ghrelin remains suppressed for at least several weeks post stimulation.

Some embodiments additionally comprise a custom setting option that allows the user to adjust or set the subset of stimulation parameters, which he is allowed to control, within constrained ranges. It should be appreciated that the number of pre-configured settings (such as mild, optimal, intense) may vary across various embodiments. Also, the stimulation protocol, with its mild, optimal and intense configurations, is only exemplary and may vary across various embodiments and for targeting specific conditions such as only appetite suppression or T2DM. For example, a stimulation protocol directed towards ghrelin modulation, and therefore appetite modulation, may include a stimulation pulse width of 200 μsec, pulse amplitude corresponding to the user's 'sensory threshold' such as 20 mA, pulse frequency of 20 Hz, stimulation session duration of 30 minutes and one session per day for 4 weeks. Another example stimulation protocol directed towards appetite suppression may include a 15 minutes stimulation session, using a current frequency of 6 Hz of 0.1 milliseconds (ms) duration starting at intensities of 1 to 20 milliampere (mA) until the intensity reaches the user's 'sensory threshold'.

In accordance with an aspect of the present specification, the Health Management application recommends and periodically adjusts the stimulation protocols or patterns based on the user's health related information, such as the user's hunger profile, standard eating and meals profile, actual eating and meals profile, energy balance, weight trends, glucose data and stimulation induced nausea, dyspepsia, habituation events. For example, if the user's energy balance is positive by about 5% beyond a pre-defined positive energy balance threshold at a certain calories consumption schedule per day, as dictated by the user's standard regular eating and meals profile, and the user is also found to be over-weight or obese, the Health Management application may suggest commencing with the optimal stimulation protocol for two weeks along with an activities regiment comprising, for example, daily or weekly goals of walking, exercising, running, swimming directed towards increasing the user's calories expenditure. The Health Management application monitors compliance of the user to the recommended optimal stimulation protocol and the activities regimen throughout the two weeks. The user's resulting energy balance and compliance profile is recorded and displayed to the user in the form of charts, graphs, tables or any other visual format as would be advantageously evident to persons of ordinary skill in the art. At the commencement or throughout the duration of the therapy, the Health Management application may also recommend a standard or customized dietary plan to the user as part of a holistic approach to improving effectiveness of the stimulation therapy. For example, Table 3 shows a 1200 Kcal/day customized diet plan (from a plurality of such diet plans pre-stored within the Health Management application) recommended by the Health Management application:

TABLE 3

| Mean values of carbohydrates 51%; proteins 23%; fats 26% | |
|---|---|
| Meal | Contents |
| Breakfast | Skimmed milk 200 cc or 2 natural skimmed yoghourts<br>Bread 50 g or 2 toasts of "biscotti" type bread |
| Mid-morning | Fruit (one piece, 100 g of apple, pear, orange, melon or kiwi) |
| Meal and dinner | Main course to choose from:<br>Vegetables 200 g: spinach, chard, eggplant, watercress, endive, lettuce, cauliflower, mushroom, leek, asparagus, escarole, cabbage, cucumber, peppers, tomatoes, alternating cooked or in a salad, or 150 g of green beans, beet, carrot, artichoke or Brussels sprouts<br>Vegetable soup<br>Skimmed broth (free consumption)<br>Andalusian gazpacho, provided it is prepare without bread and a small amount of oil, remembering not to exceed the ration of oil for the whole day<br>Pasta, semolina, rice or tapioca soup (15 g dry)<br>Second course to choose from:<br>White fish 120 g<br>Chicken, turkey, rabbit, veal meat 100 g<br>Eggs, one unit<br>Tomatoes and lettuce salad (or any other raw vegetable) 150 g only once a day<br>Dessert, to choose from:<br>Fruit (one piece, 100 g of apple, pear, orange, kiwi, melon or 200 g of watermelon)<br>Bread 25 g |

TABLE 3-continued

Mean values of carbohydrates 51%; proteins 23%; fats 26%

| Meal | Contents |
|---|---|
| Afternoon snack | 200 cc of skimmed milk, just milk or with coffee or tea |
| Oil for all day | 30 cc (2 soup spoons) |

If the user's energy balance and/or weight trend shows improvement, for example the energy balance reduces up to or below the positive energy balance threshold and/or the rate of weight reduction is within pre-defined acceptable limits, the Health Management application may recommend the user to shift to the mild stimulation protocol for the next two weeks. On the other hand, if the user's energy balance and/or weight trend deteriorates or remains same as at the commencement of the stimulation therapy due the user's non-compliance to the activities regimen (as a result of which the user is not burning a requisite amount of calories), for example if the user's energy balance is found to be positive by about M %, wherein M %>L % and/or the rate of weight reduction is below the pre-defined acceptable limits or there is no significant weight reduction, the Health Management application may recommend the user to shift to the intense stimulation protocol for the next two weeks.

Various embodiments also comprise allowing on-demand stimulation in addition to or in lieu of the standard stimulation protocol pre-configured settings (for example mild, optimal, intense). On-demand stimulations, also referred to hereinafter as "rescues", are applied at the onset of unplanned hunger events and/or at a potential occurrences of hunger events as known from the user's hunger profile. While the user is allowed on-demand stimulations as well as customized stimulation protocols, in various embodiments the Health Management application is programmed to ensure (such as by continuous monitoring, limited or restricted control access to only the subset of stimulation parameters and/or restricting the user control access to only a constrained range within the standard settings ranges) that the user does not over or under stimulate, thereby resulting in habituation or ineffective stimulation. For example, the user may be allowed to add to the number of daily sessions, over and above those scheduled based on the standard protocol settings (mild, optimal, intense), but subject to some limitations or restrictions. For example, the user may have five additional "rescues" in the first month of the stimulation therapy, declining to 4 daily in the second month, and 3 daily in the third month of therapy. It should be appreciated that the limitations are critical to avoiding habituation over time. Also, the number of stimulation sessions may be restricted and then may decline and/or the stimulation intensity, such as the amplitude and frequency, may be allowed to be adjusted up or down by a set amount, for example by +/−10%.

In some embodiments, the Health Management application is configured to be in communication with an insulin pump that the user may be using to infuse insulin while the neuro-stimulation device of the present specification uses a continuous glucose sensor, as one of the sensors 135 of FIG. 1A, to monitor the user's glucose level. Thus, for example if the user's glucose level is higher than the normal, by a predefined glucose threshold, the Health Management application may recommend commencing with the optimal stimulation protocol along with a diet plan, such as that illustrated in Table 3, for a period of 2 weeks. In various embodiments, a predefined glucose threshold comprises a fasting blood sugar level greater than 80 mg %. The Health Management application continuously monitors the user's glucose levels during the therapy and allows the user to suppress post-prandial glucose levels. When it is found that, due to the stimulation therapy, the user's glucose levels are gravitating towards normal levels the Health Management application communicates this information to the user's insulin pump to slow the insulin delivery/infusion. As discussed earlier, the stimulation protocol may be adjusted to mild or intense depending upon the effect on the glucose levels of the user.

In some embodiments, the neuro-stimulation device of the present specification is sized in the form of a percutaneous skin patch that covers both of the T6 and T7 dermatomes. In alternate embodiments, the user may use a first percutaneous electro-dermal patch on the T6 dermatome and a second percutaneous electro-dermal patch on the T7 dermatome. In such cases, the Health Management application alternatingly stimulates the T6 and T7 dermatomes to treat conditions of obesity, over-weight, eating disorders, metabolic syndrome as well as T2DM. In some embodiments, the neuro-stimulation device of the present specification is sized to cover both of the C8 and T1 dermatomes (as shown in FIG. 19C). In alternate embodiments, the user may use a first neuro-stimulation device on the C8 dermatome and a second neuro-stimulation device on the T1 dermatome. In such cases, the Health Management application alternatingly stimulates the C8 and T1 dermatomes to treat conditions of obesity, over-weight, eating disorders, metabolic syndrome. In various embodiments, a plurality of neuro-stimulation devices of the present specification are used to cover T6, T7, C8 and/or T1 dermatomes that are simultaneously or alternatingly stimulated to conditions of obesity, over-weight, eating disorders, metabolic syndrome and/or T2DM.

It should be noted, that the various suggestions and recommendations auto generated by the Health Management application, for initial fresh stimulation protocols, patterns and parameter settings as well as those related to adjusting these stimulation protocols and settings may, in various embodiments, be implemented by the user only after an approval and advice from the remote patient care facility and/or personnel. In some embodiments, however, prior approval from the remote patient care facility or personnel may not be required. The Health Management application enables the user to set an option of prior approval or disable this option.

In some embodiments, the neuro-stimulation device is driven by stimulation algorithms having different stimulation parameters to treat conditions of obesity, over-weight, eating disorders, metabolic syndrome by first enabling the patient to lose excess weight and then maintain the weight loss. For example, in one embodiment, the patient is stimulated with a first stimulation algorithm to induce weight loss. Once the patient has reached a target weight, the stimulation algorithm is changed to a second stimulation algorithm to maintain the weight loss. In some embodiments, the total stimulation energy per day provided by the first algorithm to induce weight loss is greater than the total stimulation energy per day provided by the second algorithm to maintain weight loss.

Example Stimulation Protocols for Managing Habituation, Nausea, Dyspepsia, and Skin Irritation Habituation refers to a decrease in sensory perception of a stimulus after prolonged presentation of the stimulus. In various embodiments of the present specification, in order to overcome habituation, the stimulation intensity is designed to gradually increase or decrease throughout the entire therapy session, in contrast to prior art practices of requiring the patient to manually increase or decrease intensity periodically during the therapy session. The present specification also learns the manner and frequency of the manual adjustment of the desired stimulation intensity so as to customize the stimulation parameters that modify stimulation in order to combat habituation.

In accordance with an exemplary embodiment, the stimulation intensity (comprising the pulse amplitude and/or frequency) is increased or decreased arithmetically (that is, linearly) or geometrically (that is, exponentially) with time. It should be noted, that an increase in the stimulation intensity is always above the user's 'sensory threshold' (which is already determined prior to stimulation sessions) and a decrease in the stimulation therapy is constrained in that the stimulation intensity is not allowed to fall below the 'sensory threshold'. As an example, for geometric increase or decrease, the stimulation intensity is multiplied or divided by a fixed factor per unit time. For example, the stimulation intensity may be geometrically increased or decreased by a factor Z, wherein Z is say 1.004 as an example, for every minute of a therapy session. This equates to an approximately 27% increase or decrease in stimulation intensity over a 60 minute therapy session. In various embodiments, 'Z' comprises a 10% to 50% increase or decrease of any given parameter. In another embodiment, the stimulation intensity is linearly increased or decreased by a fixed amount, such as 0.5 mA, for every minute of the therapy session. In another embodiment, the rate of increase or decrease is adjusted to account for manual changes in the stimulation intensity. For example, if the user decreases the stimulation intensity in the middle of the therapy session, then the automatic rate of increase may be too high for this user and should be decreased for subsequent therapy sessions. Similarly, if the user increases the stimulation intensity in the middle of the therapy session, then the automatic rate of increase may be too low for this user and should be increased for subsequent therapy sessions. In this fashion, the automatic habituation compensation is adaptive and responsive to the user's physiology.

In further embodiments, the stimulation continuity profile may be a step-up or a step-down profile wherein the stimulation amplitude and/or frequency may increase or decrease on a per session basis and/or the number of stimulation sessions per day may increase or decrease throughout the duration of a stimulation therapy or course to combat habituation.

In various embodiments, if the user feels nausea or dyspepsia during and/or after stimulation sessions he may provide an input to the Health Management application that a nausea and/or dyspepsia event occurred which is then automatically time stamped and stored by the application. Resultantly, the Health Management application may modify an existing stimulation protocol, for example may recommend switching the current intense stimulation protocol to the mild stimulation protocol. Additionally or alternatively, the stimulation continuity profile may be switched to the step-down profile. Still further, the Health Management application may recommend pausing the stimulation sessions for one or more days before restarting with a step-down stimulation protocol.

In accordance with another exemplary embodiment, the neuro-stimulation device of the present specification generates biphasic, symmetrical, rectangular pulses with regulated current. This pulse waveform is charge-balanced which prevents iontophoretic build-up under the electrodes that can lead to skin irritation and potential skin damage. Regulated current pulses provide more stable stimulation than regulated voltage pulses, because the stimulation current is independent of the electrode-skin impedance, which typically changes during the course of a therapy session. In order to address a wide variety of skin types and electrode quality (due to repeat use and air exposure), the maximum output voltage is 100V and the maximum output current is 50 mA. Finally, the pulse pattern is continuous stimulation with randomly varying inter-pulse intervals such that the frequency of stimulation has a uniform probability distribution between 50 Hz and 150 Hz. Alternatively, the frequency of stimulation may have a Gaussian probability distribution between 50 Hz and 150 Hz, or some other probability distribution. The benefit of providing frequency stimulation with randomly varying inter-pulse intervals (versus frequency stimulation with constant inter-pulse intervals) is that the former type of stimulation may lead to less nerve habituation.

Still further embodiments may involve relocating the neuro-stimulation device from the first stimulation spot to a second spot and alternating between the first and second stimulation spots to avoid habituation, skin irritation, nausea and/or dyspepsia.

Method of Use

In accordance with various aspects of the present specification, the PEDP device is configured to be self-implanted or self-administered by the user or implanted by a physician or medical personnel.

For self-implantation, as described earlier with reference to FIG. 1G, the user places the PEDP on the skin at an appropriate site or location to deploy a retractable needle, included on the bottom surface of the PEDP that touches the user's skin, that punctures the skin and is thereafter retracted leaving behind an electrically conductive catheter or lumen underneath the skin. In accordance with another embodiment, for self-implantation by the user, the one or more electrodes (such as the one or more electrodes 118 of FIG. 1A, for example) are configured as an array of micro-needles that enable a patient-friendly intradermal stimulation delivery solution as described earlier with reference to FIG. 1H.

In accordance with another aspect, the PEDP of the present specification is implanted by a physician or medical personnel using a percutaneous electrode insertion system (such as the system 230 described earlier with reference to FIG. 2C).

In accordance with some embodiments, for self-implantation of the PEDP, the user is enabled to apply or use the neuro-stimulation device of the present specification with no or minimal intervention from a physician. In some embodiments, the user visits his physician for just one session wherein, depending upon the user's medical condition, the physician may prescribe the neuro-stimulation device of the present specification to the user along with the stimulation depth configuration, from 0.1 mm to 60 mm, and preferably 0.1 mm to 30 mm of the dermis, of the neuro-stimulation device, as described with reference to FIG. 1A through 1F. In various embodiments, a stimulation depth through the patient's epidermal layer ranges from 0.1 mm, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2, to 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60 or any increment therein. During the session, the physician instructs the user in identifying appropriate areas of stimulation, such as T6, C8 and/or T1 dermatomes for conditions of obesity, overweight, eating disorders, metabolic syndrome and T7 for T2DM management, and also provides an orientation to the user regarding use and functions of the neuro-stimulation device. In various embodiments, the appropriate areas of stimulation may be identified, for example, by one or more temporary tattoos (such as a small dot) or an image of the user may be taken with a mark or icon locating the appropriate area on the user's body. During the session, the physician may further help the user to download the Health Management application on the user's computing device, such as his smartphone, tablet, PDA, laptop, computer and demonstrate pairing or syncing of the application to the user's computing device. The user may at this time or at a later time enable the Health Management application to be in communication with the physician or a remote patient care facility.

In various embodiments, therapy provided by the percutaneous electro-dermal patch (PEDP) devices of the present specification is driven or triggered by a plurality of variables. These variables can be entered by the patient or a medical professional into the companion device, sensed by a sensor on the PEDP, transmitted to the companion device or PEDP by a separate device, for example, a device, with physiological sensors, configured to be worn on the human body, such as around the wrist, in order to monitor, acquire, record, and/or transmit the physiological data, or can be acquired by a combination of any of the above means. In various embodiments, the variables are stored, preset, and/or measured or input on a regular, predetermined basis or time period. In some embodiments, the variables include primary variables which comprise primary drivers to any therapy regimen and secondary variables which comprise secondary indicators which may or may not affect the regimen. Some variables, such as weight in pounds, are entered into the patient diary based on their actual value while other variables, such as hunger, appetite and satiety, are given a score based on a predefined score value range or a scale such as the Visual Analogue Scale (VAS). The treatment algorithm of the companion device analyzes these scores in comparison to predefined limits and automatically modifies therapy accordingly. In some embodiments, the algorithm analyzes these scores on a daily basis. In other embodiments, the algorithm analyzes the scores every other day, every third day, every fourth day, every fifth day, every sixth day, or once per week. In various embodiments, the score values range from 0 to 100. In a preferred embodiment, the score values range from 1 to 10 and, more preferably, from 1 to 5 or 1 to 3, depending on the variable. In some embodiments, a high numerical score value indicates electrical stimulation therapy provided by the PEDP is inadequate and additional stimulation is needed. A lower numerical score value indicates electrical stimulation therapy provided by the PEDP is excessive and stimulation needs to be reduced. Conversely, in other embodiments, a high numerical score value indicates stimulation is excessive and needs to be reduced and a low numerical score value indicates stimulation is inadequate and needs to be increased. In some embodiments, a numerical score value proximate the middle of the score range indicates therapy is appropriate and can remain unchanged.

In one embodiment, the system uses one or more of the following triggers to initiate stimulation or modulate stimulation settings: a patient's glycemic level, metabolism levels, hemoglobin A1c, and/or blood sugar. Using physiological sensors or external devices which already measure metabolism, blood sugar, glycemic levels, or hemoglobin A1c, the companion device gathers such data, integrates it with existing patient status data, and generates a modulated stimulation setting, which may include a signal to initiate therapy, change therapy or cease therapy, based on an integrated patient status data profile. In one embodiment, a patient's increased blood sugar levels cause the stimulation settings to be modulated upward in order to increase the rate, frequency, or overall amount of stimulation. In another embodiment, changes in the patient status data, including increases or decreases in metabolism, blood sugar, glycemic levels, or hemoglobin A1c, may cause the companion device to recommend moving the PEDP to a different location on the patient's body to stimulate a different dermatome, such as from C8 on the hand to T1 or, for example, from T7 in the abdominal area to T6.

In some embodiments, therapy is driven by a set of three primary drivers. The primary drivers include: hunger, which is defined as the patient's desire to eat; appetite, defined as how much food the patient eats in relation to a diet plan (also considered caloric intake); and well-being, defined as simply how good the patient feels. In some embodiments, well-being is further subdivided specifically into feelings of nausea, dyspepsia, discomfort, energy level, and weakness/strength. Each of these primary drivers can be attributed a score which is entered into the companion device, as depicted in FIGS. 11, 13, and 16.

For example, for hunger, referring to FIG. 13, the patient can enter a hunger score from 1 to 5, wherein 1 indicates the patient is not hungry at all, 2 indicates the patient is almost never hungry, 3 indicates the patient is not particularly hungry, 4 indicates the patient is frequently hungry, and 5 indicates the patient is extremely hungry most of the time. In some embodiments, a hunger score having a higher numerical value indicates appetite suppression is inadequate and the patient requires greater stimulation. The treatment algorithm of the companion device recognizes the need for greater stimulation as indicated by the higher score and titrates therapy accordingly. For example, in one embodiment, if the patient enters a hunger score greater than 3 in the patient diary over a period of four to seven consecutive days within the first week, the algorithm uses the score to incrementally increase the duration of each stimulation session. If after three weeks the patient enters a hunger score greater than 3 in the patient diary for 3 consecutive days, the algorithm uses the score to increase the number of stimulation sessions per day. Conversely, a lower hunger score indicates stimulation needs to be decreased. For example, if the patient enters a hunger score of 1 for three consecutive days within the first week, stimulation sessions are decreased in duration and frequency. In other embodiments, the hunger score scale extends from 1 to 10.

In other embodiments, rather than a scale to determine the presence or absence of hunger, the system presents the patient with a scale configured to record changes in his hunger after stimulation. For example, in an embodiment, a hunger change score scale extends from 1 to 3 wherein 1 is indicative of no change, 2 is indicative of some change, and 3 is indicative of significant change in hunger after stimulation. If a patient reports a 1, no change in hunger after stimulation, stimulation parameters are increased.

For appetite, referring to FIG. 11, the patient can enter an appetite score from 1 to 5, wherein 1 indicates the patient ate substantially less than his diet, 2 indicates the patient ate a little less than his diet, 3 indicates the patient followed his diet, 4 indicates the patient somewhat exceeded his diet, and 5 indicates the patient substantially exceeded his diet. As with the hunger score discussed above, in some embodiments, an appetite score having a higher numerical value indicates appetite suppression is inadequate and the patient requires greater stimulation. The treatment algorithm of the companion device recognizes the need for greater stimulation as indicated by the higher score and titrates therapy accordingly. For example, in one embodiment, if the patient enters an appetite score greater than 3 in the patient diary over a period of four to seven consecutive days within the first week, the algorithm uses the score to incrementally increase the duration of each stimulation session. If after three weeks the patient enters an appetite score greater than 3 in the patient diary for 3 consecutive days, the algorithm uses the score to increase the number of stimulation sessions per day. Conversely, a lower appetite score indicates stimulation needs to be decreased. For example, if the patient enters an appetite score of 1 for three consecutive days within the first week, stimulation sessions are decreased in duration and frequency. In other embodiments, the appetite scale extends from 1 to 10.

As discussed earlier, in some embodiments the plurality of variables, such as hunger, appetite, satiation level, fullness, satiety, and feelings of pain, nausea, or dyspepsia, that drive or trigger therapy are alternately assessed on at least one of a plurality of scientific VAS scales. Graphs 30A through 32F represent exemplary data which the inventors believe are indicative of the therapeutic benefits of the present inventions. It should be appreciated that data may be collected and compared on a per patient basis, both before and after stimulation, on a sample group of patients, both before and after stimulation, or by using two separate groups of patients, one subjected to stimulation and the other not subjected to stimulation (as a control). Therefore the post-stimulation benefits would be achieved regardless of whether one were comparing it to the same population of users before stimulation or to a different population of users acting as a control group.

FIGS. 30A through 30I are a set of graphs illustrating effects of stimulation on a feeling of hunger as assessed on a VAS (Visual Analogue Scale) in accordance with some embodiments, while FIGS. 37A through 37I are a set of graphs illustrating effects of stimulation on a feeling of satiety as assessed on a VAS in accordance with some embodiments. Referring to FIGS. 30A through 30E, in accordance with an embodiment, a sample of 5 patients, having weight loss as an objective or goal, were assessed for their feeling of hunger (using VAS) at a first occasion, corresponding to a pre-stimulation scenario wherein the 5 patients were not subjected to stimulation therapy, and at a second occasion, corresponding to a post-stimulation scenario wherein the 5 patients were subjected to stimulation therapy using a PEDP of the present specification.

In accordance with an embodiment, the 5 patients were assessed both pre- and post-stimulation using a VAS hunger questionnaire, such as the questionnaire of FIG. 35A, having a 100 mm VAS line. At the first occasion (pre-stimulation), each patient's responses or scores to the VAS hunger questionnaire were recorded at intervals of every 60 minutes starting from a first response or score 3006a through 3006e that, in one embodiment, is recorded just prior to a meal (such as breakfast) but without subjecting any of the patients to stimulation therapy. At the second occasion (post-stimulation), each patient's responses or scores to the VAS hunger questionnaire were again recorded at intervals of every 60 minutes starting from a first response or score 3007a through 3007e recorded just prior to the meal (such as breakfast) but after having treated each of the patients with stimulation therapy prior to, for example 30 minutes before, the meal. In accordance with an embodiment, the responses or scores related to the first occasion are recorded on a first day while those related to the second occasion are recorded on a second day, preferably at the same time of day and under the same eating or fasting conditions as the first day.

Figure 30A:
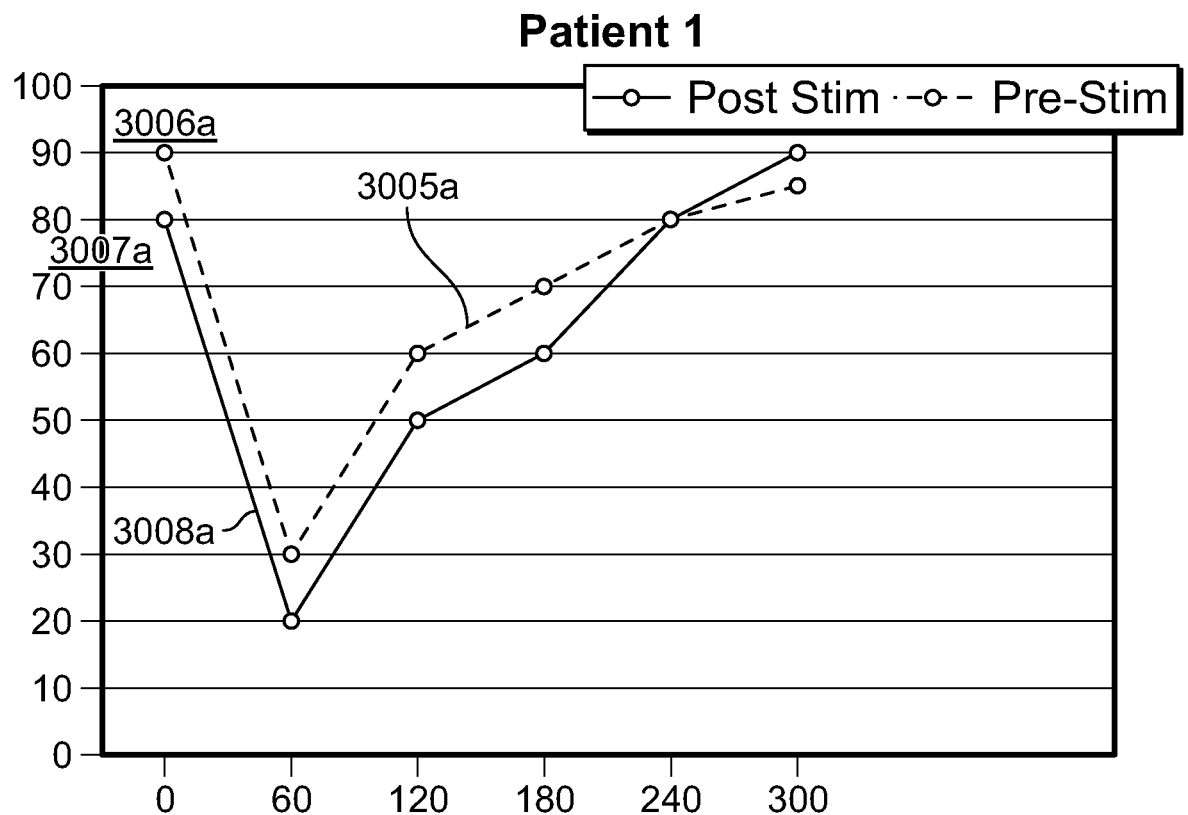
FIG. 30A is a graph illustrating pre-stimulation and post-stimulation hunger profiles of a first patient, in accordance with an embodiment.
Figure 30B:
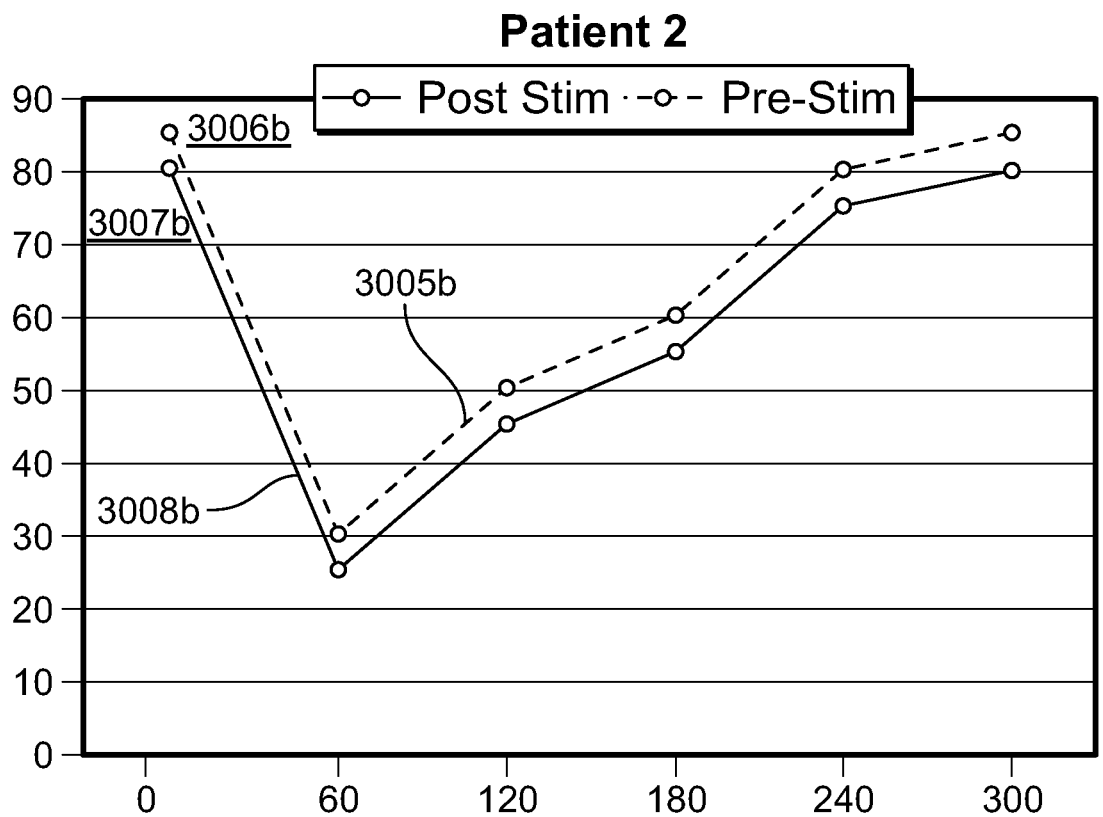
FIG. 30B is a graph illustrating pre-stimulation and post-stimulation hunger profiles of a second patient, in accordance with an embodiment.
Figure 30C:
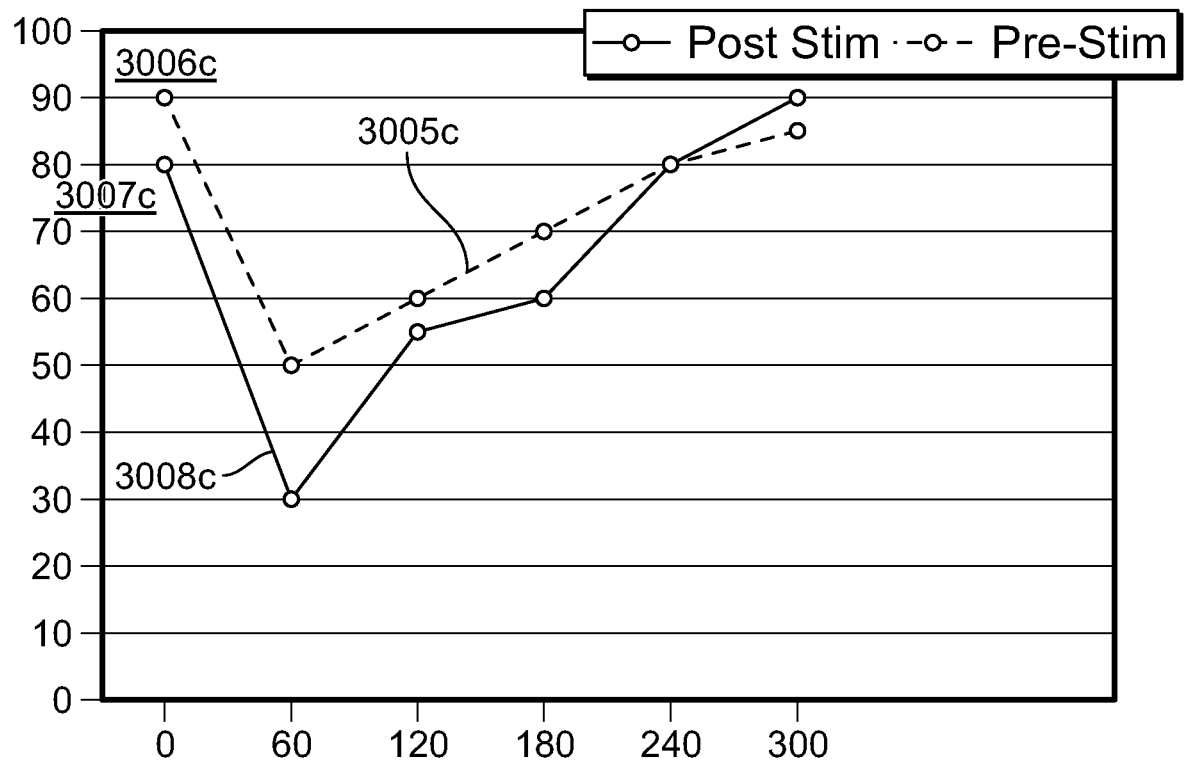
FIG. 30C is a graph illustrating pre-stimulation and post-stimulation hunger profiles of a third patient, in accordance with an embodiment.
Figure 30D:
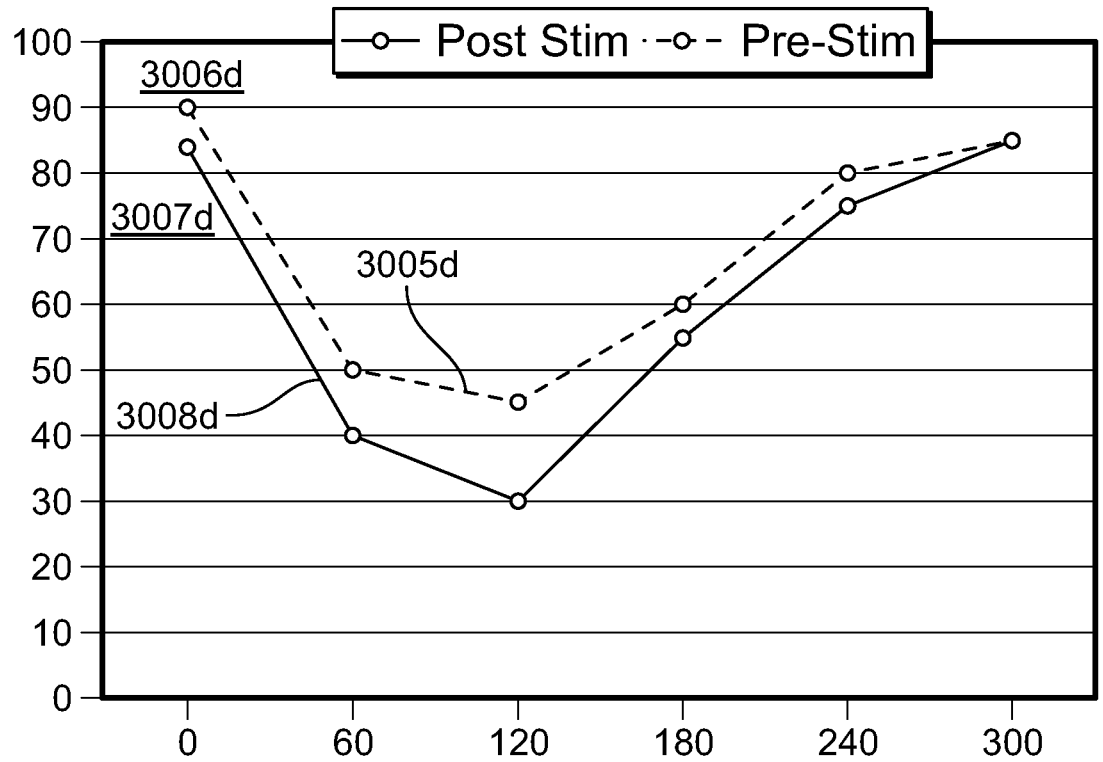
FIG. 30D is a graph illustrating pre-stimulation and post-stimulation hunger profiles of a fourth patient, in accordance with an embodiment.
Figure 30E:
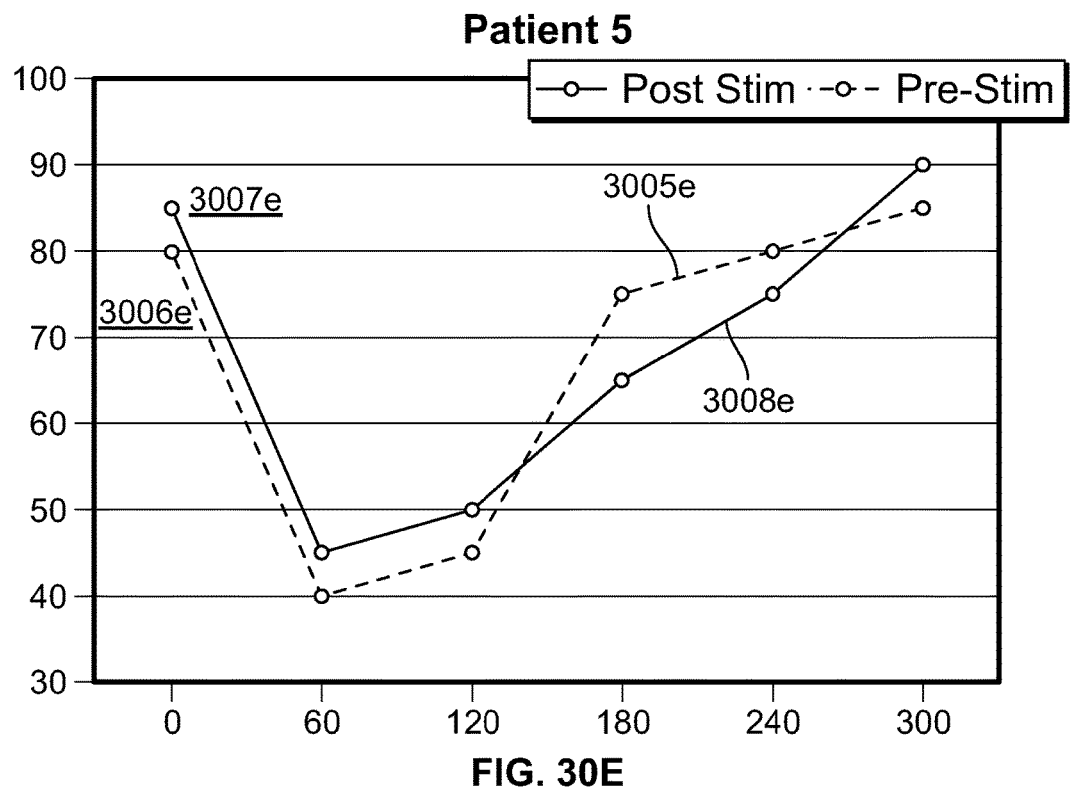
FIG. 30E is a graph illustrating pre-stimulation and post-stimulation hunger profiles of a fifth patient, in accordance with an embodiment.

As shown in FIG. 30A, the first patient's hunger responses or scores for the first occasion (that is, pre-stimulation) are recorded on a first day and plotted on a graph, whose x-axis represents time in minutes and y-axis represents VAS hunger responses or scores in millimeters, to generate a pre-stimulation hunger profile 3005a. Thereafter, the first patient is subjected to stimulation therapy, in accordance to embodiments of the present specification, and the hunger responses or scores for the second occasion (that is, post-stimulation) are also plotted on the graph to generate a post-stimulation hunger profile 3008a. Similarly, the second, third, fourth and fifth patients' responses or scores are recorded to generate the respective pre-stimulation hunger profiles 3005b, 3005c, 3005d, 3005e and the respective post-stimulation hunger profiles 3008b, 3008c, 3008d, 3008e as shown in FIGS. 30B through 30E. As can be observed from FIGS. 30A through 30E, the post-stimulation huger profiles 3008a, 3008b, 3008c, 3008d, 3008e reflect reduced hunger magnitude relative to the pre-stimulation hunger profiles 3005a, 3005b, 3005c, 3005d, 3005e. In some embodiments, the post-stimulation hunger profile of a patient reflects at least a 5% decrease in hunger magnitude relative to the patient's pre-stimulation hunger profile.

Figure 30F:
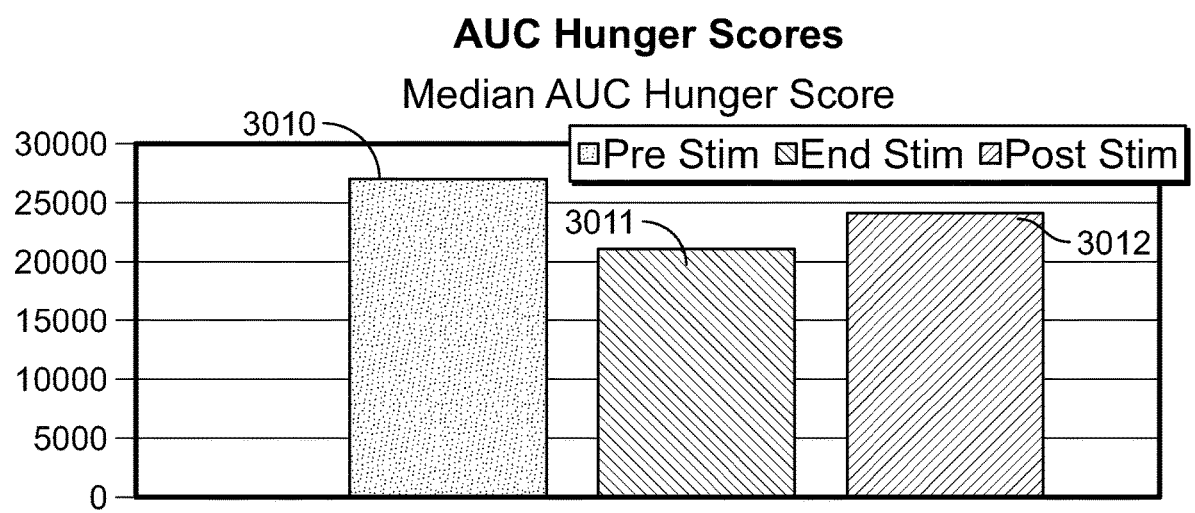
FIG. 30F is a graph illustrating median AUC (Area Under the Curve) hunger scores for pre-stimulation, end-of-stimulation and post-stimulation scenarios.

FIG. 30F shows a first bar 3010 representing a median area under curve (AUC) pre-stimulation hunger score. An AUC value is determined by calculating the area under the lines which define a given plotted profile. A second bar 3011 represents a median AUC end-of-stimulation hunger score derived from AUC values for end-of-stimulation hunger profiles (that is, the hunger profiles recorded starting immediately after the end of stimulation therapy) of the sample patients, and a third bar 3012 represents a median AUC post-stimulation hunger score derived from AUC values for post-stimulation hunger profiles of the sample patients. In various embodiments, end-of-stimulation is defined as the end of a period of stimulation lasting in a range from one session to a multitude of sessions over six months. In various embodiments, post-stimulation is defined as a time after the cessation of therapy and ranges from one day after cessation to six months after cessation. As shown in the figure, the median AUC hunger scores 3011, 3012 corresponding to end-of-stimulation and post-stimulation scenarios are reduced relative to the median AUC hunger score 3010 corresponding to the pre-stimulation scenario. In other words, the stimulation therapy of the present specification results in hunger suppression. In some embodiments, an area under the curve (AUC) of the post-stimulation hunger profile of a patient reflects at least a 5% decrease relative to the patient's AUC of the pre-stimulation hunger profile.

Figure 30G:
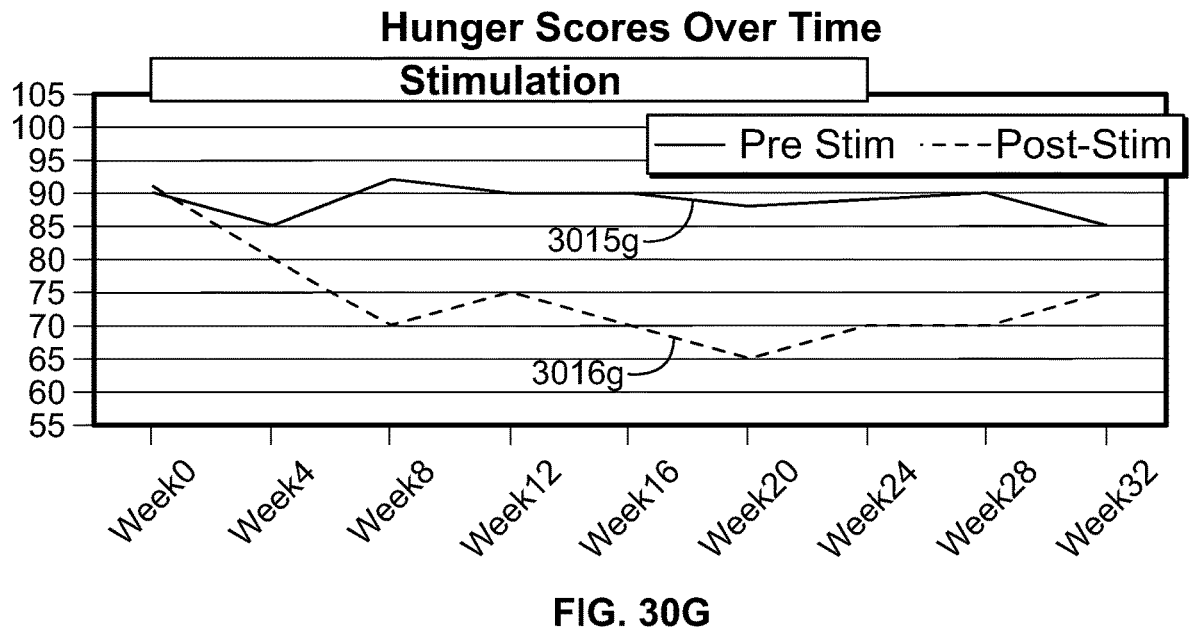
FIG. 30G is a graph illustrating pre-stimulation and post-stimulation hunger profiles over an extended period of time, in accordance with a first embodiment.
Figure 30H:
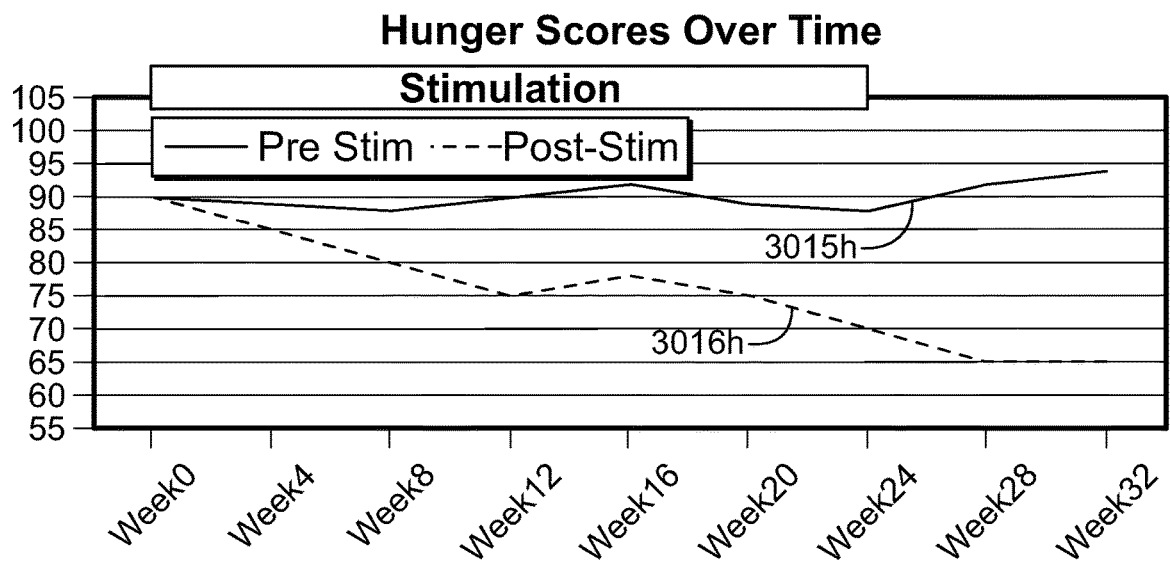
FIG. 30H is a graph illustrating pre-stimulation and post-stimulation hunger profiles over an extended period of time, in accordance with a second embodiment.

FIGS. 30G and 30H also illustrate reduced magnitude of hunger scores, for at least one patient, assessed post stimulation relative to those assessed pre-stimulation. FIGS. 30G and 30H are charts having x-axis representing time in weeks and y-axis representing hunger scores. FIG. 30G shows a pre-stimulation hunger profile 3015g relative to a post-stimulation hunger profile 3016g over extended period of times such as, in weeks and up to 32 weeks. Similarly, FIG. 30H also shows a pre-stimulation hunger profile 3015h relative to a post-stimulation hunger profile 3016h over the same extended period of times. As can be observed from the FIGS. 30G and 30H, the post-stimulation hunger profiles 3016g, 3016h show reduced hunger AUC and magnitude relative to the respective pre-stimulation hunger profiles 3015g, 3015h, even over extended periods of time.

Figure 30I:
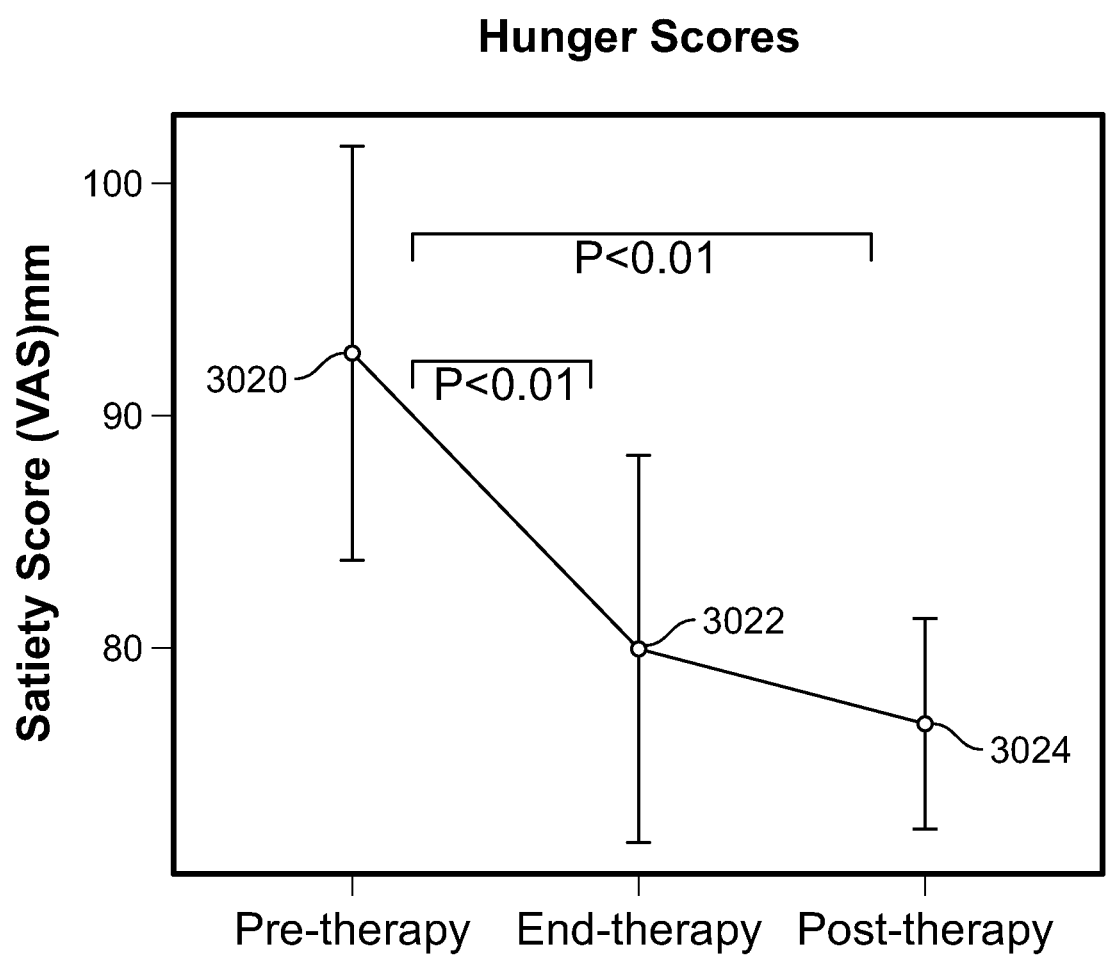
FIG. 30I is a graph illustrating hunger scores for pre-stimulation, end-of-stimulation and post-stimulation scenarios.

FIG. 30I is another graph showing a first median or average hunger score 3020 (assessed using the VAS hunger questionnaire, such as that of FIG. 29A) recorded on a first day prior to subjecting one or more patients to stimulation therapy (pre-stimulation scenario), a second median or average hunger score 3622 recorded at the end of subjecting one or more patients to stimulation therapy (end-of-stimulation scenario) and a third median or average hunger score 3624 recorded on a second day after having subjected one or more patients to stimulation therapy (post-stimulation scenario).

Referring now to FIGS. 31A through 31E, in accordance with an embodiment, a sample of 5 patients, having weight loss as an objective or goal, were assessed for their feeling of satiety (using VAS) at a first occasion, corresponding to a pre-stimulation scenario wherein the 5 patients were not subjected to stimulation therapy and at a second occasion, corresponding to a post-stimulation scenario wherein the 5 patient were subjected to stimulation therapy using a PEDP of the present specification.

In accordance with an embodiment, the 5 patients were assessed both pre and post stimulation using a VAS satiety questionnaire, such as the questionnaire of FIG. 29D, having a 100 mm VAS line. At the first occasion (pre-stimulation), each patient's responses or scores to the VAS satiety questionnaire were recorded at intervals of every 60 minutes starting from a first response or score 3106a through 3106e that, in one embodiment, is recorded just prior to a meal (such as breakfast) but without subjecting any of the patients to stimulation therapy. At the second occasion (post-stimulation), each patient's responses or scores to the VAS satiety questionnaire were again recorded at intervals of every 60 minutes starting from a first response or score 3107a through 3107e recorded just prior to the meal (such as breakfast) but after having treated each of the patients with stimulation therapy prior to, for example 30 minutes before, the meal. In accordance with an embodiment, the responses or scores related to the first occasion are recorded on a first day while those related to the second occasion are recorded on a second day, preferably at the same time of day and under the same eating or fasting conditions as the first day.

Figure 31A:
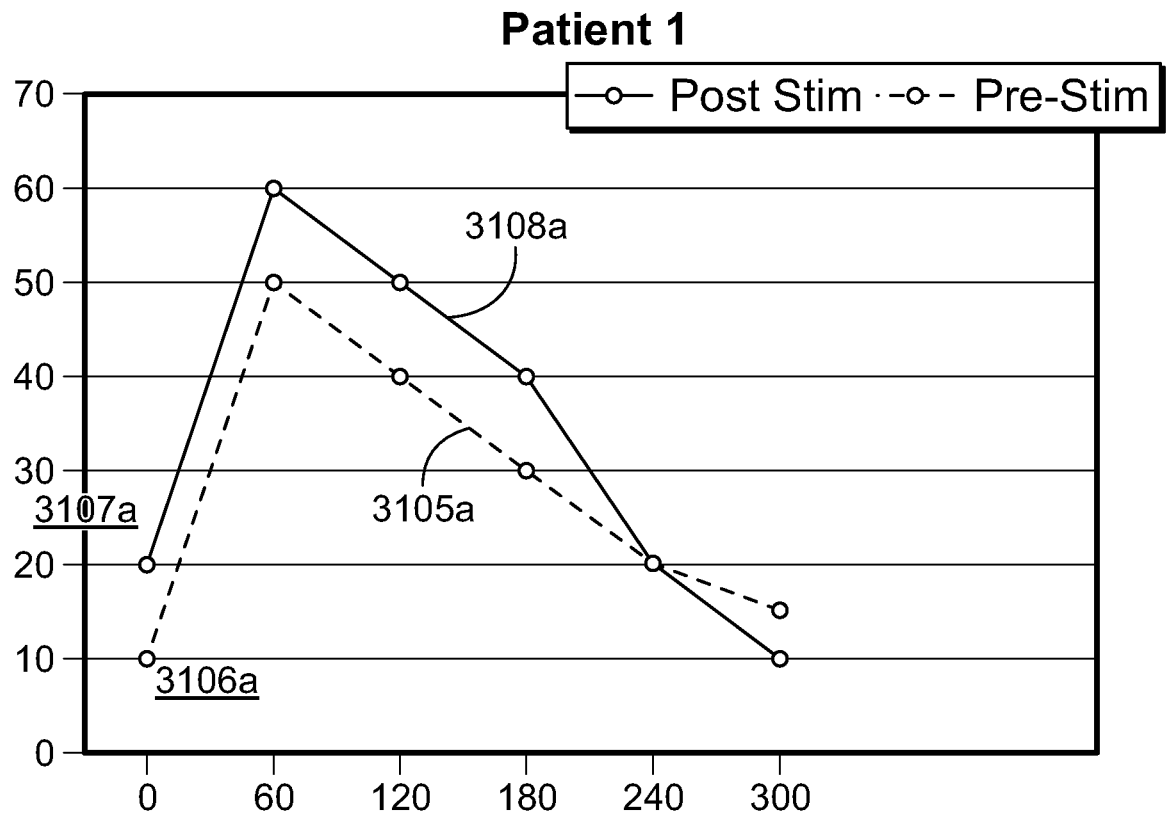
FIG. 31A is a graph illustrating pre-stimulation and post-stimulation satiety profiles of a first patient, in accordance with an embodiment.
Figure 31B:
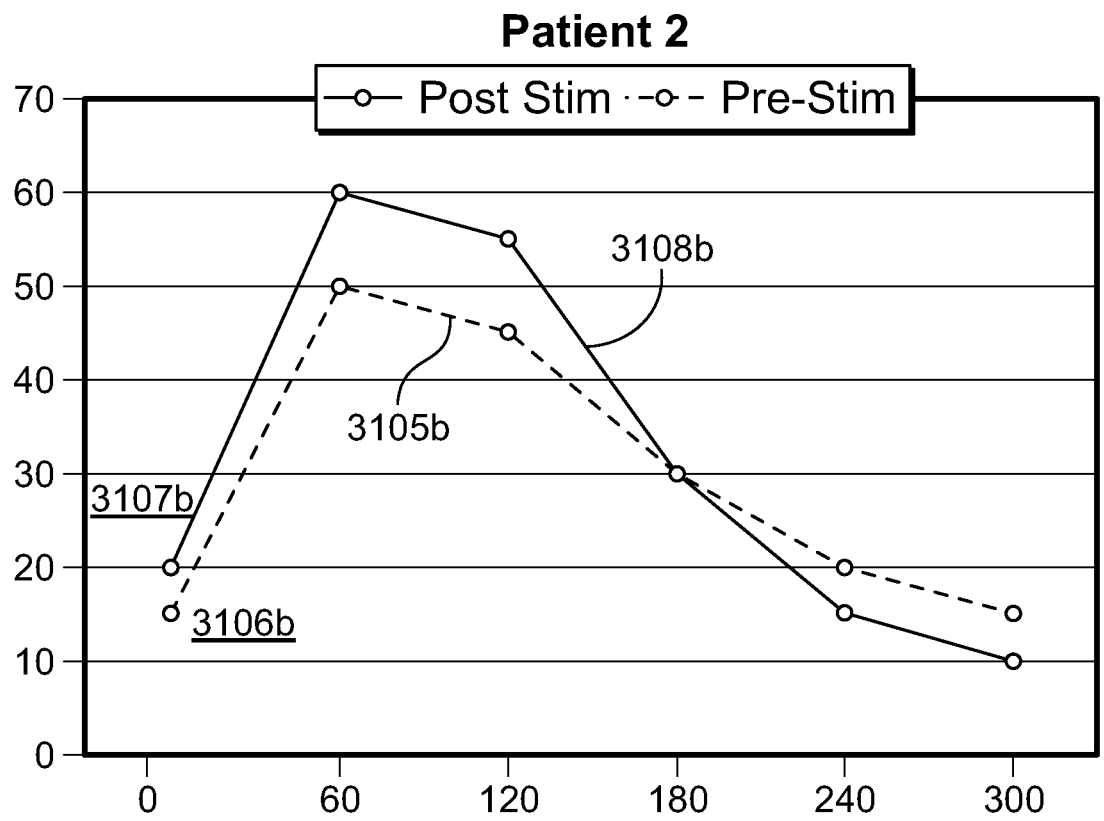
FIG. 31B is a graph illustrating pre-stimulation and post-stimulation satiety profiles of a second patient, in accordance with an embodiment.
Figure 31C:
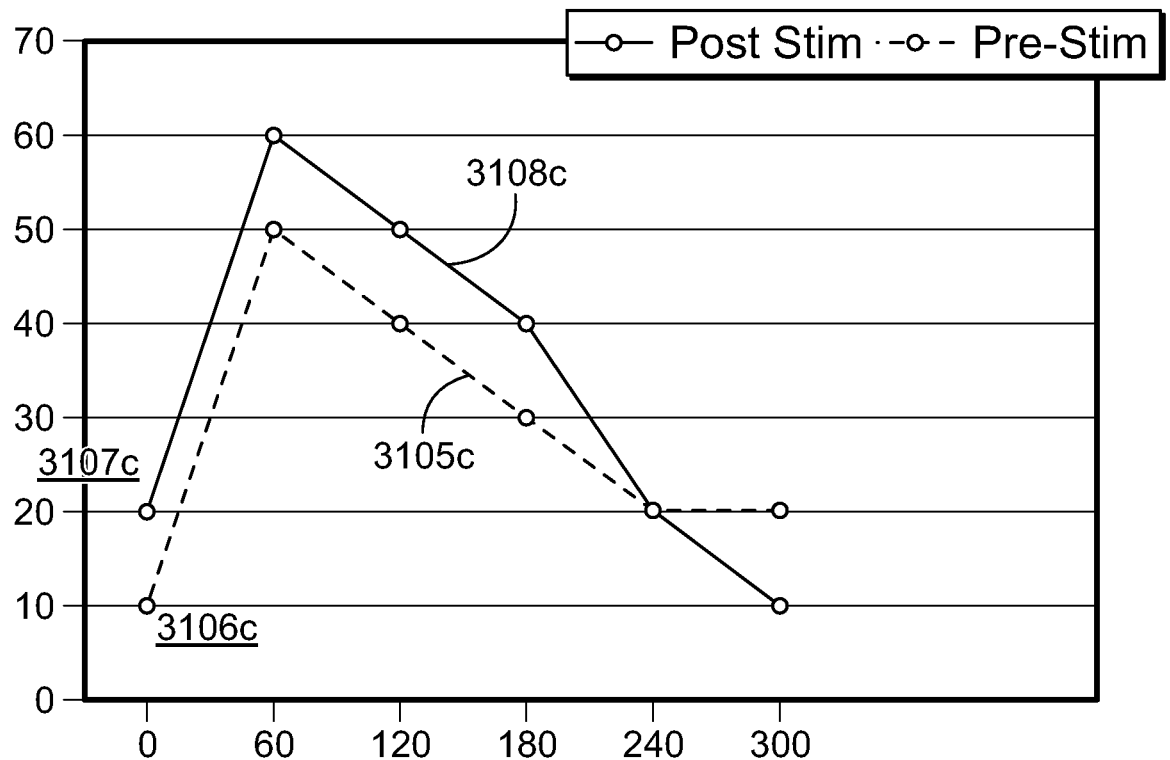
FIG. 31C is a graph illustrating pre-stimulation and post-stimulation satiety profiles of a third patient, in accordance with an embodiment.
Figure 31D:
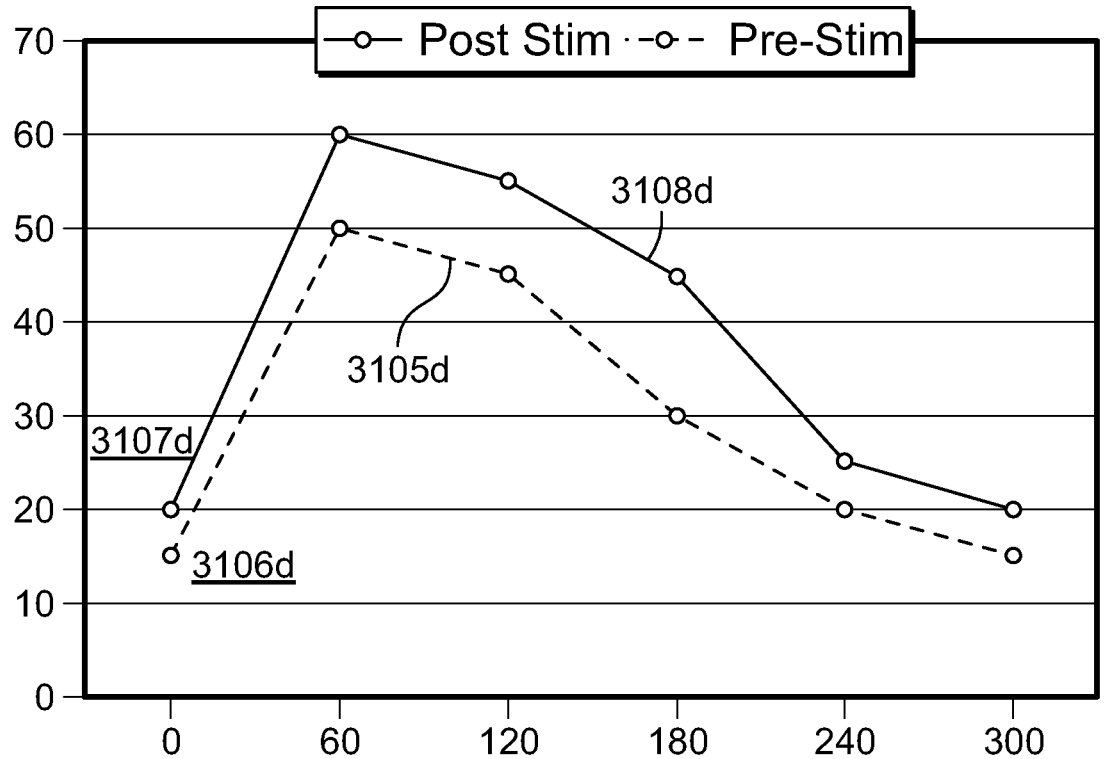
FIG. 31D is a graph illustrating pre-stimulation and post-stimulation satiety profiles of a fourth patient, in accordance with an embodiment.
Figure 31E:
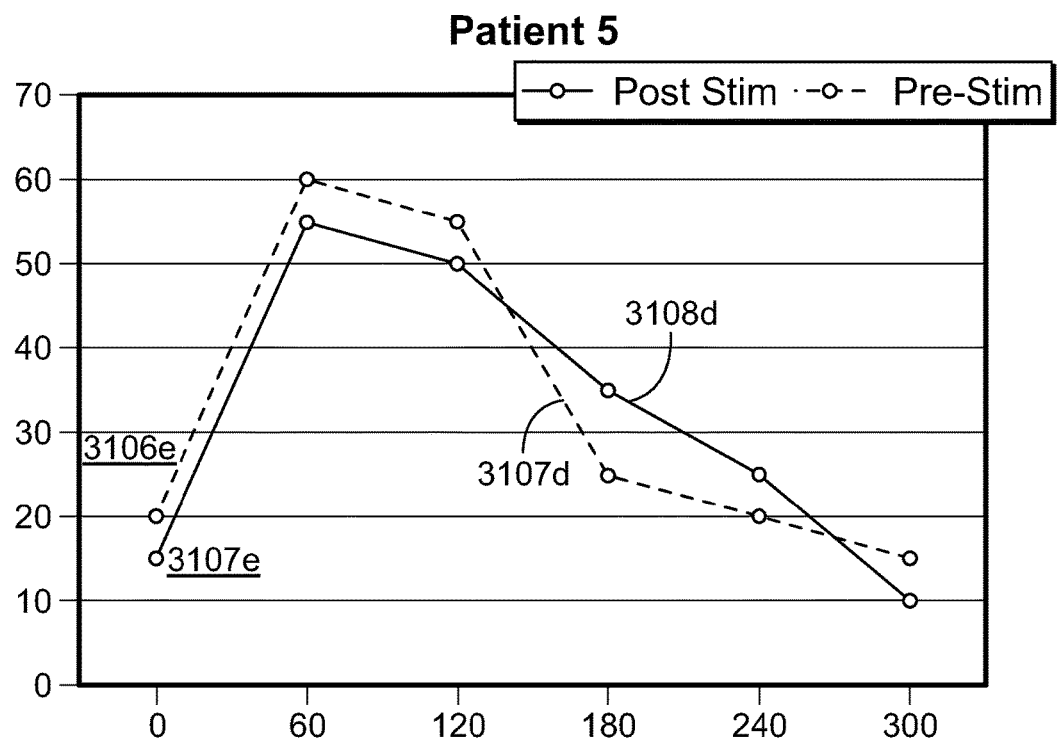
FIG. 31E is a graph illustrating pre-stimulation and post-stimulation satiety profiles of a fifth patient, in accordance with an embodiment.

As shown in FIG. 31A, the first patient's satiety responses or scores for the first occasion (that is, pre-stimulation) are recorded on a first day and plotted on a graph, whose x-axis represents time in minutes and y-axis represents VAS satiety responses or scores in millimeters, to generate a pre-stimulation satiety profile 3105a. Thereafter, the first patient is subjected to stimulation therapy, in accordance to embodiments of the present specification, and the satiety responses or scores for the second occasion (that is, post-stimulation) are also plotted on the graph to generate a post-stimulation satiety profile 3108a. Similarly, the second, third, fourth and fifth patients' responses or scores are recorded to generate the respective pre-stimulation satiety profiles 3105b, 3105c, 3105d, 3105e and the respective post-stimulation satiety profiles 3108b, 3108c, 3108d, 3108e as shown in FIGS. 31B through 31E. As can be observed from FIGS. 31A through 31E, the post-stimulation satiety profiles 3108a, 3108b, 3108c, 3108d, 3108e reflect reduced satiety magnitude relative to the pre-stimulation satiety profiles 3105a, 3105b, 3105c, 3105d, 3105e. In some embodiments, the post-stimulation satiety profile of a patient reflects at least a 5% increase in satiety magnitude relative to the patient's pre-stimulation satiety profile.

Figure 31F:
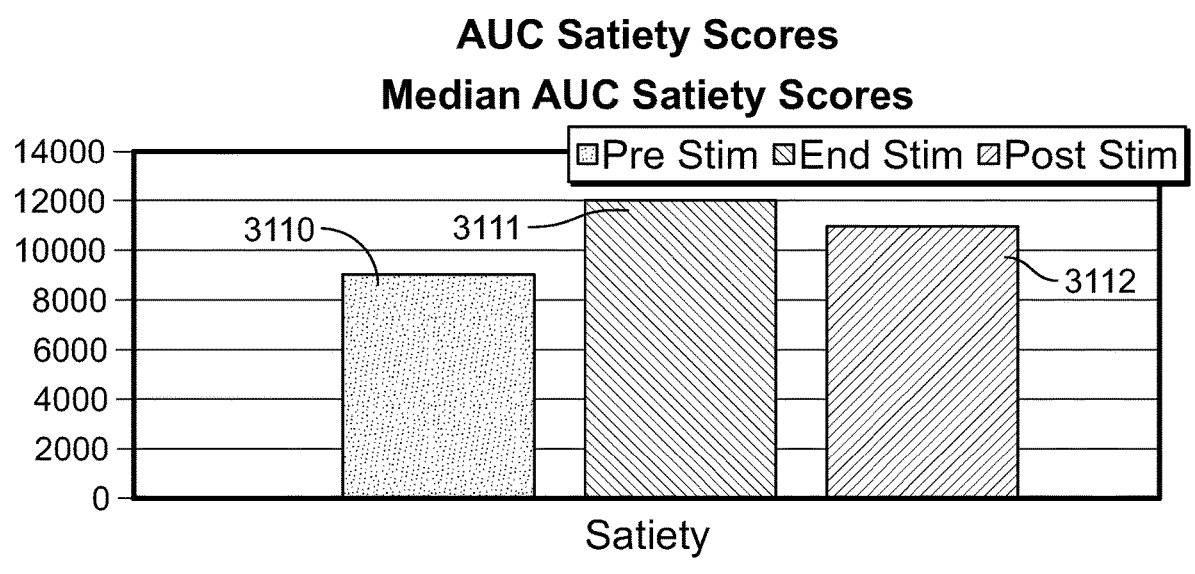
FIG. 31F is a graph illustrating median AUC (Area Under the Curve) satiety scores for pre-stimulation, end-of-stimulation and post-stimulation scenarios.

FIG. 31F shows a first bar 3110 representing a median AUC pre-stimulation satiety score derived from AUC values for pre-stimulation satiety profiles of at least one patient, a second bar 3111 representing a median AUC end-of-stimulation satiety score derived from AUC values for end-of-stimulation satiety profiles (that is, the satiety profiles recorded starting immediately after the end of stimulation therapy) of the at least one patient and third bar 3112 representing a median AUC post-stimulation satiety score derived from AUC values for post-stimulation satiety profiles of the at least one patient. In various embodiments, end-of-stimulation is defined as the end of a period of stimulation lasting in a range from one session to a multitude of sessions over six months. In various embodiments, post-stimulation is defined as a time after the cessation of therapy and ranges from one day after cessation to six months after cessation. As shown in the figure, the median AUC satiety scores 3111, 3112 corresponding to end-of-stimulation and post-stimulation scenarios are elevated or improved relative to the median AUC satiety score 3110 corresponding to the pre-stimulation scenario. In other words, the stimulation therapy of the present specification results in hunger suppression or improved satiety. In some embodiments, an area under the curve (AUC) of the post-stimulation satiety profile of a patient reflects at least a 5% increase relative to the patient's AUC of the pre-stimulation satiety profile.

Figure 31G:
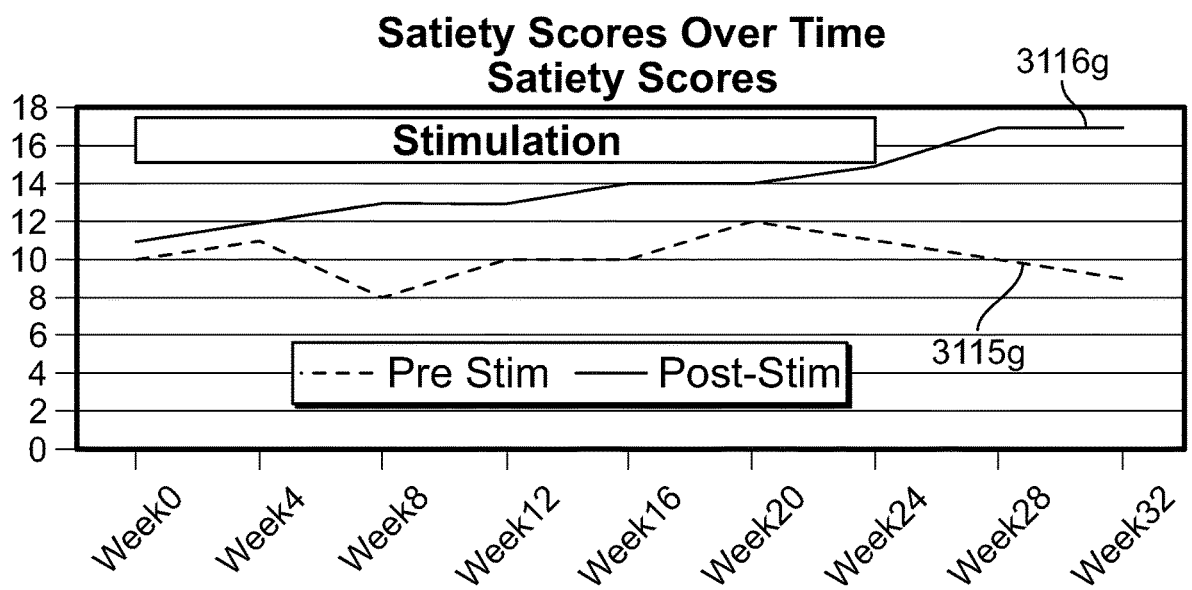
FIG. 31G is a graph illustrating pre-stimulation and post-stimulation satiety profiles over an extended period of time, in accordance with a first embodiment.
Figure 31H:
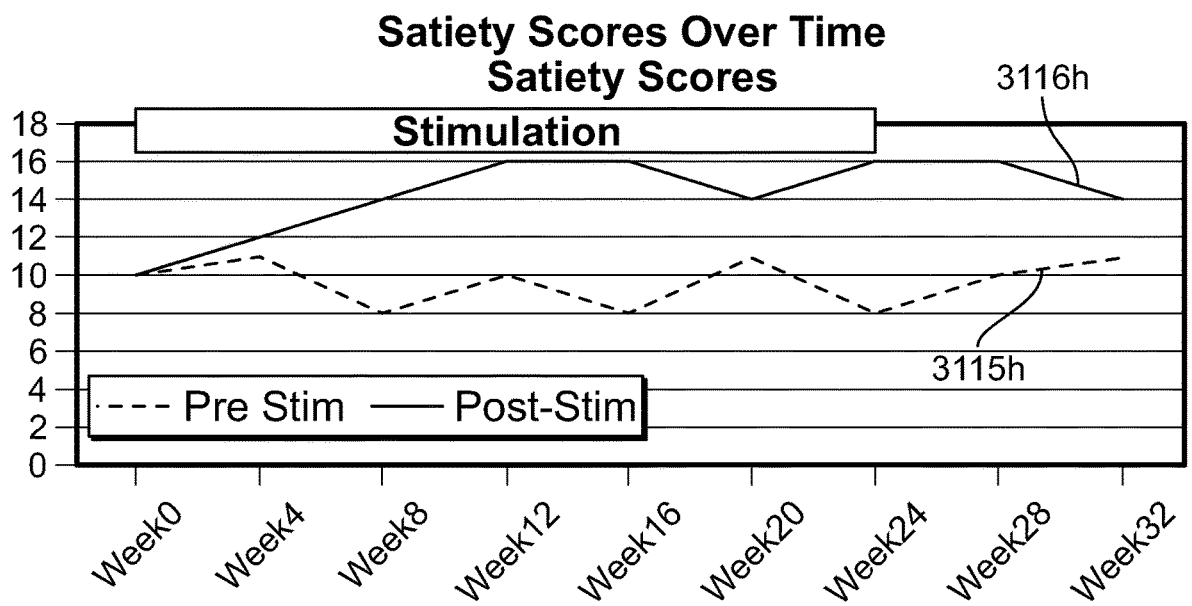
FIG. 31H is a graph illustrating pre-stimulation and post-stimulation satiety profiles over an extended period of time, in accordance with a second embodiment.

FIGS. 31G and 31H also illustrate reduced magnitude of satiety scores, for at least one patient, assessed post stimulation relative to those assessed pre-stimulation. FIGS. 31G and 31H are charts having x-axis representing time in weeks and y-axis representing satiety scores. FIG. 31G shows a pre-stimulation satiety profile 3115g relative to a post-stimulation satiety profile 3116g over extended period of times such as, in weeks and up to 32 weeks. Similarly, FIG. 31H also shows a pre-stimulation satiety profile 3115h relative to a post-stimulation satiety profile 3116h over the same extended periods of time. As can be observed from the FIGS. 31G and 31H, the post-stimulation satiety profiles 3116g, 3116h show improved or increased satiety AUC and magnitude relative to the respective pre-stimulation satiety profiles 3115g, 3115h, even over extended periods of time.

Figure 31I:
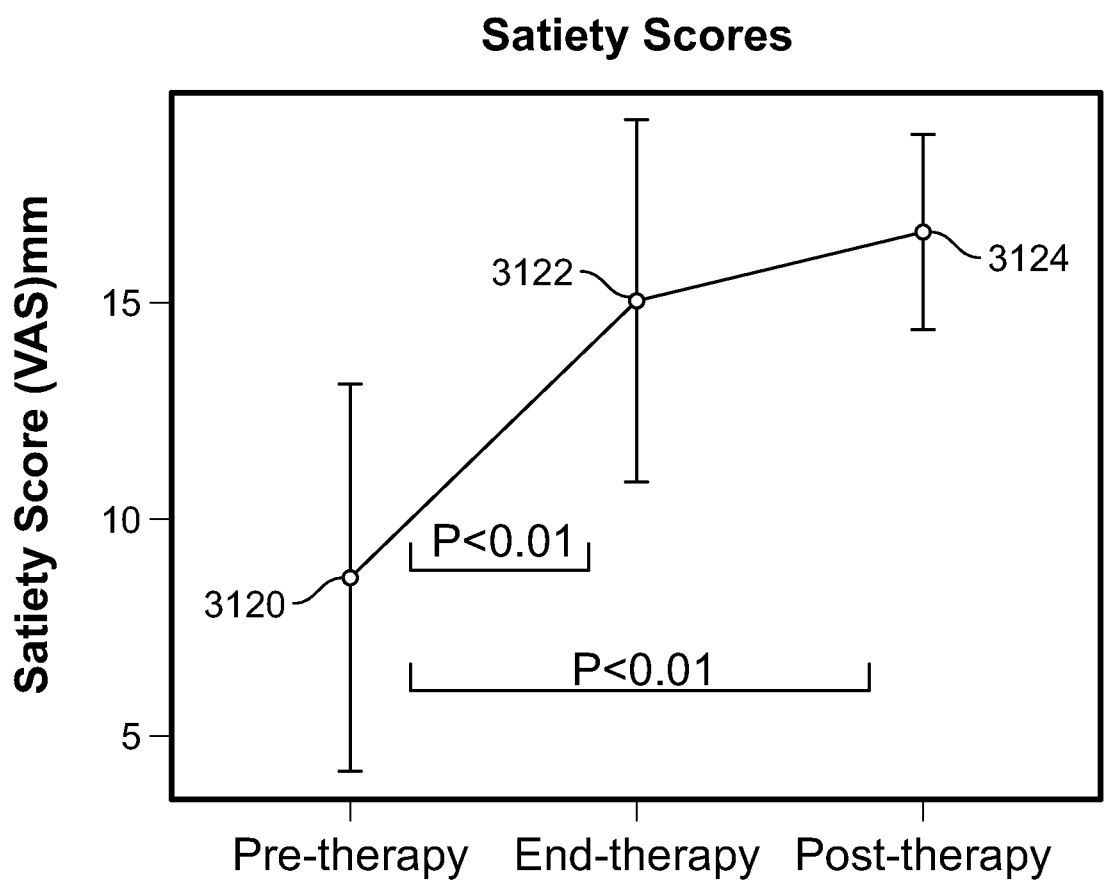
FIG. 31I is a graph illustrating satiety scores for pre-stimulation, end-of-stimulation and post-stimulation scenarios.

FIG. 31I is another graph showing a first median or average satiety score 3120 (assessed using the VAS hunger questionnaire, such as that of FIG. 29D) recorded on a first day prior to subjecting the at least one patient to stimulation therapy (pre-stimulation scenario), a second median or average satiety score 3122 recorded at the end of subjecting the at least one patient to stimulation therapy (end-of-stimulation scenario) and a third median or average satiety score 3124 recorded on a second day after having subjected the at least one patient to stimulation therapy (post-stimulation scenario).

It should be appreciated that while FIGS. 36A through 36I illustrate pre and post hunger levels and FIGS. 31A through 31I illustrate pre and post satiety levels, in various embodiments, various patient sensations such as satiation and fullness are also similarly assessed and recorded using VAS under pre and post stimulation scenarios. It should also be appreciated that the pre-stimulation levels of a patient sensations, such as hunger, appetite, satiety, satiation and fullness, are measured using a scale (such as a VAS) at predefined times of day over a first predefined period of time, and the post-stimulation levels of the patient sensations are measured, after stimulation is initiated, using the scale at the predefined times of day over a second predefined period of time, equal in duration to the first predefined period of time. In addition, in various embodiments, a patient's change in satiety, defined as an alteration in the patient's perception of gastric fullness or emptiness, is measured using a scale (such as a VAS) to determine efficacy of therapy provided by a PEDP device. Further, in various embodiments, the results obtained by the VAS, not only for change in satiety but for all patient sensations, are used to modify stimulation provided by the PEDP device.

For well-being, in one embodiment and referring to FIG. 16, the patient can enter a score from 1 to 3, wherein 1 indicates no nausea/abdominal discomfort, 2 indicates occasional nausea/abdominal discomfort, and 3 indicates the patient is experiencing frequent nausea/abdominal discomfort. In some embodiments, for well-being, a higher score indicates stimulation is too intense, causing the patient to experience nausea, and that a reduction in stimulation is needed. The treatment algorithm of the companion device recognizes the need for reduced stimulation as indicated by the higher score and titrates therapy accordingly. For example, in one embodiment, if the patient enters a well-being score of 3 in the patient diary for three consecutive days, the algorithm uses the score to incrementally reduce the number of stimulation sessions per day or week and/or the length of each stimulation session. In one embodiment, parameter modifications based on well-being scores supersede those based on hunger and/or appetite scores. These primary drivers are tracked to determine how best to modify stimulation on an on-going basis to provide the patient with the proper amount of stimulation such that the patient does not experience feelings of nausea, dyspepsia, does not experience low energy or weakness, and does not have too large an appetite or consume too much food. The tracking of these variables allows for automatic modification of stimulation parameters, based on predefined variable ranges and limits, to provide the patient with a therapeutic stimulation protocol without the need of constant management by the patient.

In some embodiments, therapy is further driven by a set of two secondary indicators. The secondary indicators include patient weight and calories expended/exercise. Weight can be entered in pounds and calories expended/exercises can be attributed a score which is entered into the companion device, as depicted in FIGS. 12 and 15. For example, for weight, referring to FIG. 15, the patient can enter his weight in pounds using a keypad on the companion device. In one embodiment, the patient enters his weight in the patient diary on a weekly basis. In other embodiments, the companion device is configured to communicate wirelessly with a wireless scale (i.e. bathroom scale) such that the patient's weight is automatically entered into the companion device when the patient weighs himself on the scale. This improves system accuracy by eliminating the possibility of the patient entering an incorrect weight. In addition, the system can track how often and when the patient weighs himself, send reminders, and titrate therapy based on the communicated weight. In another embodiment, the companion device is configured to communicate wirelessly with a separate body fat measuring device. As with the patient's weight, automatic transmission of calculated body fat to the companion device results in improved system accuracy, body fat measuring tracking and reminders, and therapy titration based on communicated body fat data. In various embodiments, the companion device is configured to communicate wirelessly with a separate device capable of measuring a plurality of physiological parameters, including, but not limited to, patient weight, body fat, lean mass, and body mass index (BMI). Data from these parameters is automatically input into a treatment algorithm of the companion device and is used to drive therapy by modifying electrical stimulation parameters.

For calories expended/exercise, referring to FIG. 12, the patient can enter an exercise score from 1 to 5, wherein 1 indicates the patient took more than 10,000 steps in a single day, 2 indicates the patient took 7,500-10,000 steps in a single day, 3 indicates the patient took 5,000-7,500 steps in a single day, 4 indicates the patient took 2,500-5,000 steps in a single day, and 5 indicates the patient took less than 2,500 steps in a single day. In some embodiments, the secondary indicators further include fitness input (from a separate device, for example, a device, with physiological sensors, configured to be worn on the human body, such as around the wrist, in order to monitor, acquire, record, and/or transmit the physiological data) and biological inputs (such as ghrelin levels).

Similar to the primary drivers, these secondary indicators can be tracked to determine how best to modify stimulation on an on-going basis to provide the patient with the proper amount of stimulation. In some embodiments, the secondary indicators possess less value compared to the primary drivers in determining how best to modify the PEDP stimulation parameters. Although embodiments having three primary drivers and two secondary indicators have been discussed, additional embodiments having greater or fewer primary drivers and/or secondary indicators are possible and the variables presented are not intended to be limiting.

The PEDP devices of the present specification can be used to enable a patient to comply with a dietary plan. In some embodiments, the system calculates, for example, via an application or software on the microprocessor of the PEDP, the timing of food consumption by the patient, the total calories consumed, and the type of food consumed (i.e. glycemic index, carbohydrate profile, and protein profile). The system then, via an algorithm through said application or software, uses the calculated information to titrate electrical stimulation therapy. For example, if the patient eats outside his normal dietary time, eats too many calories based on his diet, and/or eats foods high in glycemic index or carbohydrate profile, the system recognizes this and increases any one or combination of stimulation amplitude, frequency, number of sessions, session length, or session timing.

Specifically, in various embodiments, the system calculates timing of consumption, total calories consumed, and type of food consumed, as described above, along with other parameters such as exercise and on-going weight loss, and, based on the calculations, performs the following therapy adjustments:

If a patient consumes too many calories, based on his dietary plan, over a predetermined period (for example, 3 days), the stimulation duration, intensity, and/or number of sessions is increased.

If a patient consumes too much food at a specific time of day each day over a predetermined period (for example, 3 days), the timing of stimulation is changed to prior to (for example, a half hour or 1 hour before) the overeating time and/or an additional stimulation session is added prior to the overeating time.

If a patient consumes foods outside his dietary plan, for example, too many carbohydrates, over a predetermined period (for example, 3 days), the stimulation duration, intensity, session timing, and/or number of sessions is increased.

If a patient stops exercising for a predetermined period (for example, 3 days), stimulation parameters are increased.

If, following a course of treatment, the patient has lost a predetermined amount of target weight, the system algorithm decreases stimulation parameters, in some embodiments either by a physician or via a downloadable application.

For some patients, compliance becomes easier when the patient does not need to track the amount of calories in each piece of food consumed but rather is presented with a dietary plan with a listing of foods wherein the calorie profile of each item of food is already known. Therefore, in some embodiments, the system provides the patient with a number of breakfast, lunch, dinner, and optionally snack meal plans from which to choose. The calorie profile of each of these meal plans is pre-calculated. These calorie profiles are pre-programmed into the software or applications of the PEDP device. Patients no longer need to track the calorie content of each item of food consumed but can simply report how well they are complying with the chosen meal plans. Further, in some embodiments, the PEDP can be linked to a separate wearable device, for example, a device, with physiological sensors, configured to be worn on the human body, such as around the wrist, in order to monitor, acquire, record, and/or transmit physiological data, such as exercise data, to the PEDP so that calories expended, as tracked by the separate device, are deducted from calories consumed, as per the specific meal plans, to provide the patient and system with calorie balance information.

In some embodiments, patients are instructed to follow a 1200 calorie/day diet plan. Based on the above, too many calories consumed above the baseline 1200 and/or the wrong calories consumed (for example, a bad glycemic index, too many sugars consumed, and/or too many carbohydrates consumed) will result in an increase in stimulation. If poor eating habits (for example, too many of the wrong calories) are concentrated at a particular time of day, the system adjusts to add a session just prior to the particular time to lower hunger and improve eating behavior.

In some embodiments, stimulation is programmed to begin before (for example, 1 week prior to) the patient starts on his dietary plan. Beginning stimulation before the patient changes to a new dietary plan reduces the patient's appetite before the change in eating and results in better compliance as patients are less likely to become disheartened if they stray from their diet due to high hunger levels. In other embodiments, patients only receive stimulation therapy and do not go on a dietary plan.

Figure 21C:
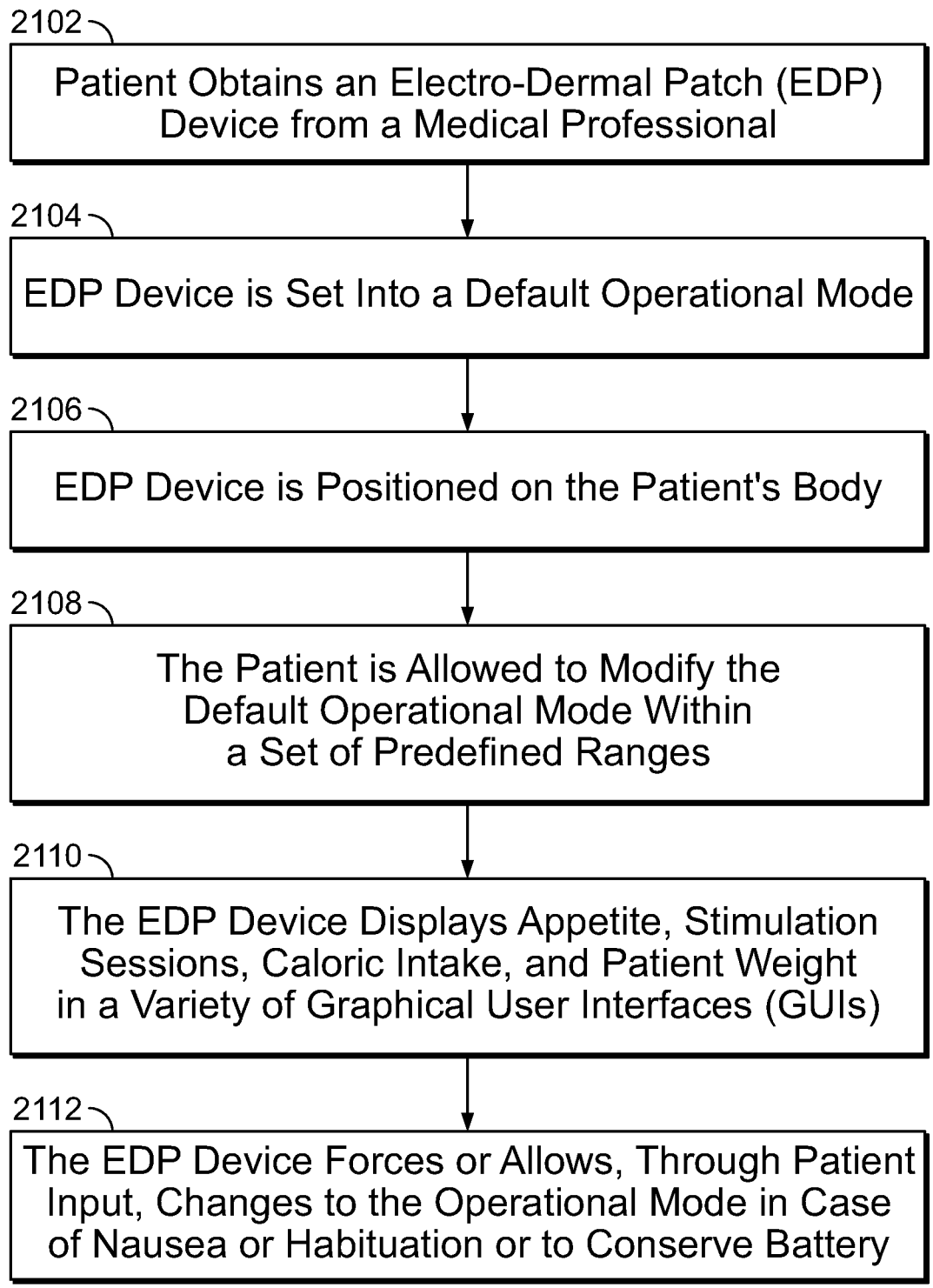
FIG. 21C is a flow chart illustrating the steps involved in a method of using a neuro-stimulation device to suppress appetite in a patient, in various embodiments of the present specification.

FIG. 21C is a flow chart illustrating the steps involved in one embodiment of a method of using an neuro-stimulation device to suppress appetite in a patient. At step 2102, a patient obtains a percutaneous electro-dermal patch (PEDP) device, in accordance with the devices disclosed in the present specification, from a medical professional.

The PEDP device is set into a default operational mode, either by the patient or by the medical professional, at step 2104. In some embodiments, the default operational mode includes the following stimulation parameters and parameter ranges: pulse width in a range of 10 μsec to 10 msec; pulse amplitude in a range of 100 μA to 500 mA; pulse frequency in a range of 1 Hz to 10,000 Hz; pulse duty cycle in a range of 1% to 100%; session duration in a range of 1 min to 120 min or substantially continuously; and 1 to 24 sessions per day. In a preferred embodiment, the default operational mode includes the following stimulation parameters: pulse width equal to 200 μsec; pulse amplitude equal to 5 mA; pulse frequency equal to 20 Hz; pulse duty cycle equaling 100%; session duration equaling 30 minutes; and 1 session per day. Then, at step 2106, the PEDP device is positioned on the patient's body, such that the at least one electrode can be implanted just underneath the patient's skin. In various embodiments, the PEDP device is either self-implanted by the patient himself or is implanted by a physician or medical personnel. The patient is allowed to modify the default operational mode within a set of predefined ranges at step 2108. The patient may modify the default operational mode based upon patient feedback or feedback provided by a separate wearable device, for example, a device, with physiological sensors, configured to be worn on the human body, such as around the wrist, in order to monitor, acquire, record, and/or transmit the physiological data. At step 2110, the PEDP device displays appetite, stimulation sessions, caloric intake, and patient weight in a variety of graphical user interfaces (GUIs). Other parameters may also be listed, and the list in step 2110 is not intended to be limiting. The PEDP device forces or allows, through patient input, changes to the operational mode in the case of nausea, dyspepsia or habituation or to conserve battery at step 2112. The PEDP device forces the changes when feedback data provided by the device or another wearable device falls outside preset ranges indicating habituation is occurring. In some embodiments, habituation occurs when hunger returns over time despite electrical stimulation via the stimulation protocols disclosed in the present specification.

The return of hunger indicates a loss of appetite suppression due to habituation of the patient to the electrical stimulation. The patient may change the operational mode if he or she is experiencing nausea and/or dyspepsia.

Figure 22:
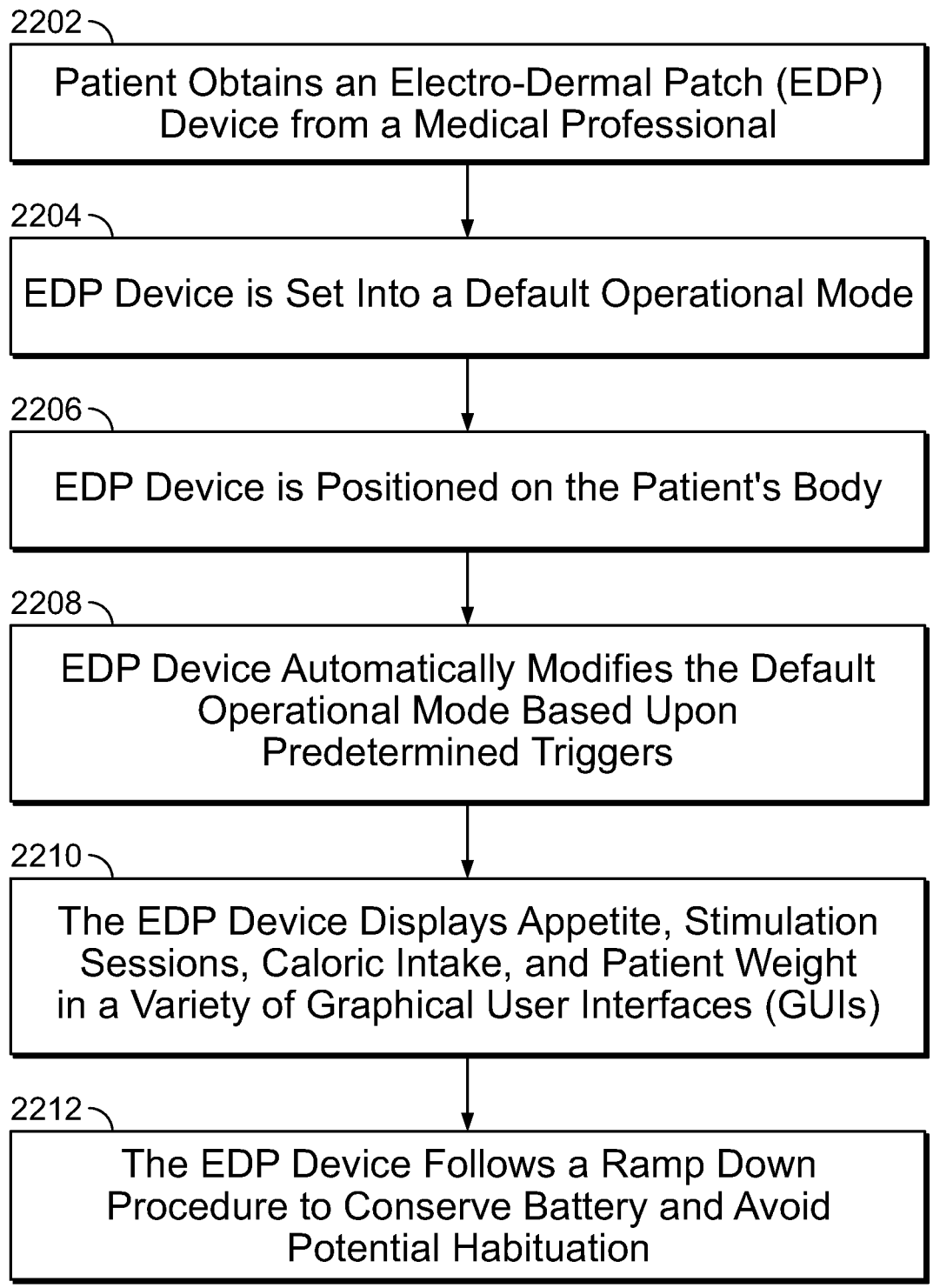
FIG. 22 is a flow chart illustrating the steps involved in a method of using a neuro-stimulation device to suppress appetite in a patient, in various embodiments of the present specification.

FIG. 22 is a flow chart illustrating the steps involved in another embodiment of a method of using an neuro-stimulation device to suppress appetite in a patient. At step 2202, a patient obtains a percutaneous electro-dermal patch (PEDP) device, in accordance with the devices disclosed in the present specification, from a medical professional. The PEDP device is set into a default operational mode, either by the patient or by the medical professional, at step 2204. In various embodiments, the default operational mode includes the stimulation parameters and parameter ranges listed above with respect to FIG. 21C. Then, at step 2206, the PEDP device is implanted just underneath the skin of the patient by a medical professional or self-implanted by the user himself. The PEDP device automatically modifies the default operational mode based upon predetermined triggers at step 2208. In various embodiments, the triggers include, but are not limited to, patient diary recording of appetite, hunger, and well-being, and data from a separate device, with physiological sensors, configured to be worn on the human body, such as around the wrist, in order to monitor, acquire, record, and/or transmit the physiological data, data transmitted to the companion device. For example, in one embodiment, the patient records an appetite diary entry with a score of 5, wherein the patient substantially exceeded his diet during his most recent meal, indicative of dietary non-compliance (that is, not conforming to a diet plan) or poor dietary compliance. In some embodiments, one or more scores of 5 on appetite triggers the companion device to automatically increase therapy parameters, for example, an increase in stimulation intensity, duration, or sessions.

In another embodiment, for example, the patient records a hunger diary entry with a score of 1, wherein the patient experienced no hunger at all at his most recent meal time. In some embodiments, one or more scores of 1 on hunger triggers the companion device to automatically decrease therapy parameters, for example, a decrease in stimulation intensity, duration, or sessions. At step 2210, the PEDP device displays appetite, stimulation sessions, caloric intake, and patient weight in a variety of graphical user interfaces (GUIs). Other parameters may also be listed, and the list in step 2210 is not intended to be limiting. The PEDP device then follows a ramp down procedure, wherein stimulation parameters are decreased sequentially, to conserve battery and avoid potential habituation at step 2212.

Figure 23:
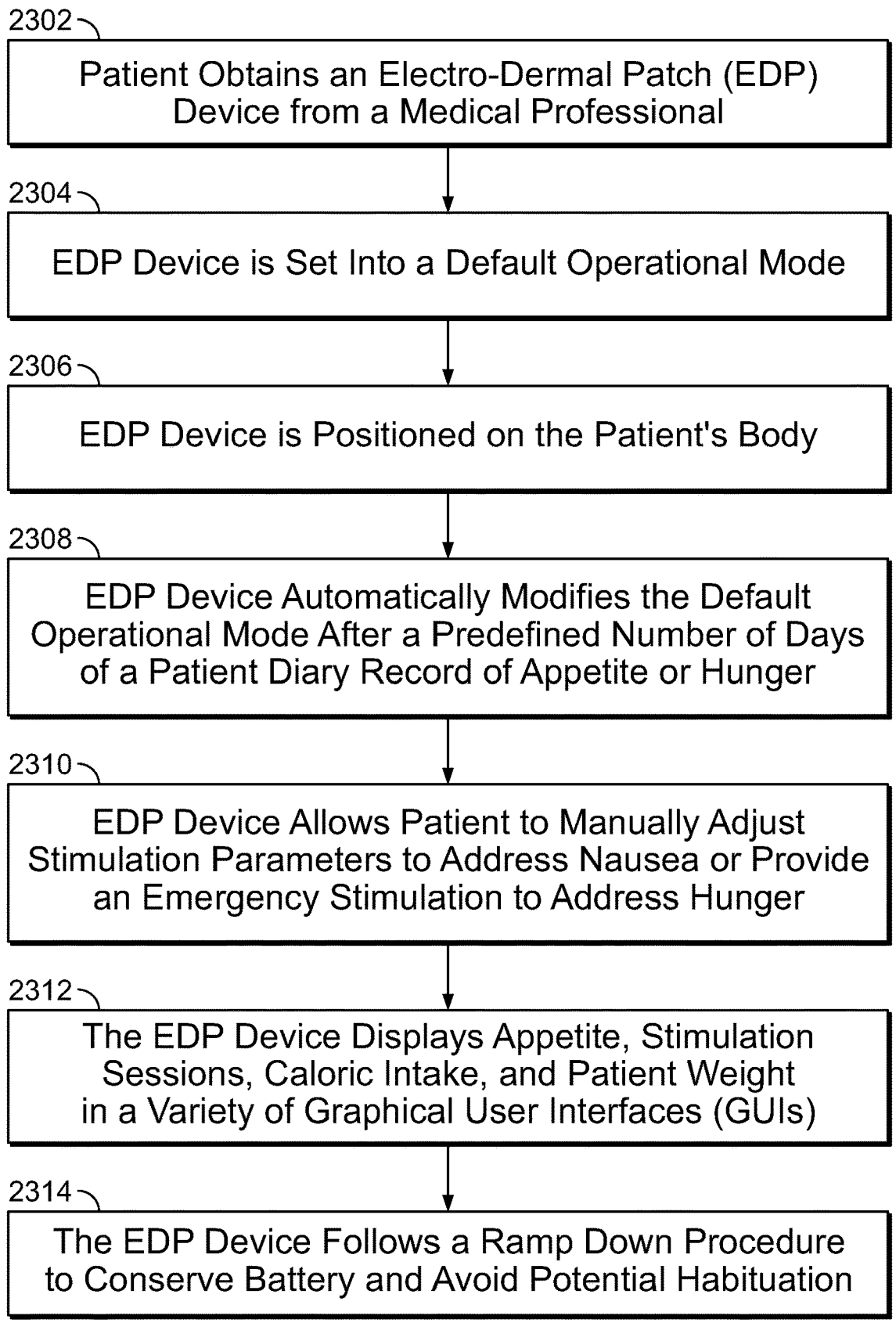
FIG. 23 is a flow chart illustrating the steps involved in a method of using a neuro-stimulation device to suppress appetite in a patient, in various embodiments of the present specification.

FIG. 23 is a flow chart illustrating the steps involved in another embodiment of a method of using an neuro-stimulation device to suppress appetite in a patient. At step 2302, a patient obtains a percutaneous electro-dermal patch (PEDP) device, in accordance with the devices disclosed in the present specification, from a medical professional. The PEDP device is set into a default operational mode, either by the patient or by the medical professional, at step 2304. In various embodiments, the default operational mode includes the stimulation parameters and parameter ranges listed above with respect to FIG. 21C. Then, at step 2306, the PEDP device is implanted within the patient's body by a medical professional or self-implanted by the user himself. The PEDP device automatically modifies the default operational mode after a predefined number of days of a patient diary record of appetite or hunger at step 2308. In various embodiments, the predefined number of days is in a range of 1 to 7 days. In one embodiment, the predefined number of days is 3 days. In one embodiment, in combination with step 2308, the PEDP device allows the patient to manually adjust stimulation parameters to address nausea, dyspepsia or provide an emergency stimulation to address hunger at step 2310. At step 2312, the PEDP device displays appetite, stimulation sessions, caloric intake, and patient weight in a variety of graphical user interfaces (GUIs). Other parameters may also be listed, and the list in step 2312 is not intended to be limiting. The PEDP device then follows a ramp down procedure, wherein stimulation parameters are decreased sequentially, to conserve battery and avoid potential habituation at step 2314.

Figure 24:
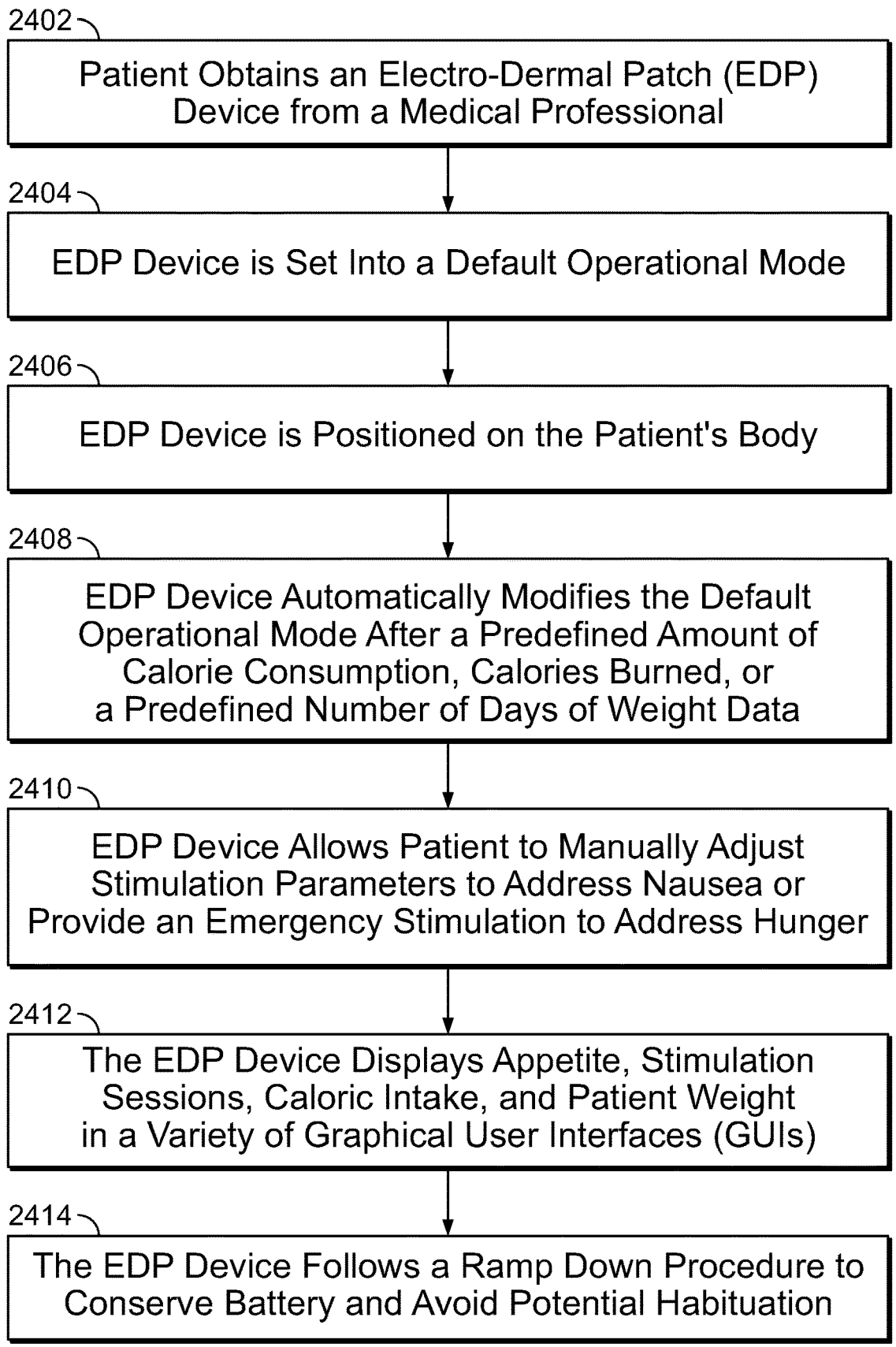
FIG. 24 is a flow chart illustrating the steps involved in a method of using a neuro-stimulation device to suppress appetite in a patient, in various embodiments of the present specification.

FIG. 24 is a flow chart illustrating the steps involved in another embodiment of a method of using an neuro-stimulation device to suppress appetite in a patient. At step 2402, a patient obtains a percutaneous electro-dermal patch (PEDP) device, in accordance with the devices disclosed in the present specification, from a medical professional. The PEDP device is set into a default operational mode, either by the patient or by the medical professional, at step 2404. In various embodiments, the default operational mode includes the stimulation parameters and parameter ranges listed above with respect to FIG. 21C. Then, at step 2406, the PEDP device is implanted within the patient's body by a medical professional or self-implanted by the user himself. The PEDP device automatically modifies the default operational mode after a predefined amount of calorie consumption or calories burned, as determined by diary entries or information gathered from a separate device, or after a predefined number of days of weight data has been recorded at step 2408. In various embodiments, the predefined number of days is in a range of 1 to 7 days. In one embodiment, the predefined number of days is 3 days. In one embodiment, in combination with step 2408, the PEDP device allows the patient to manually adjust stimulation parameters to address nausea, dyspepsia or provide an emergency stimulation to address hunger at step 2410. At step 2412, the PEDP device displays appetite, stimulation sessions, caloric intake, and patient weight in a variety of graphical user interfaces (GUIs). Other parameters may also be listed, and the list in step 2412 is not intended to be limiting. The PEDP device then follows a ramp down procedure, wherein stimulation parameters are decreased sequentially, to conserve battery and avoid potential habituation at step 2414.

Figure 25:
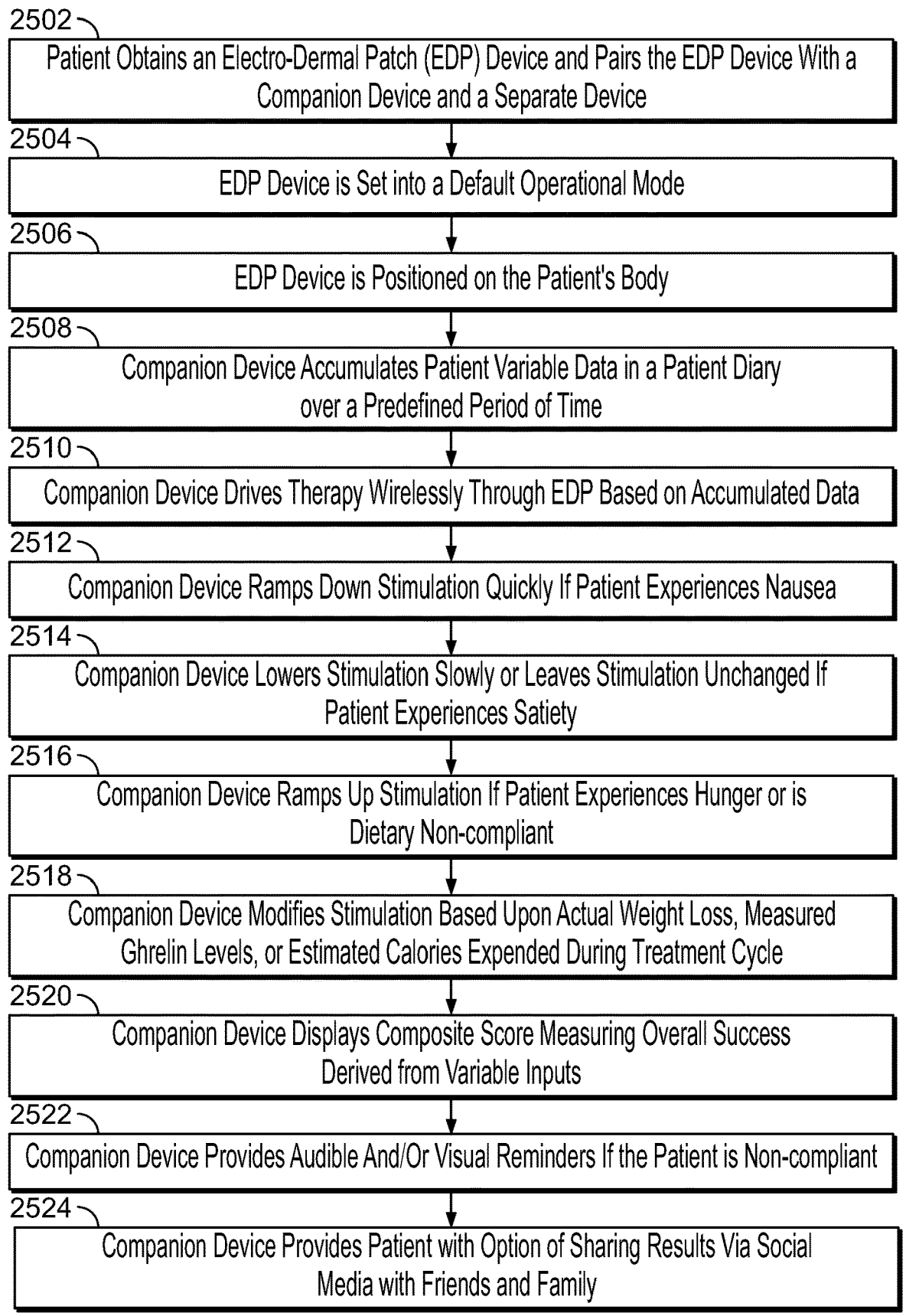
FIG. 25 is a flow chart illustrating the steps involved in a method of using a neuro-stimulation device to suppress appetite in a patient, in various embodiments of the present specification.

FIG. 25 is a flow chart illustrating the steps involved in yet another embodiment of a method of using an neuro-stimulation device to suppress appetite in a patient. At step 2502, the patient obtains a percutaneous electro-dermal patch (PEDP) device and pairs the EPD device with a companion device, such as a smartphone, and a separate device, for example, a device, with physiological sensors, configured to be worn on the human body, such as around the wrist, in order to monitor, acquire, record, and/or transmit the physiological data. In some embodiments, pairing with the separate device can be done anytime within a treatment cycle. In some embodiments, a treatment cycle lasts 3 months. At step 2504, the device is set into a default operational mode. In some embodiments, the default operational mode includes the stimulation parameters and parameter ranges listed above with respect to FIG. 21C and includes daily stimulation.

The PEDP device is implanted within the patient's body at step 2506 by a medical professional or self-implanted by the user himself. At step 2508, the companion device accumulates patient variable data, including, but not limited to, appetite, hunger, well-being, weight, and calories expended/weight loss, in a patient diary over a predefined period of time. In some embodiments, the companion device accumulates data over a range of 1 to 7 days. In one embodiment, the companion device accumulates data for 3 days. Then, at step 2510, the companion device drives stimulation therapy wirelessly through the PEDP device based on accumulated patient diary data over the treatment cycle. During the treatment cycle, if the patient experiences nausea and/or dyspepsia, the companion device ramps down stimulation parameters quickly at step 2512. During the treatment cycle, if the patient experiences satiety, defined as the absence of hunger coupled with good dietary compliance, the companion device slowly lowers stimulation to a minimum threshold, such as one 15 minute stimulation session every other day, to preserve battery and prevent habituation, or leaves stimulation unchanged at step 2514. During the treatment cycle, if the patient experiences hunger is dietary non-compliant, the companion device ramps up stimulation accordingly at step 2516. At step 2518, the companion device modifies stimulation based upon actual weight loss, measured ghrelin levels, or estimated calories expended during the treatment cycle. In one embodiment, the companion device uses a weight loss predictor algorithm based on caloric input versus caloric consumption. At step 2520, the companion device displays a composite score measuring overall success derived from the variable inputs. If the patient is non-compliant, the companion device will provide audible and/or visual reminders to the patient at step 2522. Optionally, at step 2524, the companion device provides the patient with the option of sharing his results via social media with designated friends and family.

In an alternate embodiment, the companion device first accumulates patient diary data before the PEDP device is set into the default operation mode. Referring to FIG. 25, in this alternate embodiment, step 2508 is performed prior to step 2504. The remaining steps proceed in the same order.

In other embodiments, a patient is provided with manual options of operating the PEDP device. The patient may operate the device at low, medium, and high settings, based on the patient variable data. For example, in one embodiment, a patient starts the PEDP device at a high setting but begins to experience nausea and/or dyspepsia. The patient then resets the PEDP device to the medium setting, and then to the low setting. Eventually, the patient experiences hunger and resets the PEDP device to the medium setting. In some embodiments, this protocol is driven by a therapy intensity scale, such as 1 to 5 or 1 to 10, or a graphic on the display of the companion device. In some embodiments, manual operation using low, medium, and high settings is coupled with the protocols described with reference to FIGS. 21C-25 to establish baseline PEDP device settings.

Figure 26:
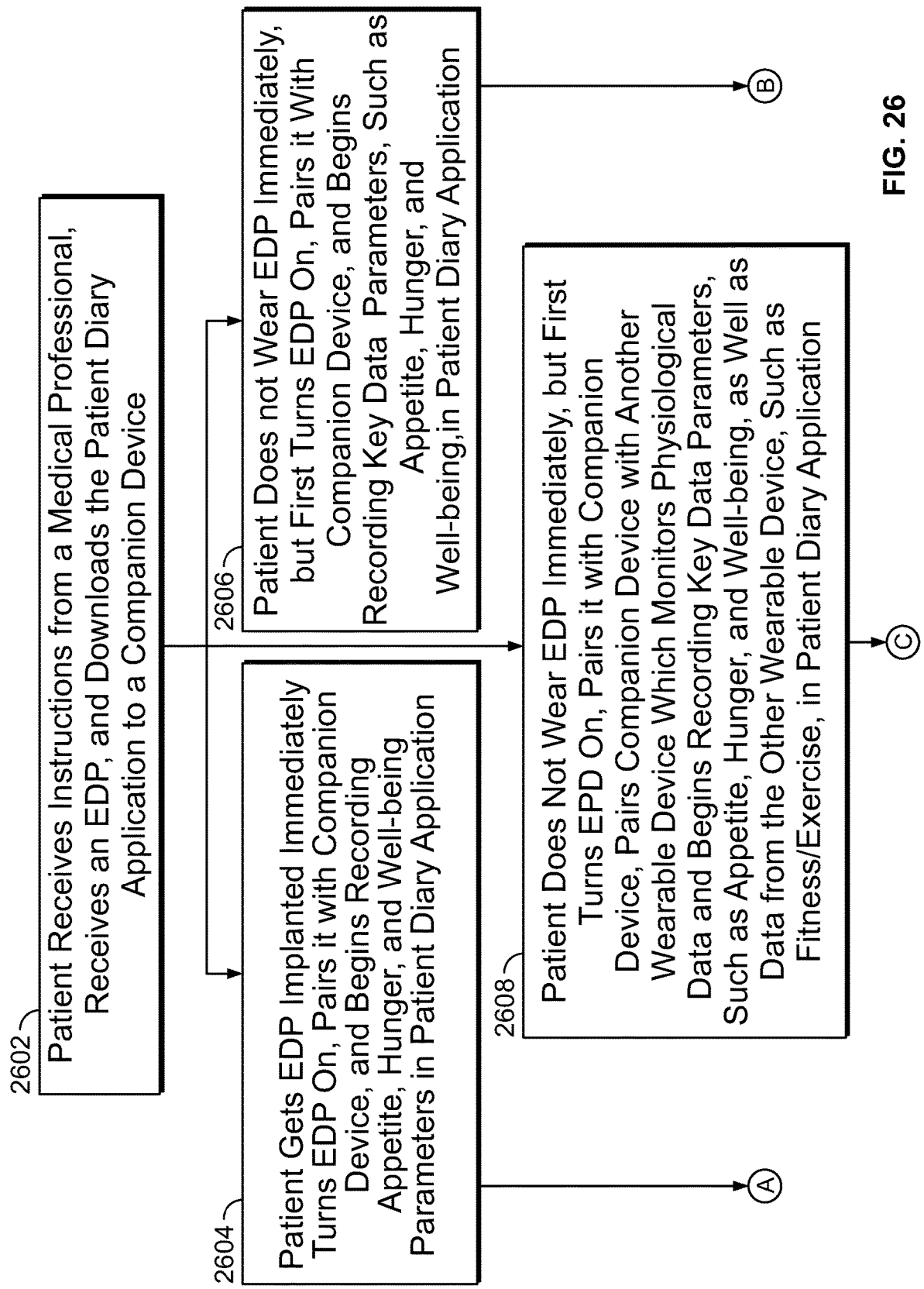
FIG. 26 is a flow chart illustrating the steps involved in methods of using a neuro-stimulation device to suppress appetite in a patient, in various embodiments of the present specification.
Figure 26:
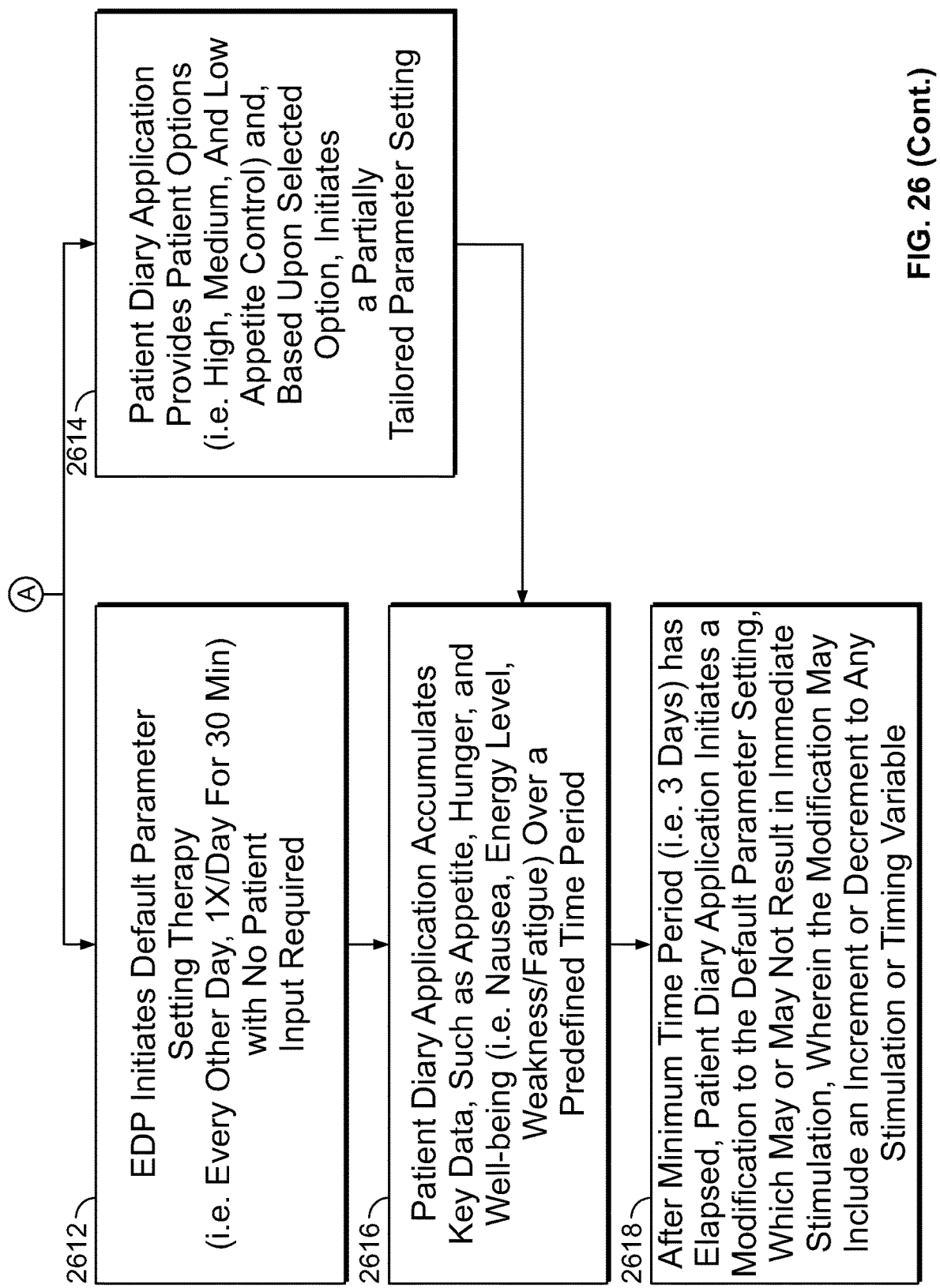
Figure 26:
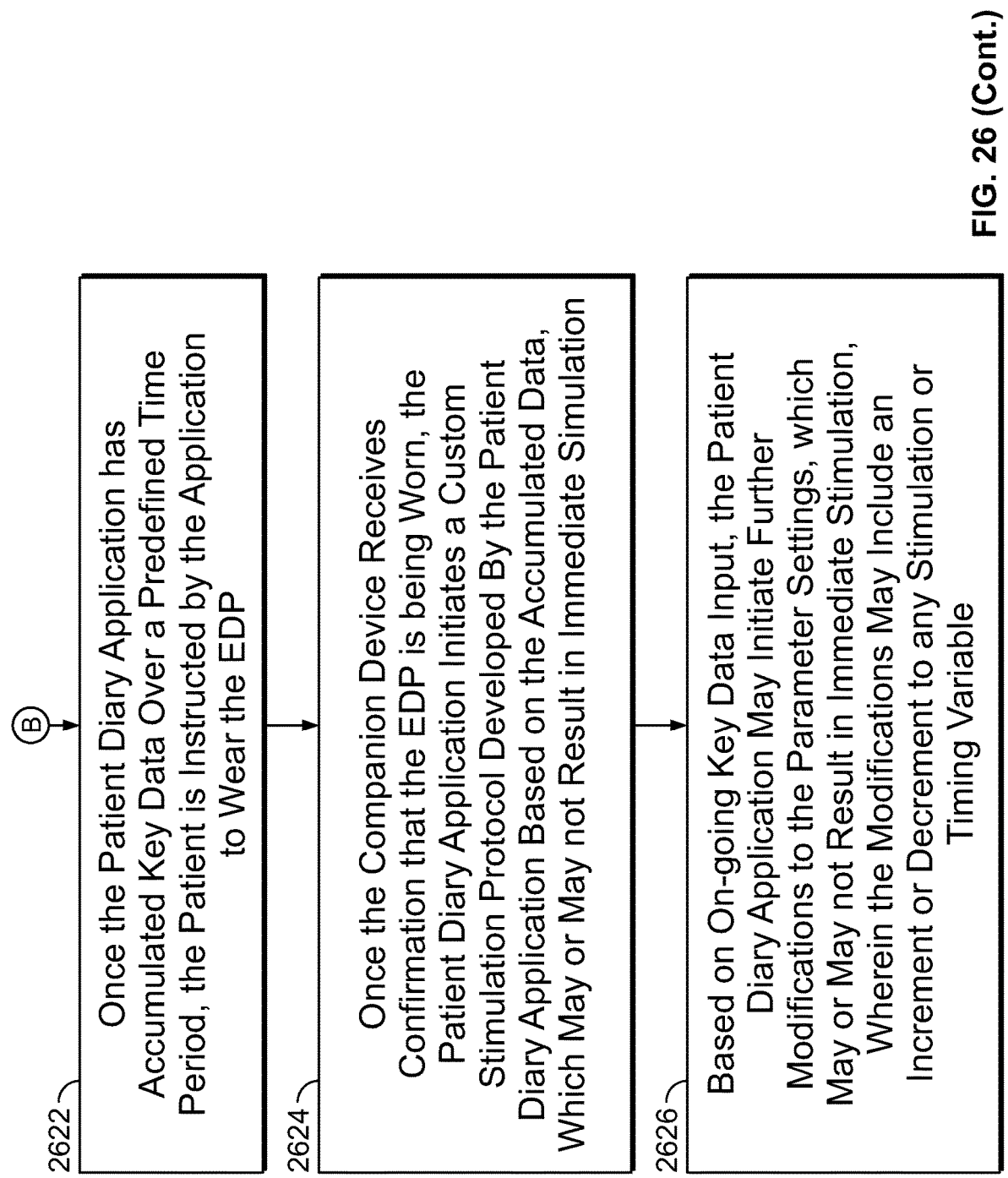
Figure 26:
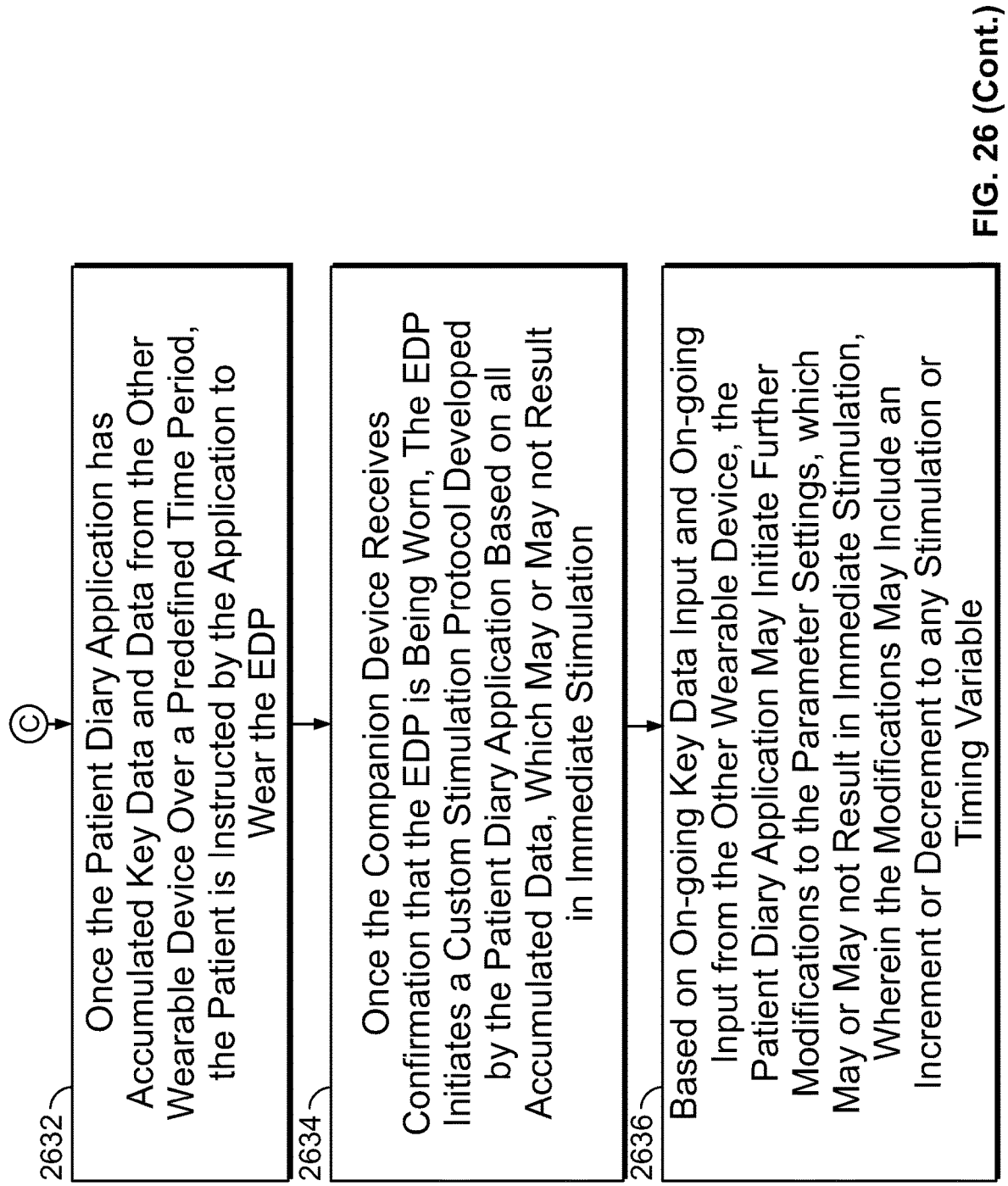

FIG. 26 is a flow chart illustrating the steps involved in yet other embodiments of methods of using an neuro-stimulation device to suppress appetite in a patient. At step 2602, a patient receives instructions from a medical professional, receives a percutaneous electro-dermal patch (PEDP) device, and downloads a patient diary application to a companion device, such as a smartphone. Optionally, at step 2604, the patient gets the PEDP implanted immediately, turns it on, and pairs it with the companion device such that the companion device begins recording appetite, hunger, and well-being parameters in the patient diary application. In various embodiments, the PEDP is implanted within the patient's body by the medical professional or self-implanted by the user himself. In one embodiment, the PEDP then initiates default parameter setting therapy (i.e. every other day, 1×/day for 30 min) with no patient input required at step 2612. The patient diary application then accumulates key data, such as appetite, hunger, and well-being (i.e. nausea, dyspepsia, energy level, weakness/fatigue) over a predefined time period at step 2616. After a minimum time period (i.e. 3 days) has elapsed at step 2618, the patient diary application initiates a modification to the default parameter setting, which may or may not result in immediate stimulation, wherein the modification may include an increment or a decrement to any stimulation or timing variable.

Alternatively, in another embodiment, following step 2604 wherein the patient gets the PEDP implanted immediately, the patient diary application provides the patient various options (i.e. high, medium, and low appetite control) at step 2614 and, based upon the selected option, initiates a partially tailored parameter setting. The patient diary application then continues to accumulate key data and initiate parameter setting modifications, as detailed in steps 2616 and 2618 respectively.

Optionally, in another embodiment, following step 2602 wherein the patient receives the PEDP and downloads the patient diary application, the patient does not wear the PEDP immediately at step 2606, but first turns the PEDP on, pairs it with the companion device, and begins recording key data parameters, such as appetite, hunger, and well-being, in the patient diary application. At step 2622, once the patient diary application has accumulated key data over a predefined time period, the patient is instructed by the application to wear the PEDP. Then, at step 2624, once the companion device receives confirmation that the PEDP is being worn, the patient diary application initiates a custom stimulation protocol developed by the patient diary application based on the accumulated data, which may or may not result in immediate stimulation. Based on on-going key data input, at step 2626, the patient diary application may initiate further modifications to the parameter settings, which may or may not result in immediate stimulation, wherein the modifications may include an increment or a decrement to any stimulation or timing variable.

Still optionally, in another embodiment, following step 2602 wherein the patient receives the PEDP and downloads the patient diary application, the patient does not self-implant or get the PEDP implanted by a physician immediately at step 2608, but first turns the PEDP on, pairs the PEDP with the companion device, pair the companion device with another wearable device, for example, a device, with physiological sensors, configured to be worn on the human body, such as around the wrist, in order to monitor, acquire, record, and/or transmit the physiological data, and begins recording key data parameters, such as appetite, hunger, and well-being, as well as data from the other wearable device, such as fitness/exercise, in the patient diary application. At step 2632, once the patient diary application has accumulated key data and data from the other wearable device over a predefined time period, the patient is instructed by the application to wear the PEDP. In various embodiments, the PEDP device is either self-implanted by the patient himself or is implanted by a physician or medical personnel. Then, at step 2634, once the companion device receives confirmation that the PEDP is being worn, the patient diary application initiates a custom stimulation protocol developed by the patient diary application based on all accumulated data, which may or may not result in immediate stimulation. Based on on-going key data input and on-going input from the other wearable device, at step 2636, the patient diary application may initiate further modifications to the parameter settings, which may or may not result in immediate stimulation, wherein the modifications may include an increment or a decrement to any stimulation or timing variable.

Figure 27:
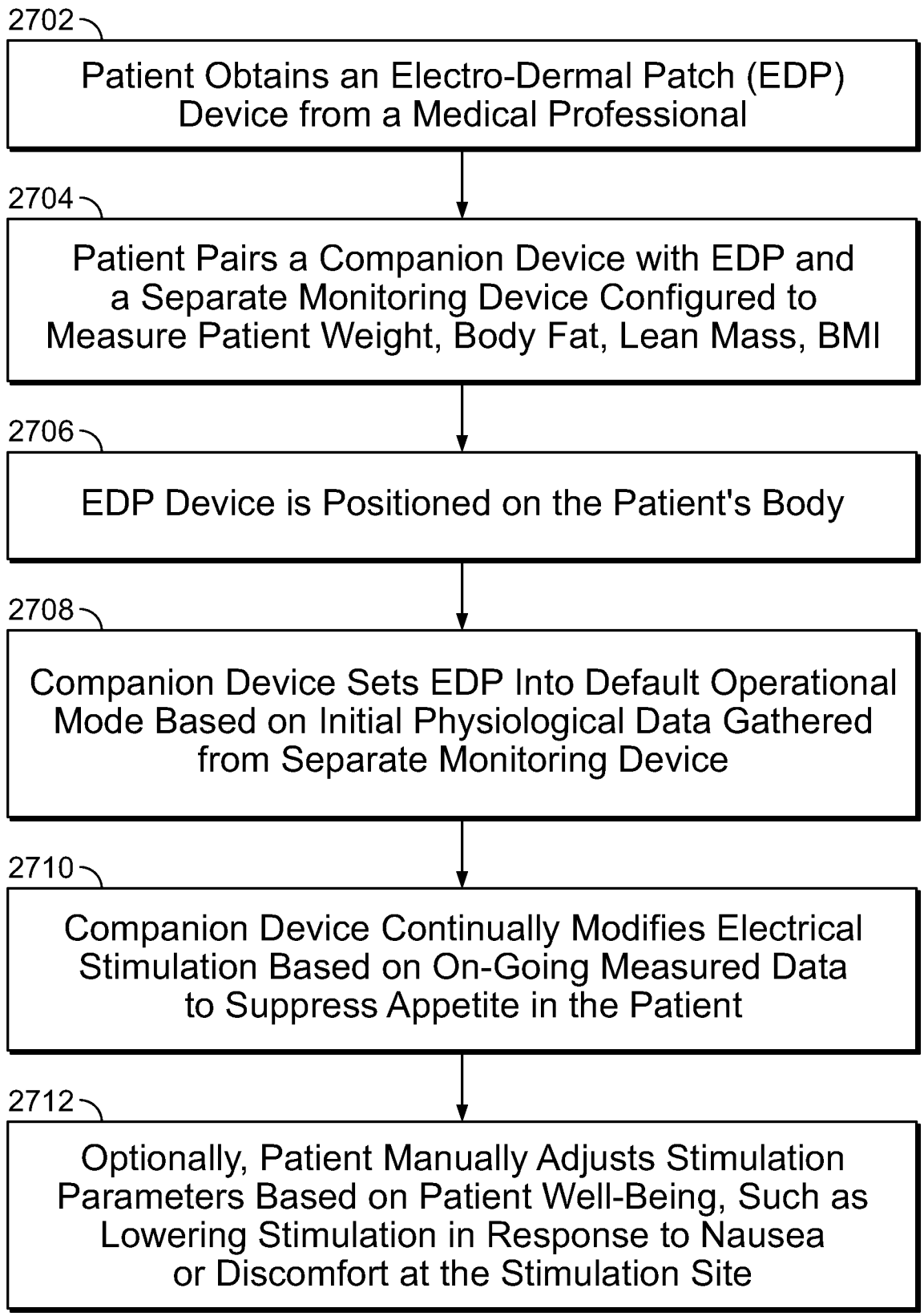
FIG. 27 is a flow chart illustrating the steps involved in a using a neuro-stimulation device and a companion device, paired with a separate monitoring device, to suppress appetite in a patient, in accordance with an embodiment of the present specification.

FIG. 27 is a flow chart illustrating the steps involved in a using an neuro-stimulation device and a companion device, paired with a separate monitoring device, to suppress appetite in a patient, in accordance with one embodiment of the present specification. At step 2702, the patient obtains a PEDP from a medical professional. The patient pairs a companion device with the PEDP and with a separate monitoring device at step 2704. The separate monitoring device is configured to measure a plurality of physiological parameters, including, but not limited to, patient weight, body fat, lean mass, and BMI, and wirelessly transmit monitored data to the companion device. The patient then gets the device implanted on his body by the medical professional at step 2706. Alternatively, the patient self-implants the device on his body at step 2706. At step 2708, the companion device sets the PEDP into a default stimulation mode based on initial physiological data gathered from the separate monitoring device. Based on on-going data gathering an input, the companion device continually modifies the electrical stimulation provided by the PEDP in an effort to suppress appetite in the patient at step 2710. Optionally, at step 2712, the patient manually adjusts stimulation parameters based on patient well-being, for example, lowering stimulation parameters if the patient is experiencing nausea, dyspepsia or discomfort at the stimulation site.

Figure 28:
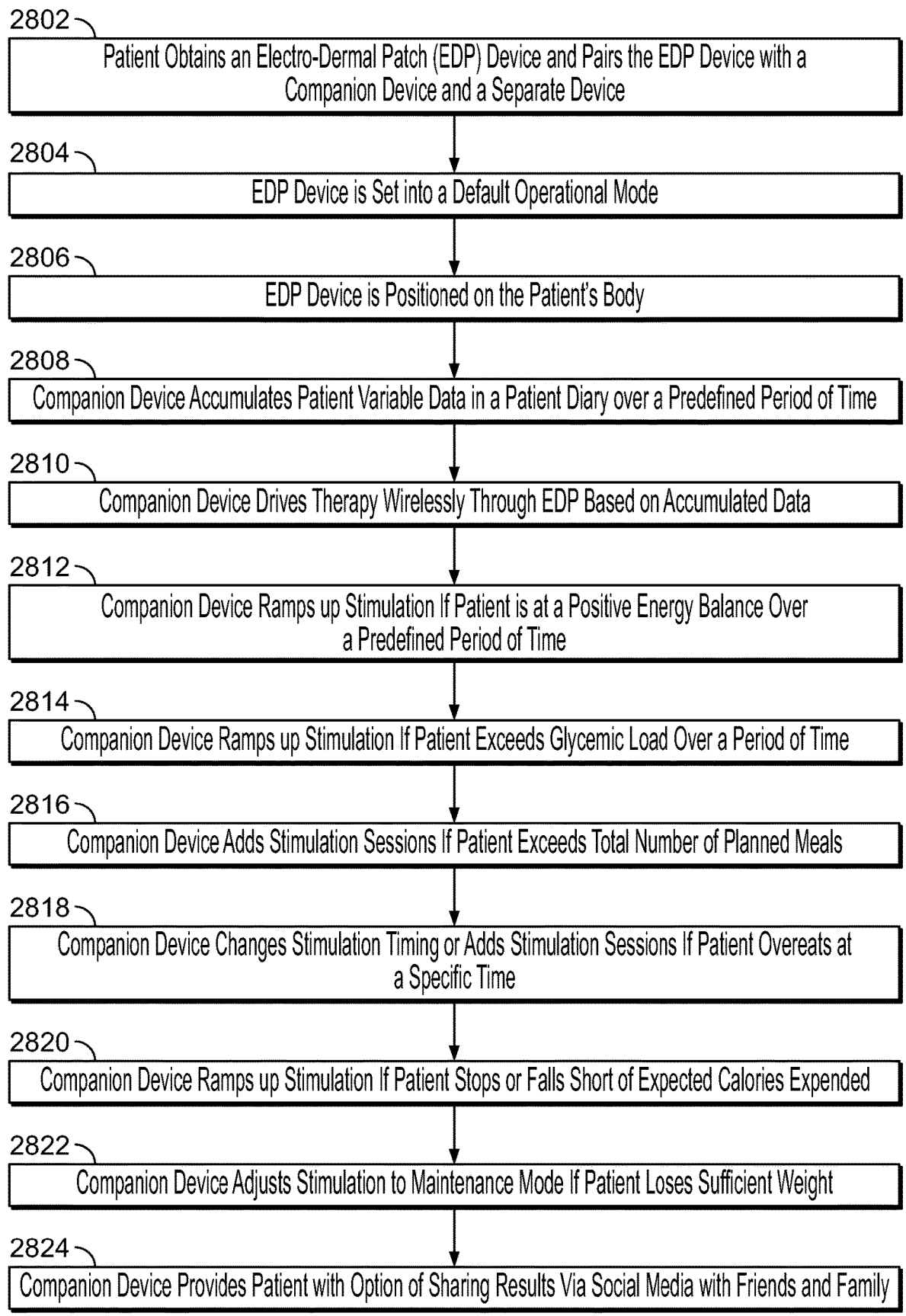
FIG. 28 is a flow chart illustrating steps involved in methods of using a neuro-stimulation device to suppress appetite in a patient, in various embodiments of the present specification.

FIG. 28 is a flow chart illustrating the steps involved in still another embodiment of a method of using an neuro-stimulation device to suppress appetite in a patient. At step 2802, the patient obtains a percutaneous electro-dermal patch (PEDP) device and pairs the EPD device with a companion device, such as a smartphone, and a separate device, for example, a device, with physiological sensors, configured to be worn on the human body, such as around the wrist, in order to monitor, acquire, record, and/or transmit the physiological data. In some embodiments, pairing with the separate device can be done anytime within a treatment cycle. In some embodiments, a treatment cycle lasts 3 months. At step 2804, the device is set into a default operational mode. In some embodiments, the default operational mode includes the stimulation parameters and parameter ranges listed above with respect to FIG. 21C and includes daily stimulation.

The PEDP device is implanted on the patient's body at step 2806. In accordance with various embodiments, the PEDP device is implanted within the patient's body by a medical professional or self-implanted by the user himself At step 2808, the companion device accumulates patient variable data, including, but not limited to, actual eating and meals profile of the user such as the time of consumption of a meal in a day and the type and amount of food eaten at the meal, standard regular eating and meals routine of the user, such as a standard diet plan (such as, but not limited to, Mediterranean, Zone Diet, Atkins Diet, Ketogenic Diet, Intermittent Fasting, Jenny Craig, and Custom Plan), appetite, hunger, well-being, weight, and calories expended/weight loss, in a patient diary over a predefined period of time. In some embodiments, the companion device accumulates data over a range of 1 to 7 days. In one embodiment, the companion device accumulates data for 3 days. Then, at step 2810, the companion device drives stimulation therapy wirelessly through the PEDP device based on accumulated patient diary data over the treatment cycle.

During the treatment cycle, if the patient has a positive or surplus energy balance (representative of more actual calories consumed in comparison to the calories expended) over a predefined period of time, for example, 3 days, the companion device ramps up stimulation parameters (such as, by increasing the stimulation duration, intensity and/or number of sessions) at step 2812. During the treatment cycle, if the patient exceeds the glycemic load (calculated based on the patient's actual eating and meals profile input into the patient diary), compared to the allowed glycemic load as estimated based on the patient's standard diet plan, over a predefined period of time, for example, 3 to 5 days, the companion device ramps up stimulation parameters at step 2814. Alternatively or additionally, at steps 2812 and 2814, the companion device ramps up stimulation parameters if the patient records an appetite diary entry with a score of 5, for example, for 3 to 5 days, indicative of poor or no dietary compliance with reference to the patient's standard diet plan. Thus, in some embodiments, the Health Management application uses the appetite parameter, which is indicative of the patient's dietary compliance, to assess if the patient is likely to be at a surplus energy balance and exceed the allowable glycemic load.

During the treatment cycle, if the patient exceeds the total number of meals per day over a predefined period of time, compared to the number of meals allowed according to the patient's standard diet plan, the companion device may include additional stimulation sessions just prior (for example, a half hour or an hour prior) to the extra meal events at step 2816. At step 2818, if the patient overeats at a specific time and continues to depict such overeating behavior over a predefined period of time, for example, 3 to 5 days, the companion device may change the timing of stimulation to just prior (for example, a half hour or an hour prior) to the overeating meal event or time or may include an additional stimulation session just prior to the overeating meal event. In some embodiments, the energy balance and glycemic load are calculated for every meal of the day, which in turn enables calculation of the meal that contributes the highest percentage of calories (or energy surplus) and glycemic load for the day. This meal, which contributes the highest percentage of calories and glycemic load per day over a predefined period of time, is identified as the overeating meal event.

During the treatment cycle, if the patient stops exercising for a predefined period of time, for example 3 to 5 days, or if the patient has an exercise score of 5 (FIG. 12), indicating the least level of expected exercising and therefore calories expended, and is also at a surplus energy balance for a predefined period of time (for example 3 to 5 days), the companion device ramps up stimulation parameters at step 2820. At step 2822, following a treatment course or cycle, once the patient has lost sufficient weight or achieved a target weight, the companion device modifies stimulation parameters to a maintenance mode wherein the stimulation parameters such as stimulation intensity, duration and number of sessions are all lowered.

Optionally, at step 2824, the companion device provides the patient with the option of sharing his results via social media with designated friends and family. In an alternate embodiment, the companion device first accumulates patient diary data before the PEDP device is set into the default operation mode. Referring to FIG. 28, in this alternate embodiment, step 2808 is performed prior to step 2804. The remaining steps proceed in the same order.

Therapeutic Objectives

In various embodiments, the systems and methods of the present specification employ a percutaneous electro-dermal patch that provides pre-programmed and/or customized stimulation protocols to induce changes in antral and gastric motility to slow passage of food. In various embodiments, a Health Management application software, as described above, provides and/or enables the programming, either pre-programmed or set 'on demand' by the patient or medical personnel (in real time), of a plurality of therapeutic goals which are also customizable or adjustable in order to modulate gut hormones, modulate gut microbiota, assess antral and gastric motility, suppress appetite, achieve dietary compliance, suppress hunger, or elevate fullness, satiation, or satiety. It should be noted herein that any or a plurality of the methods of use or treatment examples provided above may be employed to achieve the therapeutic objectives.

It should also be noted that the percent changes in value listed below are represented by the following formula: [(New Value)−(Old Value)]/(Old Value)]. Thus, where a certain parameter is measured in percentage, the percentage change is reflected by the above formula and not a delta value.

The following are a plurality of non-limiting, exemplary goals:

In some embodiments, after at least one stimulation session or determinable time period after when stimulation terminates, the rate, level or amount of any patient parameter, as discussed throughout this specification is modified relative to the rate, level or amount of that patient parameter before stimulation. In one instance, after at least one stimulation session or determinable time period after when stimulation terminates, the rate, level or amount of that patient parameter is reduced relative to the rate, level or amount of that patient parameter before stimulation. In another instance, after at least one stimulation session or determinable time period after when stimulation terminates, the rate, level or amount of that patient parameter is increased relative to the rate, level or amount of that patient parameter before stimulation.

In some embodiments, after stimulation terminates, or at least one minute from when stimulation terminates, the patient experiences a decrease in appetite or hunger by at least 5%.

In some embodiments, after at least one minute from when stimulation terminates or after at least one stimulation session, the patient experiences a decrease in appetite or hunger such that it is equal to, or less than, 95% of the pre-stimulation appetite or hunger levels.

In some embodiments, after at least one minute from when stimulation is initiated, the patient experiences a perceptible decrease in appetite or hunger.

In some embodiments, after at least one minute from when stimulation is initiated, the patient experiences an increase in satiety, satiation or fullness levels by at least 5%.

In some embodiments, after at least one minute from when stimulation terminates or after at least one stimulation session, the patient experiences an increase in satiety, satiation or fullness levels such that it is equal to, or greater than, 105% of the pre-stimulation satiety, satiation or fullness levels.

In some embodiments, after at least one stimulation session, a patient's compliance with a target daily caloric intake increases relative to the patient's compliance with the target daily caloric intake before stimulation.

In some embodiments, the systems and methods of the present specification result in a decrease in the post-stimulation daily caloric intake of a patient relative to a pre-stimulation daily caloric intake of the patient, wherein the pre-stimulation daily caloric intake is a function of an amount of calories consumed by the patient over a first predefined period of time prior to stimulation, and wherein the post-stimulation daily caloric intake is a function of an amount of calories consumed by the patient over a second predefined period of time equal in duration to the first predefined period of time, after stimulation is initiated. For example, the decrease may be quantified as equal to or less than 99% of the pre-stimulation caloric intake, where the caloric intake decreases to a range of 600 to 1600 calories, decreases from over 2000 calories per day to less than 2000 calories per day, or decreases from over 1600 calories per day to less than 1600 calories per day.

In some embodiments, after at least one stimulation session, an amount or rate of a patient's antral motility, gastric motility, gastric emptying, hunger or appetite level is modified, relative to the corresponding amount before stimulation.

In some embodiments, after at least one stimulation session, the rate of a patient's antral motility, gastric motility, or gastric emptying is modified relative to the rate of the patient's antral motility, gastric motility, or gastric emptying before stimulation, and preferably the rate of a patient's antral motility, gastric motility, or gastric emptying is reduced relative to the rate of the patient's antral motility, gastric motility, or gastric emptying before stimulation.

In some embodiments, a patient's appetite or hunger level, in a first state, is greater that the appetite or hunger in a second state, wherein the first state is defined by a first area under the curve (AUC) corresponding to a pre-stimulation appetite or hunger level and the second state is defined by a second AUC corresponding to a post-stimulation appetite or hunger level, and wherein the first AUC differs from the second AUC by at least 5%, thereby representing a decrease in the appetite or hunger level of the patient.

In some embodiments, a patient's satiety, satiation or fullness level, in a first state, is less than the satiety, satiation or fullness level in a second state, wherein the first state is defined by a first AUC corresponding to a pre-stimulation satiety, satiation or fullness level and the second state is defined by a second AUC corresponding to a post-stimulation satiety, satiation or fullness level, and wherein the first AUC differs from the second AUC by at least 5%, thereby representing an increase in the satiety, satiation or fullness level of the patient.

In some embodiments, after at least one stimulation session, an amount of a patient's satiety, satiation or fullness levels increases relative to the corresponding amount before stimulation.

In some embodiments, after at least one stimulation session, a patient's appetite or hunger level decreases, over a predefined period of time, relative to the patient's appetite or hunger level before stimulation and the patient's nausea and/or dyspepsia level does not increase, over the predefined period of time, relative to the patient's nausea level before stimulation, wherein the stimulation does not cause the patient to experience a pain sensation.

In some embodiments, after at least one stimulation session, a patient's satiety, satiation or fullness level increases, over a predefined period of time, relative to the patient's satiety, satiation or fullness level before stimulation and the patient's nausea and/or dyspepsia level does not increase, over the predefined period of time, relative to the patient's nausea level before stimulation, wherein the stimulation does not cause the patient to experience a pain sensation.

In some embodiments, after at least one stimulation session, a patient's total body weight reduces by at least 1% relative to the patient's total body weight before stimulation. In some embodiments, after at least one stimulation session, a patient's total body weight reduces by at least 3% relative to the patient's total body weight before stimulation. In some embodiments, after at least one stimulation session, a patient's total body weight reduces by at least 1% relative to the patient's total body weight before stimulation and the patient's well-being level does not reduce more than 5% relative to the patient's well-being level before stimulation. In some embodiments, after at least one stimulation session, a patient's total body weight reduces by at least 3% relative to the patient's total body weight before stimulation and the patient's well-being level does not reduce more than 5% relative to the patient's well-being level before stimulation.

In some embodiments, after at least one stimulation session, a patient's pre-prandial ghrelin level reduces by at least 1%, and preferably at least 3%, relative to the patient's pre-prandial ghrelin level before stimulation. In some embodiments, after at least one stimulation session, a patient's post-prandial ghrelin level reduces by at least 1%, and preferably at least 3%, relative to the patient's post-prandial ghrelin level before stimulation.

In some embodiments, after at least one stimulation session, a post-stimulation ghrelin level of a patient decreases by at least 1%, and preferably at least 3%, relative to a pre-stimulation ghrelin level of the patient, wherein the pre-stimulation ghrelin level is measured prior to stimulation and wherein the post-stimulation ghrelin level is measured more than ten weeks after the at least one stimulation session.

In some embodiments, after at least one stimulation session, the level of a patient's glucagon-like peptide-1, leptin, serotonin, peptide YY, beta-endorphin levels, resting metabolic rate, and/or cholecystokinin increases relative to the corresponding level of a patient's glucagon-like peptide- 1, leptin, serotonin, peptide YY, beta-endorphin levels, resting metabolic rate, and/or cholecystokinin before stimulation.

In some embodiments, after at least one stimulation session, the level of a patient's triglycerides, cholesterol, lipopolysaccharides, and/or motilin-related peptide decreases relative to the corresponding level of a patient's triglycerides, cholesterol, lipopolysaccharides, and/or motilin-related peptide.

In some embodiments, after at least one stimulation session, a patient's glucagon-like peptide-1 level increases by at least 1%, and preferably at least 3%, relative to the patient's glucagon-like peptide-1 level before stimulation.

In some embodiments, after at least one stimulation session, a patient's leptin level increases by at least 1%, and preferably at least 3%, relative to the patient's leptin level before stimulation.

In some embodiments, after at least one stimulation session, a patient's serotonin level increases by at least 1%, and preferably at least 3%, relative to the patient's serotonin level before stimulation.

In some embodiments, after at least one stimulation session, a patient's peptide YY level increases by at least 1%, and preferably at least 3%, relative to the patient's peptide YY level before stimulation.

In some embodiments, after at least one stimulation session, a patient's beta-endorphin level increases by at least 1%, and preferably at least 3%, relative to the patient's beta-endorphin level before stimulation.

In some embodiments, after at least one stimulation session, a patient's resting metabolic rate increases by at least 1%, and preferably at least 3%, relative to the patient's resting metabolic rate before stimulation.

In some embodiments, after at least one stimulation session, a patient's cholecystokinin level increases by at least 1%, and preferably at least 3%, relative to the patient's cholecystokinin level before stimulation.

In some embodiments, after at least one stimulation session, a patient's lipopolysaccharide level reduces by at least 1%, and preferably at least 3%, relative to the patient's lipopolysaccharide level before stimulation. In some embodiments, a reduction in the lipopolysaccharide level also reduces metabolic inflammation and insulin resistance.

In some embodiments, after at least one stimulation session, a patient's motilin-related peptide level reduces by at least 1%, and preferably at least 3%, relative to the patient's motilin-related peptide level before stimulation.

In some embodiments, after at least one stimulation session, a patient's triglycerides level reduces by at least 1%, and preferably at least 3%, relative to the patient's triglycerides level before stimulation.

In some embodiments, after at least one stimulation session, a patient's degree of glycemia improves by at least 1%, and preferably at least 3% relative to the patient's degree of glycemia before stimulation.

In some embodiments, after at least one stimulation session, a non-diabetic or a non-pre-diabetic patient's glucose is reduced to a fasting level of less than 100 mg/dl, reducing the overall changes of the patient developing pre-diabetes in the future.

In some embodiments, after at least one stimulation session, a patient's glycemic control is improved. In some embodiments, after at least one stimulation session, a patient's glycemic control is modified relative to the patient's glycemic control before stimulation, and preferably the patient's glycemic control is increased relative to the patient's glycemic control before stimulation. In some embodiments, after at least one stimulation session, the level of hemoglobin A1C decreases by at least 1%, and preferably at least 3% relative to the patient's level of hemoglobin A1C before stimulation. In some embodiments, after at least one stimulation session, the level of hemoglobin A1C decreases by ≥5% relative to the patient's level of hemoglobin A1C before stimulation. In some embodiments, after at least one stimulation session, the level of hemoglobin A1C decreases by 0.5% relative to the patient's level of hemoglobin A1C before stimulation. Because hemoglobin A1C is measured in terms of percentage, it should be noted that what is described here is the percentage change relative to its level before stimulation. For example, if the baseline hemoglobin A1C level is measured at 7%, a 5% decrease is calculated as a decrement of 0.35% and therefore a decreased hemoglobin A1C level of 6.75%.

In some embodiments, after at least one stimulation session, a patient's glucose homeostasis improves by at least 1%, and preferably at least 3% relative to the patient's glucose homeostasis before stimulation. Optionally, glucose homeostasis is quantified by decreasing HOMA-IR (Homeostasis Model Assessment—estimated Insulin Resistance) by ≥5% compared to a baseline HOMA-IR and is calculated as described above with respect to hemoglobin A1C. In some T2DM patients, after at least one stimulation session, fasting blood glucose is decreased by 20 mg/dl.

In some embodiments, after at least one stimulation session, the patient experiences a decrease in a fasting plasma insulin level of ≥5% compared to a baseline fasting plasma insulin level.

In some embodiments, after at least one stimulation session, the patient experiences a decrease in a fasting plasma glucose level of ≥5% compared to a baseline fasting plasma glucose level.

In some embodiments, after at least one stimulation session, a patient's degree of insulin resistance is modified relative to the patient's degree of insulin resistance before stimulation, and preferably the patient's degree of insulin resistance is increased relative to the patient's degree of insulin resistance before stimulation. In some embodiments, after at least one stimulation session, a patient's degree of insulin resistance improves by at least 1%, and preferably at least 3% relative to the patient's degree of insulin resistance before stimulation.

In some embodiments, after at least one stimulation session, a patient's level of total blood cholesterol decreases by at least 1%, and preferably at least 3%, relative to the patient's level of total blood cholesterol before stimulation.

In some embodiments, after at least one stimulation session, a composition of a patient's gut microbiota is modified relative to a composition of a patient's gut microbiota before stimulation. In some embodiments, after at least one stimulation session, a composition of a patient's gut microbiota modulates from a first state to a second state, wherein the first state has a first level of bacteroidetes and a first level of firmicutes, wherein the second state has a second level of bacteroidetes and a second level of firmicutes, wherein the second level of bacteroidetes is greater than the first level of bacteroidetes by at least 1%, and preferably at least 3%, and wherein the second level of firmicutes is less than the first level of firmicutes by at least 1%, and preferably at least 3%.

In some embodiments, after at least one session of stimulation session, the patient experiences a modification, and preferably, a perceptible decrease in appetite or hunger which lasts for at least one day.

In some embodiments, a patient's appetite is reduced by 5% over at least 1 day of stimulation therapy.

In some embodiments, after at least one session of stimulation, a patient reports "improved" dietary compliance, wherein dietary compliance is achieving a daily caloric consumption target. In some embodiments, "improved" dietary compliance is at least 5% closer to a defined or set daily calorie consumption target using the PEDP device of the present specification.

In some embodiments, a patient has reached a therapeutic goal if they achieve greater than at least 1%, and more preferably 2%, 5%, 10%, and any increment therein, TWL (Total Weight Loss) or at least 1%, and more preferably 2%, 5%, 10%, and any increment therein, EWL (Excess Weight Loss) in six months of stimulation therapy.

In some embodiments, a patient has reached a therapeutic goal if they are able to change their metabolism rate (such as RMR or BMR) by 10%. In some embodiments, a stimulation therapy is intended to affect at least 5% improvement in RMR.

In some embodiments, application of electrical stimulation via the PEDP embodiments disclosed herein result in a person having an altered perception of gastric fullness or emptiness. Specifically, when the PEDP therapy is applied, the stimulation parameters are selected such that, after at least one stimulation session, the perception of gastric fullness or gastric emptiness of the patient increases by at least 1% relative to the perception of gastric fullness or gastric emptiness of the patient before stimulation. This may be measured over a single day, week, month or other time period.

In some embodiments, application of electrical stimulation via the PEDP embodiments disclosed herein result in a person having increased exercise output, defined as the amount of calories burned in a given time period or steps taken in a given time period. Specifically, when the PEDP therapy is applied, the stimulation parameters are selected such that, after at least one stimulation session, exercise output of the patient increases by at least 1% relative to the exercise output of the patient before stimulation. This exercise output may be measured over a single day, week, month or other time period.

Achieving Dietary Compliance

In one embodiment, use of the PEDP device, in accordance with the methods described herein, result in patients being able to better comply with a predefined dietary regime, including being better able to restrict daily caloric intake to a predefined amount, being better able to adhere to a diet designed to maximize particular nutritional components, such as vitamins, minerals, and proteins, and decrease undesirable nutritional components, such as carbohydrates, fat, and sugars, and being better able to adhere to a diet designed to have a glycemic index that is equal to or less than a predefined amount. The present specification facilitates adhering to dietary objectives for overweight (body mass index of 25-29.9) or obese (body mass index of 30 or greater) individuals, particularly given that willpower alone or even willpower with exercise is an ineffectual approach to dietary compliance and either weight loss or weight management.

Therapeutically, the PEDP device can be used in conjunction with predefined diet plans, comprising a nutritional profile, a set of foods, and/or a maximum number of calories, to ensure that a patient adheres to the predefined plan.

Therefore, in one embodiment, the present specification enables increased dietary compliance. A patient is provided the PEDP device, adheres it to his or her epidermal layer, and initiates a stimulation regime. The patient also receives a diet plan, either manually or electronically into an application executing on an external device, that defines a diet plan. The diet plan may establish a maximum daily caloric intake, such as between 600 and 1600 calories, may require a particular nutritional profile, such as a certain number or type of vegetables, proteins, and/or supplements, and/or may require the avoidance of certain types of foods, such as carbohydrates, sugars, and/or foods with high glycemic indexes. The parameters of the diet plan may be based on receiving, electronically into an application executing on an external device or manually, an indication of how active the patient is (sedentary, moderately active, active), the patient's gender, the patient's age, the patient's weight, the patient's height, the patient's percentage of body fat, and/or the patient's body mass index. As the patient uses the device and records his or her food consumption, either into the program in the external device in communication with the PEDP device or into a separate third party program which then transmits the information to the program in communication with the PEDP device, the program in communication with the PEDP device determines if the patient is complying with the diet regimen. If the patient is not avoiding certain types of food, not eating a particular nutritional profile, and/or exceeding the maximum daily caloric intake, the program modulates stimulation parameters in order to decrease appetite and/or hunger levels and transmits those modulated stimulation parameters to the PEDP device, which then increases stimulation strength, duration, and/or frequency, thereby causing the decrease appetite and/or hunger levels and enabling the patient to better comply with the diet regimen. Conversely, if the patient is not getting enough calories, the program modulates stimulation parameters in order to increase appetite and/or hunger levels and transmits those modulated stimulation parameters to the PEDP device, which then decreases stimulation strength, duration, and/or frequency, thereby causing the increase appetite and/or hunger levels and, again, enabling the patient to better comply with the diet regimen.

In another embodiment, the present specification enables improved dietary management. One substantial problem that physicians and diet programs have is keeping a patient on the prescribed diet. The present specification enables improved dietary management. A third party manager, such as a physician or health care provider, provides a patient with the PEDP device and programs the PEDP device with an initial stimulation regime based upon a prescribed diet plan. The diet plan may establish a maximum daily caloric intake, such as in the range of 600 to 1600 calories, may require a particular nutritional profile, such as a certain number or type of vegetables, proteins, and/or supplements, and/or may require the avoidance of certain types of foods, such as carbohydrates, sugars, and/or foods with high glycemic indexes. The parameters of the diet plan may be based on receiving, electronically into an application executing on an external device or manually, an indication of how active the patient is (sedentary, moderately active, active), the patient's gender, the patient's age, the patient's weight, the patient's height, the patient's percentage of body fat, and/or the patient's body mass index. As the patient uses the device and records his or her food consumption, either into the program in the external device in communication with the PEDP device or into a separate third party program which then transmits the information to the program in communication with the PEDP device, the program in communication with the PEDP device determines if the patient is complying with the diet regimen. If the patient is not avoiding certain types of food, not eating a particular nutritional profile, and/or exceeding the maximum daily caloric intake, the third party manager may modulate stimulation parameters in order to decrease appetite and/or hunger levels and transmits those modulated stimulation parameters to the PEDP device, which then increases stimulation strength, duration, and/or frequency, thereby causing the decrease appetite and/or hunger levels and enabling the patient to better comply with the diet regimen. Conversely, if the patient is not getting enough calories, the third party manager may modulate stimulation parameters in order to increase appetite and/or hunger levels and transmit those modulated stimulation parameters to the PEDP device, which then decreases stimulation strength, duration, and/or frequency, thereby causing the increase appetite and/or hunger levels and, again, enabling the patient to better comply with the diet regimen.

In another embodiment, the present specification enables improved dietary maintenance and preventing the regaining of weight. After meeting a weight goal, through any of the aforementioned treatment methods, the patient's diet plan is adjusted to a new diet plan reflecting a weight maintenance, instead of a weight loss, objective. Such a diet plan, which may be received either manually or electronically into an application executing on an external device, may establish a higher maximum daily caloric intake than the previous diet plan, such as between 1600 and 2800 calories, a different nutritional profile, and/or less emphasis on avoiding of certain types of foods, such as carbohydrates, sugars, and/or foods with high glycemic indexes. The parameters of the new diet plan may be based on receiving, electronically into an application executing on an external device or manually, an indication of how active the patient is (sedentary, moderately active, active), the patient's gender, the patient's age, the patient's weight, the patient's height, the patient's percentage of body fat, and/or the patient's body mass index. As the patient uses the device and records his or her food consumption, either into the program in the external device in communication with the PEDP device or into a separate third party program which then transmits the information to the program in communication with the PEDP device, the program in communication with the PEDP device determines if the patient is complying with the new diet regimen. If the patient is not avoiding certain types of food, not eating a particular nutritional profile, and/or exceeding the new maximum daily caloric intake, the program modulates stimulation parameters in order to decrease appetite and/or hunger levels and transmits those modulated stimulation parameters to the PEDP device, which then increases stimulation strength, duration, and/or frequency, thereby causing the decrease appetite and/or hunger levels and enabling the patient to better comply with the diet regimen. Conversely, if the patient is not eating enough calories, the program modulates stimulation parameters in order to increase appetite and/or hunger levels and transmits those modulated stimulation parameters to the PEDP device, which then decreases stimulation strength, duration, and/or frequency, thereby causing the increase appetite and/or hunger levels and, again, enabling the patient to better comply with the diet regimen.

Alternatively, instead of modulating the stimulation parameters if the patient is not avoiding certain types of food, not eating a particular nutritional profile, and/or exceeding the new maximum daily caloric intake, the program, either in direct communication with the PEDP device, a remote server, or a third party application executing on an external device, may change the diet plan itself by increasing or decreasing the maximum daily caloric intake, changing the nutritional profile, and/or changing what types of foods to avoid.

Figure 32A:
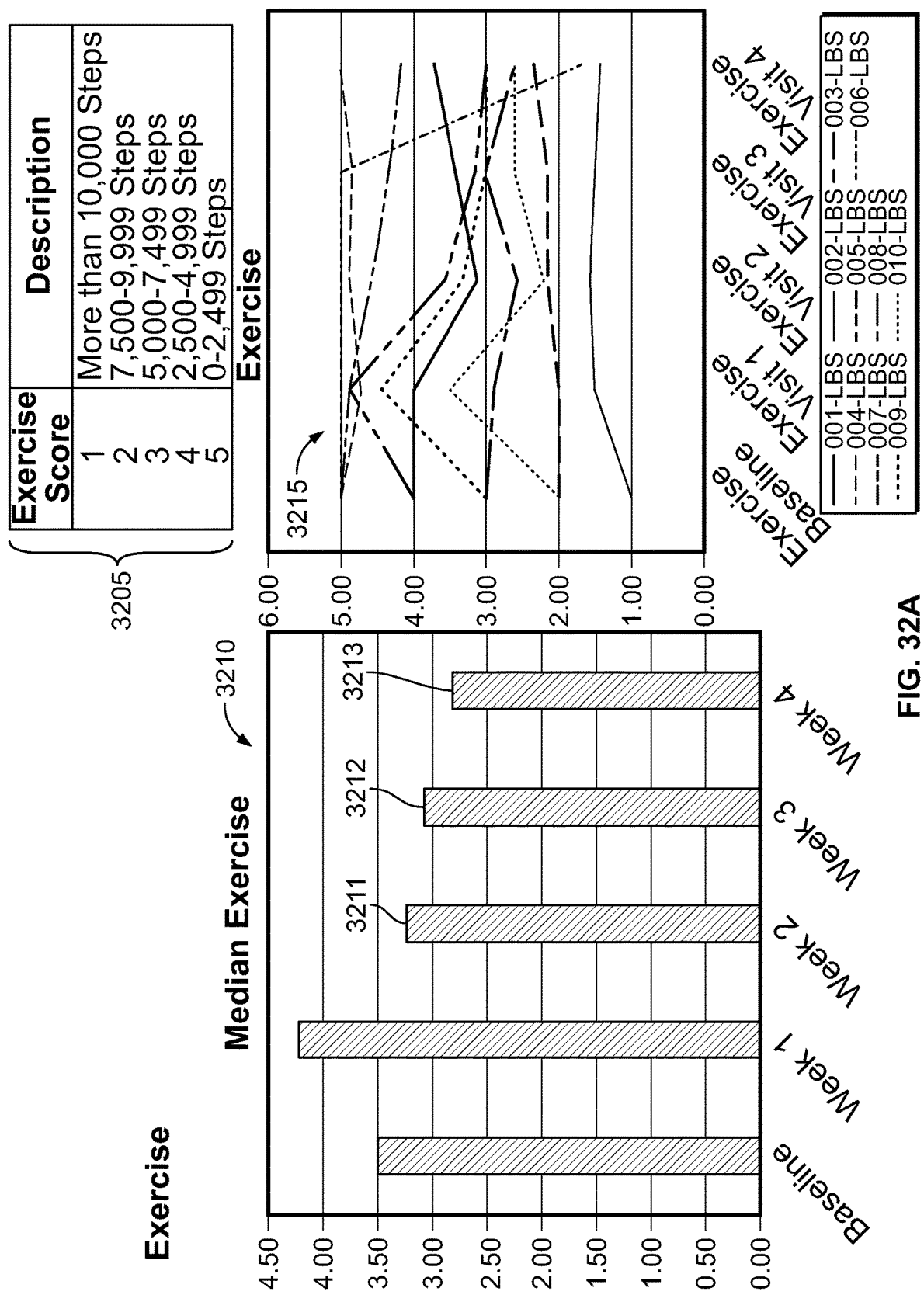
FIG. 32A is a graph illustrating exercise scores of a sample of patients treated with stimulation therapy, in accordance with an embodiment of the present specification.

FIGS. 32A through 32F show charts illustrating how the stimulation therapy of the present specification affects or modulates a plurality of patient variables or parameters such as, weight, BMI (Body Mass Index), appetite, dietary compliance and well-being for a sample of 10 patients. In accordance with an embodiment, the sample of 10 patients, having weight loss as an objective or goal, were treated with the stimulation therapy of the present specification over a duration of 4 weeks and the patients recorded their status on the plurality of variables or parameters throughout the duration of the 4 weeks using their companion devices. As shown in FIG. 32A, the 10 patients also exercised through the duration of 4 weeks and recorded their exercise scores 3205 using their companion devices (as described earlier with reference to FIG. 12). The bar graph 3210 shows median exercise scores per week, calculated from the exercise scores of the sample of 10 patients, while the line graphs 3215 show exercise scores per week of each of the 10 patients. As can be observed from the bar graph 3210, the median exercise scores 3211, 3212, 3213 improved during the second, third and fourth weeks.

Figure 32B:
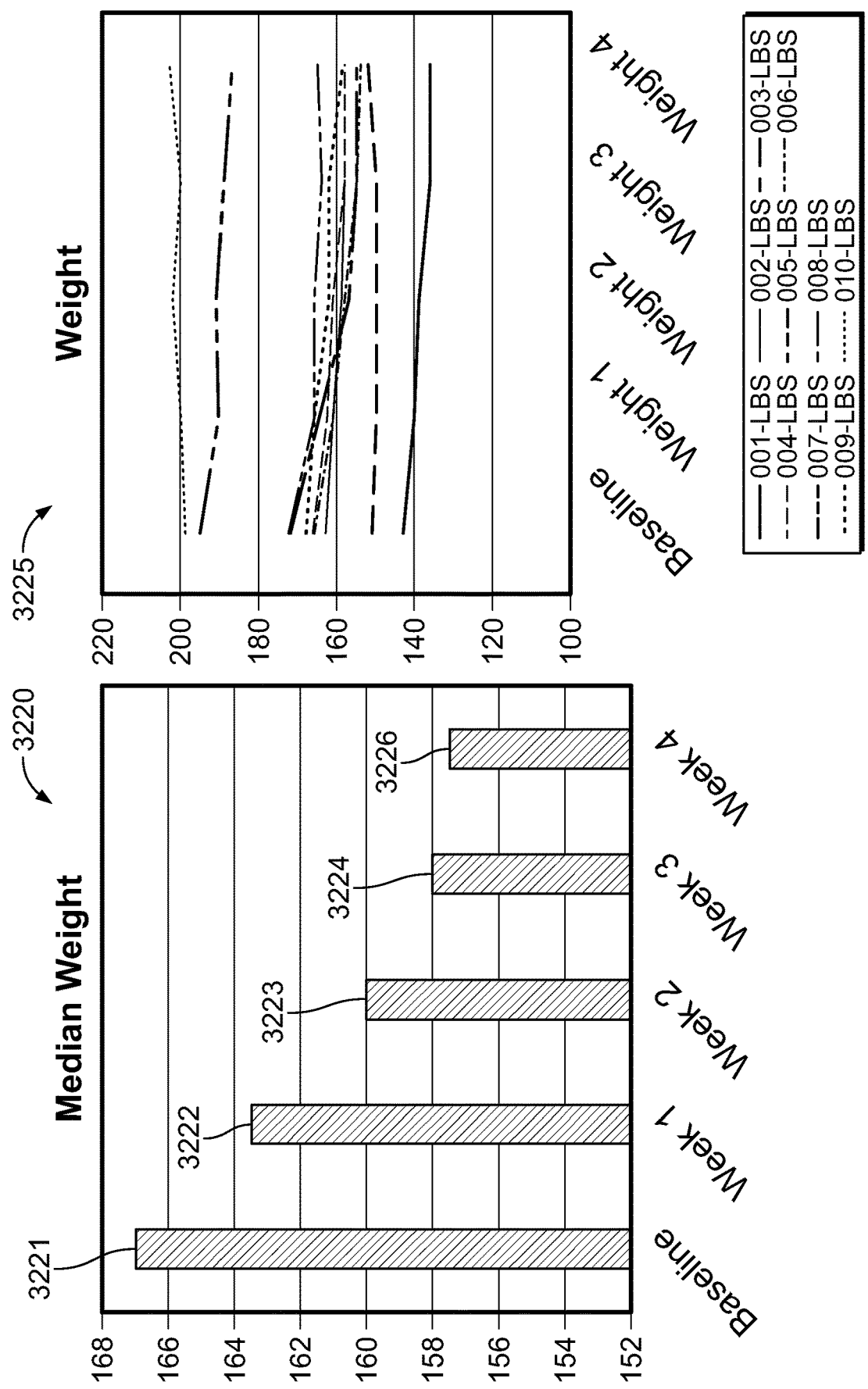
FIG. 32B is a graph illustrating weights of a sample of patients treated with stimulation therapy, in accordance with an embodiment of the present specification.

FIG. 32B shows charts illustrating how the weight parameter, for the sample of 10 patients, varied during the course of the 4 weeks, while the patients exercised, received stimulation therapy and recorded their weight using their companion devices (as described earlier with reference to FIG. 15). The bar graph 3220 shows median weights per week, calculated from the weights of the sample of 10 patients, while the line graphs 3225 show weights per week of each of the 10 patients. As can be observed from the bar graph 3220, the median weights 3222, 3223, 3224, 3226 continued to reduce during the first, second, third and fourth weeks relative to the median weight 3221 at the baseline (that is, prior to receiving stimulation therapy).

Figure 32C:
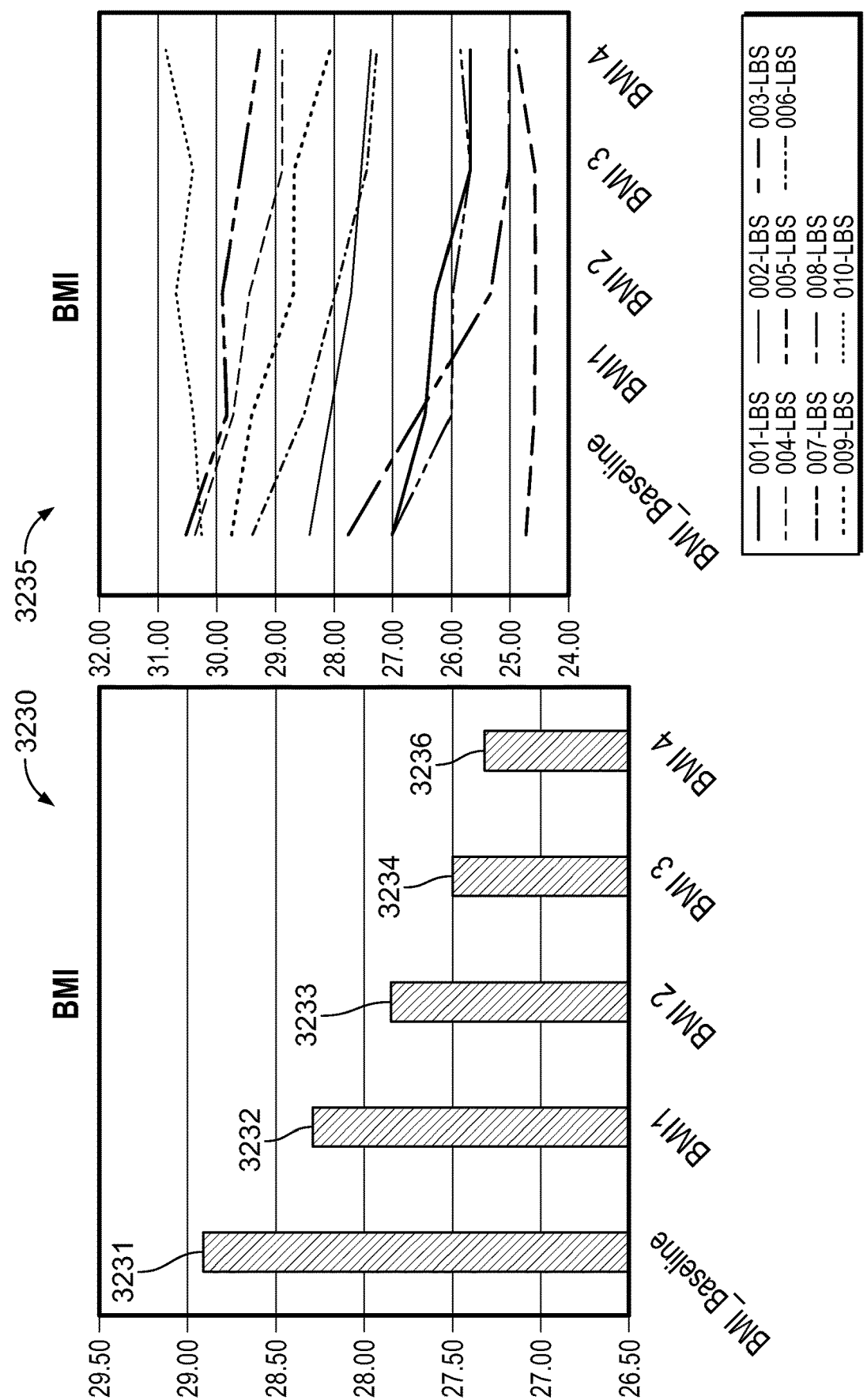
FIG. 32C is a graph illustrating BMIs (Body Mass Index) of a sample of patients treated with stimulation therapy, in accordance with an embodiment of the present specification.

FIG. 32C shows charts illustrating how the BMI parameter, for the sample of 10 patients, varied during the course of the 4 weeks, while the patients exercised and received stimulation therapy. The bar graph 3230 shows median BMI per week, calculated from the BMIs of the sample of 10 patients, while the line graphs 3235 show BMIs per week of each of the 10 patients. As can be observed from the bar graph 3230, the median BMIs 3232, 3233, 3234, 3236 continued to reduce during the first, second, third and fourth weeks relative to the median BMI 3231 at the baseline (that is, prior to receiving stimulation therapy).

Figure 32D:
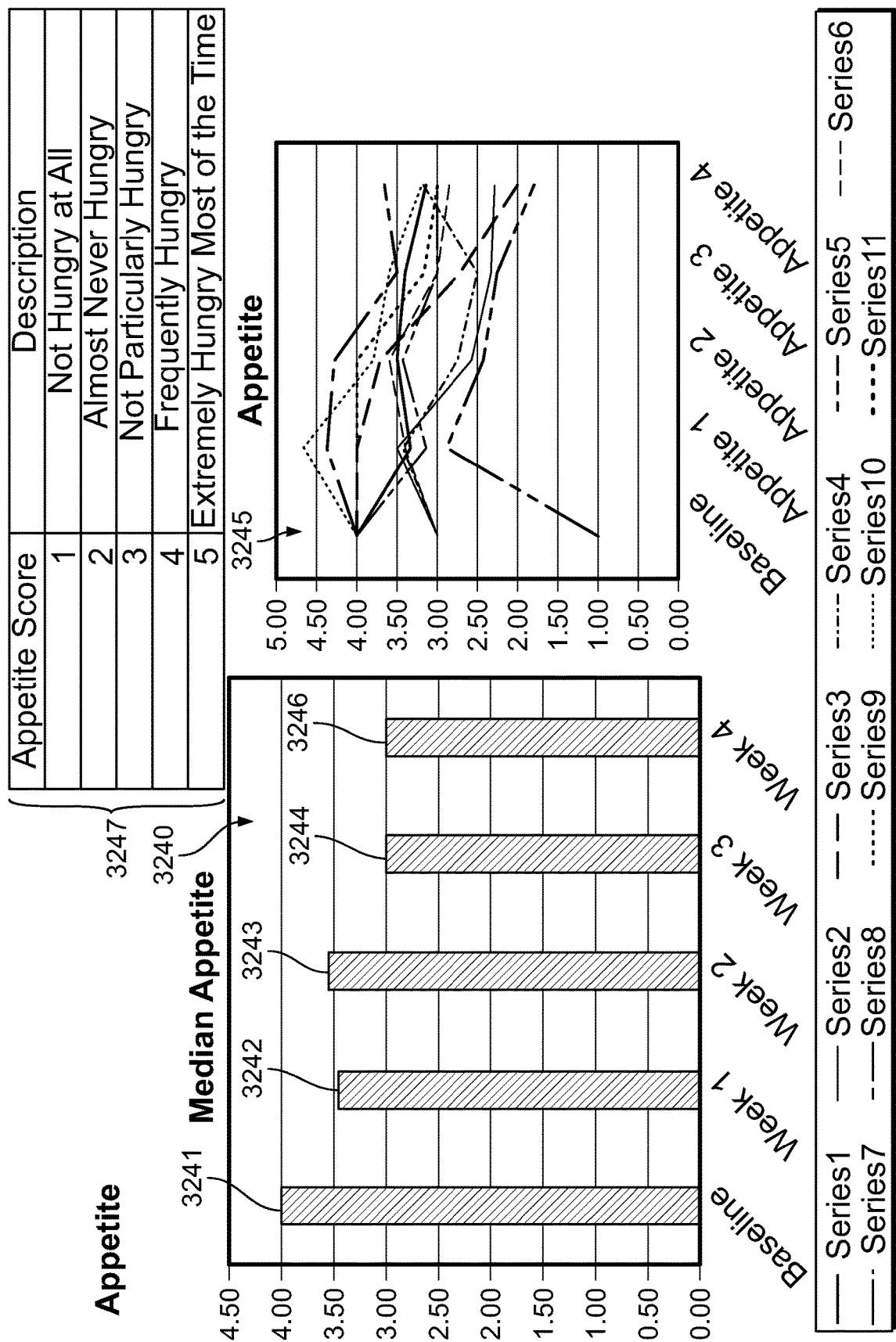
FIG. 32D is a graph illustrating appetite scores of a sample of patients treated with stimulation therapy, in accordance with an embodiment of the present specification.

FIG. 32D shows charts illustrating how the appetite parameter, for the sample of 10 patients, varied during the course of the 4 weeks, while the patients exercised, received stimulation therapy and recorded their appetite scores 3247 using their companion devices (as described earlier with reference to FIG. 11). The bar graph 3240 shows median appetite scores per week, calculated from the appetite scores of the sample of 10 patients, while the line graphs 3245 show appetite scores per week of each of the 10 patients. As can be observed from the bar graph 3240, the median appetite scores 3242, 3243, 3244, 3246 continued to reduce during the first, second, third and fourth weeks relative to the median appetite score 3241 at the baseline (that is, prior to receiving stimulation therapy).

Figure 32E:
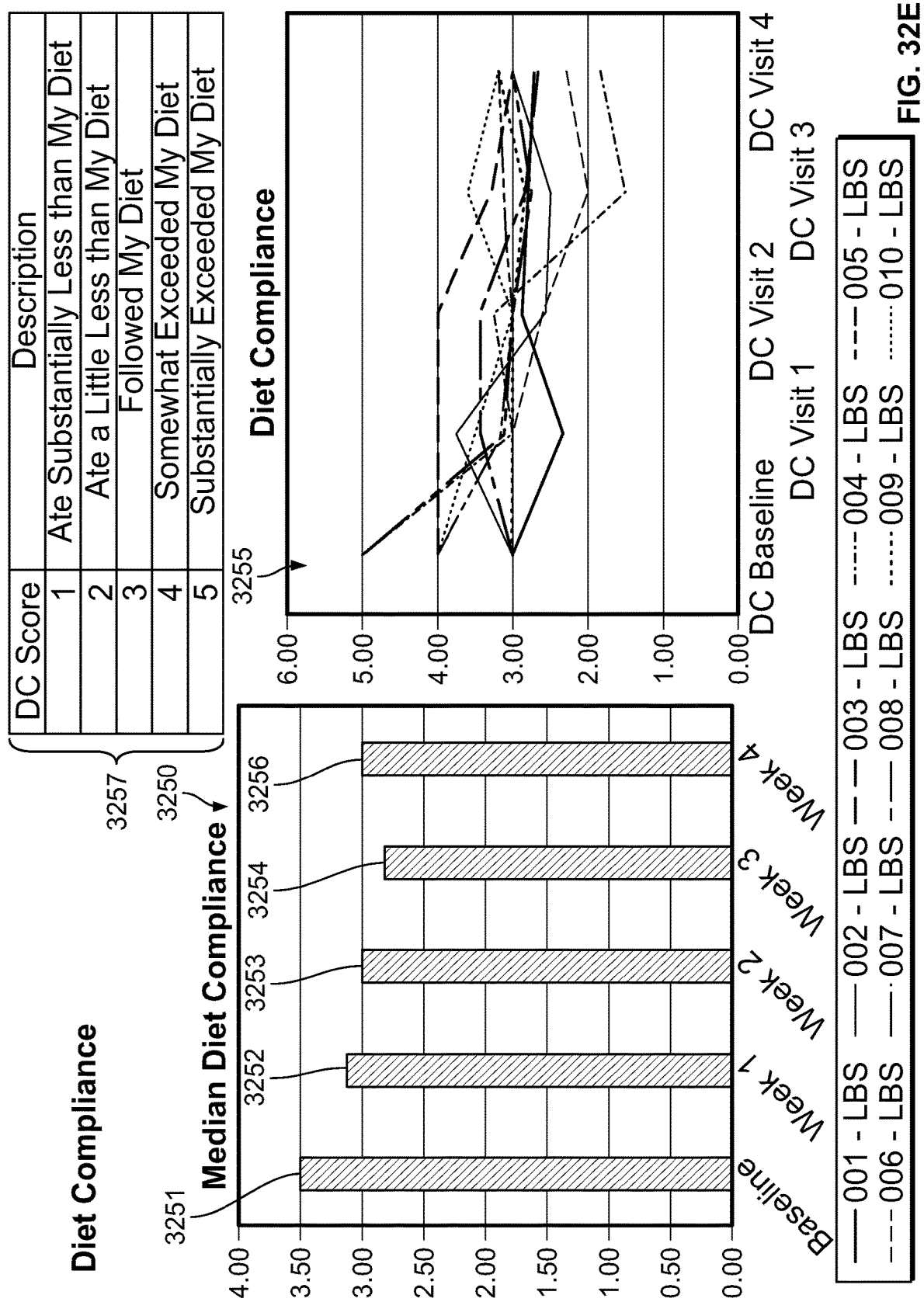
FIG. 32E is a graph illustrating dietary compliance scores of a sample of patients treated with stimulation therapy, in accordance with an embodiment of the present specification.

FIG. 32E shows charts illustrating how the dietary compliance parameter, for the sample of 10 patients, varied during the course of the 4 weeks, while the patients exercised, received stimulation therapy and recorded their dietary compliance scores 3257 using their companion devices. The bar graph 3250 shows median dietary compliance scores per week, calculated from the dietary compliance scores of the sample of 10 patients, while the line graphs 3255 show dietary compliance scores per week of each of the 10 patients. As can be observed from the bar graph 3250, the median dietary compliance scores 3252, 3253, 3254, 3256 improved during the first, second, third and fourth weeks relative to the median dietary compliance score 3251 at the baseline (that is, prior to receiving stimulation therapy). The graph 3250 highlights key advantages of the wearable neuro-stimulation device of the present specification, specifically in terms of greater patient independence and improved patient compliance to stimulation protocols, with resultant increased dietary compliance.

Figure 32F:
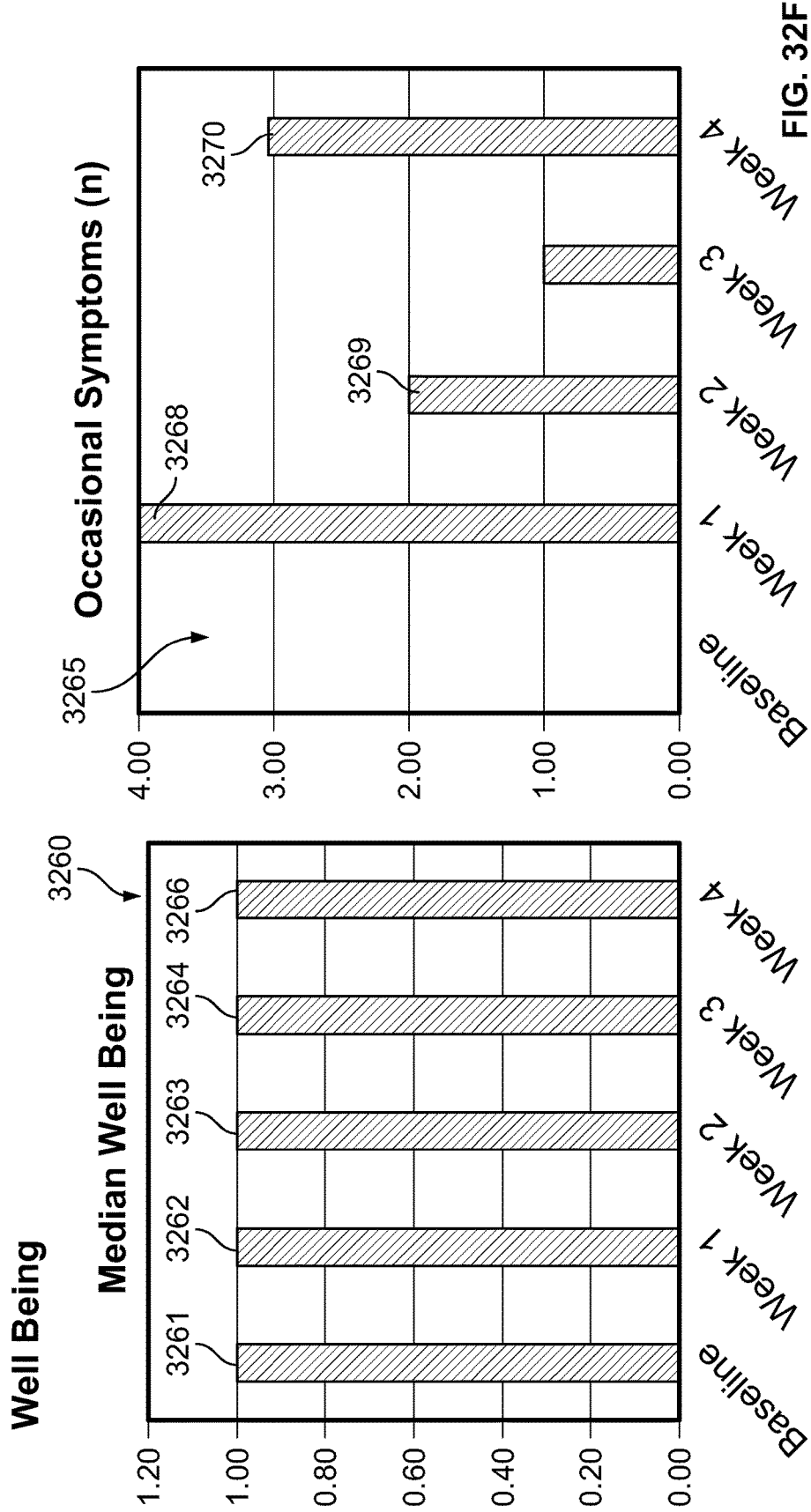
FIG. 32F is a graph illustrating well-being scores of a sample of patients treated with stimulation therapy, in accordance with an embodiment of the present specification.

FIG. 32F shows charts illustrating how the well-being parameter, for the sample of 10 patients, varied during the course of the 4 weeks, while the patients exercised, received stimulation therapy and recorded their well-being scores 3267 using their companion devices (as described earlier with reference to FIG. 16). The bar graph 3260 shows median well-being scores per week, calculated from the well-being scores of the sample of 10 patients, while the bar graphs 3265 show variation in well-being scores for a number of patients (y-axis) reporting symptoms of nausea/abdominal pain at each week. As can be observed from the bar graph 3260, the median well-being scores 3262, 3263, 3264, 3266 remained stable during the first, second, third and fourth weeks relative to the median well-being score 3261 at the baseline (that is, prior to receiving stimulation therapy) although there were occasional deterioration of well-being scores per week (such as the well-being scores 3268, 3269, 3270 for 4, 2 and 3 patients respectively) for some patients, as can be observed from the bar graphs 3265.

It should be appreciated that the pre-stimulation levels of the plurality of patient variables or parameters (such as, but not limited to, weight, BMI (Body Mass Index), appetite, dietary compliance and well-being) are measured using a scale (such as a VAS) at predefined times of the day over a first predefined period of time (such as 4 weeks, for example), and the post-stimulation levels of the patient variables or parameters are measured, after stimulation is initiated, using the scale at the predefined times of the day over a second predefined period of time, equal in duration to the first predefined period of time.

It should be appreciated that each of the pre-stimulation and post-stimulation levels, profiles or measurements may be assessed by comparing data from a single individual or by first aggregating pre-stimulation data from multiple individuals and post-stimulation data from multiple individuals and comparing the two aggregated data sets. Additionally, it should be appreciated that the effects of stimulation may be assessed by comparing measured parameters, as described above, from either an individual or group (in the form of aggregated data) to a control individual or group which has not undergone stimulation. In such cases, one would be comparing post-stimulation effects to no stimulation in a different individual or group of individuals (control) as opposed to comparing post-stimulation effects to pre-stimulation measurements from the same individual or group of individuals.

Telemedicine

As discussed earlier, the neuro-stimulation device is in data communication with and controlled by the companion device. The companion device is further capable of being in data communication with one or more remote patient care facilities and/or patient care personnel enabling telehealth or e-health and therefore allowing health care professionals to evaluate, diagnose and treat patients in remote locations using telecommunications technology.

In accordance with an aspect of the present specification, the user's plurality of health related information, such as the user's hunger profile, standard eating and meals profile, actual eating and meals profile, energy balance, weight trends, glucose data, daily or periodic scores related to hunger, appetite, exercise and well-being, stimulation induced nausea, dyspepsia and habituation events, including stimulation protocols, setting and parameters are recorded, archived and stored by the Health Management application software on the Cloud (for example). In various embodiments, such recorded and archived health related information as well stimulation protocols, settings and parameters of the user are communicated to one or more remote care facilities and/or patient care personnel in real time, on-demand and/or periodically.

This enables the user to communicate his health status, trends, treatment or therapy details as well as therapeutic outcomes to the remote care facility and/or patient care personnel for evaluation, advice, support and further treatment and/or medication options. For example, weight loss programs focused on diets often fail due to weight gain after the termination of the program. However, the Health Management application software, which may be HIPAA compliant, enables continuous weight maintenance by: enabling remote monitoring of the user's weight, blood glucose, blood pressure, and overall activity level, for example; supporting a plurality of modes of communication such as, but not limited to, video-conferencing, tele-conferencing, email, and chat to enable interactive, real-time and/or asynchronous weight maintenance related advice or stimulation regimen for the user. For example, the user's nutrition specialist, fitness trainer and/or a concierge service associated with the PEDP device and Health Management application of the present specification may access, process and analyze the user's health related information and provide interventions in the form of adjusted or modified stimulation parameters, settings and protocols; modifications to exercising routines, forms, frequency and period; and/or adjustments to the user's dietary plan.

Hydrolysis of Adipose Tissues

In accordance with an aspect, stimulation of the sympathetic nerves using the PEDP device of the present specification allows for innervation of white adipose tissue to hydrolyze them. Even after losing weight, there are spots or areas that remain with a high amount of adipose tissue (for example hip or upper arm or love handles on the trunk). In some embodiments, these spots or areas are stimulated over long periods of time, for example daily, to hydrolyze the adipose tissue accumulated in these spots or areas.

The above examples are merely illustrative of the many applications of the methods and systems of present specification. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An electrical dermal patch adapted to be adhered to a patient's skin configured to modulate at least one of the patient's appetite, hunger, level of satiety, or level of satiation level, the electrical dermal patch comprising:

a housing, wherein the housing is defined by a thickness, a width, and a length and wherein the thickness is less than either the width or length;

a controller positioned in the housing;

at least a first electrode partially positioned in the housing and adapted to be implanted to a depth of 0.1 mm to 30 mm within said patient's skin;

a non-transient memory positioned in the housing;

a pulse generator positioned in the housing and in electrical communication with the controller and said at least first electrode; and a plurality of programmatic instructions, stored in the non-transient memory, wherein, when executed by the controller, the plurality of programmatic instructions cause the pulse generator to generate a plurality of electrical pulses, wherein the plurality of electrical pulses comprise a pulse width in a range of 10 μsec to 100 msec, a pulse amplitude in a range of 100 μA to 500 mA, and a pulse frequency in a range of 1 Hz to 10,000 Hz, and wherein at least one of the pulse width, pulse amplitude or pulse frequency is selected such that the patient's appetite, hunger, level of satiety or level of satiation is modulated.

2. The electrical dermal patch of claim 1 further comprising a second electrode adapted to be positioned on a surface of the patient's skin.

3. The electrical dermal patch of claim 1 further comprising a second percutaneous electrode adapted to be implanted to a depth of 0.1 mm to 30 mm within said patient's skin.

4. The electrical dermal patch of claim 1 wherein the pulse generator is configured to generate a corresponding electrical field, wherein the electrical field is adapted to penetrate a range of 0.1 mm to 30 mm through the patient's skin.

5. The electrical dermal patch of claim 1 wherein the at least first electrode is positioned outside said housing.

6. The electrical dermal patch of claim 4 wherein the electrical field is adapted to contact at least one of the patient's T2 frontal and lateral thoracic dermatome, T3 frontal and lateral thoracic dermatome, T4 frontal and lateral thoracic dermatome, T5 frontal and lateral thoracic dermatome, T6 frontal and lateral thoracic dermatome, T7 frontal and lateral thoracic dermatome, T8 frontal and lateral thoracic dermatome, T9 frontal and lateral thoracic dermatome, or T10 frontal and lateral thoracic dermatome.

7. The electrical dermal patch of claim 4 wherein the electrical field is adapted to contact at least one of the patient's T2 frontal and lateral thoracic dermatome, T3 frontal and lateral thoracic dermatome, T4 frontal and lateral thoracic dermatome, T5 frontal and lateral thoracic dermatome, T6 frontal and lateral thoracic dermatome, T7 frontal and lateral thoracic dermatome, T8 frontal and lateral thoracic dermatome, T9 frontal and lateral thoracic dermatome, and T10 frontal and lateral thoracic dermatome and is not positioned within a range of 0.1 mm to 25 mm from any one of the patient's T2 posterior thoracic dermatome, T3 posterior thoracic dermatome, T4 posterior thoracic dermatome, T5 posterior thoracic dermatome, T6 posterior thoracic dermatome, T7 posterior thoracic dermatome, T8 posterior thoracic dermatome, T9 posterior thoracic dermatome, and T10 posterior thoracic dermatome.

8. The electrical dermal patch of claim 4 wherein the electrical field is adapted to contact at least one of the patient's C8 anterior or posterior dermatome located on the patient's hand, wrist, elbow, and fingers, C8 anterior or posterior dermatome located on the patient's arm, C8 dermatome located on the patient's upper trunk, T1 anterior or posterior dermatome located on the patient's arm, T1 anterior or posterior dermatome located on the patient's wrist, elbow, and hand, and T1 anterior or posterior dermatome located on the patient's upper trunk is electrically stimulated.

9. The electrical dermal patch claim 1 further comprising an adhesive layer positioned on a bottom surface of the electrical dermal patch, such that when the adhesive layer is adhered to the patient's skin, the electrical dermal patch has an average minimum peel strength in a range of 1.3 to 1.7 newtons.

* * * * *